(12) United States Patent
Clark et al.

(10) Patent No.: US 7,807,690 B2
(45) Date of Patent: Oct. 5, 2010

(54) 2,3-DIHYDRO-IMINOISOINDOLE DERIVATIVES

(75) Inventors: Richard Clark, Tsukuba (JP); Atsushi Takemura, Tsukuba (JP); Nobuhisa Watanabe, Tsukuba (JP); Osamu Asano, Tsukuba (JP); Tadashi Nagakura, Tsukuba (JP); Kimiyo Tabata, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 12/234,116

(22) Filed: Sep. 19, 2008

(65) Prior Publication Data

US 2009/0270433 A1 Oct. 29, 2009

Related U.S. Application Data

(60) Provisional application No. 60/975,055, filed on Sep. 25, 2007.

(30) Foreign Application Priority Data

Sep. 21, 2007 (JP) .............................. 2007-245988

(51) Int. Cl.
| | |
|---|---|
| A61K 31/506 | (2006.01) |
| A61K 31/4439 | (2006.01) |
| A61K 31/427 | (2006.01) |
| A61K 31/422 | (2006.01) |
| A61K 31/4196 | (2006.01) |
| C07D 401/14 | (2006.01) |
| C07D 403/14 | (2006.01) |
| C07D 413/14 | (2006.01) |
| C07D 417/14 | (2006.01) |
| C07D 249/12 | (2006.01) |

(52) U.S. Cl. .................. 514/275; 514/339; 514/370; 514/377; 514/384; 544/331; 546/272.4; 548/181; 548/233; 548/264.2

(58) Field of Classification Search ................ None
See application file for complete search history.

(56) References Cited

U.S. PATENT DOCUMENTS

| | | |
|---|---|---|
| 6,916,837 B2 | 7/2005 | Satoh et al. |
| 7,576,098 B2 | 8/2009 | Glunz et al. |
| 2002/0004608 A1 | 1/2002 | Alig et al. |
| 2002/0052417 A1 | 5/2002 | Klingler et al. |
| 2003/0181766 A1 | 9/2003 | Satoh et al. |
| 2004/0242627 A1 | 12/2004 | Suzuki et al. |
| 2004/0254376 A1 | 12/2004 | Suzuki et al. |
| 2005/0004197 A1 | 1/2005 | Suzuki et al. |
| 2005/0004204 A1 | 1/2005 | Suzuki et al. |
| 2005/0245592 A1 | 11/2005 | Suzuki et al. |
| 2008/0015199 A1 | 1/2008 | Clark et al. |
| 2008/0132507 A1 | 6/2008 | Clark et al. |

| | | |
|---|---|---|
| 2009/0270433 A1 | 10/2009 | Clark et al. |

FOREIGN PATENT DOCUMENTS

| | | |
|---|---|---|
| AU | 58281/80 | 11/1980 |
| EP | 0 019 586 | 11/1980 |
| EP | 1 020 434 A1 | 7/2000 |
| EP | 1 078 917 A1 | 2/2001 |
| EP | 1 312 602 A1 | 5/2003 |
| JP | 2002-509924 A | 4/2002 |
| JP | 2002-543176 A | 12/2002 |
| JP | 2003-212837 A | 7/2003 |
| JP | 2003-534311 A | 11/2003 |
| JP | 2003-535844 A | 12/2003 |
| SU | 1512055 | 7/1992 |
| WO | WO-99/10316 A1 | 3/1999 |
| WO | WO-99/41231 A1 | 8/1999 |
| WO | WO-99/50255 A2 | 10/1999 |
| WO | WO-00/35858 A1 | 6/2000 |
| WO | WO-00/41531 A2 | 7/2000 |
| WO | WO-00/58346 A1 | 10/2000 |
| WO | WO-00/66545 A1 | 11/2000 |
| WO | WO-02/085855 A1 | 10/2002 |
| WO | WO-2004/032846 A2 | 4/2004 |
| WO | WO-2004/101555 A1 | 11/2004 |
| WO | WO-2006/062972 A2 | 6/2006 |
| WO | WO 2007/111212 | * 10/2007 |
| WO | WO-2007/111212 A1 | 10/2007 |

OTHER PUBLICATIONS

"cancer." MedLine Plus. (2009). Accessed Mar. 17, 2009. <http://www.nlm.nih.gov/medlineplus/cancer.html>.*

Golub et al. "Molecular Classification of Cancer: Class Discovery and Class Prediction by Gene Expression Monitoring." Science (1999), vol. 286, 521-537.*

(Continued)

*Primary Examiner*—Golam M. M. Shameem
*Assistant Examiner*—Alicia L Fierro
(74) *Attorney, Agent, or Firm*—Birch, Stewart, Kolasch & Birch, LLP

(57) ABSTRACT

A compound represented by the following general formula (1), or a salt thereof has serine protease inhibiting activity, and particularly excellent inhibiting activity against clotting factor VIIa. This compound or a salt thereof is useful as therapeutic and/or prophylactic agents for diseases associated with thrombus formation.

(1)

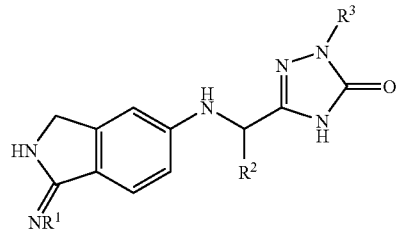

[wherein $R^1$ represents hydrogen, $R^2$ represents optionally substituted phenyl, etc., $R^3$ represents optionally substituted C6-10 aryl, etc.].

25 Claims, No Drawings

OTHER PUBLICATIONS

Lala et al. "Role of nitric oxide in tumor progression: Lessons from experimental tumors." Cancer and Metastasis Reviews (1998), 17(1), 91-106.*

Roussel, P. et al., "Inhibition of the Tissue Factor/Factor Vlla Complex—Lead Optimisation Using Combinatorial Chemistry", Tetrahedron vol. 55, 1999, pp. 6219-6230.

Vippagunta et al., "Crystalline Solids," *Adv. Drug Delivery Rev.*, 48, pp. 3-26 (2001).

McMahon et al., "VEGF Receptor Signaling in Tumor Angiogenesis," *The Oncologist*, 5 (suppl 1): pp. 3-10 (2000).

Jinrong Fu et al., "Anti-apoptotic role . . . ," *Biochemical and Biophysical Research Comm.*, 349, pp. 504-512 (2006).

Pinedo et al., "Translational Research . . . ," *The Oncologist*, 5 (suppl 1): pp. 1-2 (2000).

Office Action of Dec. 28, 2009 in U.S. Appl. No. 11/723,893.
Office Action of Jul. 20, 2009 in U.S. Appl. No. 11/723,893.
Office Action of Jun. 24, 2009 in U.S. Appl. No. 11/665,385.
Database WPI Week 199323, Thomson Scientific, London, GB 1993-186830, XP002540626.
International Preliminary Report on Patentability dated Apr. 15, 2010, PCT/JP2008/066944.
International Preliminary Report on Patentability dated Oct. 30, 2008, PCT/JP2007/055813.
Notice of Allowance of Feb. 23, 2010 in U.S. Appl. No. 11/665,385.
Notice of Allowance of May 6, 2010 in U.S. Appl. No. 11/723,893.
Office Action of Feb. 25, 2009 in U.S. Appl. No. 11/665,385.
Office Action of Mar. 30, 2009 in U.S. Appl. No. 11/723,893.

* cited by examiner

2,3-DIHYDRO-IMINOISOINDOLE DERIVATIVES

CROSS-REFERENCE TO RELATED APPLICATION

This application claims priority to U.S. Provisional Application 60/975,055 filed on Sep. 25, 2007 as well as Japanese Patent Application 2007-245988 filed on Sep. 21, 2007, all of which are herein incorporated by reference in their entirety.

BACKGROUND OF THE INVENTION

1. Field of the Invention

The present invention relates to novel 2,3-dihydro-iminoisoindole derivatives that are useful as pharmaceuticals, to their pharmacologically acceptable salts, and to therapeutic or prophylactic agents for diseases associated with thrombus formation that contain the foregoing as active ingredients.

2. Related Background Art

Living organisms with damaged blood vessels avoid hemorrhage death by rapid production of thrombin. However, excess production of thrombin by inflammatory reaction in damaged blood vessels causes thrombosis, which impairs the function of essential organs. Thrombin inhibitors such as heparin and warfarin, which inhibit thrombin production or directly block thrombin activity, have long been used as anticoagulants to treat or prevent thrombosis. Currently, new anticoagulants are being sought that exhibit a more reliable dose-dependent medicament effect, and which are safer and suitable for oral administration.

The blood clotting mechanism has been classified into two pathways, the "intrinsic clotting pathway" which begins with activation of factor XII (FXII) upon contact with negatively charged substances, and the "extrinsic clotting pathway" which is activated by tissue factor (TF) and factor VII (FVII), and since the pathology of thrombosis onset is associated with specific expression of TF, it has been suggested that extrinsic clotting is of major importance. Compounds that inhibit clotting factor VIIa, which is furthest upstream in the extrinsic clotting pathway of the clotting cascade, are thought to have potential use as therapeutic and/or prophylactic agents for diseases associated with thrombus formation, such as thrombosis, in which the extrinsic clotting mechanism plays a part.

As compounds that inhibit clotting factor VIIa there are known in the prior art amidinonaphthol derivatives (see Non-patent document 1), amidino derivatives (see Patent document 1), N-sulfonyldipeptide derivatives (see Patent document 2), 6-[[(allyl)oxy]methyl]naphthalene-2-carboxyimidamide derivatives (see Patent document 3) and phenylglycine derivatives (Patent documents 4 and 5).

However, these known compounds have still been inadequate from the standpoint of inhibiting activity against clotting factor VIIa, blood clotting effects and thrombosis-treating effects.

[Non-patent document 1] Tetrahedron, 55, p. 6219, 1999
[Patent document 1] EP 1078917
[Patent document 2] WO 00/58346
[Patent document 3] WO 00/66545
[Patent document 4] WO 00/35858
[Patent document 5] WO 00/41531

SUMMARY OF THE INVENTION

It is an object of the present invention, which has been accomplished in light of the aforementioned problems of the prior art, to provide novel 2,3-dihydro-iminoisoindole derivatives having serine protease inhibiting activity, and particularly excellent inhibiting activity against clotting factor VIIa, as well as their pharmacologically acceptable salts, and therapeutic and/or prophylactic agents for diseases associated with thrombus formation, that employ the foregoing.

As a result of much diligent research in light of the circumstances described above, the present inventors have succeeded in synthesizing novel 2,3-dihydro-iminoisoindole derivatives having a specific chemical structure, and have completed this invention upon discovering that these compounds have excellent inhibiting activity against clotting factor VIIa, and particularly that they are useful as therapeutic and/or prophylactic agents for diseases associated with thrombus formation. In other words, the present invention provides the following [1]-[35].

[1] A compound represented by general formula (I), or a salt thereof:

[Chemical Formula 1]

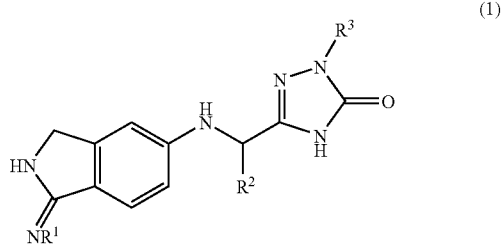

(1)

wherein $R^1$ represents hydrogen;

$R^2$ represents a C6-10 aryl optionally having 1-5 substituents selected from Group A1 below, a 5- to 10-membered heteroaryl group optionally having 1-5 substituents selected from Group A1 below or a 9- to 12-membered benzene-fused cyclic group optionally having 1-5 substituents selected from Group A1 below; and $R^3$ represents a 5- or 6-membered non-aromatic heterocyclic group optionally having 1-S substituents selected from Group A1 below, a C6-10 aryl optionally having 1-5 substituents selected from Group A1 below or a 5- to 10-membered heteroaryl group optionally having 1-5 substituents selected from Group A1 below, wherein Group A1 consists of hydroxyl, halogen, cyano, nitro, oxo, C1-6 alkyl optionally having 1-3 substituents selected from Group B1 below, C3-8 cycloalkyl optionally having 1-5 substituents selected from Group B1 below, C2-6 alkenyl, C2-6 alkynyl, C1-6 alkoxy optionally having 1-3 substituents selected from Group B1 below, C3-8 cycloalkyloxy optionally having 1-5 substituents selected from Group B1 below, C2-6 alkenyloxy, C2-6 alkynyloxy, C1-6 alkylthio, C1-6 alkylsulfinyl, C1-6 alkylsulfonyl, C1-6 alkylsulfonyloxy, C6-10 aryl optionally having 1-5 substituents selected from Group B1 below, C6-10 aryloxy optionally having 1-5 substituents selected from Group B1 below, 5- to 10-membered heteroaryl group optionally having 1-5 substituents selected from Group B1 below, 5- to 10-membered heteroaryloxy optionally having 1-5 substituents selected from Group B1 below, a 5- or 6-membered non-aromatic heterocyclic group optionally having 1-5 substituents selected from Group B1 below, 5- or 6-membered non-aromatic heterocyclooxy optionally having 1-5 substituents selected from Group B1 below, a group represented by —$NR^{1'}$—$R^{2'}$ and a group represented by —CO—$R^{3'}$;

where $R^{1'}$ and $R^{2'}$ each independently represent hydrogen, C1-6 alkyl optionally having 1-3 substituents selected from Group B1 below, C2-6 alkenyl, C2-7 alkylcarbonyl optionally having 1-3 substituents selected from Group B13 below, C2-7 alkoxycarbonyl optionally having 1-3 substituents selected from Group B1 below, C1-6 alkylsulfonyl optionally having 1-3 substituents selected from Group B1 below, carbamoyl, aminosulfonyl, C6-10 aryl optionally having 1-5 substituents selected from Group B1 below or 5- to 10-membered heteroaryl group optionally having 1-5 substituents selected from Group B1 below, and $R^{3'}$ represents hydroxyl, C1-6 alkyl optionally having 1-3 substituents selected from Group B1 below, C1-6 alkoxy optionally having 1-3 substituents selected from Group B1 below, amino, mono(C1-6 alkyl)amino optionally having 1-3 substituents selected from Group B1 below or di(C1-6 alkyl)amino optionally having 1-3 substituents selected from Group B1 below, wherein Group B1 consists of hydroxyl, halogen, cyano, oxo, C1-6 alkoxy optionally having halogen, C3-8 cycloalkyl, amino, mono(C1-6 alkyl)amino, di(C1-6 alkyl)amino, carbamoyl, mono(C1-6 alkyl)aminocarbonyl, di(C1-6 alkyl)aminocarbonyl, C6-10 aryl optionally having 1-5 substituents selected from Group C1 below, and 5- to 10-membered heteroaryl group optionally having 1-5 substituents selected from Group C1 below, wherein Group C1 consists of halogen, C1-6 alkyl and C1-6 alkoxy.

[2] A compound represented by general formula (1-1), or a salt thereof:

[Chemical Formula 2]

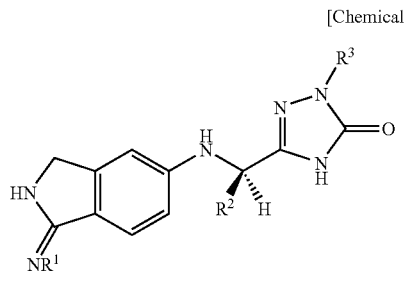

(1-1)

wherein $R^1$, $R^2$ and $R^3$ have the same definitions as $R^1$, $R^2$ and $R^3$ in [1] above.

[3] A compound represented by general formula (1-2), or a salt thereof:

[Chemical Formula 3]

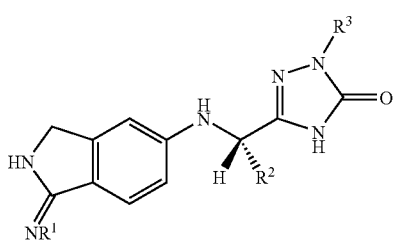

(1-2)

wherein $R^1$, $R^2$ and $R^3$ have the same definitions as $R^1$, $R^2$ and $R^3$ in [1] above.

[4] A compound represented by the following general formula, or a salt thereof:

[Chemical Formula 4]

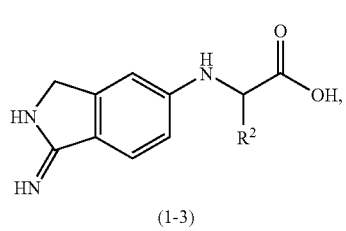

(1-3)

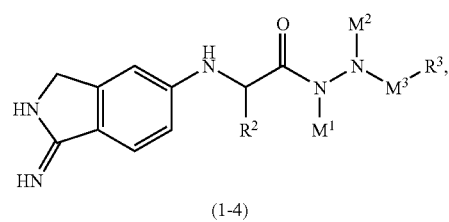

(1-4)

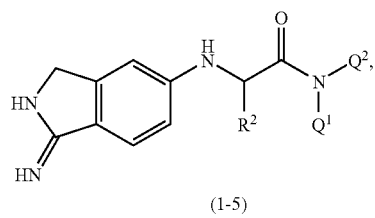

(1-5)

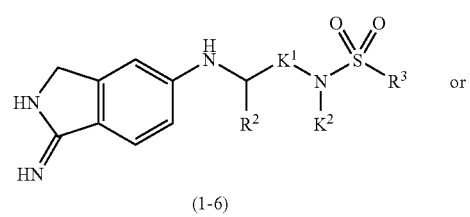

(1-6)

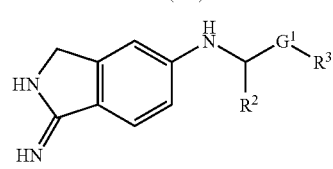

(1-7)

wherein $R^2$ and $R^3$ have the same definitions as $R^2$ and $R^3$ in [1] above;

$M^1$ represents hydrogen or C1-6 alkyl; $M^2$ represents hydrogen or C1-6 alkyl; $M^3$ represents a single bond, —$SO_2$—, —CO— or —CS—;

$Q^1$ represents hydrogen or C1-6 alkyl; $Q^2$ represents morpholino or a group represented by the following formula:

[Chemical Formula 5]

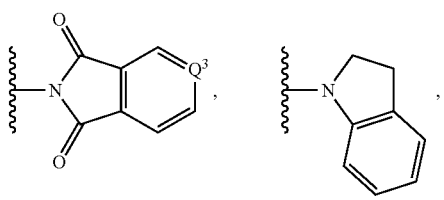

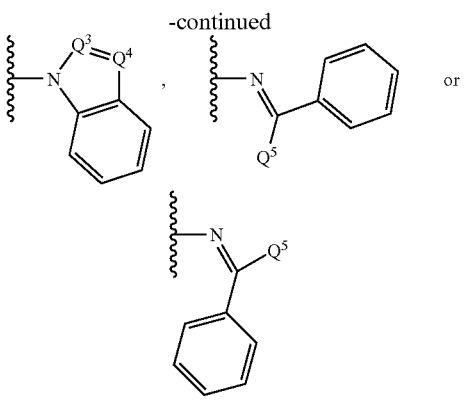

wherein $Q^5$ represents hydrogen or C1-6 alkyl, and $Q^3$ and $Q^4$ each independently represent methyne or nitrogen, where $Q^2$ optionally has 1-3 substituents selected from Group A1 in [1] above;

$K^1$ represents methylene or carbonyl; $K^2$ represents hydrogen or C1-6 alkyl;

$G^1$ represents a 5- to 10-membered heterocyclic group selected from the following Group G1: Group G1 is the group consisting of furyl, thienyl, pyrolyl, imidazolyl, triazolyl, tetrazolyl, thiazolyl, pyrazolyl, oxazolyl, isooxazolyl, isothiazolyl, furazanyl, thiadiazolyl, oxadiazolyl, pyridyl, pyrazinyl, pyridazinyl, pyrimidinyl, triazinyl, purinyl, pteridinyl, quinolyl, isoquinolyl, naphthylidinyl, quinoxalinyl, cinnolinyl, quinazolinyl, phthaladinyl, imidazopyridyl, imidazothiazolyl, imidazooxazolyl, benzothiazolyl, benzooxazolyl, benzoimidazolyl, indolyl, isoindolyl, indazolyl, pyrrolopyridyl, thienopyridyl, furopyridyl, benzothiadiazolyl, benzooxadiazolyl, pyridopyrimidinyl, benzofuryl, benzothienyl, benzo[1,3]dioxole, thienofuryl, N-oxypyridyl, N—C1-6 alkylpyridinium, 5,6,7,8-tetrahydroquinolyl and 4,5,6,7-tetrahydro-1H-benzo[d]imidazolyl.

[5] A compound or a salt thereof according to any one of [1] to [4] above, wherein $R^2$ is phenyl optionally having 1-4 substituents selected from Group D1 below, pyridyl optionally having 1-3 substituents selected from Group D1 below or a 9- to 12-membered benzene-fused cyclic group optionally having 1-4 substituents selected from Group D1 below, wherein Group D1 consists of hydroxyl, halogen, C1-6 alkyl optionally having 1-3 substituents selected from Group D2 below, C2-6 alkenyl, C2-6 alkynyl, C1-6 alkoxy optionally having 1-3 substituents selected from Group D2 below, C2-6 alkenyloxy, C1-6 alkylsulfonyloxy, 5- or 6-membered non-aromatic heteroclooxy optionally having 1-3 substituents selected from Group D2 below and C2-7 alkylcarbonyl, wherein Group D2 consists of hydroxyl, halogen, cyano, oxo, C1-6 alkoxy optionally having halogen, mono(C1-6 alkyl)amino, di(C1-6 alkyl)amino, mono(C1-6 alkyl)aminocarbonyl and di(C1-6 alkyl)aminocarbonyl.

[6] A compound or a salt thereof according to any one of [1] to [4] above, wherein $R^2$ is phenyl optionally having 1-4 substituents selected from Group D1 below, wherein Group D1 consists of hydroxyl, halogen, C1-6 alkyl optionally having 1-3 substituents selected from Group D2 below, C2-6 alkenyl, C2-6 alkynyl, C6-6 alkoxy optionally having 1-3 substituents selected from Group D2 below, C2-6 alkenyloxy, C1-6 alkylsulfonyloxy, 5- or 6-membered non-aromatic heteroclooxy optionally having 1-3 substituents selected from Group D2 below and C2-7 alkylcarbonyl, wherein Group D2 consists of hydroxyl, halogen, cyano, oxo, C1-6 alkoxy optionally having halogen, mono(C1-6 alkyl)amino, di(C1-6 alkyl)amino, mono(C1-6 alkyl)aminocarbonyl and di(C1-6 alkyl)aminocarbonyl.

[7] A compound or a salt thereof according to any one of [1] to [4] above, wherein $R^2$ is phenyl optionally having 2 or 3 substituents selected from Group D3 below, wherein Group D3 consists of fluorine, chlorine, methyl optionally having 1 substituent selected from Group D4 below, ethyl optionally having 1 substituent selected from Group D4 below, vinyl, ethynyl, methoxy optionally having 1 or 2 substituents selected from Group D4 below, ethoxy optionally having 1 or 2 substituents selected from Group D4 below, 1-propyloxy optionally having 1 or 2 substituents selected from Group D4 below, 2-propyloxy optionally having 1 or 2 substituents selected from Group D4 below, allyloxy, tetrahydrofuryloxy, tetrahydropyranyloxy and acetyl, wherein Group D4 consists of hydroxyl, fluorine, cyano, methoxy, methylamino, dimethylamino, methylaminocarbonyl and dimethylaminocarbonyl.

[8] A compound or a salt thereof according to any one of [1] to [4] above, wherein $R^2$ is a group represented by the following formula:

[Chemical Formula 6]

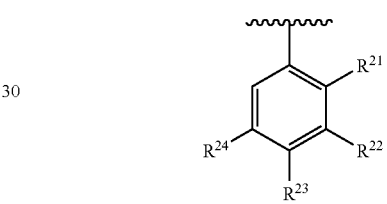

wherein $R^{21}$ represents hydrogen, benzyloxy, fluorine or chlorine;

$R^{22}$ represents hydrogen, hydroxyl, methyl optionally having 1 substituent selected from Group D5 below, ethyl optionally having 1 substituent selected from Group D5 below, methoxy optionally having 1 substituent selected from Group D5 below, ethoxy optionally having 1 or 2 substituents selected from Group D5 below, 1-propyloxy optionally having 1 substituent selected from Group D5 below, 2-propyloxy optionally having 1 substituent selected from Group D5 below, allyloxy, tetrahydrofuryloxy, tetrahydropyranyloxy or acetyl;

$R^{23}$ represents hydrogen, fluorine, hydroxyl, methoxy optionally having 1 substituent selected from Group D6 below, ethoxy optionally having 1 substituent selected from Group D6 below or 2-propyloxy optionally having 1 substituent selected from Group D6 below; and $R^{24}$ represents hydrogen, fluorine, hydroxyl, methyl optionally having 1 substituent selected from Group 1)₇ below, ethyl, vinyl, ethynyl, methoxy optionally having 1 substituent selected from Group D7 below, ethoxy optionally having 1 substituent selected from Group D7 below, 2-propyloxy or allyloxy, wherein Group D5 consists of hydroxyl, fluorine, cyano, methoxy, dimethylamino, dimethylaminocarbonyl, 2-fluoroethoxy and 2-hydroxyethoxy, wherein Group D6 consists of fluorine, cyano, methoxy, dimethylamino, methylaminocarbonyl and dimethylaminocarbonyl, wherein Group D7 consists of hydroxyl, fluorine, cyano and ethoxy having one methoxy group.

[9] A compound or a salt thereof according to [8] above, wherein $R^{21}$ is hydrogen or fluorine.

[10] A compound or a salt thereof according to [8] or [9], wherein $R^{22}$ is hydrogen, hydroxyl, cyanomethyl, methoxymethyl, methoxy, dimethylaminocarbonylmethoxy, ethoxy, 2-fluoroethoxy, 2-hydroxyethoxy, 2-methoxyethoxy, 2-(dimethylamino)ethoxy, tetrahydrofuryloxy, tetrahydropyranyloxy, fluoromethoxy, 3-hydroxypropyloxy, 2-fluoroethoxymethyl or 2-hydroxyethoxymethyl.

[11] A compound or a salt thereof according to any one of [8] to [10] above, wherein $R^{23}$ is hydrogen, fluorine, methoxy, cyanomethoxy, ethoxy, 2-propyloxy or 2-methoxyethoxy.

[12] A compound or a salt thereof according to any one of [8] to [1,1] above, wherein $R^{24}$ is hydrogen, hydroxyl, methyl, methoxymethyl, ethyl, vinyl, ethynyl, methoxy, ethoxy or 2-fluoroethoxy.

[13] A compound or a salt thereof according to any one of [1] to [4] above, wherein $R^2$ is pyridyl optionally having 1-3 substituents selected from Group D1 below, wherein Group D1 consists of hydroxyl, halogen, C1-6 alkyl optionally having 1-3 substituents selected from Group D2 below, C2-6 alkenyl, C2-6 alkynyl, C1-6 alkoxy optionally having 1-3 substituents selected from Group D2 below, C2-6 alkenyloxy, C1-6 alkylsulfonyloxy, 5- or 6-membered non-aromatic heterocyclooxy optionally having 1-3 substituents selected from Group D2 below and C2-7 alkylcarbonyl, wherein Group D2 consists of hydroxyl, halogen, cyano, oxo, C1-6 alkoxy optionally having halogen, mono(C1-6 alkyl)amino, di(C1-6 alkyl)amino, mono(C1-6 alkyl)aminocarbonyl and di(C1-6 alkyl)aminocarbonyl.

[14] A compound or a salt thereof according to any one of [1] to [4] above, wherein $R^2$ is pyridyl having two substituents selected from the group consisting of C1-6 alkyl and C1-6 alkoxy.

[15] A compound or a salt thereof according to any one of [1] to [4] above, wherein $R^2$ is pyridyl having two substituents selected from the group consisting of methyl, methoxy and ethoxy.

[16] A compound or a salt thereof according to any one of [1] to [4] above, wherein $R^2$ is a group represented by the following formula:

[Chemical Formula 7]

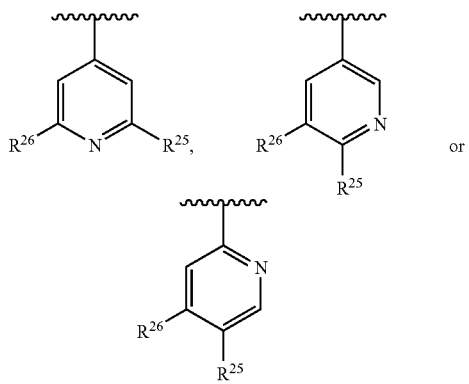

wherein $R^{25}$ is methyl or methoxy, and $R^{26}$ is methoxy or ethoxy.

[17] A compound or a salt thereof according to any one of [1] to [4] above, wherein $R^2$ is a 9- to 12-membered benzene-fused cyclic group optionally having 1-4 substituents selected from Group D1 below, wherein Group D1 consists of hydroxyl, halogen, C1-6 alkyl optionally having 1-3 substituents selected from Group D2 below, C2-6 alkenyl, C2-6 alkynyl, C1-6 alkoxy optionally having 1-3 substituents selected from Group D2 below, C2-6 alkenyloxy, C1-6 alkylsulfonyloxy, 5- or 6-membered non-aromatic heterocyclooxy optionally having 1-3 substituents selected from Group D2 below and C2-7 alkylcarbonyl, wherein Group D2 consists of hydroxyl, halogen, cyano, oxo, C1-6 alkoxy optionally having halogen, mono(C1-6 alkyl)amino, di(C1-6 alkyl)amino, mono(C1-6 alkyl)aminocarbonyl and di(C1-6 alkyl)aminocarbonyl,

[18] A compound or a salt thereof according to any one of [1] to [4] above, wherein $R^2$ is a group represented by the following formula:

[Chemical Formula 8]

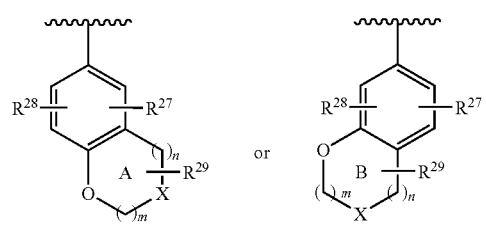

wherein $R^{27}$ represents hydrogen or halogen;

$R^{28}$ represents hydrogen, hydroxyl, halogen, C1-6 alkyl optionally having 1-3 substituents selected from Group D8 below, C2-6 alkenyl, C2-6 alkynyl, C1-6 alkoxy optionally having 1-3 substituents selected from Group D8 below, or C2-7 alkylcarbonyl;

$R^{29}$ represents hydrogen, cyano, C1-6 alkyl optionally having 1-3 substituents selected from Group D8 below, C1-6 alkoxy optionally having 1-3 substituents selected from Group D8 below or carbamoyl;

X represents carbon optionally having 1 or 2 substituents selected from Group D8 below, nitrogen optionally having 1 substituent selected from Group D8 below or oxygen;

m represents an integer from 0 to 3 and n represents an integer from 0 to 2, with the proviso that the sum of m and n is 1-4; and Rings A and B optionally contain one double bond in the ring and optionally have an oxo group on the ring, wherein Group D8 consists of hydrogen, hydroxyl, halogen, C1-6 alkoxy, mono(C1-6 alkyl)amino, di(C1-6 alkyl)amino, mono(C1-6 alkyl)aminocarbonyl, di(C1-6 alkyl)aminocarbonyl and C1-6 alkyl optionally having halogen.

[19] A compound or a salt thereof according to [1,8] above, wherein $R^2$ is a group represented by the following formula:

[Chemical Formula 9]

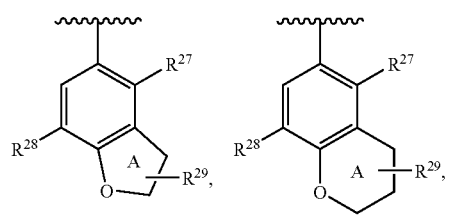

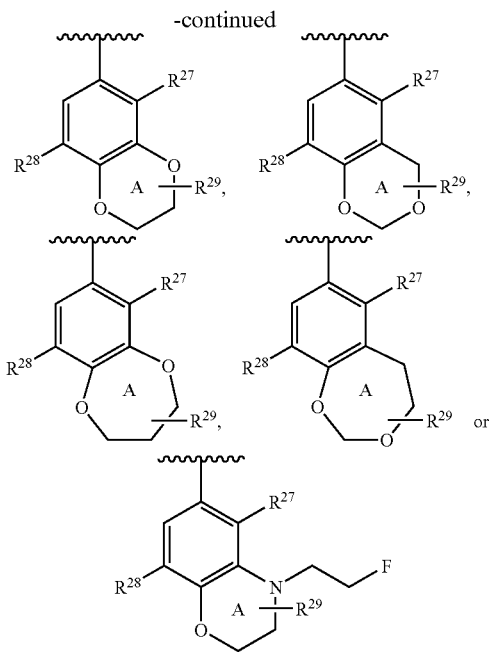

wherein R²⁷ represents hydrogen or halogen;

R²⁸ represents hydrogen, hydroxyl, C1-6 alkyl optionally having 1-3 substituents selected from Group D8 below, C2-6 alkenyl, C2-6 alkynyl, C1-6 alkoxy optionally having 1-3 substituents selected from Group D8 below or C2-7 alkylcarbonyl;

R²⁹ represents hydrogen, cyano, C1-6 alkyl optionally having 1-3 substituents selected from Group D8 below, C1-6 alkoxy optionally having 1-3 substituents selected from Group D8 below or aminocarbonyl; and Ring A optionally has an oxo group on the ring, wherein Group D8 consists of hydrogen, hydroxyl, halogen, C1-6 alkoxy, mono(C1-6 alkyl)amino, di(C1-6 alkyl)amino, mono(C1-6 alkyl)aminocarbonyl, di(C1-6 alkyl)aminocarbonyl and C1-6 alkyl optionally having halogen.

[20] A compound or a salt thereof according to [19] above, wherein R²⁸ is methyl, ethyl, methoxy, ethoxy, vinyl or ethynyl.

[21] A compound or a salt thereof according to [19] or [20] above, wherein R²⁹ is hydrogen.

[22] A compound or a salt thereof according to any one of [1] to [21] above, wherein R³ is phenyl optionally having 1-3 substituents selected from Group E1 below, pyridyl optionally having 1-3 substituents selected from Group E1 below, N-oxypyridyl optionally having 1-3 substituents selected from Group E1 below, N—C1-6 alkylpyridinium optionally having 1-3 substituents selected from Group E1 below, pyrazinyl optionally having 1-3 substituents selected from Group E1 below, pyridazinyl optionally having 1-3 substituents selected from Group E1 below, pyrimidinyl optionally having 1-3 substituents selected from Group E1 below, pyrazolyl optionally having 1 or 2 substituents selected from Group E1 below, imidazolyl optionally having 1 or 2 substituents selected from Group E1 below, thiazolyl optionally having 1 or 2 substituents selected from Group E1 below, thienyl optionally having 1-3 substituents selected from Group E1 below, oxazolyl optionally having 1-3 substituents selected from Group E1 below or dihydropyrazinyl having an oxo group, with the proviso that when R³ is N—C1-6 alkylpyridinium, R³ forms an ion pair with an anion in the molecule, wherein Group E1 consists of hydroxyl, halogen, cyano, C1-6 alkyl, C1-6 alkoxy, a group represented by the formula —NH—R²¹ʳ and a group represented by the formula —CO—R³¹ʳ;

where R²¹ʳ represents hydrogen, C1-6 alkyl, C2-6 alkenyl, C2-7 alkylcarbonyl optionally having 1-3 substituents selected from Group E2 below, C2-7 alkoxycarbonyl optionally having 1-3 substituents selected from Group E2 below, C1-6 alkylsulfonyl, carbamoyl or aminosulfonyl, and R³¹ʳ represents hydroxyl, C1-6 alkyl, C1-6 alkoxy, amino, mono(C1-6 alkyl)amino or di(C1-6 alkyl)amino, wherein Group E2 consists of hydroxyl, C1-6 alkoxy and C3-8 cycloalkyl.

[23] A compound or a salt thereof according to any one of [1] to [21] above, wherein R³ is phenyl optionally having 1 or 2 substituents selected from Group E3 below, pyridyl optionally having 1 or 2 substituents selected from Group E3 below, N-oxypyridyl optionally having 1 or 2 substituents selected from Group E3 below, pyrazinyl optionally having 1 or 2 substituents selected from Group E3 below, pyridazinyl optionally having 1 or 2 substituents selected from Group E3 below, pyrimidinyl optionally having 1 or 2 substituents selected from Group E3 below, pyrazolyl optionally having 1 or 2 substituents selected from Group E3 below, imidazolyl optionally having 1 or 2 substituents selected from Group E3 below, thiazolyl optionally having 1 or 2 substituents selected from Group E3 below, thienyl optionally having 1 or 2 substituents selected from Group E3 below, oxazolyl optionally having 1 or 2 substituents selected from Group E3 below or dihydropyrazinyl having an oxo group, wherein Group E3 consists of halogen, C1-6 alkyl, C1-6 alkoxy, a group represented by the formula —NH—R²²ʳ, nitro and a group represented by the formula —CO—R³²ʳ;

where R²²ʳ is hydrogen or C2-7 alkoxycarbonyl, and R³²ʳ is hydroxyl, C1-6 alkoxy or amino.

[24] A compound or a salt thereof according to any one of [1] to [21] above, wherein R³ is phenyl optionally having one group selected from Group E4 below, pyridyl optionally having one group selected from Group E5 below, N-oxypyridyl, pyrazinyl, pyridazinyl, pyrimidinyl, pyrazolyl optionally having one group selected from Group E4 below, imidazolyl optionally having one group selected from Group E4 below, thiazolyl optionally having one group selected from Group E4 below, thienyl optionally having one group selected from Group E4 below, oxazolyl optionally having one group selected from Group E4 below or dihydropyrazinyl having an oxo group, wherein Group E4 consists of methoxy, a group represented by the formula —NH—R²²ʳ, nitro, carboxyl, carbamoyl, methoxycarbonyl and methoxycarbonylamino, where R²²ʳ is hydrogen or C2-7 alkoxycarbonyl, wherein Group E5 consists of fluorine, methyl, methoxy and amino.

[25] A medicament comprising a compound or a salt thereof according to any one of [1] to [24].

[26] A therapeutic and/or prophylactic agent for a disease associated with thrombus formation, which comprises a compound or a salt thereof according to any one of [1] to [24].

[27] A therapeutic and/or prophylactic agent for a disease selected from Group F1 below, which comprises a compound or a salt thereof according to any one of [1] to [24], wherein Group F1 consists of thrombosis, deep vein thrombosis, pulmonary embolism, cerebral infarction, myocardial infarction, acute coronary syndrome, vascular restenosis, disseminated intravascular coagulation syndrome and malignant tumor.

[28] A therapeutic and/or prophylactic agent for a disease selected from Group F2 below, which comprises a compound or a salt thereof according to any one of [1] to [24],
wherein Group F2 consists of thrombosis, deep vein thrombosis, pulmonary embolism, cerebral infarction, myocardial infarction, acute coronary syndrome, vascular restenosis and disseminated intravascular coagulation syndrome.

[29] A method for treatment and/or prevention of a disease associated with thrombus formation, which involves administration of a pharmacologically effective dose of a compound or a salt thereof according to any one of [1] to [24].

[30] A method for treatment and/or prevention of a disease selected from Group F1 below, which involves administration of a pharmacologically effective dose of a compound or a salt thereof according to any one of [1] to [24],
wherein Group F1 consists of thrombosis, deep vein thrombosis, pulmonary embolism, cerebral infarction, myocardial infarction, acute coronary syndrome, vascular restenosis, disseminated intravascular coagulation syndrome and malignant tumor.

[31] A method for treatment and/or prevention of a disease selected from Group F2 below, which involves administration of a pharmacologically effective dose of a compound or a salt thereof according to any one of [1] to [24],
wherein Group F2 consists of thrombosis, deep vein thrombosis, pulmonary embolism, cerebral infarction, myocardial infarction, acute coronary syndrome, vascular restenosis and disseminated intravascular coagulation syndrome.

[32] Use of a compound or a salt thereof according to any one of [1] to [24] for production of a therapeutic and/or prophylactic agent for a disease associated with thrombus formation.

[33] Use of a compound or a salt thereof according to any one of [1] to [24] for production of a therapeutic and/or prophylactic agent for a disease selected from Group F1 below,
wherein Group F1 consists of thrombosis, deep vein thrombosis, pulmonary embolism, cerebral infarction, myocardial infarction, acute coronary syndrome, vascular restenosis, disseminated intravascular coagulation syndrome and malignant tumor.

[34] Use of a compound or a salt thereof according to any one of [1] to [24] for production of a therapeutic and/or prophylactic agent for a disease selected from Group F2 below,
wherein Group F2 consists of thrombosis, deep vein thrombosis, pulmonary embolism, cerebral infarction, myocardial infarction, acute coronary syndrome, vascular restenosis and disseminated intravascular coagulation syndrome.

[35] A compound represented by the following general formula (1-3), or a salt thereof:

[Chemical Formula 10]

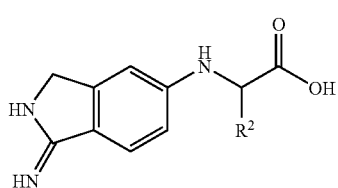

(1-3)

wherein $R^2$ has the same definition as $R^2$ in [1] above.

[36] A compound represented by the following general formula (1-4), or a salt thereof:

[Chemical Formula 11]

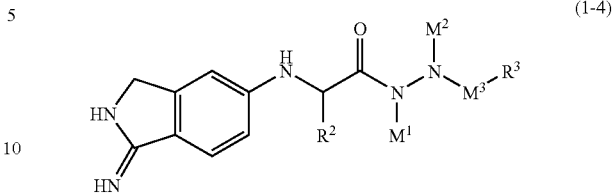

(1-4)

wherein $R^2$ and $R^3$ have the same definitions as $R^2$ and $R^3$ in [1] above;

$M^1$ represents hydrogen or C1-6 alkyl;

$M^2$ represents hydrogen or C1-6 alkyl; and $M^3$ represents a single bond, —$SO_2$—, —CO— or —CS—.

[37] A compound represented by the following general formula (1-5), or a salt thereof:

[Chemical Formula 12]

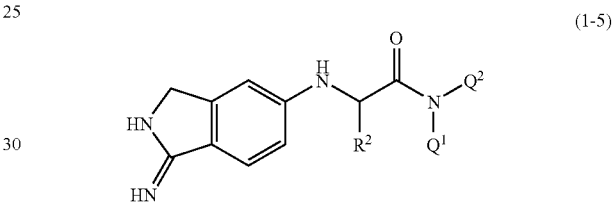

(1-5)

wherein $R^2$ has the same definition as $R^2$ in [1] above;

$Q^1$ represents hydrogen or C1-6 alkyl; and $Q^2$ represents morpholino or a group represented by the following formula:

[Chemical Formula 13]

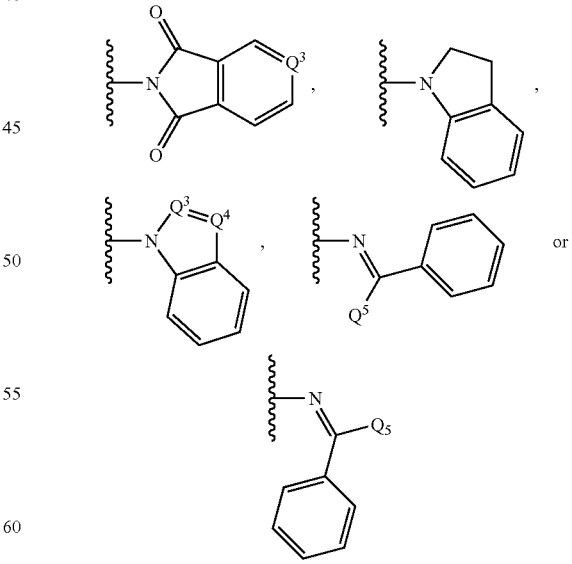

wherein $Q^5$ represents hydrogen or C1-6 alkyl, and $Q^3$ and $Q^4$ each independently represent methyne or nitrogen, where $Q^2$ optionally has 1-3 substituents selected from Group A1 in [1] above.

[38] A compound represented by the following general formula (1-6), or a salt thereof:

[Chemical Formula 14]

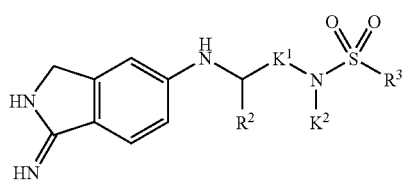

wherein $R^2$ and $R^3$ have the same definitions as $R^2$ and $R^3$ in [1] above, $K^1$ represents methylene or carbonyl and $K^2$ represents hydrogen or C1-6 alkyl

[39] A compound represented by the following general formula (1-8), or a salt thereof;

[Chemical Formula 15]

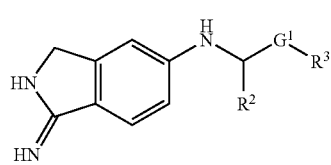

wherein $R^2$ and $R^3$ have the same definitions as $R^2$ and $R^3$ in [1] above and $G^1$ represents a 5- to 10-membered heterocyclic group selected from Group G1: Group G1 is the group consisting of furyl, thienyl, pyrolyl, imidazolyl, triazolyl, tetrazolyl, thiazolyl, pyrazolyl, oxazolyl, isooxazolyl, isothiazolyl, furazanyl, thiadiazolyl, oxadiazolyl, pyridyl, pyrazinyl, pyridazinyl, pyrimidinyl, triazinyl, purinyl, pteridinyl, quinolyl, isoquinolyl, naphthylidinyl, quinoxalinyl, cinnolinyl, quinazolinyl, phthaladinyl, imidazopyridyl, imidazothiazolyl, imidazooxazolyl, benzothiazolyl, benzooxazolyl, benzoimidazolyl, indolyl, isoindolyl, indazolyl, pyrrolopyridyl, thienopyridyl, furopyridyl, benzothiadiazolyl, benzooxadiazolyl, pyridopyrimidinyl, benzofuryl, benzothienyl, benzo[1,3]dioxole, thienofuryl, N-oxypyridyl, N—C1-6 alkylpyridinium, 5,6,7,8-tetrahydroquinolyl and 4,5,6,7-tetrahydro-1H-benzo[d]imidazolyl.

EFFECT OF THE INVENTION

The compounds of the invention have excellent inhibiting effects against clotting factor VIIa and excellent anticoagulant effects, and are therefore useful as therapeutic and/or prophylactic agents for diseases associated with thrombus formation (for example, thrombosis, deep vein thrombosis, pulmonary embolism, cerebral infarction, myocardial infarction, acute coronary syndrome, vascular restenosis or disseminated intravascular coagulation syndrome)(Johannes Ruef & Hugo A Katus, New antithrombotic drugs on the horizon, Expert Opin. Investig. Drugs (2003) 12(5):781-797).

Substances with inhibiting effects against clotting factor VIIa have also been reported to exhibit malignant tumor metastasis suppression and reduction. The compounds of the invention that exhibit excellent inhibition against clotting factor VIIa are therefore useful as therapeutic and/or prophylactic agents for malignant tumors (Mattias Belting et al., Regulation of angiogenesis by tissue factor cytoplasmic domain signaling, Nature Medicine (2004) 10(5):502-509; X Jiang et al., Formation of tissue factor-factor VIIa-factor Xa complex promotes cellular signaling and migration of human breast cancer cells, J Thromb Haemost, (2004) 2:93-101; Hembrough T A. Swartz G M. Papathanassiu A. Vlasuk G P. Rote W E. Green S J. Pribluda V S., Tissue factor/factor VIIa inhibitors block angiogenesis and tumor growth through a nonhemostatic mechanism. Cancer Research. (2003) 63(11): 2997-3000).

Since the compounds of the invention have excellent suppressing effects against blood clotting, and are safer with suitable physicochemical stability, they are useful as medicaments, and especially as therapeutic and/or prophylactic agents for diseases associated with thrombus formation.

DESCRIPTION OF THE PREFERRED EMBODIMENTS

The present invention will now be explained in detail.

1) Compounds Represented by General Formula (1)

Throughout the present specification, the structural formulas for the compounds will show only one specific isomer for convenience, but the invention includes all isomers such as geometric isomers, optical isomers, stereoisomers and tautomers implied by the compound structures, as well as their isomer mixtures, and the compounds may therefore be any of the isomers or their mixtures, without being limited to the formulas shown for convenience. Therefore, the compounds of the invention may exist as optically active forms or racemic mixtures, all of which are included without limitations according to the invention. Polymorphic crystals may also exist, and there may be used any crystal form or a mixture thereof without any restrictions, while the compounds of the invention include both anhydrous and hydrated forms.

2) Compounds Represented by General Formulas (1-1) and (1-2)

Throughout the present specification, the structural formulas for compounds will represent only one isomer for convenience, but the invention includes all isomers including geometric isomers, stereoisomers and tautomers, as well as isomer mixtures, implied by the compound structure, being not limited to the formula shown for convenience, and may relate to any one of the isomers or a mixture thereof. Polymorphic crystals may also exist, and there may be used any crystal form or a mixture thereof without any restrictions, while the compounds of the invention include both anhydrous and hydrated forms.

As tautomers of the compounds represented by general formula (I) there may be mentioned compounds represented by the following general formulas (1p), (1q), (1r), (1s) and (1t).

[Chemical Formula 16]

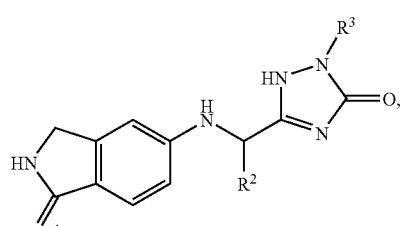

(1p)

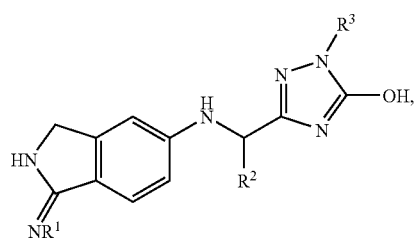
(1q)
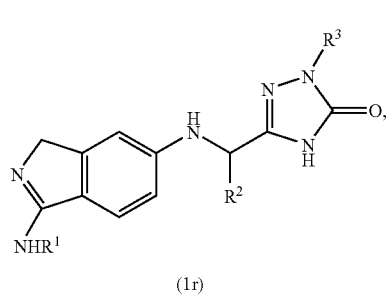
(1r)
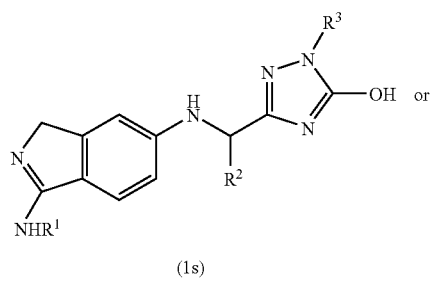
(1s)
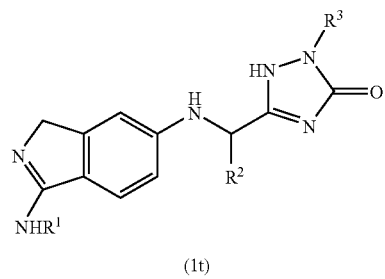
(1t)
As tautomers of compounds represented by general formula (1-1) there may be mentioned compounds represented by the following general formulas (1p-1), (1q-1), (1r-1), (1s-1) and (1t-1).
[Chemical Formula 17]
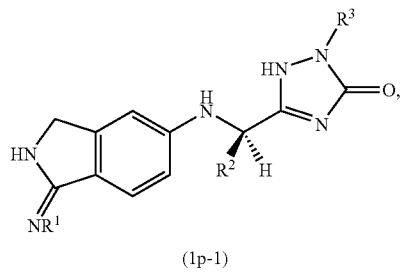
(1p-1)
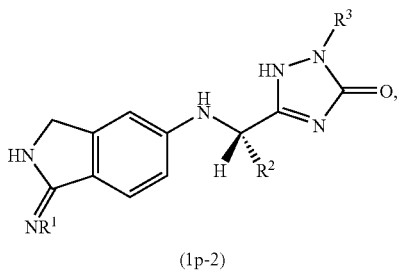
(1q-1)
(1r-1)
(1s-1)
(1t-1)
As tautomers of compounds represented by general formula (1-2) there may be mentioned compounds represented by the following general formulas (1p-2), (1q-2), (1r-2), (1s-2) and (1t-2).
[Chemical Formula 18]
(1p-2)

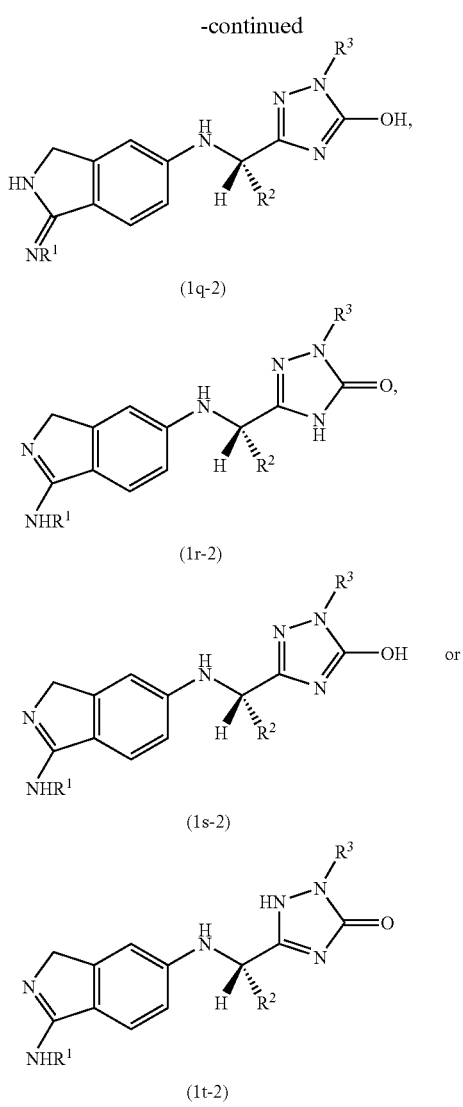

(1q-2)

(1r-2)

(1s-2)

(1t-2)

The definitions of the terms and symbols used throughout the present specification will now be explained, prior to a more detailed description of the invention.

The term "disease associated with thrombus formation" is not particularly restricted so long as it is a disease with onset directly or indirectly caused by thrombus formation, and as specific examples there may be mentioned thrombosis, deep vein thrombosis, pulmonary embolism, cerebral infarction, myocardial infarction, acute coronary syndrome, vascular restenosis, disseminated intravascular coagulation syndrome and malignant tumor, and preferably thrombosis, deep vein thrombosis, pulmonary embolism, cerebral infarction, myocardial infarction, acute coronary syndrome, vascular restenosis and disseminated intravascular coagulation syndrome.

The term "halogen" refers to fluorine, chlorine, bromine and iodine. As preferred examples of "halogen" there may be mentioned fluorine and chlorine.

The term "C1-6 alkyl" refers to C1-6 straight-chain or branched alkyl groups, and as specific examples there may be mentioned methyl, ethyl, 1-propyl(n-propyl), 2-propyl(i-propyl), 2-methyl-1-propyl (1-butyl), 2-methyl-2-propyl(t-butyl), 1-butyl(n-butyl), 2-butyl(s-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,3-dimethyl-1-butyl, 3,3-dimethyl-1-butyl, 2,2-dimethyl-1-butyl, 2-ethyl-1-butyl, 3,3-dimethyl-2-butyl and 2,3-dimethyl-2-butyl.

The term "C2-6 alkenyl" refers to C2-6 straight-chain or branched alkenyl groups with one double bond, and as specific examples there may be mentioned vinyl(ethenyl), allyl (2-propenyl), 1-propenyl, isopropenyl (1-methylvinyl), 1-butenyl, 2-butenyl, 3-butenyl, pentenyl and hexenyl.

The term "C2-6 alkynyl" refers to a C2-6 straight-chain or branched alkynyl group with one triple bond, and as specific examples there may be mentioned ethynyl, 1-propynyl, 2-propynyl, butynyl, pentynyl and hexynyl.

The term "C3-8 cycloalkyl" refers to a C3-8 monocyclic saturated aliphatic hydrocarbon, and as specific examples there may be mentioned cyclopropyl, cyclobutyl, cyclopentyl, cyclohexyl, cycloheptyl and cyclooctyl.

The term "C6-10 aryl" refers to a C6-10 aromatic hydrocarbon ring group, and as specific examples there may be mentioned phenyl and naphthyl.

The term "5- to 10-membered heteroaryl group" refers to an aromatic ring group having 5-10 atoms composing the ring and containing 1-5 heteroatoms among the atoms composing the ring, and as specific examples there may be mentioned furyl, thienyl, pyrolyl, imidazolyl, triazolyl, tetrazolyl, thiazolyl, pyrazolyl, oxazolyl, isooxazolyl, isothiazolyl, furazanyl, thiadiazolyl, oxadiazolyl, pyridyl, pyrazinyl, pyridazinyl, pyrimidinyl, triazinyl, purinyl, pteridinyl, quinolyl, isoquinolyl, naphthylidinyl, quinoxalinyl, cinnolinyl, quinazolinyl, phthaladinyl, imidazopyridyl, imidazothiazolyl, imidazooxazolyl, benzothiazolyl, benzooxazolyl, benzoimidazolyl, indolyl, isoindolyl, indazolyl, pyrrolopyridyl, thienopyridyl, furopyridyl, benzothiadiazolyl, benzooxadiazolyl, pyridopyrimidinyl, benzofuryl, benzothienyl, benzo[1,3] dioxole, thienofuryl, N-oxypyridyl and N—C1-6 alkylpyridinium.

The term "5- or 6-membered non-aromatic heterocyclic group" refers to (1) a non-aromatic cyclic group (2) having 5 or 6 atoms composing the ring, (3) containing 1 or 2 heteroatoms among the atoms composing the ring, (4) optionally having 1 or 2 double bonds in the ring and (5) optionally having 1 or 2 oxo groups (carbonyl groups) on the ring, and as specific examples there may be mentioned pyrrolidinyl, piperidinyl, morpholinyl, thiomorpholinyl, tetrahydrofuryl, tetrahydropyranyl, pyridonyl and dihydropyrazinyl.

The term "5- to 8-membered heterocycle" refers to a ring (1) having 5-8 atoms composing the ring, (2) containing 1-2 heteroatoms among the atoms composing the ring, (3) optionally having 1-2 double bonds in the ring and (4) optionally having 1-2 oxo groups (carbonyl groups) on the ring, and as specific examples there may be mentioned pyrrolidine, piperidine, azepane, azocane, piperazine, diazepane, diazocane, morpholine, thiomorpholine, tetrahydrofuran, tetrahydropyran, oxepane, dioxane, dioxepane, dihydrofuran, tetrahydrothiophene, tetrahydrothiopyran, oxazolidine, thiazolidine, pyridone and dihydropyrazine rings.

The term "9- to 12-membered benzene-fused cyclic group" refers to a cyclic group having a "5- to 8-membered heterocycle" as defined above fused with a phenyl group, and as specific preferred examples there may be mentioned a group represented by the following formula:

[Chemical Formula 19]

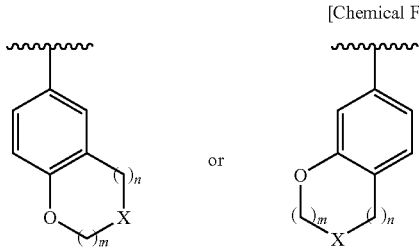

wherein the symbols have the same definitions as above, and more preferably a group represented by the following formula.

[Chemical Formula 20]

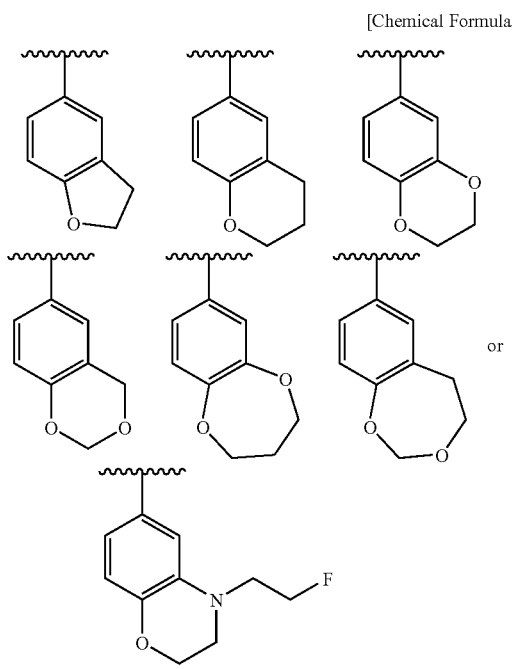

The term "C1-6 alkoxy" refers to an oxy group bonded to "C1-6 alkyl" as defined above, and as specific examples there may be mentioned methoxy, ethoxy, 1-propyloxy, 2-propyloxy, 2-methyl-1-propyloxy, 2-methyl-2-propyloxy, 1-butyloxy, 2-butyloxy, 1-pentyloxy, 2-pentyloxy, 3-pentyloxy, 2-methyl-1-butyloxy, 3-methyl-1-butyloxy, 2-methyl-2-butyloxy, 3-methyl-2-butyloxy, 2,2-dimethyl-1-propyloxy, 1-hexyloxy, 2-hexyloxy, 3-hexyloxy, 2-methyl-1-pentyloxy, 3-methyl-1-pentyloxy, 4-methyl-1-pentyloxy, 2-methyl-2-pentyloxy, 3-methyl-2-pentyloxy, 4-methyl-2-pentyloxy, 2-methyl-3-pentyloxy, 3-methyl-3-pentyloxy, 2,3-dimethyl-1-butyloxy, 3,3-dimethyl-1-butyloxy, 2,2-dimethyl-1-butyloxy, 2-ethyl-1-butyloxy, 3,3-dimethyl-2-butyloxy and 2,3-dimethyl-2-butyloxy.

The term "C3-8 cycloalkyloxy" refers to an oxy group bonded to "C3-8 cycloalkyl" as defined above, and as specific examples there may be mentioned cyclopropyloxy, cyclobutyloxy, cyclopentyloxy, cyclohexyloxy, cycloheptyloxy and cyclooctyloxy.

The term "C2-6 alkenyloxy" refers to an oxy group bonded to "C2-6 alkenyl" as defined above, and as specific examples there may be mentioned vinyloxy(ethenyloxy), allyloxy(2-propenyloxy), 1-propenyloxy, isopropenyloxy(1-methylvinyloxy), 1-butenyloxy, 2-butenyloxy, 3-butenyloxy, pentenyloxy and hexenyloxy.

The term "C2-6 alkynyloxy" refers to an oxy group bonded to "C2-6 alkynyl" as defined above, and as specific examples there may be mentioned ethynyloxy, 1-propynyloxy, 2-propynyloxy, butynyloxy, pentynyloxy and hexynyloxy.

The term "C1-6 alkylthio" refers to a thio group bonded to "C1-6 alkyl" as defined above, and as specific examples there may be mentioned methylthio, ethylthio, 1-propylthio, 2-propylthio, butylthio and pentylthio.

The term "C1-6 alkylsulfinyl" refers to a sulfinyl group bonded to "C1-6 alkyl" as defined above, and as specific examples there may be mentioned methylsulfinyl, ethylsulfinyl, 1-propylsulfinyl, 2-propylsulfinyl, butylsulfinyl and pentylsulfinyl.

The term "C1-6 alkylsulfonyl" refers to a sulfonyl group bonded to "C1-6 alkyl" as defined above, and as specific examples there may be mentioned methylsulfonyl, ethylsulfonyl, 1-propylsulfonyl, 2-propylsulfonyl, butylsulfonyl and pentylsulfonyl.

The term "C2-7 alkylcarbonyl" refers to a carbonyl group bonded to "C1-6 alkyl" as defined above, and as specific examples there may be mentioned acetyl, propionyl, isopropionyl, butyryl, isobutyryl, valeryl, isovaleryl and pivaloyl.

The term "C2-7 alkoxycarbonyl" refers to a carbonyl group bonded to "C1-6 alkoxy" as defined above, and as specific examples there may be mentioned methoxycarbonyl, ethoxycarbonyl, 1-propyloxycarbonyl and 2-propyloxycarbonyl.

The term "C6-10 aryloxy" refers to an oxy group bonded to "C6-10 aryl" as defined above, and as specific examples there may be mentioned phenyloxy, 1-naphthyloxy and 2-naphthyloxy.

The term "5- to 10-membered heteroaryloxy" refers to an oxy group bonded to "5- to 10-membered heteroaryl group" as defined above, and as specific examples there may be mentioned furyloxy, thienyloxy, pyrrolyloxy, imidazolyloxy, pyridyloxy and pyrazinyloxy.

The term "5- or 6-membered non-aromatic heterocyclooxy" refers to a group consisting of an oxy group bonded to a "5- or 6-membered non-aromatic heterocyclic group" as defined above, and as specific examples there may be mentioned pyrrolidinyloxy, piperidinyloxy, morpholinyloxy, thiomorpholinyloxy, tetrahydrofuryloxy and tetrahydropyranyloxy.

The term "C1-6 alkylsulfonyloxy" refers to an oxy group bonded to "C1-6 alkylsulfonyl" as defined above, and as specific examples there may be mentioned methylsulfonyloxy, ethylsulfonyloxy, 1-propylsulfonyloxy, 2-propylsulfonyloxy, butylsulfonyloxy and pentylsulfonyloxy.

The term "C6-10 arylmethyl" refers to a methyl group bonded to "C6-10 aryl" as defined above, and as specific examples there may be mentioned benzyl, 1-naphthylmethyl and 2-naphthylmethyl.

The term "C6-10 arylamino" refers to an amino group bonded to "C6-10 aryl" as defined above, and as specific examples there may be mentioned phenylamino, 1-naphthylamino and 2-naphthylamino.

The term "mono(C1-6 alkyl)amino" refers to an amino group bonded to one "C1-6 alkyl" group as defined above, and as specific examples there may be mentioned methylamino and ethylamino.

The term "di(C1-6 alkyl)amino" refers to an amino group bonded to two "C1-6 alkyl" groups as defined above, and as specific examples there may be mentioned dimethylamino and methylethylamino.

The term "mono(C1-6 alkyl)aminocarbonyl" refers to a carbonyl group bonded to "mono(C1-6 alkyl)amino" as defined above, and as specific examples there may be mentioned methylaminocarbonyl and ethylaminocarbonyl.

The term "di(C1-6 alkyl)aminocarbonyl" refers to a carbonyl group bonded to "di(C1-6 alkyl)amino" as defined above, and as specific examples there may be mentioned dimethylaminocarbonyl and methylethylaminocarbonyl.

The term "pyridyl" refers to a monovalent group derived by removing one hydrogen from any position of a pyridine ring, and specifically there may be mentioned 2-pyridyl, 3-pyridyl and 4-pyridyl.

The term "N-oxypyridyl" refers to "pyridyl" wherein the nitrogen atom of the ring has been oxidized, and specifically there may be mentioned N-oxy-2-pyridyl, N-oxy-3-pyridyl and N-oxy-4-pyridyl.

The term "N—C1-6 alkylpyridinium" refers to a cyclic group wherein "C1-6 alkyl" is bonded to the nitrogen atom on a "pyridyl" ring, and specifically there may be mentioned N-methyl-2-pyridinium, N-methyl-3-pyridinium and N-methyl-4-pyridinium. An "N—C1-6 alkylpyridinium" group forms an ion pair with an anion in the molecule, and as examples of such anions there may be mentioned acetate ion and trifluoroacetate ion.

The term "pyrazinyl" refers to a monovalent group derived by removing one hydrogen from any position of a pyrazine ring.

The term "pyridazinyl" refers to a monovalent group derived by removing one hydrogen from any position of a pyridazine ring, and specifically there may be mentioned 2-pyridazinyl and 3-pyridazinyl.

The term "pyrimidinyl" refers to a monovalent group derived by removing one hydrogen from any position of a pyrimidine ring, and specifically there may be mentioned 2-pyrimidinyl, 4-pyrimidinyl and 5-pyrimidinyl.

The term "pyrazolyl" refers to a monovalent group derived by removing one hydrogen from any position of a pyrazole ring, and specifically there may be mentioned 3-pyrazolyl, 4-pyrazolyl and 5-pyrazolyl.

The term "imidazolyl" refers to a monovalent group derived by removing one hydrogen from any position of an imidazole ring, and specifically there may be mentioned 2-imidazolyl, 4-imidazolyl and 5-imidazolyl.

The term "thiazolyl" refers to a monovalent group derived by removing one hydrogen from any position of a thiazole ring, and specifically there may be mentioned 2-thiazolyl, 4-thiazolyl and 5-thiazolyl.

The term "oxazolyl" refers to a monovalent group derived by removing one hydrogen from any position of an oxazole ring, and specifically there may be mentioned 2-oxazolyl, 4-oxazolyl and 5-oxazolyl.

The term "thienyl" refers to a monovalent group derived by removing one hydrogen from any position of a thiophene ring, and specifically there may be mentioned 2-thienyl and 3-thienyl.

The term "pyridonyl" refers to a monovalent group derived by removing one hydrogen from any position of a pyridone ring, and specifically there may be mentioned a group represented by the following formula.

[Chemical Formula 21]

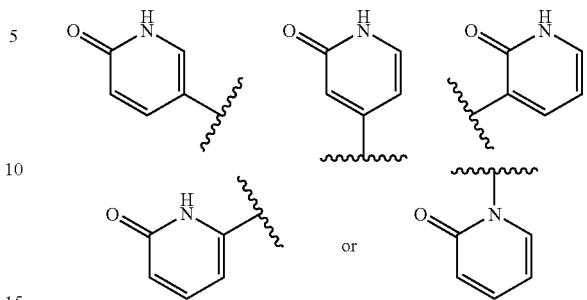

The term "dihydropyrazinyl having an oxo group" refers to a monovalent group having one oxo group (carbonyl group) on a dihydropyrazine ring and derived by removing one hydrogen from any position of a dihydropyrazine ring, and specifically there may be mentioned a group represented by the following formula.

[Chemical Formula 22]

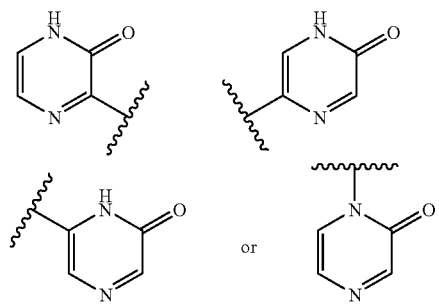

The term r"tetrahydrofuryloxy" refers to an oxy group bonded to "a monovalent group derived by removing one hydrogen from any position of a tetrahydrofuran ring", and specifically there may be mentioned 2-tetrahydrofuryloxy and 3-tetrahydrofuryloxy.

The term "tetrahydropyranyloxy" refers to an oxy group bonded to "a monovalent group derived by removing one hydrogen from any position of a tetrahydropyran ring", and specifically there may be mentioned 2-tetrahydropyranyloxy, 3-tetrahydropyranyloxy and 4-tetrahydropyranyloxy.

The term "optionally having substituents" means that the compound may have one or more substituents in any desired combination at substitutable positions.

A "salt" as referred to throughout the present specification is not particularly restricted so long as it is formed with the compound of the invention and is pharmacologically acceptable, and as examples there may be mentioned inorganic acid salts, organic acid salts, inorganic base salts, organic base salts and acidic or basic amino acid salts.

As preferred examples of inorganic acid salts there may be mentioned hydrochloric acid salts, hydrobromic acid salts, sulfuric acid salts, nitric acid salts, phosphoric acid salts and the like, and as preferred examples of organic acid salts there may be mentioned acetic acid salts, succinic acid salts, fumaric acid salts, maleic acid salts, tartaric acid salts, citric acid salts, lactic acid salts, stearic acid salts, benzoic acid salts, methanesulfonic acid salts, ethanesulfonic acid salts, p-toluenesulfonic acid salts, benzenesulfonic acid salts and the like.

As preferred examples of inorganic base salts there may be mentioned alkali metal salts such as sodium salts and potassium salts, alkaline earth metal salts such as calcium salts and magnesium salts, and aluminum salts, ammonium salts and the like, and as preferred examples of organic base salts there may be mentioned diethylamine salts, diethanolamine salts, meglumine salts, N,N'-dibenzylethylenediamine salts and the like.

As preferred examples of acidic amino acid salts there may be mentioned aspartic acid salts and glutamic acid salts, and as preferred examples of basic amino acid salts there may be mentioned arginine salts, lysine salts and ornithine salts.

The substituents for compounds of the invention represented by general formulas (1), (1-1), (1-2), (1-3), (1-4), (1-5), (1-6) and (1-7) above will now be explained.

$R^1$ represents hydrogen.

$R^2$ represents C6-10 aryl optionally having 1-5 substituents selected from Group A1 below, a 5- to 10-membered heteroaryl group optionally having 1-5 substituents selected from Group A1 below or a 9- to 12-membered benzene-fused cyclic group optionally having 1-5 substituents selected from Group A1 below.

As preferred examples of $R^2$ there may be mentioned phenyl optionally having 1-4 substituents selected from Group D1 below, pyridyl optionally having 1-3 substituents selected from Group D1 below or a 9- to 12-membered benzene-fused cyclic group optionally having 1-4 substituents selected from Group D1 below.

As preferred examples where $R^2$ is optionally substituted phenyl, there may be mentioned phenyl optionally having 2 or 3 substituents selected from Group D3 below.

As preferred examples where $R^2$ is optionally substituted phenyl there may be mentioned a group represented by the following formula:

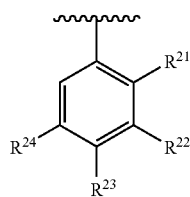

[Chemical Formula 23]

wherein $R^{21}$ represents hydrogen, benzyloxy, fluorine or chlorine;

$R^{22}$ represents hydrogen, hydroxyl, methyl optionally having 1 substituent selected from Group D5 below, ethyl optionally having 1 substituent selected from Group D5 below, methoxy optionally having 1 substituent selected from Group D5 below, ethoxy optionally having 1 or 2 substituents selected from Group D5 below, 1-propyloxy optionally having 1 substituent selected from Group D5 below, 2-propyloxy optionally having 1 substituent selected from Group D5 below, allyloxy, tetrahydrofuryloxy, tetrahydropyranyloxy or acetyl;

$R^{23}$ represents hydrogen, fluorine, hydroxyl, methoxy optionally having 1 substituent selected from Group D6 below, ethoxy optionally having 1 substituent selected from Group D6 below or 2-propyloxy optionally having 1 substituent selected from Group D6 below; and $R^{24}$ represents hydrogen, fluorine, hydroxyl, methyl optionally having 1 substituent selected from Group D7 below, ethyl, vinyl, ethynyl, methoxy optionally having 1 substituent selected from Group D7 below, ethoxy optionally having 1 substituent selected from Group D7 below, 2-propyloxy or allyloxy.

As preferred examples of $R^{21}$ there may be mentioned hydrogen and fluorine, as preferred examples of $R^{22}$ there may be mentioned hydrogen, hydroxyl, cyanomethyl, methoxymethyl, methoxy, dimethylaminocarbonylmethoxy, ethoxy, 2-fluoroethoxy, 2-hydroxyethoxy, 2-methoxyethoxy, 2-(dimethylamino)ethoxy, tetrahydro furyloxy, tetrahydropyranyloxy, fluoromethoxy, 3-hydroxypropyloxy, 2-fluoroethoxymethyl and 2-hydroxyethoxymethyl, as preferred examples of $R^{23}$ there may be mentioned hydrogen, fluorine, methoxy, cyanomethoxy, ethoxy, 2-propyloxy and 2-methoxyethoxy, and as preferred examples of $R^{24}$ there may be mentioned hydrogen, hydroxyl, methyl, methoxymethyl, ethyl, vinyl, ethynyl, methoxy, ethoxy and 2-fluoroethoxy.

As preferred examples where $R^2$ is optionally substituted phenyl there may be mentioned a group represented by the following formula.

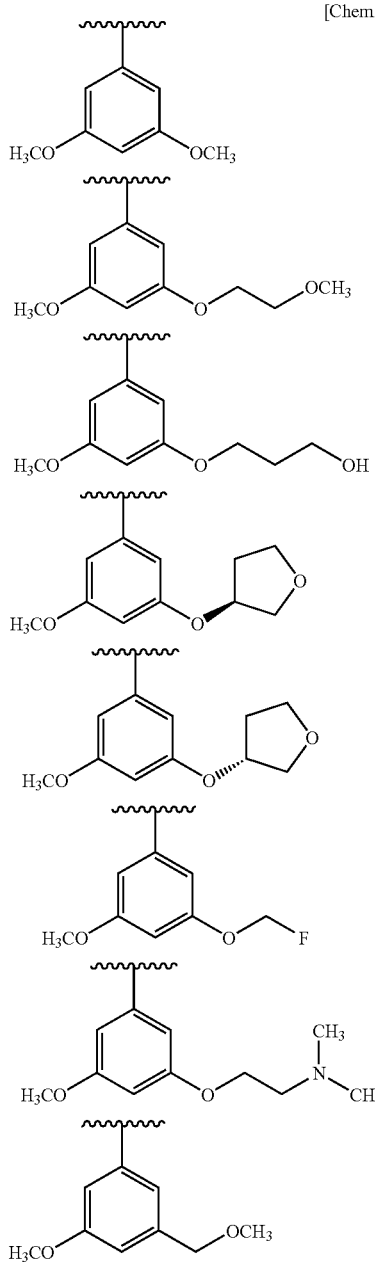

[Chemical Formula 24]

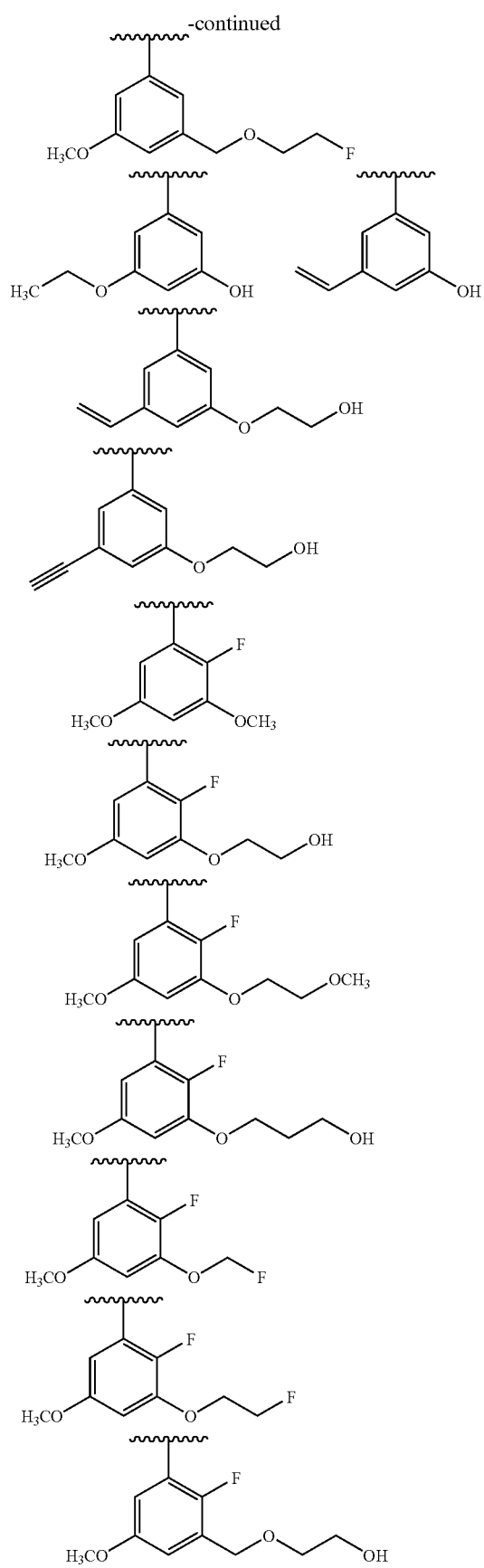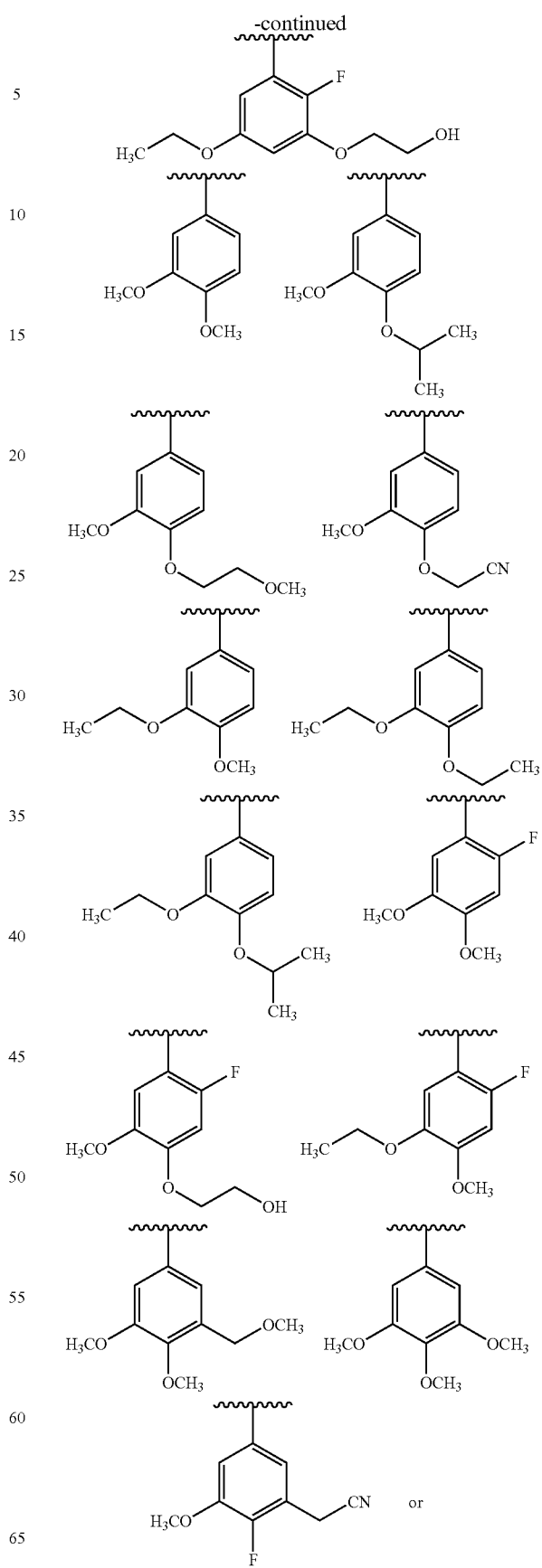

-continued

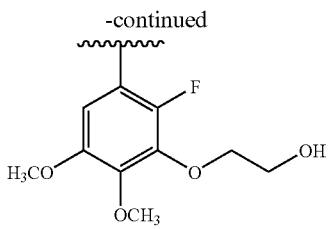

As preferred examples where R² is optionally substituted pyridyl there may be mentioned pyridyl having two substituents selected from the group consisting of C1-6 alkyl and C1-6 alkoxy, more preferably pyridyl having two substituents selected from the group consisting of methyl, methoxy and ethoxy, and even more preferably a group represented by the following formula:

[Chemical Formula 25]

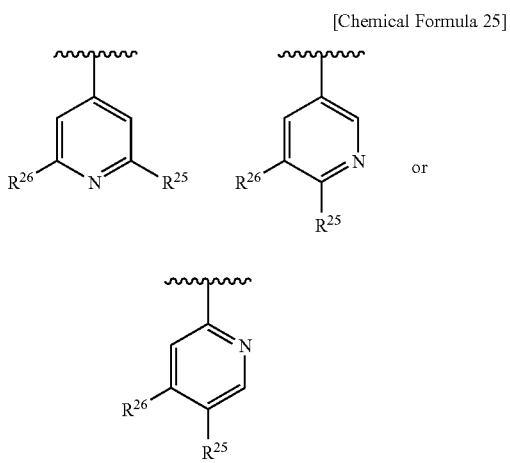

wherein $R^{25}$ represents methyl or methoxy, and $R^{26}$ represents methoxy or ethoxy.

As preferred examples where R² is optionally substituted pyridyl there may be mentioned a group represented by the following formula.

[Chemical Formula 26]

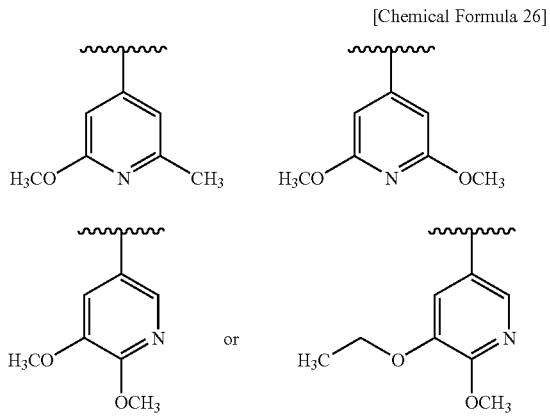

As preferred examples where R² is an optionally substituted 9- to 12-membered benzene-fused cyclic group, there may be mentioned a group represented by the following formula:

[Chemical Formula 27]

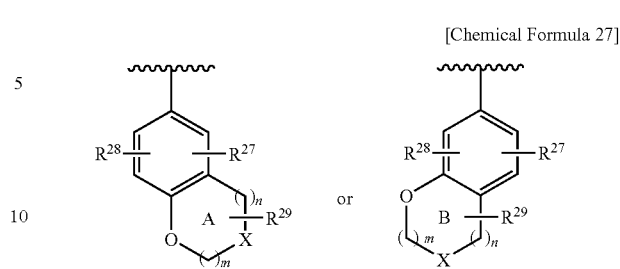

wherein $R^{27}$ represents hydrogen or halogen;

$R^{28}$ represents hydrogen, hydroxyl, halogen, C1-6 alkyl optionally having 1-3 substituents selected from Group D8 below, C2-6 alkenyl, C2-6 alkynyl, C1-6 alkoxy optionally having 1-3 substituents selected from Group D8 below, or C2-7 alkylcarbonyl;

$R^{29}$ represents hydrogen, cyano, C1-6 alkyl optionally having 1-3 substituents selected from Group D8 below, C1-6 alkoxy optionally having 1-3 substituents selected from Group D8 below or carbamoyl;

X represents carbon optionally having 1 or 2 substituents selected from Group D8 below, nitrogen optionally having 1 substituent selected from Group D8 below or oxygen;

m represents an integer from 0 to 3 and n represents an integer from 0 to 2, with the proviso that the sum of m and n is 1-4; and Rings A and B optionally contain one double bond in the ring and optionally have an oxo group on the ring, and as more preferred examples there may be mentioned a group represented by the following formula:

[Chemical Formula 28]

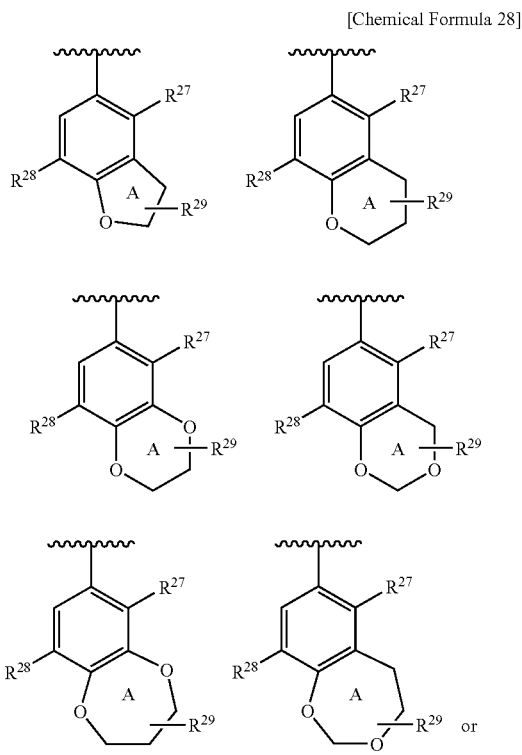

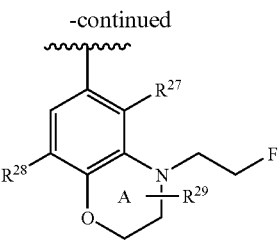

wherein $R^{27}$, $R^{28}$ and $R^{29}$ have the same definitions as above, and Ring A optionally has an oxo group on the ring.

As preferred examples of $R^{28}$ there may be mentioned methyl, ethyl, methoxy, ethoxy, vinyl and ethynyl, and as a preferred example of $R^{29}$ there may be mentioned hydrogen.

As preferred examples where $R^2$ is an optionally substituted 9- to 12-membered benzene-fused cyclic group there may be mentioned a group represented by the following formula.

[Chemical Formula 29]

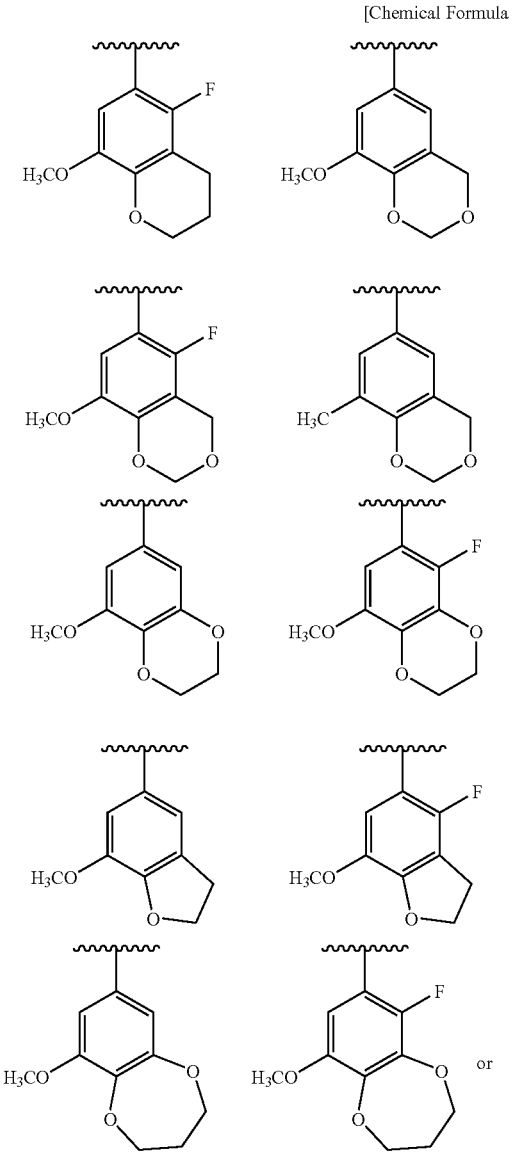

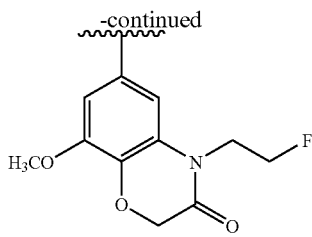

$R^3$ represents a 5- or 6-membered non-aromatic heterocyclic group optionally having 1-5 substituents selected from Group A1 below, a C6-10 aryl optionally having 1-5 substituents selected from Group A1 below or a 5- to 10-membered heteroaryl group optionally having 1-5 substituents selected from Group A1 below.

As preferred examples of $R^3$ there may be mentioned phenyl optionally having 1-3 substituents selected from Group E1 below, pyridyl optionally having 1-3 substituents selected from Group E1 below, N-oxypyridyl optionally having 1-3 substituents selected from Group E1 below, N—C1-6 alkylpyridinium optionally having 1-3 substituents selected from Group E1 below, pyrazinyl optionally having 1-3 substituents selected from Group E1 below, pyridazinyl optionally having 1-3 substituents selected from Group E1 below, pyrimidinyl optionally having 1-3 substituents selected from Group E1 below, pyrazolyl optionally having 1 or 2 substituents selected from Group E1 below, imidazolyl optionally having 1 or 2 substituents selected from Group E1 below, thiazolyl optionally having 1 or 2 substituents selected from Group E1 below, thienyl optionally having 1-3 substituents selected from Group E1 below, and dihydropyrazinyl having an oxo group, with the proviso that when $R^3$ is N—C1-6 alkylpyridinium, $R^3$ forms an ion pair with an anion in the molecule.

As more preferred examples of $R^3$ there may be mentioned phenyl optionally having 1 or 2 substituents selected from Group E3 below, pyridyl optionally having 1 or 2 substituents selected from Group E3 below, N-oxypyridyl optionally having 1 or 2 substituents selected from Group E3 below, pyrazinyl optionally having 1 or 2 substituents selected from Group E3 below, pyridazinyl optionally having 1 or 2 substituents selected from Group E3 below, pyrimidinyl optionally having 1 or 2 substituents selected from Group E3 below, pyrazolyl optionally having 1 or 2 substituents selected from Group E3 below, imidazolyl optionally having 1 or 2 substituents selected from Group E3 below, thiazolyl optionally having 1 or 2 substituents selected from Group E3 below, thienyl optionally having 1 or 2 substituents selected from Group E3 below, oxazolyl optionally having 1 or 2 substituents selected from Group E3 below and dihydropyrazinyl having an oxo group.

As even more preferred examples of $R^3$ there may be mentioned phenyl optionally having one group selected from Group E4 below, pyridyl optionally having one group selected from Group E5 below, N-oxypyridyl, pyrazinyl, pyridazinyl, pyrimidinyl, pyrazolyl optionally having one group selected from Group E4 below, imidazolyl optionally having one group selected from Group E4 below, thiazolyl optionally having one group selected from Group E4 below, thienyl optionally having one group selected from Group E4 below, oxazolyl optionally having one group selected from Group E4 below or dihydropyrazinyl having an oxo group.

As specific preferred examples of $R^3$ there may be mentioned a group represented by the following formula:

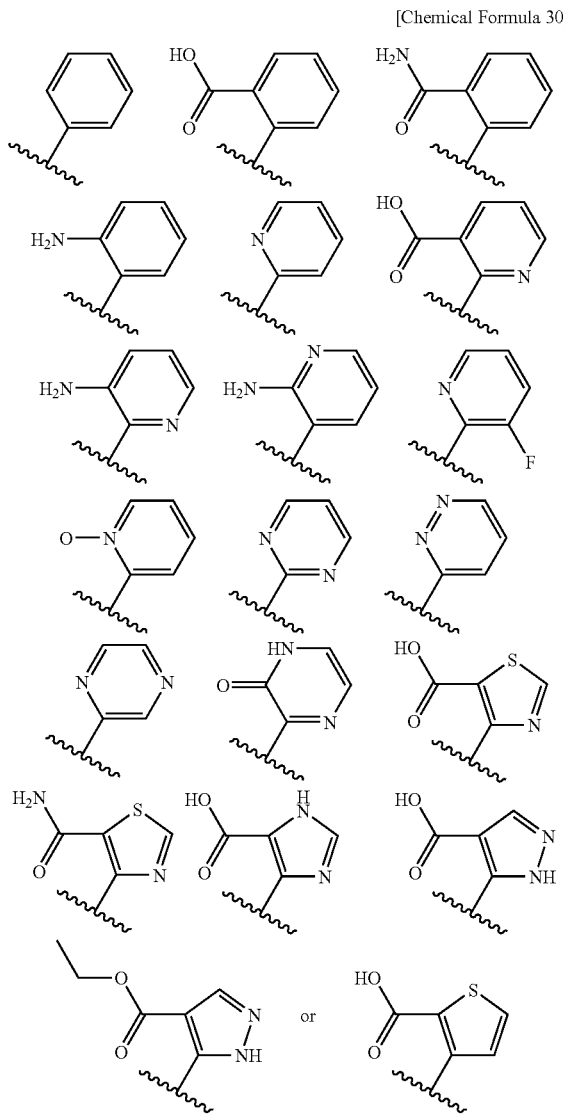

or

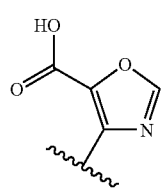

Group A1: Hydroxyl, halogen, cyano, nitro, oxo, C1-6 alkyl optionally having 1-3 substituents selected from Group B1 below, C3-8 cycloalkyl optionally having 1-5 substituents selected from Group B1 below, 2-6 alkenyl, C2-6 alkynyl, C1-6 alkoxy optionally having 1-3 substituents selected from Group B1 below, C3-8 cycloalkyloxy optionally having 1-5 substituents selected from Group B1 below, C2-6 alkenyloxy, C2-6 alkynyloxy, C1-6 alkylthio, C1-6 alkylsulfinyl, C1-6 alkylsulfonyl, C1-6 alkylsulfonyloxy, C6-10 aryl optionally having 1-5 substituents selected from Group B1 below, C6-10 aryloxy optionally having 1-5 substituents selected from Group B1 below, 5- to 10-membered heteroaryl group optionally having 1-5 substituents selected from Group B1 below, 5- to 10-membered heteroaryloxy optionally having 1-5 substituents selected from Group B1 below, a 5 or 6-membered non-aromatic heterocyclic group optionally having 1-5 substituents selected from Group B1 below, 5- or 6-membered non-aromatic heterocyclooxy optionally having 1-5 substituents selected from Group B1 below, a group represented by —$NR^{1t}$—$R^{2t}$ and a group represented by —CO—$R^{3t}$, where $R^{1t}$ and $R^{2t}$ each independently represent hydrogen, C1-6 alkyl optionally having 1-3 substituents selected from Group B1 below, C2-6 alkenyl, C2-7 alkylcarbonyl optionally having 1-3 substituents selected from Group B1 below, C2-7 alkoxycarbonyl optionally having 1-3 substituents selected from Group B1 below, C1-6 alkylsulfonyl optionally having 1-3 substituents selected from Group B1 below, carbamoyl, aminosulfonyl, C6-10 aryl optionally having 1-5 substituents selected from Group B1 below or 5- to 10-membered heteroaryl group optionally having 1-5 substituents selected from Group B1 below, and $R^{3t}$ represents hydroxyl, C1-6 alkyl optionally having 1-3 substituents selected from Group B1 below, C1-6 alkoxy optionally having 1-3 substituents selected from Group B1 below, amino, mono(C1-6 alkyl)amino optionally having 1-3 substituents selected from Group B1 below or di(C1-6 alkyl)amino optionally having 1-3 substituents selected from Group B1 below.

Group B1: Hydroxyl, halogen, cyano, oxo, C1-6 alkoxy optionally having halogen, C3-8 cycloalkyl, amino, mono(C1-6 alkyl)amino, di(C1-6 alkyl)amino, carbamoyl, mono(C1-6 alkyl)aminocarbonyl, di(C1-6 alkyl)aminocarbonyl, C6-10 aryl optionally having 1-5 substituents selected from Group C1 below, and 5- to 10-membered heteroaryl group optionally having 1-5 substituents selected from Group C1 below.

Group C1: Halogen, C1-6 alkyl and C1-6 alkoxy.

Group D1: Hydroxyl, halogen, C1-6 alkyl optionally having 1-3 substituents selected from Group D2 below, C2-6 alkenyl, C2-6 alkynyl, C1-6 alkoxy optionally having 1-3 substituents selected from Group D2 below, C2-6 alkenyloxy, C1-6 alkylsulfonyloxy, 5- or 6-membered non-aromatic heterocyclooxy optionally having 1-3 substituents selected from Group D2 below and C2-7 alkylcarbonyl.

Group D2: Hydroxyl, halogen, cyano, oxo, C1-6 alkoxy optionally having halogen, mono(C1-6 alkyl)amino, di(C1-6 alkyl)amino, mono(C1-6 alkyl)aminocarbonyl and di(C1-6 alkyl)aminocarbonyl.

Group D3: Fluorine, chlorine, methyl optionally having 1 substituent selected from Group D4 below, ethyl optionally having 1 substituent selected from Group D4 below, vinyl, ethynyl, methoxy optionally having 1 or 2 substituents selected from Group D4 below, ethoxy optionally having 1 or 2 substituents selected from Group D4 below, 1-propyloxy optionally having 1 or 2 substituents selected from Group D4 below, 2-propyloxy optionally having 1 or 2 substituents selected from Group D4 below, allyloxy, tetrahydrofuryloxy, tetrahydropyranyloxy and acetyl.

Group D4: Hydroxyl, fluorine, cyano, methoxy, methylamino, dimethylamino, methylaminocarbonyl and dimethylaminocarbonyl.

Group D5: Hydroxyl, fluorine, cyano, methoxy, dimethylamino, dimethylaminocarbonyl, 2-fluoroethoxy and 2-hydroxyethoxy.

Group D6; Fluorine, cyano, methoxy, dimethylamino, methylaminocarbonyl and dimethylaminocarbonyl.

Group D7: Hydroxyl, fluorine, cyano and ethoxy having one methoxy group.

Group D8: Hydrogen, hydroxyl, halogen, C1-6 alkoxy, mono(C1-6 alkyl)amino, di(C1-6 alkyl)amino, mono(C1-6 alkyl)aminocarbonyl, di(C1-6 alkyl)aminocarbonyl and C1-6 alkyl optionally having halogen.

Group E1: Hydroxyl, halogen, cyano, C1-6 alkyl, C1-6 alkoxy, a group represented by the formula —NH—$R^{21t}$ and a group represented by the formula —CO—$R^{31t}$, where $R^{21t}$ represents hydrogen, C1-6 alkyl, C2-6 alkenyl, C2-7 alkylcarbonyl optionally having 1-3 substituents selected from Group E2 below, C2-7 alkoxycarbonyl optionally having 1-3 substituents selected from Group E2 below, C1-6 alkylsulfonyl, carbamoyl or aminosulfonyl, and $R^{31t}$ represents hydroxyl, C1-6 alkyl, C1-6 alkoxy, amino, mono(C1-6 alkyl)amino or di(C1-6 alkyl)amino.

Group E2: Hydroxyl, C1-6 alkoxy and C3-s cycloalkyl.

Group E3: Halogen, C1-6 alkyl, C1-6 alkoxy, a group represented by the formula —NH—$R^{22}$, nitro and a group represented by the formula —CO—$R^{32t}$, where $R^{22t}$ is hydrogen or C2-7 alkoxycarbonyl, and $R^{32t}$ is hydroxyl, C1-6 alkoxy or amino.

Group E4: Methoxy, a group represented by the formula —NH—$R^{22t}$, nitro, carboxyl, carbamoyl, methoxycarbonyl and methoxycarbonylamino.

where $R^{22t}$ is hydrogen or C2-7 alkoxycarbonyl.

Group E5: Fluorine, methyl, methoxy and amino.

[General Production Processes for Compounds of the Invention]

The compounds of the invention may be produced by the processes described below. However, the processes for production of the compounds of the invention are not restricted to these alone.

These processes will now be explained.

[Production Process A] Production Process for Invention Compound Intermediate (14a)

[Chemical Formula 32]

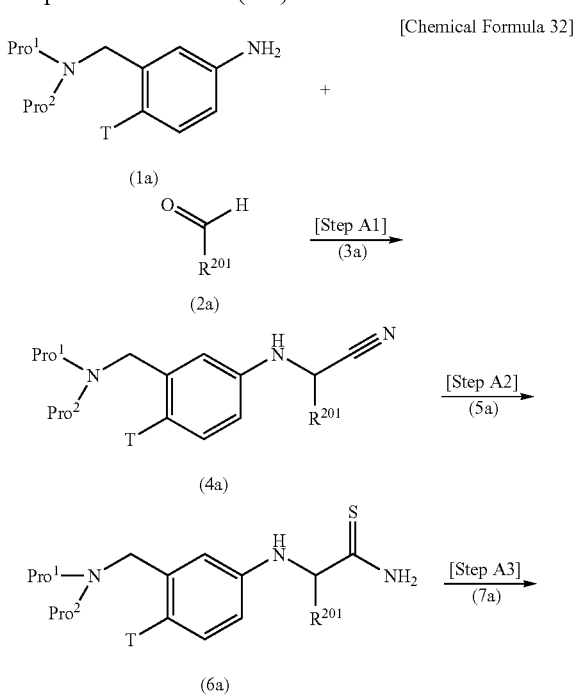

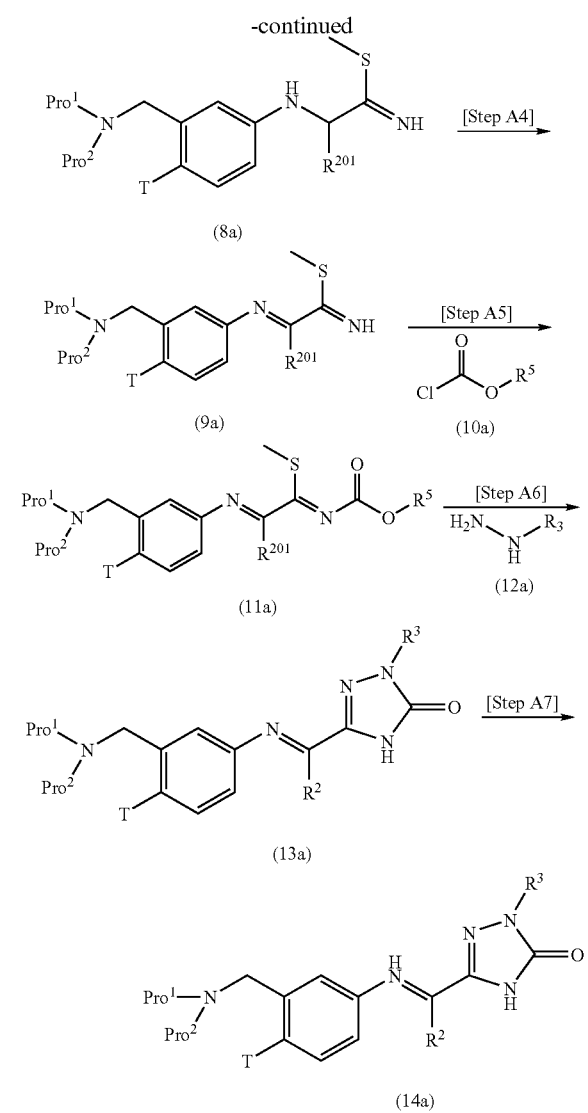

In this formula, $R^2$ and $R^3$ have the same definitions as above. $R^{201}$ represents C6-10 aryl optionally having 1-5 substituents selected from Group A1 above, a 5- to 10-membered heteroaryl group optionally having 1-5 substituents selected from Group A1 above or a 9- to 12-membered benzene-fused cyclic group optionally having 1-5 substituents selected from Group A1 above. When the substituent selected from Group A1 above is hydroxyl, the hydroxyl may be protected. $R^5$ represents C1-6 alkyl optionally substituted with a C6-10 aryl. T represents a cyano group or bromine. $Pro^1$ and $Pro^2$ each independently represent hydrogen or an amino protecting group such as t-butoxycarbonyl group (BOC), (2-trimethylsilanyl)ethylcarbonyl or benzylcarbonyl, with the proviso that $Pro^1$ and $Pro^2$ are not both hydrogen.

[Step A1]

This is a step of reacting compound (1a), compound (2a) and a cyanating agent such as trimethylsilyl cyanide or hydrogen cyanide (3a) in a solvent, in the presence or in the absence of a suitable Lewis acid catalyst and in the presence or in the absence of a suitable dehydrating agent, to produce compound (4a).

This step may be carried out by a commonly employed protocol as described in SYNLETT, 1997, 115-116.

The step may also be carried out under a stream or in an atmosphere of an inert gas such as nitrogen or argon.

As compound (1a) there may be used the compounds described in Examples 1, 3 and 14, publicly known compounds, commercially available compounds, or compounds that can be synthesized from commercially available compounds by methods ordinarily employed by those skilled in the art, or based on the same reaction conditions as in Examples 1, 3 and 14.

As compound (2a) there may be used publicly known compounds, commercially available compounds or compounds that can be produced from commercially available compounds by processes ordinarily carried out by those skilled in the art or by the processes described in the production examples below.

The solvent used for the reaction is not particularly restricted so long as it dissolves the starting materials to some degree and does not interfere with the reaction, and for example, there may be used halogen solvents such as dichloromethane, 1,2-dichloroethane and chloroform, ether solvents such as tetrahydrofuran, 1,2-dimethoxyethane, t-butyl methyl ether, diethyl ether and 1,4-dioxane, ester solvents such as ethyl acetate, nitrile solvents such as acetonitrile, aromatic hydrocarbon solvents such as benzene and toluene, aliphatic hydrocarbon solvents such as heptane and hexane, or mixtures thereof. Of these solvents, dichloromethane or tetrahydrofuran is preferred.

As examples of Lewis acids to be used for the reaction there may be mentioned ytterbium(III) trifluoromethanesulfonate hydrate, scandium(III) trifluoromethanesulfonate, bismuth (III) chloride, ruthenium(III) chloride, nickel(II) chloride, lithium perchlorate and the like, with ytterbium(III) trifluoromethanesulfonate hydrate being preferred.

As examples of dehydrating agents for the reaction there may be used Molecular Sieves 3A, Molecular Sieves 4A, anhydrous magnesium sulfate, anhydrous sodium sulfate and the like, among which Molecular Sieves 3A is preferred.

The reaction temperature will generally differ depending on the starting materials, solvent and other reagents used in the reaction, but it is preferably between −20° C. and 50° C., and more preferably 10° C.-30° C.

The reaction time will generally differ depending on the starting materials, solvent and other reagents used in the reaction, and on the reaction temperature, but preferably stirring is carried out for 1-96 hours and more preferably 12-48 hours at the aforementioned reaction temperature after addition of the reagents.

Compound (1a) may be used in a 1- to 2-fold molar amount with respect to compound (2a), but preferably it is used in a 1- to 1.2-fold molar amount and more preferably in a 1- to 1.05-fold molar amount.

The cyanating agent (3a) may be used in a 1- to 3-fold molar amount with respect to compound (2a), but preferably it is used in a 1- to 2-fold molar amount and more preferably in a 1.5- to 2-fold molar amount.

The Lewis acid catalyst may be used in a 0.01- to 2-fold molar amount with respect to compound (2a), but preferably it is used in a 0.05- to 0.2-fold molar amount and more preferably in a 0.1-fold molar amount.

[Step A2]

This is a step of reacting compound (4a) with a sulfidizing agent (5a) such as aqueous ammonium sulfide in a solvent to produce compound (6a).

The step may also be carried out under a stream or in an atmosphere of an inert gas such as nitrogen or argon.

The solvent used for the reaction is not particularly restricted so long as it dissolves the starting materials to some degree and does not interfere with the reaction, and for example, there may be used alcohol solvents such as methanol, ethanol and 2-propanol or ether solvents such as tetrahydrofuran, 1,2-dimethoxyethane, t-butyl methyl ether, diethyl ether and 1,4-dioxane, or mixtures thereof. Of these solvents, methanol and tetrahydrofuran mixed solvents are preferred.

The reaction temperature will generally differ depending on the starting materials, solvent and other reagents used in the reaction, but it is preferably between 0° C. and 80° C., and more preferably 10-50° C.

The reaction time will generally differ depending on the starting materials, solvent and other reagents used in the reaction, and on the reaction temperature, but preferably stirring is carried out for 1-48 hours and more preferably 2-12 hours at the aforementioned reaction temperature after addition of the reagents.

The sulfidizing agent (5a) may be used in a 1- to 10-fold molar amount with respect to compound (4a), but preferably it is used in a 2- to 6-fold molar amount and more preferably in a 3- to 5-fold molar amount.

[Step A3]

This is a step of reacting compound (6a) with a methylating agent (7a) such as trimethyloxonium tetrafluoroborate in a solvent to produce compound (8a).

The step may also be carried out under a stream or in an atmosphere of an inert gas such as nitrogen or argon.

The solvent used for the reaction is not particularly restricted so long as it dissolves the starting materials to some degree and does not interfere with the reaction, and for example, there may be used halogen solvents such as dichloromethane, 1,2-dichloroethane and chloroform, aromatic hydrocarbon solvents such as benzene and toluene, aliphatic hydrocarbon solvents such as heptane and hexane, nitrile solvents such as acetonitrile, nitro solvents such as nitromethane, or mixtures thereof. Of these solvents, dichloromethane or acetonitrile is preferred.

The reaction temperature will generally differ depending on the starting materials, solvent and other reagents used in the reaction, but it is preferably between −20° C. and 50° C., and more preferably 0-30° C.

The reaction time will generally differ depending on the starting materials, solvent and other reagents used in the reaction, and on the reaction temperature, but preferably stirring is carried out for between 10 minutes and 14 hours and more preferably between 10 minutes and 2 hours at the aforementioned reaction temperature after addition of the reagents.

The methylating agent (7a) may be used in a 1- to 1.5-fold molar amount with respect to compound (6a), but preferably it is used in a 1- to 1.2-fold molar amount and more preferably in a 1.05-fold molar amount.

[Step A4]

This is a step of converting compound (8a) to compound (9a) with an appropriate oxidizing agent in a solvent.

The solvent used for the reaction is not particularly restricted so long as it dissolves the starting materials to some degree and does not interfere with the reaction, and for example, there may be used halogen solvents such as dichloromethane, 1,2-dichloroethane and chloroform, ester solvents such as ethyl acetate, ether solvents such as tetrahydrofuran, 1,2-dimethoxyethane, t-butyl methyl ether, diethyl ether and 1,4-dioxane, aromatic hydrocarbon solvents such as benzene and toluene, aliphatic hydrocarbon solvents such as heptane and hexane, ketone solvents such as acetone, or mixtures thereof. Of these solvents, dichloromethane or ethyl acetate is preferred.

As examples of oxidizing agents for the reaction there may be used manganese dioxide, m-chloroperbenzoic acid and 2,3-dichloro-5,6-dicyano-p-benzoquinone, among which manganese dioxide is preferred.

The reaction temperature will generally differ depending on the starting materials, solvent and oxidizing agent used in the reaction, but it is preferably between 0° C. and 50° C., and more preferably 10-30° C.

The reaction time will generally differ depending on the starting materials, solvent and other reagents used in the reaction, and on the reaction temperature, but preferably stirring is carried out for between 10 minutes and 12 hours and more preferably between 30 minutes and 4 hours at the aforementioned reaction temperature after addition of the reagents.

The oxidizing agent may be used in a 1- to 20-fold molar amount with respect to compound (8a), but preferably it is used in a 5- to 15-fold molar amount.

[Step A5]

This is a step of reacting compound (9a) with a chloroformic acid ester (10a) such as methyl chloroformate or ethyl chloroformate in a solvent, in the presence of a suitable base, to produce compound (11a).

The step may also be carried out under a stream or in an atmosphere of an inert gas such as nitrogen or argon.

The solvent used for the reaction is not particularly restricted so long as it dissolves the starting materials to some degree and does not interfere with the reaction, and for example, there may be used ether solvents such as tetrahydrofuran, 1,2-dimethoxyethane, t-butyl methyl ether, diethyl ether and 1,4-dioxane, halogen solvents such as dichloromethane, 1,2-dichloroethane and chloroform, aromatic hydrocarbon solvents such as benzene, toluene and xylene, aliphatic hydrocarbon solvents such as heptane and hexane, or mixtures thereof. Of these solvents, toluene is preferred.

As specific bases for the reaction there may be used organic bases such as collidine, pyridine and lutidine, among which collidine is preferred.

The reaction temperature will generally differ depending on the starting materials, solvent and other reagents used in the reaction, but it is preferably between 0° C. and 120° C., and more preferably 60-100° C.

The reaction time will generally differ depending on the starting materials, solvent and other reagents used in the reaction, and on the reaction temperature, but preferably stirring is carried out for 1-24 hours and more preferably 1-14 hours at the aforementioned reaction temperature after addition of the reagents.

The chloroformic acid ester (10a) may be used in a 1- to 3-fold molar amount with respect to compound (9a), but preferably it is used in a 1- to 2-fold molar amount and more preferably in a 1.2- to 1.6-fold molar amount.

The base may be used in a 1- to 5-fold molar amount with respect to compound (9a), but preferably it is used in a 1- to 3-fold molar amount and more preferably in a 1.5- to 2.5-fold molar amount.

[Step A6]

This is a step of reacting compound (11a) with compound (12a) in a solvent, in the presence or in the absence of a suitable base, to produce compound (13a).

As compound (12a) there may be used a publicly known compound, a commercially available compound or a compound that can be produced from a commercially available compound by a process ordinarily carried out by those skilled in the art or by the processes described in the production examples below. Also, compound (12a) may be used in free form or as a salt.

The step may also be carried out under a stream or in an atmosphere of an inert gas such as nitrogen or argon.

The solvent used for the reaction is not particularly restricted so long as it dissolves the starting materials to some degree and does not interfere with the reaction, and for example, there may be used amide solvents such as N,N-dimethylformamide and N,N-dimethylacetamide, sulfoxide solvents such as dimethyl sulfoxide, ether solvents such as tetrahydrofuran, 1,2-dimethoxyethane, t-butyl methyl ether, diethyl ether and 1,4-dioxane, aromatic hydrocarbon solvents such as benzene and toluene, aliphatic hydrocarbon solvents such as heptane and hexane, alcohol solvents such as methanol, ethanol and 2-propanol, halogen solvents such as dichloromethane, 1,2-dichloroethane and chloroform, or mixtures thereof. Of these solvents, N,N-dimethylformamide is preferred.

As specific examples of bases for the reaction there may be used organic bases such as triethylamine, diisopropylethylamine, collidine and pyridine, among which triethylamine is preferred.

The reaction temperature will generally differ depending on the starting materials, solvent and other reagents used in the reaction, but it is preferably between 10° C. and 100° C., and more preferably 60-90° C.

The reaction time will generally differ depending on the starting materials, solvent and other reagents used in the reaction, and on the reaction temperature, but preferably stirring is carried out for 1-48 hours and more preferably about 14 hours at the aforementioned reaction temperature after addition of the reagents.

Compound (12a) may be used in a 1- to 3-fold molar amount with respect to compound (11a), but preferably it is used in a 1- to 1.2-fold molar amount and more preferably in a 1- to 1.05-fold molar amount.

The base may be used in a 1- to 3-fold molar amount with respect to compound (12a), but preferably it is used in a 1- to 2-fold molar amount.

When $R^{201}$ is C6-10 aryl having a protected hydroxyl group, a 5- to 10-membered heteroaryl group having a protected hydroxyl group or a 9- to 12-membered benzene-fused cyclic group having a protected hydroxyl group, this step may be preceded by 1) removal of the hydroxyl-protecting group and 2) alkylation of the hydroxyl group.

Removal of the protecting group may be accomplished by a method that is generally known in the field of synthetic organic chemistry, and for example by a method described in T. W. Greene, (Protective Groups in Organic Synthesis), John Wiley & Sons.

For example, when the hydroxyl-protecting group is a silyl protecting group such as t-butyldimethylsilyl or triisopropylsilyl, the removal may be accomplished by reacting a deprotecting agent such as tetrabutylammonium fluoride with compound (11a) in a solvent such as tetrahydrofuran.

Alkylation of the hydroxyl group may be accomplished by a method that is generally known in the field of synthetic organic chemistry, and for example, by reacting compound (11a) deprotected at the hydroxyl-protecting group (hereinafter referred to as "deprotected compound") with an alkylating agent such as 2-dimethylaminoethyl chloride hydrochloride or (2-iodoethoxy)triisopropylsilane in a solvent such as N,N-dimethylformamide, in the presence or in the absence of a base such as cesium carbonate or potassium carbonate. It may also be accomplished by reacting the deprotected compound with an alcohol such as 3-hydroxytetrahydrofuran, 1-methylpiperidin-4-ol or 2-dimethylaminoethanol in a solvent such as tetrahydrofuran, in the presence of triphenylphosphine and in the presence of an azodicarboxylic acid diester such as diethyl azodicarboxylate or diisopropyl azodicarboxylate.

[Step A7]

This is step of reacting compound (13a) with a suitable reducing agent in a solvent in the presence or in the absence of a suitable acid, for conversion to compound (14a).

This step may be carried out by a commonly employed method as described in Jikken Kagaku Koza 20 (4th Edition, The Chemical Society of Japan, Maruzen Publishing, pp. 282-284).

The step may also be carried out under a stream or in an atmosphere of an inert gas such as nitrogen or argon.

The solvent used for the reaction is not particularly restricted so long as it dissolves the starting materials to some degree and does not interfere with the reaction, and for example, there may be used alcohol solvents such as methanol, ethanol and 2-propanol, amide solvents such as N,N-dimethylformamide and N,N-dimethylacetamide, sulfoxide solvents such as dimethyl sulfoxide, ether solvents such as tetrahydrofuran, 1,2-dimethoxyethane, t-butyl methyl ether, diethyl ether and 1,4-dioxane, aromatic hydrocarbon solvents such as benzene and toluene, aliphatic hydrocarbon solvents such as heptane and hexane, halogen solvents such as dichloromethane, 1,2-dichloroethane and chloroform, or mixtures thereof. Of these solvents, a mixture of methanol and tetrahydrofuran is preferred.

Examples of reducing agents to be used for the invention include metal hydrogen complexes such as sodium cyanotrihydroborate, diisobutylaluminum hydride, lithium aluminum hydride, sodium bis(2-methoxyethoxy)aluminum hydride, sodium borohydride, sodium triacetoxyborohydride, lithium borohydride, lithium triethylborohydride and lithium tri(s-butyl)borohydride, borane-tetrahydrofuran complex, borane-dimethyl sulfide complex, thexylborane, catecholborane, 9-borabicyclo[3,3,1]nonane and the like, among which sodium cyanotrihydroborate is preferred.

As examples of acids for the reaction there may be used acetic acid, formic acid, hydrochloric acid and the like, among which acetic acid is preferred.

The reaction temperature will generally differ depending on the starting materials, solvent and other reagents used in the reaction, but it is preferably between –20° C. and 80° C., and more preferably 10-30° C.

The reaction time will also generally differ depending on the starting materials, solvent and other reagents used in the reaction, and on the reaction temperature, but preferably stirring is carried out for 1-24 hours and more preferably about 3 hours at the aforementioned reaction temperature after addition of the reagents.

The reducing agent may be used in a 1- to 10-fold molar amount with respect to compound (13a), but preferably it is used in a 3- to 6-fold molar amount and more preferably in a 5-fold molar amount.

Alternatively, compound (13a) may be converted to compound (14a) by catalytic hydrogenation in the presence of a suitable metal catalyst.

The metal catalyst used for the reaction may be palladium-carbon, platinum(IV) oxide or the like, with palladium-carbon being preferred.

The solvent used for the reaction is not particularly restricted so long as it dissolves the starting materials to some degree and does not interfere with the reaction, and for example, there may be used alcohol solvents such as methanol, ethanol and 2-propanol, esteric solvents such as ethyl acetate, ether solvents such as tetrahydrofuran, 1,2-dimethoxyethane, t-butyl methyl ether, diethyl ether and 1,4-dioxane, aromatic hydrocarbon solvents such as benzene and toluene, organic acids such as acetic acid and formic acid, water, or mixtures thereof, with ethanol and acetic acid mixed solvents being preferred.

The reaction temperature will generally differ depending on the starting materials, solvent and other reagents used in the reaction, but it is preferably between 10° C. and 80° C., and more preferably 10-30° C.

The reaction time will also generally differ depending on the starting materials, solvent and other reagents used in the reaction, as well as on the reaction temperature, but preferably stirring is carried out for 1-24 hours and more preferably about 12 hours at the aforementioned reaction temperature after addition of the reagents.

The metal catalyst may be used in a 0.01- to 2-fold molar amount with respect to compound (13a), but preferably it is used in a 0.05- to 1-fold molar amount.

Alternatively, compound (13a) may be converted to compound (14a) in the presence of a suitable metal reagent.

The step may also be carried out under a stream or in an atmosphere of an inert gas such as nitrogen or argon.

The metal reagent used for the invention may be iron powder, zinc, Raney nickel or the like, with iron powder being preferred.

The solvent used for the reaction is not particularly restricted so long as it dissolves the starting materials to some degree and does not interfere with the reaction, and for example, there may be used alcohol solvents such as methanol, ethanol and 2-propanol, organic acids such as acetic acid and formic acid, water, or mixtures thereof. Of these solvents, methanol, acetic acid and water mixed solvents are preferred.

The reaction temperature will generally differ depending on the starting materials, solvent and other reagents used in the reaction, but it is preferably between 10° C. and 80° C., and more preferably 50-70° C.

The reaction time will also generally differ depending on the starting materials, solvent and other reagents used in the reaction, as well as on the reaction temperature, but preferably stirring is carried out for 1-48 hours and more preferably about 24 hours at the aforementioned reaction temperature after addition of the reagents.

The metal reagent may be used in a 1- to 50-fold molar amount with respect to compound (13a), but preferably it is used in a 10- to 30-fold molar amount.

[Chemical Formula 33]

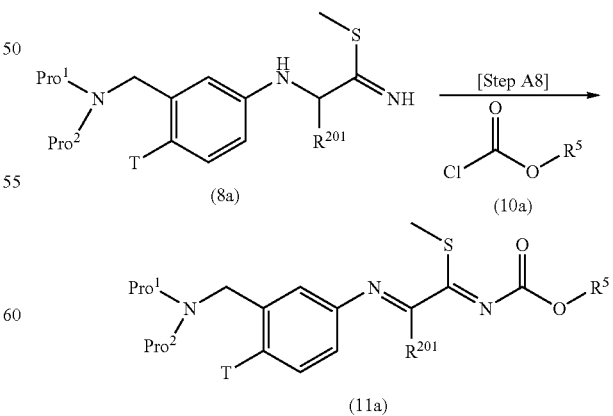

In this formula, $R^{201}$, $R^5$, T, $Pro^1$ and $Pro^2$ have the same definitions as above.

[Step A8]

This is a step of reacting compound (8a) with a chloroformic acid ester (10a) such as methyl chloroformate or ethyl chloroformate in a solvent, in the presence of a suitable base, to produce compound (11a).

The step may also be carried out under a stream or in an atmosphere of an inert gas such as nitrogen or argon.

The solvent used for the reaction is not particularly restricted so long as it dissolves the starting materials to some degree and does not interfere with the reaction, and for example, there may be used ether solvents such as tetrahydrofuran, 1,2-dimethoxyethane, t-butyl methyl ether, diethyl ether and 1,4-dioxane, aromatic hydrocarbon solvents such as benzene and toluene, aliphatic hydrocarbon solvents such as heptane and hexane, halogen solvents such as dichloromethane, 1,2-dichloroethane and chloroform, or mixtures thereof. Of these solvents, toluene is preferred.

As specific bases for the reaction there may be used collidine, pyridine and lutidine, among which collidine is preferred.

The reaction temperature will generally differ depending on the starting materials, solvent and other reagents used in the reaction, but it is preferably between 0° C. and 100° C., and more preferably 60-80° C.

The reaction time will also generally differ depending on the starting materials, solvent and other reagents used in the reaction, as well as on the reaction temperature, but preferably stirring is carried out for 1-24 hours and more preferably 1-14 hours at the aforementioned reaction temperature after addition of the reagents.

The chloroformic acid ester (10a) may be used in a 1- to 5-fold molar amount with respect to compound (8a), but preferably it is used in a 1.5- to 3.5-fold molar amount and more preferably in a 2- to 3-fold molar amount.

The base may be used in a 1- to 7-fold molar amount with respect to compound (8a), but preferably it is used in a 2- to 4-fold molar amount.

[Production Process B] Production Process (1) for Invention Compounds

[Chemical Formula 34]

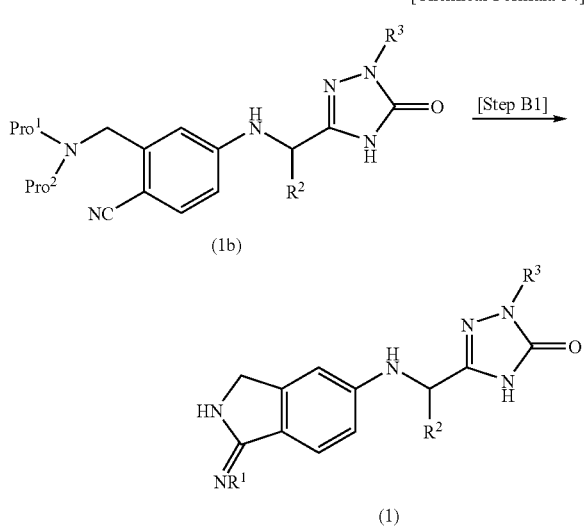

In this formula, $R^1$, $R^2$, $R^3$, $Pro^1$ and $Pro^2$ have the same definitions as $R^1$, $R^2$, $R^3$, $Pro^1$ and $Pro^2$ above.

[Step B1]

This is a step of deprotection of the amino-protecting group in compound (1b)(compound (14a) above wherein T is a cyano group) in a solvent or without a solvent (elimination of $Pro^1$ and $Pro^2$) followed by intramolecular cyclization reaction, to produce compound (1).

Elimination of the protecting group may be accomplished by a method that is generally known in the field of synthetic organic chemistry, and for example, by the method described in T. W. Greene, (Protective Groups in Organic Synthesis), John Wiley & Sons.

<1>

When the amino-protecting group is a t-butoxycarbonyl group, compound (1b) may be reacted in the presence of an acid such as anhydrous hydrogen chloride-ethyl acetate solution, anhydrous hydrogen chloride-methanol solution, anhydrous hydrogen chloride-ethanol solution, anhydrous hydrogen chloride-dioxane solution, trifluoroacetic acid or formic acid, to obtain compound (1).

The step may also be carried out under a stream or in an atmosphere of an inert gas such as nitrogen or argon.

The solvent used for this reaction is not particularly restricted so long as it dissolves the starting materials to some degree and does not interfere with the reaction, and for example, there may be used ether solvents such as tetrahydrofuran, 1,4-dioxane, 1,2-dimethoxyethane, methyl-t-butyl ether, cyclopentyl methyl ether, diethyl ether, diisopropyl ether, dibutyl ether and dicyclopentyl ether, aromatic hydrocarbon solvents such as benzene and toluene, halogen solvents such as dichloromethane, alcohol solvents such as methanol, ethanol and 2-propanol and esteric solvents such as ethyl acetate and propyl acetate, as well as mixtures of these. Of these solvents, dichloromethane is preferred.

The reaction temperature will generally differ depending on the starting materials, solvent and other reagents used in the reaction, but it is preferably between −20° C. and 50° C. (reactor internal temperature), and more preferably O-30° C. (reactor internal temperature).

<2>

When the amino-protecting group is a (2-trimethylsilanyl)ethylcarbonyl group, compound (1b) may be reacted in the presence of a deprotecting agent to obtain compound (1).

The step may also be carried out under a stream or in an atmosphere of an inert gas such as nitrogen or argon.

The solvent used for this reaction is not particularly restricted so long as it dissolves the starting materials to some degree and does not interfere with the reaction, and for example, there may be used ether solvents such as tetrahydrofuran, 1,2-dimethoxyethane, methyl-t-butyl ether, cyclopentyl methyl ether, diethyl ether, diisopropyl ether, dibutyl ether and dicyclopentyl ether, nitrile solvents such as acetonitrile and propionitrile, amide solvents such as N,N-dimethylformamide and sulfoxide solvents such as dimethyl sulfoxide, as well as mixtures of these. Of these solvents, acetonitrile is preferred.

As deprotecting agents for this reaction there may be used tetrabutylammonium fluoride, cesium fluoride, potassium fluoride and the like, with tetrabutylammonium fluoride being preferred.

The reaction temperature will generally differ depending on the starting materials, solvent and other reagents used in the reaction, but it is preferably between 20° C. and 100° C. (reactor internal temperature), and more preferably 30-70° C. (reactor internal temperature).

<3>

When the amino-protecting group is an allyl or alkylcarbonyl group, compound (1b) may be reacted in the presence of a hydroxide compound to obtain compound (1).

The step may also be carried out under a stream or in an atmosphere of an inert gas such as nitrogen or argon.

The solvent used for this reaction is not particularly restricted so long as it dissolves the starting materials to some degree and does not interfere with the reaction, and for example, there may be used ether solvents such as tetrahydrofuran, 1,2-dimethoxyethane, methyl-t-butyl ether, cyclopentyl methyl ether, diethyl ether, diisopropyl ether, dibutyl ether and dicyclopentyl ether, alcohol solvents such as methanol and ethanol, amide solvents such as N,N-dimethylformamide and sulfoxide solvents such as dimethyl sulfoxide, as well as mixtures of these. Of these solvents, methanol and tetrahydrofuran mixed solvents are preferred.

As hydroxides for this reaction there may be used sodium hydroxide, potassium hydroxide and the like, among which sodium hydroxide is preferred.

The reaction temperature will generally differ depending on the starting materials, solvent and other reagents used in the reaction, but it is preferably between 20° C. and 100° C. (reactor internal temperature), and more preferably 40-80° C. (reactor internal temperature).

[Production Process C] Production Process for Compound (1) of the Invention

[Chemical Formula 35]

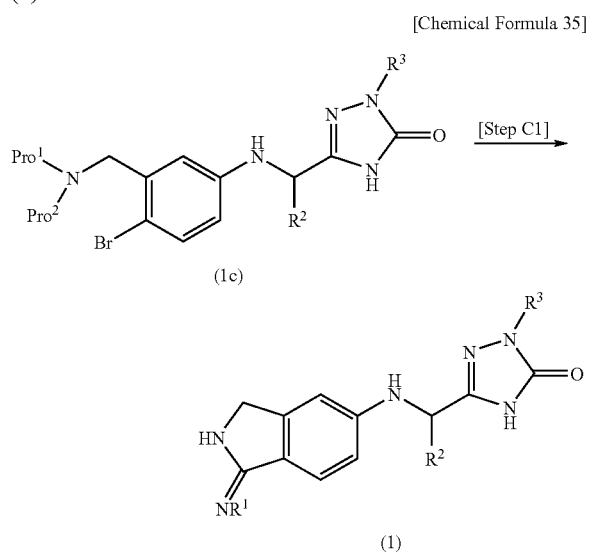

In this formula, $R^1$, $R^2$, $R^3$, $Pro^1$ and $Pro^2$ have the same definitions as $R^1$, $R^2$, $R^3$, $Pro^1$ and $Pro^2$ above.

[Step C1]

This is a step of reaction of compound (1c)(compound (14a) above wherein T is bromine) with a cyanating agent in a solvent, in the presence or in the absence of a suitable catalyst (cyanating coupling reaction) and ligand (cyanating coupling reaction), and then deprotection of the amino-protecting group (elimination of $Pro^1$ and $Pro^2$) followed by intramolecular cyclization reaction to produce compound (1).

The step may also be carried out under a stream or in an atmosphere of an inert gas such as nitrogen or argon.

The solvent used for this reaction is not particularly restricted so long as it dissolves the starting materials to some degree and does not interfere with the reaction, and for example, there may be used ether solvents such as tetrahydrofuran, 1,2-dimethoxyethane, methyl-t-butyl ether, cyclopentyl methyl ether, diethyl ether, diisopropyl ether, dibutyl ether and dicyclopentyl ether, amide solvents such as N,N-dimethylformamide and 1-methyl-2-pyrrolidone and sulfoxide solvents such as dimethyl sulfoxide, as well as mixtures of these. Of these solvents, N,N-dimethylformamide is preferred.

As cyanating agents for this reaction there may be used zinc cyanide, copper cyanide, acetone cyanohydrin and the like: among which zinc cyanide is preferred.

As cyanating reaction catalysts for this reaction there may be used tris(dibenzylideneacetone)dipalladium(0), palladium(II) acetate and the like, with tris(dibenzylideneacetone) dipalladium(0) being preferred.

As ligands for the reaction there may be used 1,1'-bis (diphenylphosphino)ferrocene, tri-t-butylphosphine and the like, with 1,1'-bis(diphenylphosphino)ferrocene being preferred.

The reaction temperature will generally differ depending on the starting materials, solvent and other reagents used in the reaction, but it is preferably between 20° C. and 200° C. (reactor internal temperature), and more preferably 60-150° C. (reactor internal temperature).

[Production Process D] Production Process for Compounds of the Invention [Compound (1-3), Compound (1-4), Compound (1-5), Compound (1-6), Compound (1-7)]

Compound (1-3), compound (1-4), compound (1-5), compound (1-6) and compound (1-7) as compounds of the invention can be obtained

[1] using compound (1a) above as starting material,
[2] by the same procedures under the same conditions as in the examples, based on production process A, production process B, or the common production processes described in WO 00/35858, WO 06/41119, WO 00/41531, WO 06/62972 or WO 07/76431.

Upon completion of the reaction in each step of the processes described above, the target compound of each step may be recovered from the reaction mixture by a usual method.

For example, in the case of the entire reaction mixture is a solution, the reaction mixture may be returned to room temperature or cooled on ice, and acid, alkali, oxidizing agent or reducing agent may be appropriately neutralized as desired, prior to addition of water and an organic solvent that is immiscible therewith and does not react with the target compound, such as ethyl acetate, and separation of the layer containing the target compound. Next, a solvent that is immiscible with the obtained layer and does not react with the target compound may be added, and then the layer containing the target compound washed and separated. When this layer is an organic layer, it may be dried using a desiccant such as anhydrous magnesium sulfate or anhydrous sodium sulfate, and the solvent distilled off to recover the target compound. When the layer is an aqueous layer, it may be electrically desalted and then freeze-dried to recover the target compound.

When the entire reaction mixture is a solution, it may be possible to recover the target compound simply by distilling off the components other than the target compound (for example, solvent, reagents, etc.) at ordinary pressure or under reduced pressure.

On the other hand, when the reagents or catalyst are the only solids present, or when the entire reaction mixture is a solution and the reagents or catalyst alone precipitate as solid during the recovery process, with the target compound remaining dissolved in solution, the reagents or catalyst may be first filtered by a filtration method, the filtered reagents or catalyst washed with a suitable organic or inorganic solvent, and the obtained wash combined with the mother liquor to obtain a liquid mixture, which may then be treated in the same manner as if the entire reaction mixture were a solution, in order to obtain the target compound.

The reaction mixture may be used directly for subsequent steps without isolation of the target compound in cases where components other than the target compound in the reaction mixture will not inhibit reaction in the subsequent steps.

Purity of the target compound recovered by such methods can be increased by appropriately carrying out recrystallization, different chromatography methods or distillation.

When the recovered target compound is a solid, purity of the target compound can usually be improved by recrystallization. For recrystallization there may be used a simple solvent or a multiple solvent mixture that does not react with the target compound. Specifically, the target compound may first be dissolved at room temperature or with heating in the simple solvent or solvent mixture that does not react with the target compound. The obtained mixture may then be cooled with ice water or the like or allowed to stand at room temperature to cause precipitation of the target compound from the mixture.

The recovered target compound may subjected to different types of chromatography methods such as normal phase column chromatography or reverse phase column chromatography, to improve the purity of the target compound. In most cases a weakly acidic silica gel such as silica gel 60 (70-230 mesh or 340-400 mesh) by Merck, Ltd. or BW-300 (300 mesh) by Fuji Silysia Chemical, Ltd. may be used. If the target compound is basic and adsorption onto the aforementioned silica gel types is too strong, there may be used propylamine-coated silica gel (200-350 mesh) by Fuji Silysia Chemical, Ltd. If the target compound is dipolar or requires elution with a highly polar solvent such as methanol, there may be used NAM-200H or NAM-300H by Nagara Science Co., Ltd. Purification by chromatography may be accomplished by normal phase silica gel column chromatography using a FLASH+Cartridge (KP-SIL, 60 Å, 32-63 μm) by Biotage or a Hi-Flash™ Column (40 μm 60 Å) by Yamazen Corp., or by reverse phase silica gel column chromatography using YMC*GEL ODS-A by YMC Co., Ltd. Using these silica gels, the target compound may be eluted in a simple solvent or solvent mixture that does not react with the target compound and the solvent distilled off to obtain the target compound with enhanced purity.

When the recovered target compound is a liquid, purity of the target compound can also be improved by distillation. For distillation, the target compound may be placed under reduced pressure at room temperature or with heating to achieve distillation of the target compound.

Representative examples of production processes for compounds according to the invention were described above, but the starting compounds and reagents for production of the invention compounds may form salts, hydrates or solvates, and will differ depending on the starting materials and solvents used, without any particular restrictions so long as they do not inhibit the reaction. The solvent used will also differ depending on the starting materials and reagents, and of course is not particularly restricted so long as it can dissolve the starting materials to some degree and does not inhibit the reaction. When a compound of the invention is obtained in free form, it may be converted to an acceptable salt of the compound by an ordinary method.

Conversely, when a compound of the invention is obtained as a salt or hydrate, it may be converted to the free form of the compound by an ordinary method.

Various isomers (for example, geometric isomers, optical isomers, rotational isomers, stereoisomers, tautomers and the like) obtained for compounds of the invention may be purified and isolated using ordinary separation means such as, for example, recrystallization, a diastereomer salt method, enzymatic resolution or chromatography methods (for example, thin-layer chromatography, column chromatography, gas chromatography, etc.).

When a compound of the invention is to be used as a medicament, the compound of the invention will usually be used after mixture and formulation with appropriate additives. However, this does not negate the use of the compounds of the invention in simple forms as medicaments.

As additives there may be mentioned excipients, binders, lubricants, disintegrators, coloring agents, taste correctives, emulsifiers, surfactants, dissolving aids, suspending agents, isotonizing agents, buffering agents, antiseptic agents, antioxidants, stabilizers, absorption accelerators and the like which are commonly used in medicaments, and these may also be used in appropriate combinations as desired.

As examples of excipients there may be mentioned lactose, saccharose, glucose, corn starch, mannitol, sorbitol, starch, pregelatinized starch, dextrin, crystalline cellulose, light silicic anhydride, aluminum silicate, calcium silicate, magnesium aluminate metasilicate, calcium hydrogenphosphate and the like.

As examples of binders there may be mentioned polyvinyl alcohol, methylcellulose, ethylcellulose, gum arabic, tragacanth, gelatin, shellac, hydroxypropylmethylcellulose, hydroxypropylcellulose, carboxymethylcellulose sodium, polyvinylpyrrolidone, macrogol and the like.

As examples of lubricants there may be mentioned magnesium stearate, calcium stearate, sodium stearyl fumarate, talc, polyethylene glycol, colloidal silica and the like.

As examples of disintegrators there may be mentioned crystalline cellulose, agar, gelatin, calcium carbonate, sodium hydrogencarbonate, calcium citrate, dextrin, pectin, low-substituted hydroxypropylcellulose, carboxymethylcellulose, carboxymethylcellulose calcium, croscarmellose sodium, carboxymethyl starch, carboxymethyl starch sodium and the like.

As coloring agents there may be mentioned those approved for addition to pharmaceuticals, such as iron sesquioxide, yellow iron sesquioxide, calamine, caramel, β-carotene, titanium oxide, talc, riboflavin sodium phosphate, yellow aluminum lake and the like.

As taste correctives there may be mentioned cocoa powder, menthol, aromatic powders, peppermint oil, camphor, cinnamon powder and the like.

As emulsifying agents or surfactants there may be mentioned stearyltriethanolamine, sodium lauryl sulfate, laurylaminopropionic acid, lecithin, glycerin monostearate, sucrose fatty acid esters, glycerin fatty acid esters and the like.

As dissolving aids there may be mentioned polyethylene glycol, propylene glycol, benzyl benzoate, ethanol, cholesterol, triethanolamine, sodium carbonate, sodium citrate, polysorbate 80, nicotinamide and the like.

As suspending agents there may be mentioned the aforementioned surfactants, as well as hydrophilic polymers such as polyvinyl alcohol, polyvinylpyrrolidone, methylcellulose, hydroxymethylcellulose, hydroxyethylcellulose and hydroxypropylcellulose.

As isotonizing agents there may be mentioned glucose, sodium chloride, mannitol, sorbitol and the like.

As buffering agents there may be mentioned buffers of phosphate, acetate, carbonate, citrate and the like.

As antiseptic agents there may be mentioned methylparaben, propylparaben, chlorobutanol, benzyl alcohol, phenethyl alcohol, dehydroacetic acid, sorbic acid and the like.

As antioxidants there may be mentioned sulfurous acid salts, ascorbic acid, α-tocopherol and the like.

As stabilizers there may be mentioned those commonly used in medicaments.

As absorption accelerators there may also be mentioned those commonly used in medicaments.

As formulations there may be mentioned oral forms such as tablets, powders, granules, capsules, syrups, lozenges and inhalants; external preparations such as suppositories, ointments, eye salves, tapes, eye drops, nose drops, ear drops, poultices, lotions, and the like; and injections.

The aforementioned oral forms may be formulated with appropriate combinations of the additives mentioned above. Their surfaces may also be coated if necessary.

The aforementioned external preparations may be formulated with appropriate combinations of the additives mentioned above, and especially excipients, binders, taste correctives, emulsifiers, surfactants, dissolving aids, suspending agents, isotonizing agents, antiseptic agents, antioxidants, stabilizers and absorption accelerators.

Injections may also be formulated with appropriate combinations of the additives mentioned above, and especially emulsifiers, surfactants, dissolving aids, suspending agents, isotonizing agents, buffering agents, antiseptic agents, antioxidants, stabilizers and absorption accelerators.

The dosage of a medicament according to the invention will differ depending on the severity of symptoms, patient age, gender and body weight, type of dosage form/salt, patient medicament sensitivity and specific nature of the disease, but the dosage per day for adults will generally be about 1 mg to about 1000 mg (preferably about 10 mg to about 300 mg) for oral administration, about 1 mg to about 1000 mg (preferably about 10 to about 300 mg) for external application, and in the case of an injection, about 1 µg to about 3000 µg (preferably about 3 µg to about 3000 fig) per kilogram of body weight, either administered at a single time or divided into 2 to 6 times per day.

These values are the actual administered amounts in the case of oral formulations and injections, and are the amounts actually absorbed by the body in the case of external formulations.

EXAMPLES

The compounds of the invention may be produced by the processes described in the following examples, and the effects of the compounds may be confirmed by the methods described in the following testing examples. However, these specific examples are merely illustrative and not intended to restrict the invention in any way, while various modifications may be implemented such as are within the scope of the invention.

Compounds mentioned with reference to published documents are produced in the manner described in those documents.

Unless otherwise specified, the "silica gel" in "silica gel column chromatography" mentioned throughout the examples is either Silica Gel 60 (70-230 mesh or 340-400 mesh) by Merck, Ltd. or FLASH+Cartridge (KP-SIL, 60 Å, 32-63 µm) by Biotage.

Also, unless otherwise specified, the "silica gel" in "silica gel column chromatography" mentioned throughout the examples also includes Hi-Flash™ Column (40 µm, 60 Å) by Yamazen Corp., in addition to the two silica gels mentioned above.

Also, unless otherwise specified, the "reverse phase silica gel" in "reverse phase silica gel column chromatography" mentioned throughout the examples is YMC*GEL ODS-A (12 nm, S-50 µm) by YMC Co., Ltd.

Also unless otherwise specified, the "NH silica gel" in "NH silica gel column chromatography" mentioned throughout the examples is propylamine-coated silica gel (200-350 mesh) by Fuji Silysia Chemical, Ltd.

The "NAM silica gel" in "NAM silica gel column chromatography" mentioned throughout the examples is either NAM-200H or NAM-300H by Nagara Science Co., Ltd.

Also, unless specifically stated otherwise, the "purification by reverse-phase high performance liquid chromatography" mentioned throughout the examples was carried out under the following conditions.

[Column]

One of the following columns was selected for use.
Manufacturer: SHISEIDO
Name: CAPCELL PAK C18
Size: 50 mm×20 mm I.D.
Type: ACR 5 µm
Manufacturer: YMC
Name: YMC CombiPrep ODS-A
Size: 50 mm×20 mm I.D.
Type: S-5 µm
Manufacturer: WAKO
Name: WAKOpak Combi ODS-A
Size: 50 mm×20 mm I.D.
[Mobile Phase]

A combination of (1) and (2) below or a combination of (3) and (4) below was prepared with a gradient in a 100:0-0:100 proportion range for use as the moving bed for liquid chromatography.
(1) 99.9% water (0.1% trifluoroacetic acid)
(2) 99.9% acetonitrile (0.1% trifluoroacetic acid)
(3) 99.9% water (0.1% acetic acid)
(4) 99.9% acetonitrile (0.1% acetic acid)

Unless specifically stated otherwise, "the optical resolution using a SUMICHIRAL OA-2500 column" mentioned throughout the examples was carried out under the following conditions.

[Column]
Name: SUMICHIRAL OA-2500, 20 mmφ×25 cm
Manufacturer: Sumika Chemical Analysis Service, Ltd.
[Mobile Phase and Elution Rate]
0.05 M Ammonium acetate methanol solution, 10 ml/min Unless otherwise specified, the term "HPLC retention time" used throughout the examples is the retention time for optical resolution under the following conditions.
[Column]
Name: SUMICHIRAL OA-2500, 20 mmφ×25 cm
Manufacturer: Sumika Chemical Analysis Service, Ltd.
[Mobile Phase and Elution Rate]
0.05 M Ammonium acetate methanol solution, 10 ml/min Unless otherwise specified, the term "manganese dioxide" used throughout the examples refers to CMD-1 by Chuo Denki Kogyo Co., Ltd.

The term "room temperature" in the examples ordinarily refers to a temperature between about 10° C. and 35° C. The percentage values are weight percentages, unless otherwise specified. The other symbols used in the examples stand for the following.

$^1$H-NMR: Proton nuclear magnetic resonance
δ: Chemical shift
s: singlet
d: doublet
t: triplet
q: quartet
quint: quintet
m: multiplet
br: broad
sept: septet
J: coupling constant
Hz: Hertz M: mol/L
n-: normal
s-: secondary
t-: tertiary
N: normality
CDCl$_3$: Deutero chloroform
d$_6$-DMSO: Deutero dimethylsulfoxide
CD$_3$OD: Deutero methanol
CD$_3$CO$_2$D: Deutero acetic acid
CD$_3$CN: Deutero acetonitrile
DMF: N,N-Dimethylformamide
THF: Tetrahydrofuran
DMSO: Dimethyl sulfoxide
DIAD: Diisopropyl azodicarboxylate
DEAD: Diethyl azodicarboxylate
MS3A: Molecular Sieves 3A
Yb(OTf)$_3$: Ytterbium(III) trifluoromethanesulfonate hydrate
Me$_3$O$^+$BF$_4$$^-$: Trimethyloxonium tetrafluoroborate
TBAF: Tetrabutylammonium fluoride Production Example 1a 3-Fluoro-2-(3-hydroxypropyl)-6-methoxyphenol

[Chemical Formula 36]

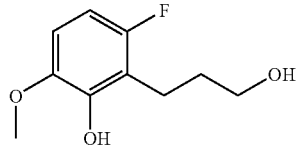

To a 50 ml solution of 4.46 g of 6-fluoro-2-hydroxy-3-methoxybenzaldehyde in dichloromethane there was added 10 g of (triphenylphosphoranilidene)acetic acid ethyl ester while cooling on ice. After stirring at room temperature for 30 minutes, the reaction mixture was poured into a silica gel column and elution was performed with heptane-ethyl acetate=3:1. The eluate was concentrated under reduced pressure. The residue was dissolved in 100 ml of ethyl acetate, and 1 g of 10% palladium-carbon was added prior to stirring for 7 hours at room temperature under a hydrogen atmosphere. The reaction mixture was filtered through Celite, and the filtrate was concentrated under reduced pressure. The residue was dissolved in 100 ml of THF, 2 g of lithium borohydride was added while cooling on ice and the mixture was stirred overnight at room temperature. After then adding 1N hydrochloric acid to the reaction mixture while cooling on ice, extraction was performed with ethyl acetate. The organic layer was dried over anhydrous magnesium sulfate. The desiccant was filtered out and the filtrate was concentrated under reduced pressure. The residue was purified by silica gel column chromatography (ethyl acetate-heptane system) to obtain the target compound (4.78 g) as a solid.

$^1$H-NMR (CDCl$_3$) δ 1.85 (sept, J=6.8 Hz, 2H) 2.80 (dt, J=1.6, 6.8 Hz, 2H) 3.59 (t, J=6.0 Hz, 2H) 3.86(s, 3H) 6.54 (t, J=9.2 Hz, 1H) 6.64 (dd, J=4.8, 8.8 Hz, 1H)

Production Example 1b

5-Fluoro-8-methoxychromane

[Chemical Formula 37]

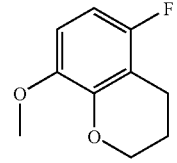

After dissolving 4.78 g of 3-fluoro-2-(3-hydroxypropyl)-6-methoxyphenol and 9.4 g of triphenylphosphine in 70 ml of THF under a nitrogen atmosphere, the mixture was cooled to −74° C. Next, 7 ml of DIAD was added to the reaction mixture, which was then raised to room temperature and stirred overnight. The reaction mixture was concentrated and the residue was purified by silica gel column chromatography (ethyl acetate-heptane system) to obtain the target compound (3.6 g) as an oil.

Production Example 1c

5-Fluoro-8-methoxychroman-6-carboaldehyde

[Chemical Formula 38]

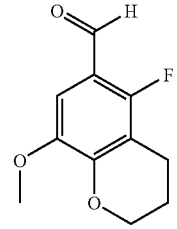

To a 130 ml THF solution containing 3.6 g of 5-fluoro-8-methoxychromane and 4.2 ml of N,N,N',N',N"-pentamethyldiethylenetriamine there was added dropwise 8 ml of n-butyllithium (2.55 M, hexane solution) at −74° C. After stirring at −74° C. for 1 hour, N-formylmorpholine was added. Stirring was continued for 1 hour at room temperature, and then 1N hydrochloric acid was added to the reaction mixture while cooling on ice, and the mixture was extracted with ethyl acetate and dried over anhydrous magnesium sulfate. The desiccant was filtered out and the filtrate was concentrated under reduced pressure. The residue was purified by silica gel column chromatography (ethyl acetate-heptane system) to obtain the target compound (1.50 g) as a colorless solid.

$^1$H-NMR (CDCl$_3$) δ 2.03-2.10 (m, 2H) 2.80 (t, J=6.4 Hz, 2H) 3.90(s, 3H) 4.36 (t, J=5.2 Hz, 2H) 7.16 (d, J=6.4 Hz, 1H) 10.24 (s: 1H)

Production Example 2a

4-Amino-2-methanesulfonylthiazole-5-carboxylic acid methyl ester

[Chemical Formula 39]

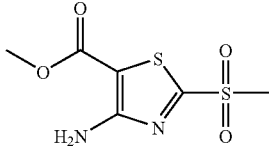

After adding 45.2 g of 4-amino-2-methylsulfanylthiazole-5-carboxylic acid methyl ester [CAS No. 60093-05-2] to 2 l of a water:methanol=1:1 mixed solvent at room temperature, 408 g of Oxone® was gradually added over a period of 30 minutes while stirring. Stirring was continued for 24 hours at room temperature, and then the reaction mixture was poured into a mixture of 10 l of ethyl acetate and 10 l of water. The organic layer was washed with 5 l of brine and dried over anhydrous magnesium sulfate. The desiccant was filtered out and the filtrate was concentrated under reduced pressure to obtain the target compound (37.6 g) as a colorless solid.

$^1$H-NMR (CDCl$_3$) δ 3.29(s, 3H) 3.90(s, 3H) 6.00(br.s, 2H)

Production Example 2b

4-Aminothiazole-5-carboxylic acid methyl ester

[Chemical Formula 40]

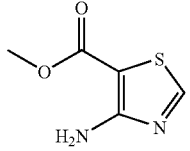

To a 1 l solution of 37.6 g of 4-amino-2-methanesulfonylthiazole-5-carboxylic acid methyl ester in a methanol:THF=1:1 mixed solvent at room temperature, there was gradually added 15 g of sodium borohydride over a period of 10 hours. Stirring was continued for 40 hours at room temperature, and then the reaction mixture was poured into a mixture of 6 l of ethyl acetate and 3 l of water. The organic layer was washed with 3 l of water and 3 l of brine, and the aqueous layer was extracted again with ethyl acetate. The organic layers were combined and dried over anhydrous magnesium sulfate. The desiccant was filtered out and the filtrate was concentrated under reduced pressure. The residue was purified by silica gel column chromatography (ethyl acetate-heptane system) to obtain the target compound (15.3 g) as an off-white solid.

$^1$H-NMR (CDCl$_3$) δ 3.85(s, 3H) 5.87(br.s, 211) 8.54(s, 1H)

Production Example 2c

4-Hydrazinothiazole-5-carboxylic acid methyl ester

[Chemical Formula 41]

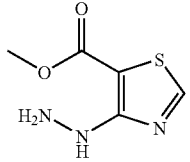

An aqueous solution (10 ml) of sodium nitrite (7.32 g) was added dropwise to a concentrated hydrochloric acid solution (90 ml) of 4-aminothiazole-5-carboxylic acid methyl ester (15.3 g) at 0-10° C. The mixture was then stirred at 0° C. for 30 minutes. To this mixture there was added dropwise a concentrated hydrochloric acid solution (100 ml) containing tin(II) chloride (73.2 g) at 0-10° C., and the mixture was stirred at the same temperature for 2 hours. The mixture was filtered and the filtrate was carefully added to a suspension of potassium carbonate and Celite in ethyl acetate (3 l) while stirring, with regular addition of potassium carbonate to prevent solution acidity. After adding the filtered substance to this ethyl acetate suspension, it was rendered basic with a 5N aqueous sodium hydroxide solution. The mixture was allowed to stand, and then most of the supernatant (organic layer A) was separated off. The remaining suspension was filtered through Celite and the filtrate was separated into organic layer B and aqueous layer A. Ethyl acetate (500 ml) and anhydrous magnesium sulfate were added to the filtered substance, and the mixture was stirred and then filtered. Aqueous layer A was re-extracted with the resulting filtrate. Washing of the filtered substance and re-extraction of aqueous layer A were repeated 4 times in the same manner. Organic layer A and organic layer B were combined with the obtained organic layer, and the mixture was dried over anhydrous magnesium sulfate. The desiccant was filtered out and the filtrate was concentrated under reduced pressure. The residue was purified by silica gel column chromatography (ethyl acetate-methanol system) to obtain the target compound (11.6 g) as an off-white solid.

$^1$H-NMR (CDCl$_3$) δ 3.83(s, 3H) 4.14(br.s, 2H) 7.55(br.s, 1H) 8.61(s, 1H)

Production Example 3a

4-Bromo-2-hydroxymethyl-6-methoxyphenol

[Chemical Formula 42]

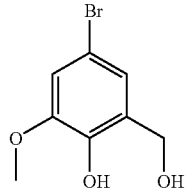

To a 200 ml solution of 50 g of 5-bromo-2-hydroxy-3-methoxybenzaldehyde in an ethanol:THF=1:1 mixed solvent there was added 16.4 g of sodium borohydride while cooling on ice. After stirring for 2 hours at room temperature, 1N hydrochloric acid was added to the reaction mixture while cooling on ice. The organic layer was extracted with ethyl acetate and dried over anhydrous magnesium sulfate. The desiccant was filtered out and the filtrate was concentrated under reduced pressure to obtain the target compound (50 g) as a crude product.

Production Example 3b

6-Bromo-8-methoxy-4H-benzo-[1,3]dioxine

[Chemical Formula 43]

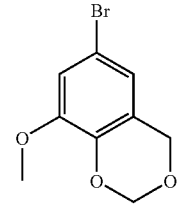

To a 450 ml solution of 50 g of 4-bromo-2-hydroxymethyl-6-methoxyphenol in DMF there was added 20 g of sodium hydride (60% mineral oil suspension) while cooling on ice, and the mixture was stirred at room temperature for 30 minutes. After then adding 15 ml of bromochloromethane and 3.2 g of sodium iodide to the reaction mixture, it was stirred at 80° C. for 6 hours under a nitrogen atmosphere. A saturated ammonium chloride aqueous solution was added to the reaction mixture and extraction was performed with ethyl acetate. The organic layer was dried over anhydrous magnesium sulfate. The desiccant was filtered out and the filtrate was concentrated under reduced pressure. The residue was purified by silica gel column chromatography (ethyl acetate-heptane system) to obtain the target compound (31.2 g) as a colorless solid.

$^1$H-NMR (CDCl$_3$) δ 3.87(s, 3H) 4.85(s, 2H) 5.28(s, 2H) 6.73(s, 1H) 6.88(s, 1H)

Production Example 3c

8-Methoxy-4H-benzo[1,3] dioxin-6-carboaldehyde

[Chemical Formula 44]

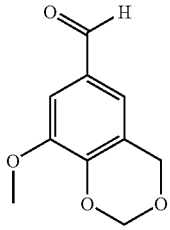

To 500 ml of a THF solution containing 31.2 g of 6-bromo-8-methoxy-4H-benzo[1,3]dioxine there was added dropwise 55 ml of n-butyllithium (2.55 M, hexane solution) at –70° C. under a nitrogen atmosphere. After stirring for 30 minutes at –72° C., 20 ml of N-formylmorpholine was added and the temperature was raised from –78° C. to 0° C. over a period of 30 minutes. A saturated ammonium chloride aqueous solution was added to the reaction mixture and extraction was performed with ethyl acetate. The organic layer was dried over anhydrous magnesium sulfate. The desiccant was filtered out and the filtrate was concentrated under reduced pressure. The residue was purified by silica gel column chromatography (ethyl acetate-heptane system) to obtain the target compound (21.28 g) as a colorless solid.

$^1$H-NMR (CDCl$_3$) δ 3.95(s, 3H) 4.95(s, 2H) 5.37(s, 2H) 7.13(dd, J=0.8, 2.0 Hz, 1H) 7.31(d, J=2.0 Hz, 1H), 9.82 (s, 1H)

Production Example 3a) 5-Ethyl-2-fluorophenol

[Chemical Formula 45]

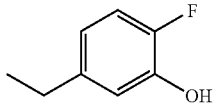

A 500 ml THF solution containing 15.5 g of 4-ethylfluorobenzene and 14.6 g of N,N,N'N'-tetramethylethylenediamine was cooled to –75° C. under a nitrogen atmosphere, and then 126 ml of s-butyllithium (0.99 M, cyclohexane solution) was added and the mixture was stirred for 2 hours. Next, 28 ml of trimethyl borate was added, the reaction mixture temperature was raised to room temperature and 14.4 ml of acetic acid was added. After stirring for 30 minutes, the reaction mixture was cooled to 0° C., 28.4 ml of a 30% aqueous solution of hydrogen peroxide was added and stirring was continued at room temperature for 18 hours. Next, 500 ml of a saturated aqueous solution of sodium sulfite was added to the reaction mixture, which was then extracted with 1 l of diethyl ether. The organic layer was washed with 500 ml of water and 500 ml of saturated aqueous sodium chloride in that order and dried over anhydrous magnesium sulfate, the desiccant was filtered out, and the filtrate was concentrated under reduced pressure. The residue was distilled to obtain the target compound (16.35 g) as a colorless liquid (boiling point: 76-80° C., 17 mmHg).

$^1$H-NMR (CDCl$_3$) δ 1.30(t, J=7.7 Hz, 3H) 2.57(q, J=7.7 Hz, 2H) 6.65(ddd, J=8.5, 4.7, 2.1 Hz, 1H) 6.83(dd, J=8.5, 2.1 Hz, 1H) 6.95 (dd, J=10.6, 8.5 Hz, Production Example 3b t-butyl-(5-ethyl-2-fluorophenoxy)dimethylsilane

[Chemical Formula 46]

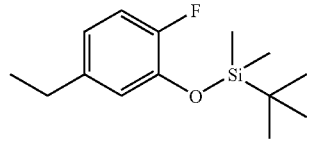

To a 40 ml solution of 16.4 g of 5-ethyl-2-fluorophenol in DMF there were added 9.16 g of imidazole and 19.4 g of t-butyldimethylchlorosilane, and the reaction mixture was stirred at room temperature for 18 hours. After then adding 500 ml of diethyl ether and 500 ml of water to the reaction mixture, the organic layer was washed twice with 100 ml of water and once with 100 ml of saturated aqueous sodium chloride in that order and then dried over anhydrous magnesium sulfate, the desiccant was filtered out, and the filtrate was concentrated under reduced pressure. The residue was distilled to obtain the target compound (25.38 g) as a colorless liquid (boiling point: 133-135° C., 20 mmHg).

$^1$H-NMR (CDCl$_3$) δ 0.19(s, 6H) 1.01(s, 9H) 1.38(t, J=7.7 Hz, 3H) 2.55(q, J=7.7 Hz, 2H) 6.67(ddd, J=8.3, 4.3, 2.2 Hz, 1H) 6.72(dd, J=8.3, 2.2 Hz, 1H) 6.94(dd, J=10.8, 8.3 Hz, 1H)

Production Example 3c 3-(t-butyldimethylsilanyloxy)-5-ethyl-2-fluorobenzaldehyde

[Chemical Formula 47]

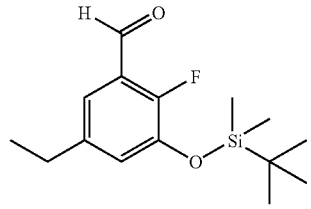

A 250 ml THF solution containing 12.7 g of t-butyl-(5-ethyl-2-fluorophenoxy)dimethylsilane and 7.5 g of N,N,N'N'-tetramethylethylenediamine was cooled to –75° C. under a nitrogen atmosphere, and then 55.6 ml of s-butyllithium (0.99 M, cyclohexane solution) was added and the mixture was stirred for 2 hours. After then adding 7.74 ml of DMF, the mixture was stirred at –75° C. for 1 hour and the temperature was raised to room temperature. Next, 500 ml of diethyl ether and 500 ml of a 5% aqueous ammonium chloride solution were added to the reaction mixture, the organic layer was washed twice with 500 ml of water and once with 500 ml of saturated aqueous sodium chloride in that order, and the aqueous layer was extracted with 100 ml of diethyl ether. The organic layers were combined and dried over anhydrous magnesium sulfate, the desiccant was filtered out, and the filtrate was concentrated under reduced pressure. The residue was purified by silica gel column chromatography (ethyl acetate-heptane system) to obtain the target compound (12.6 g) as a colorless solid.

$^1$H-NMR (CDCl$_3$) δ 0.24(s, 6H) 1.01(s, 9H) 1.24(t, J=7.7 Hz, 3H) 2.60(q, J=7.7 Hz, 2H) 6.99 (dd, J=10.0, 2.2 Hz, 1H) 7.25(dd, J=4.8, 2.2 Hz, 1H) 10.30(s, 1H)

Production Example 5

The same procedure was carried out under the same reaction conditions as (135b)-(135c) above to obtain 3-triisopropylsilanyloxy-5-ethyl-2-fluorobenzaldehyde, except that triisopropylchlorosilane was used instead of the t-butyldimethylchlorosilane in (135b)-(135c).

Production Example 6a (2-Fluoro-5-methoxyphenoxy)triisopropylsilane

[Chemical Formula 48]

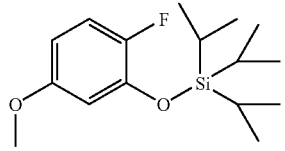

To a 200 ml THF solution containing 50.1 g of 1-fluoro-4-methoxybenzene and 70 g of N,N,N',N',N''-pentamethyldiethylenetriamine there was added dropwise 150 ml of n-butyllithium (2.66 M, hexane solution) at –74° C. over a period of 30 minutes, under a nitrogen atmosphere. After stirring between –74° C. and –70° C. for 3 hours, 100 ml of trimethyl borate was added. The temperature of the reaction mixture was then slowly raised to room temperature. Next, 70 ml of acetic acid and 75 ml of a 30% hydrogen peroxide aqueous solution were added and the reaction mixture was stirred overnight at room temperature. After the addition of water to the reaction mixture, it was extracted with a hexane/ethyl acetate mixture and dried over anhydrous magnesium sulfate. The desiccant was filtered out, and the filtrate was concentrated under reduced pressure to obtain a crude product of 1-fluoro-2-hydroxy-4-methoxybenzene (65.59 g) as a colorless solid.

This compound was dissolved in 500 ml of DMF, and then 40 g of imidazole and 85 g of chlorotriisopropylsilane were added and the mixture was stirred overnight at room temperature. Water was added to the reaction mixture and extraction was performed with t-butyl methyl ether. The organic layers were combined and washed with 0.5N hydrochloric acid and brine in that order. The organic layer was dried over anhydrous magnesium sulfate. The desiccant was filtered out and the filtrate was concentrated under reduced pressure. The residue was purified by silica gel column chromatography (t-butyl methyl ether-heptane system) to obtain the target compound (113.04 g) as an oil.

$^1$H-NMR (CDCl$_3$) δ 1.11(d, J=7.2 Hz, 18H) 1.23-1.32 (m, 3H) 3.75(s, 3H) 6.39(dt, J=2.8, 8.8 Hz, 1H) 6.50(dd, J=3.2, 7.2 Hz, 1H) 6.93(dd, J=8.0, 10.4 Hz, 1H)

Production Example 6b

2-Fluoro-5-methoxy-3-triisopropylsilanyloxybenzaldehyde

[Chemical Formula 49]

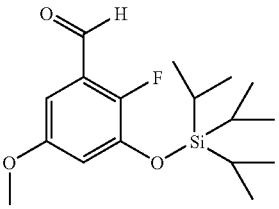

To a 240 ml THF solution containing 113 g of (2-fluoro-5-methoxyphenoxy)triisopropylsilane and 70 g of N,N,N',N',N''-pentamethyldiethylenetriamine there was added dropwise 150 ml of n-butyllithium (2.66 M, hexane solution) at –74° C., over a period of 50 minutes. After stirring at –60° C. for 3 hours, 70 ml of N-formylmorpholine was added. The temperature of the reaction mixture was slowly raised to 6° C. Next, 1N hydrochloric acid was added to the reaction mixture while cooling on ice, and then it was extracted with a mixture of hexane and t-butyl methyl ether and dried over anhydrous magnesium sulfate. The desiccant was filtered out and the filtrate was concentrated under reduced pressure. The residue was purified by silica gel column chromatography (t-butyl methyl ether-heptane system) to obtain the target compound (113.26 g) as an oil.

$^1$H-NMR (CDCl$_3$) δ 1.11(d, J=7.2 Hz, 18H) 1.22-1.35 (m, 3H) 3.80(s, 3H) 6.77(dd, J=2.8, 7.2 Hz, 1H) 6.87(dd, J=3.2, 4.0 Hz, 1H) 10.33 (s, 1H)

Production Example 7

3-Allyl-5-hydrazino-3H-imidazole-4-carboxylic acid ethyl ester hydrochloride

[Chemical Formula 50]

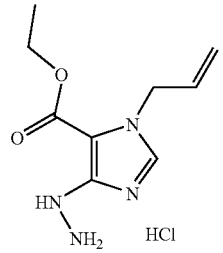

To a mixture of N-cyanoformimidate ethyl ester [CAS No. 4428-98-2] (6.79 g) and diethyl ether (20 mL) there was added dropwise allylamineacetic acid benzyl ester [CAS No. 197900-94-0] (14.2 g) under a nitrogen atmosphere. The mixture was stirred at room temperature for 1 hour and concentrated under reduced pressure.

Sodium (1.67 g) was added to ethanol (50 mL) under a nitrogen atmosphere, and when generation of hydrogen ceased, the mixture was cooled to 0° C. and the previous reaction residue was added dropwise. The mixture was then stirred overnight at room temperature, and ethyl acetate (400 mL) and half-saturated aqueous ammonium chloride (200 mL) were added. The mixture was sufficiently shaken, and the organic layer was separated off, washed with water (200 mL) and saturated aqueous sodium chloride (200 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain 3-allyl-5-amino-3H-imidazole-4-carboxylic acid ethyl ester (7.81 g) as a colorless solid.

A mixture of this compound (5.86 g) and a 35% hydrochloric acid solution (50 mL) was cooled to 0° C., and a mixture of sodium nitrite (2.17 g) and water (6 mL) was added dropwise at 0-5° C. The reaction mixture was stirred at 0° C. for 30 minutes, and then a mixture of tin(II) chloride (22.8 g) and a concentrated hydrochloric acid solution (20 ml) was added dropwise at 0-10° C., and the reaction mixture was stirred at 0° C. for 2 hours. The precipitate was collected by filtration, washed with a small amount of water and dried under reduced pressure. A mixture of this solid with water (100 mL) and dichloromethane (100 mL) was adjusted to basic with potassium carbonate, and then di-t-butyl dicarbonate (9.82 g) was added and the mixture was stirred overnight at room temperature. The reaction mixture was filtered, and after sufficiently shaking the filtrate, the organic layer was separated off. The filtered product was washed with dichloromethane (100 mL) and this solution was used for extraction of the previous aqueous layer. The organic layers were combined and dried over anhydrous magnesium sulfate. The desiccant was removed and the solvent in the filtrate was distilled off under reduced pressure. The residue was purified by silica gel column chromatography (ethyl acetate-heptane mixture) to obtain 3-allyl-5-(N'-t-butoxycarbonylhydrazino)-3H-imidazole-4-carboxylic acid ethyl ester (6.66 g) as a colorless solid.

Trifluoroacetic acid (20 mL) was added to a mixture of this compound (6.66 g) and dichloromethane (60 mL), and the mixture was stirred at room temperature for 4 hours. Toluene (100 mL) was added, and the solvent in the reaction mixture was distilled off under reduced pressure. Ethanol (100 mL) and concentrated hydrochloric acid (10 mL) were added to the residue, and after heating to reflux for 8 hours, the solvent in the reaction mixture was distilled off under reduced pressure. Ethanol (50 mL) was added to the residue and the solvent was distilled off under reduced pressure. This procedure was repeated twice, and then a mixture of the residue, ethyl acetate (20 mL) and t-butyl methyl ether (50 mL) was tritiated and the solid was collected by filtration. The solvent in the filtrate was distilled off under reduced pressure, ethyl acetate (10 mL) and t-butyl methyl ether (20 mL) were added to the residue, the mixture was tritiated and the solid was collected by filtration, The collected products were combined to obtain the target compound (5.05 g) as a colorless solid.

$^1$H-NMR (CD$_3$OD) δ 1.37(t, J=7.3 Hz, 3H) 4.25(q, J=7.3 Hz, 2H) 4.90(dt, J=5.7, 1.6 Hz, 2H) 5.09(dq, J=16.8, 1.6 Hz, 1H) 5.22(dq, J=10.9, 1.6 Hz, 1H) 6.03(ddt, J=16.8, 10.9, 5.7 Hz, 1H) 7.72(s, 1H)

Production Example 8

1-Oxypyridin-2-yl)hydrazine

[Chemical Formula 51]

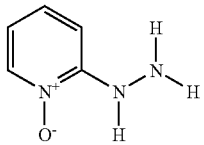

After adding 6 ml of hydrazine monohydrate to 1.66 ml of 2-chloropyridine N-oxide hydrochloride, the mixture was stirred at room temperature for 15 hours. Following concentration under reduced pressure, the residue was purified by NAM silica gel column chromatography (methanol-ethyl acetate system) to obtain the target compound (888 mg) as a yellowish colorless solid.

$^1$H-NMR (CD$_3$OD) δ 6.70(td, J=8.3, 1.5 Hz, 1H) 7.33(ddd, J=8.3, 1.2, 0.6 Hz, 1H) 7.46(ddd, J=8.3, 7.1, 1.2 Hz, 1H) 8.00(ddd, J=7.1, 1.5, 0.6 Hz, 1H)

Production Example 9a 3-(N'-t-Butoxycarbonylhydrazino)-1H-pyrazole-4-carboxylic acid ethyl ester

[Chemical Formula 52]

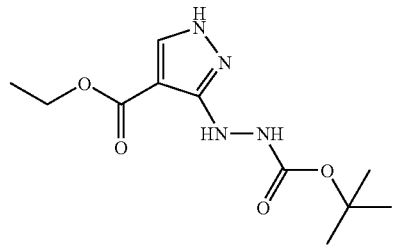

To 65 ml of a 35% hydrochloric acid solution containing 15.7 g of 3-amino-1H-pyrazole-4-carboxylic acid ethyl ester there were added 10 ml of an aqueous solution containing 6.66 g of sodium nitrite and 100 ml of a 35% hydrochloric acid solution containing 64.3 g of tin(II) chloride dihydrate in that order while cooling on ice, and the mixture was stirred for 2 hours. The precipitate was collected by filtration and dissolved in 150 ml of water. After then adding 300 ml of dichloromethane, the mixture was adjusted to alkaline with potassium carbonate, and then 33.1 g of di-t-butyl dicarbonate was added and the mixture was stirred for 60 hours at room temperature. The solution was separated, the aqueous solution was extracted twice with 200 ml of dichloromethane, and the organic layers were combined and dried over anhydrous magnesium sulfate. The desiccant was filtered out and the filtrate was concentrated under reduced pressure. The residue was purified by silica gel column chromatography (heptane-ethyl acetate system) to obtain the target compound (4.35 g) as a colorless solid.

$^1$H-NMR (CDCl$_3$) δ 1.34(t, J=7.3 Hz, 3H) 1.43(s, 9H) 1.67(br.s, 2H) 4.29(q, J=7.3 Hz, 2H) 6.92(br.s, 1H) 7.79(s, 1H)

Production Example 9b

3-Hydrazino-1H-pyrazole-4-carboxylic acid Ethyl ester Bishydrochloride

[Chemical Formula 53]

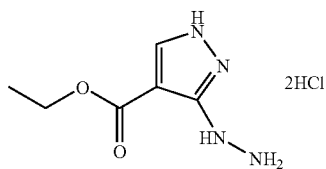

After adding 25 ml of trifluoroacetic acid to a 50 ml solution of 3.30 g of 3-(N'-t-butoxycarbonylhydrazino)-1H-pyrazole-4-carboxylic acid ethyl ester in dichloromethane, the mixture was stirred for 2 hours at room temperature. Next, 100 ml of toluene was added and the solvent was removed under reduced pressure. The residue was dissolved in a small amount of methanol, and after adding a 4N hydrogen chloride-ethyl acetate solution until the solution reached acidity, the solvent was removed under reduced pressure. The residue was treated with 50 ml of t-butyl methyl ether, and the solid was collected by filtration and dried under reduced pressure to obtain the target compound (3.30 g) as a colorless solid.

$^1$H-NMR (d$_6$-DMSO) δ 1.25(t, J=7.3 Hz, 3H) 4.19(q, J=7.3 Hz, 2H) 8.18(br.s, 1H) 8.23(s, 1H) 9.90(br.s, 4H) 12.55 (br.s, 1H)

Example 1

(R)- and (S)-4-{3-[(5-Fluoro-8-methoxychroman-6-yl)-1-imino-2,3-dihydro-1H-isoindol-5-ylamino) methyl]-5-oxo-4,5-dihydro-[1,2,4]triazol-1-yl}thiazole-5-carboxylic acid (1a)(2-Bromo-5-nitrophenyl)methanol

[Chemical Formula 54]

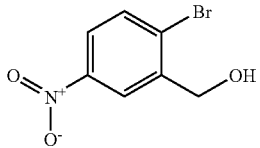

To a mixture of 2-bromo-5-nitrobenzoic acid (15.6 g) and THF (130 mL) there were added dropwise triethylamine (9.33 mL) and isobutyl chloroformate (8.67 mL) in that order at −20 Cc under a nitrogen atmosphere. The mixture was stirred for 2 hours and then filtered, and a mixture of sodium borohydride (7.23 g) and water (10 mL) was added dropwise to the filtrate at −20° C. The mixture was stirred overnight at room temperature, and then a small amount of water was added, and ethyl acetate (500 mL) and 1N hydrochloric acid (200 mL) were further added. The mixture was sufficiently shaken, and then the organic layer was separated off, washed with saturated aqueous sodium hydrogen carbonate (200 mL), water (200 mL) and saturated aqueous sodium chloride (200 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (6.32 g) as a colorless solid.

$^1$H-NMR (CDCl$_3$) δ 2.11(t, J=5.2 Hz, 1H) 4.86(d, J=5.2 Hz, 2H) 7.73(d, J=9.2 Hz, 1H) 8.03(dd, J=9.2, 3.0 Hz, 1H) 8.44(d, J=3.0 Hz, 1H)

(1b) 1-Bromo-2-chloromethyl-4-nitrobenzene

[Chemical Formula 55]

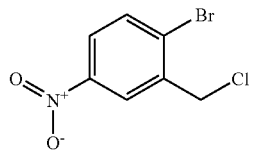

To a mixture of (2-bromo-5-nitrophenyl)methanol (6.32 g) and THF (150 mL) there were added diisopropylethylamine (5.21 mL) and methanesulfonyl chloride (2.32 mL) dropwise in that order at −10° C. under a nitrogen atmosphere. The mixture was stirred overnight at room temperature, and then ethyl acetate (400 mL) and water (200 mL) were added. The mixture was sufficiently shaken, and then the organic layer was separated oft washed with water (200 mL) and saturated aqueous sodium chloride (200 mL) in that order, and dried over anhydrous magnesium sulfate. The mixture was filtered to obtain a filtrate and the solvent in the filtrate was distilled off under reduced pressure to obtain the target compound (7.35 g) as a brown solid, which was used without purification as starting material for the following reaction (1c).

(1c) 2-Azidomethyl-1-bromo-4-nitrobenzene

[Chemical Formula 56]

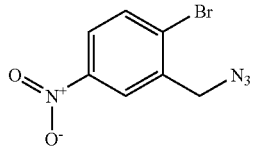

To a mixture of the 1-bromo-2-chloromethyl-4-nitrobenzene (7.35 g) obtained in (1b) above and DMF (100 mL) there was added sodium azide (2.1 g) at 0° C. The mixture was stirred overnight at room temperature, and then ethyl acetate (400 mL) and water (200 mL) were added. The mixture was sufficiently shaken, and then the organic layer was separated off, washed twice with water (200 mL) and once with saturated aqueous sodium chloride (200 mL) in that order, and dried over anhydrous magnesium sulfate. The mixture was filtered to obtain a filtrate, and the solvent in the filtrate was distilled off under reduced pressure and the residue was purified by silica gel column chromatography (ethyl acetate-heptane mixture) to obtain the target compound (6.57 g) as a brown solid.

$^1$H-NMR (CDCl$_3$) δ 4.61(s, 2H) 7.79(d, J=9.4 Hz, 1H) 8.07(dd, J=9.4, 3.0 Hz, 1H) 8.31(d, J=3.0 Hz, 1H)

(1d) 2-Bromo-5-nitrobenzylamine

[Chemical Formula 57]

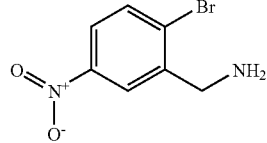

To a mixture of 2-azidomethyl-1-bromo-4-nitrobenzene (6.57 g) and THF (50 mL) there was added triphenylphosphine (7.05 g) at 0° C. under a nitrogen atmosphere. The mixture was stirred at 0° C. for 1 hour and then at room temperature for 2 hours, after which water (10 mL) was added and the mixture was heated to reflux for 15 hours. The solvent in the mixture was distilled off under reduced pressure and the residue was purified by NH silica gel column chromatography (ethyl acetate-heptane mixture) to obtain the target compound (5.64 g) as a colorless solid.

$^1$H-NMR (CDCl$_3$) δ 4.02(s, 2H) 7.63(d, J=9.0 Hz, 1H) 7.98(dd, J=9.0, 2.7 Hz, 1H) 8.37(d, J=2.7 Hz, 1H)

(1e)(2-Bromo-5-nitrobenzyl)carbamic acid t-butyl ester

[Chemical Formula 58]

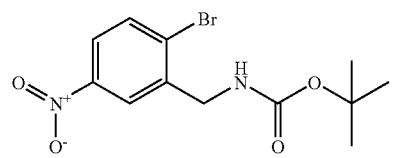

To a mixture of t-butyl methyl ether (100 mL) and water (50 mL) there was added 2-bromo-5-nitrobenzylamine (5.64 g), and then sodium hydrogen carbonate (10.2 g) and di-t-butyl dicarbonate (10.7 g) were added in that order while stirring. After stirring at room temperature for 4 hours, the organic layer was separated off and the organic layer was dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (8.17 g) as a colorless solid.

$^1$H-NMR (CDCl$_3$) δ 1.49(s, 9H) 4.45(d, J=6.6 Hz, 2H) 5.12(br.s, 1H) 7.74(d, J=9.3 Hz, 1H) 8.00(dd, J=9.3, 2.5 Hz, 1H) 8.37(d, J=2.5 Hz, 1H)

(1f)(2-Cyano-5-nitrobenzyl)carbamic acid t-butyl ester

[Chemical Formula 59]

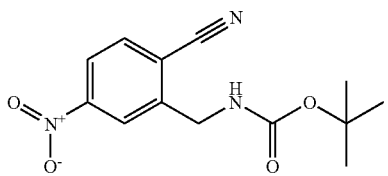

To a mixture of (2-bromo-5-nitrobenzyl)carbamic acid t-butyl ester (8.17 g), tris(dibenzylideneacetone)dipalladium (0)(1.13 g), zinc cyanide (5.22 g) and zinc (0.040 g) there was added deaerated DMF (100 mL) under a nitrogen atmosphere, and then tri-t-butylphosphine (0.500 g) was added while stirring at room temperature. The mixture was stirred overnight at room temperature, and then ethyl acetate (500 mL) and water (300 mL) were added. The mixture was sufficiently shaken, and then the organic layer was separated off, washed twice with water (200 mL) and once with saturated aqueous sodium chloride (200 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (2.39 g) as a colorless solid.

$^1$H-NMR (CDCl$_3$) δ 1.46(s, 9H) 4.61(d, J=6.2 Hz, 2H) 5.22(br.s, 1H) 7.85(d, J=8.7 Hz, 1H) 8.23(dd, J=8.7, 2.0 Hz, 1H) 8.37(d, J=2.0 Hz, 1H) (1g)(5-Amino-2-cyanobenzyl)carbamic acid t-butyl ester

[Chemical Formula 60]

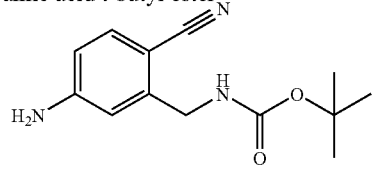

To a mixture of (2-cyano-5-nitrobenzyl)carbamic acid t-butyl ester (2.39 g) and ethanol (180 mL) there were added water (12 mL), saturated aqueous ammonium chloride (5 mL) and iron powder (2.02 g), under a nitrogen atmosphere. The mixture was heated to reflux for 2 hours and then filtered through Celite to obtain a filtrate, and the solvent in the filtrate was distilled off under reduced pressure to obtain a residue. The Celite and filtered substance were washed with ethyl acetate (400 mL) and water (200 mL) in that order, and this washed solution was combined with the previous residue. After sufficiently shaking the mixture, the organic layer was separated off and the organic layer was dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (1.97 g) as an off-white solid.

$^1$H-NMR (CDCl$_3$) δ 1.46(s, 911) 4.17(br.s, 2H) 4.37(d, J=6.7 Hz, 2H) 5.11(br.s, 1H) 6.54(dd, J=8.8, 2.5 Hz, 1H) 6.70(d, J=2.5 Hz, 1H) 7.29(d, J=8.8 Hz, 1H)

(1 h) (2-Cyano-5-{[cyano-(5-fluoro-8-methoxychroman-6-yl)methyl]amino}benzyl)carbamic acid t-butyl ester

[Chemical Formula 61]

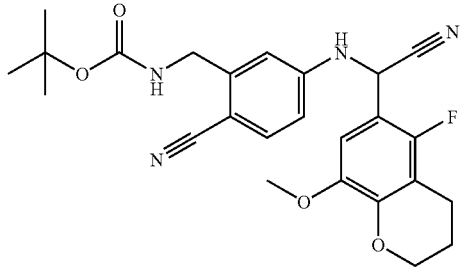

To a mixture of ytterbium(III) trifluoromethanesulfonate hydrate (hereinafter abbreviated as Yb(OTf)$_3$)(0.177 g) and THF (8 mL) there were added (5-amino-2-cyanobenzyl)carbamic acid t-butyl ester (0.465 g), 5-fluoro-8-methoxychroman-6-carboaldehyde (0.395 g), Molecular Sieves 3A (hereinafter abbreviated as MS3A)(0.5 g) and trimethylsilyl cyanide (0.501 mL) in that order under a nitrogen atmosphere, and the mixture was stirred at room temperature for 14 hours. Ethyl acetate (300 mL) and water (200 mL) were added to the mixture, and after sufficiently shaking the mixture, the organic layer was separated off and washed with saturated aqueous sodium chloride (200 mL) and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (0.899 g) as a colorless solid.

$^1$H-NMR (CDCl$_3$) δ 1.46(s, 9H) 2.04(quint, J-6.8 Hz, 2H) 2.77(t, J=6.8 Hz, 2H) 3.90(s, 3H) 4.29(t, J=6.8 Hz, 2H) 4.42 (d, J=6.4 Hz, 2H) 4.51(d, J=7.0 Hz, 1H) 5.15(br.t, J=6.4 Hz, 1H) 5.55(d, J=7.0 Hz, 14) 6.67(dd, J=8.0, 2.4 Hz, 1H) 6.83(d, J=2.4 Hz, 1H) 6.86(d, J=6.9 Hz, 1H) 7.53(d, J=8.0 Hz, 1H)

(1i) (2-Cyano-5-{[(5-fluoro-8-methoxychroman-6-yl)thiocarbamoylmethyl]amino}benzyl)carbamic acid t-butyl ester

[Chemical Formula 62]

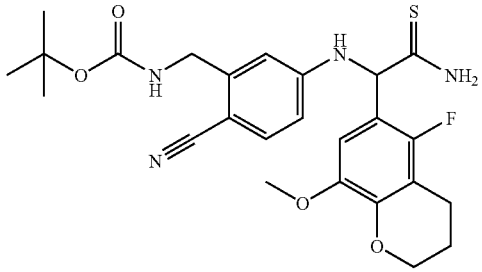

20% aqueous solution of ammonium sulfide (3.29 mL) was added to (2-cyano-5-{[cyano-(5-fluoro-8-methoxychroman-6-yl)methyl]amino}benzyl)carbamic acid t-butyl ester (0.899 g) and a methanol:THF (2:1) mixed solvent (15 mL), and the mixture was stirred overnight at room temperature. Ethyl acetate (300 mL) and water (200 mL) were added to the mixture, and after sufficiently shaking the mixture, the organic layer was separated off and washed with water (200 mL) and saturated aqueous sodium chloride (200 mL) in that order and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (0.702 g) as a colorless solid.

$^1$H-NMR (CDCl$_3$) δ 1.46(s, 9H) 2.04(m, 2H) 2.81(m, 2H) 3.79(s, 3H) 4.27(m, 2H) 4.37(d, J=6.3 Hz, 2H) 5.09(br.t, J=6.3 Hz, 1H) 5.40(d, J=4.8 Hz, 1H) 5.83(d, J=4.8 Hz, 1H) 6.45(d, J=8.6 Hz, 1H) 6.67(d, J=7.0 Hz, 1H) 6.72(s, 1H) 7.40(d, J=8.6 Hz, 1H) 7.51(br.s, 1H) 7.54(br.s, 1H)

(1j) {2-[3-(t-Butoxycarbonylaminomethyl)-4-cyanophenylimino]-2-(5-fluoro-8-methoxychroman-6-yl)-1-methylsulfanylethylidene}carbamic acid methyl ester

[Chemical Formula 63]

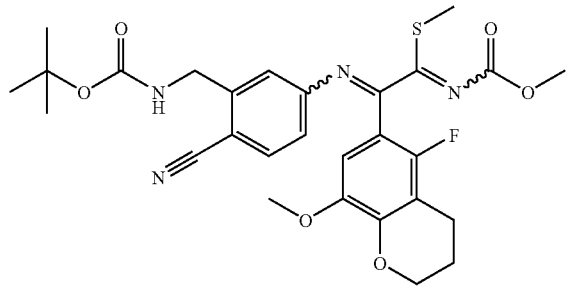

To a mixture of (2-cyano-5-{[(5-fluoro-8-methoxychroman-6-yl)thiocarbamoylmethyl] amino}benzyl)carbamic acid t-butyl ester (0.702 g) and acetonitrile (50 mL) there was added trimethyloxonium tetrafluoroborate (0.217 g) under a nitrogen atmosphere, and the mixture was stirred at room temperature for 1 hour. Ethyl acetate (500 mL) and saturated aqueous sodium hydrogen carbonate (200 mL) were added to the mixture, and after sufficiently shaking the mixture, the organic layer was separated off and the organic layer was dried over anhydrous magnesium sulfate. The mixture was filtered to obtain a filtrate, and the solvent in the filtrate was distilled off under reduced pressure.

Ethyl acetate (10 mL) and manganese dioxide (1.83 g) were added to the residue in that order, and the mixture was stirred at room temperature for 6 hours. The mixture was filtered through Celite and the Celite was washed with ethyl acetate (100 mL). The organic layers were combined and the solvent in the combined organic layer was distilled off under reduced pressure.

Toluene (30 mL), 2,4,6-collidine (0.407 mL) and methyl chloroformate (0.195 mL) were added to the residue in that order, and the mixture was stirred at 80° C. for 8 hours under a nitrogen atmosphere. The mixture was cooled to room temperature, and then ethyl acetate (200 mL) and 1N hydrochloric acid (100 mL) were added. The mixture was sufficiently shaken, and then the organic layer was separated off, washed with saturated aqueous sodium hydrogen carbonate (100 mL) and saturated aqueous sodium chloride (100 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (0.535 g) as an off-white solid.

$^1$H-NMR (CDCl$_3$) Main isomer δ 1.44(s, 9H) 2.04(m, 2H) 2.33(s, 3H) 2.81(t, J=6.0 Hz, 2H) 3.64(s, 3H) 3.94(s, 3H) 4.33(t, J=6.0 Hz, 2H) 4.50(d, J=5.9 Hz, 2H) 5.09(br.t, J=5.9 Hz, 1H) 6.96(m, 2H) 7.12(s, 1H) 7.57(d, J=8.4 Hz, 1H)

(1k) 4-(3-{[3-(t-Butoxycarbonylaminomethyl)-4-cyanophenylamino]-(5-fluoro-8-methoxychroman-6-yl)methyl}-5-oxo-4,5-dihydro-[1,2,4]triazol-1-yl) thiazole-5-carboxylic acid methyl ester

[Chemical Formula 64]

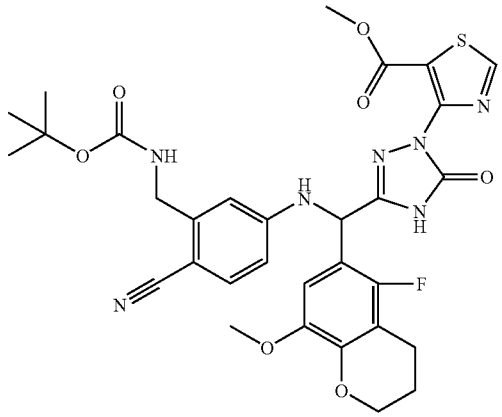

To a mixture of {2-[3-(t-butoxycarbonylaminomethyl)-4-cyanophenylimino]-2-(5-fluoro-8-methoxychroman-6-yl)-1-methylsulfanylethylidene}carbamic acid methyl ester (104 mg) and THF (2.0 mL) there were added 4-hydrazinothiazole-5-carboxylic acid methyl ester (33.1 mg) and triethylamine (27.9 μL), and the mixture was stirred at 65° C. for 18 hours under a nitrogen atmosphere. The solvent in the mixture was distilled off, DMF (2.0 mL) was added to the residue, and the mixture was stirred at 85° C. for 30 hours under a nitrogen atmosphere. The solvent in the mixture was distilled off.

Methanol (1.0 mL), THF (1.0 mL) and acetic acid (52.1 μL) were added to the residue. Sodium cyanotrihydroborate (114 mg) was then added and the mixture was stirred at room temperature for 3 hours. Water and ethyl acetate were added to the mixture, and after sufficiently shaking the mixture, the organic layer was separated off, ethyl acetate was added to the remaining aqueous layer, the mixture was sufficiently shaken and the organic layer was separated off. The combined organic layers were washed with water and saturated aqueous sodium chloride in that order and dried over anhydrous magnesium sulfate. The mixture was filtered to obtain a filtrate, and the solvent in the filtrate was distilled off under reduced pressure. The residue was purified by NAM silica gel column chromatography (ethyl acetate-heptane mixture) to obtain the target compound (74 mg) as an off-white solid.

$^1$H-NMR (CDCl$_3$) δ 1.40(s, 9H) 1.96(m, 2H) 2.69(m, 2H) 3.71(s, 3H) 3.79(s, 3H) 4.22(t, J=5.0 Hz, 2H) 4.33(d, J=6.0 Hz, 2H) 5.30(m, 1H) 5.54(s, 1H) 5.80(d, J=5.6 Hz, 1H) 6.52 (dd, J=8.4, 2.0 Hz, 1H) 6.72(s, 1H) 6.73(d, J=6.8 Hz, 1H) 7.34(d, J=8.4 Hz, 1H) 8.90(s, 1H) 11.1(s, 1H)

(11)
4-{3-[(5-Fluoro-8-methoxychroman-6-yl)-(1-imino-2,3-dihydro-1H-isoindol-5-ylamino)methyl]-5-oxo-4,5-dihydro-[1,2,4]triazol-1-yl}thiazole-5-carboxylic acid

[Chemical Formula 65]

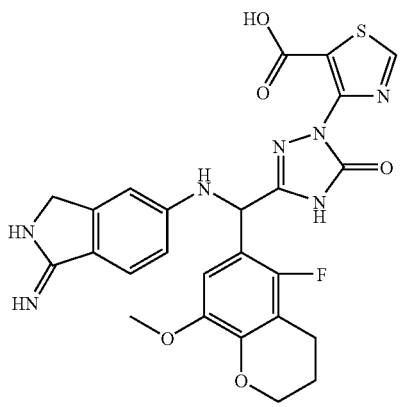

To a mixture of 4-(3-{[3-(t-butoxycarbonylaminomethyl)-4-cyanophenylamino]-(5-fluoro-8-methoxychroman-6-yl)methyl}-5-oxo-4,5-dihydro-[1,2,4]triazol-1-yl)thiazole-5-carboxylic acid methyl ester (74 mg) and methanol (2.0 mL) there was added aqueous 5N sodium hydroxide (111 μL), and the mixture was stirred at room temperature for 3 hours and 15 minutes. After adding acetic acid (52 μL) to the mixture, the solvent in the mixture was distilled off under reduced pressure. Dichloromethane (2.0 mL) was added to the residue, TFA (400 μL) was added to the resulting solution and the mixture was stirred at room temperature for 5 hours. Dichloromethane (50 mL) was added to the mixture, which was then stirred at room temperature for 14 hours. Toluene (10 mL) was added to the mixture, and the solvent in the mixture was distilled off. The residue was purified by reverse-phase high performance liquid chromatography (acetonitrile/water mixed solvent, 0.1% acetic acid) to obtain the target compound (21 mg).

$^1$H-NMR ($d_6$-DMSO) δ 1.92(m, 2H) 2.70(m, 2H) 3.77(s, 3H) 3.97(m, 2H) 4.16(t, J=5.0 Hz, 2H) 5.51(s, 1H) 6.85(s, 1H) 6.93-7.01(m, 2H) 7.22(m, 1H) 7.54(d, J=8.8 Hz, 1H) 8.94(s, 1H) 9.41(s, 1H) 11.9(brs, 1H)

Mass spectrum (ESI) m/z: 552 (M+H)$^+$ (1m)(R)- and (S)-4-{3-[(5-Fluoro-8-methoxychroman-6-yl)-(1-imino-2,3-dihydro-1H-isoindol-5-ylamino)methyl]-5-oxo-4,5-dihydro-[1,2,4]triazol-1-yl}thiazole-5-carboxylic acid

[Chemical Formula 66]

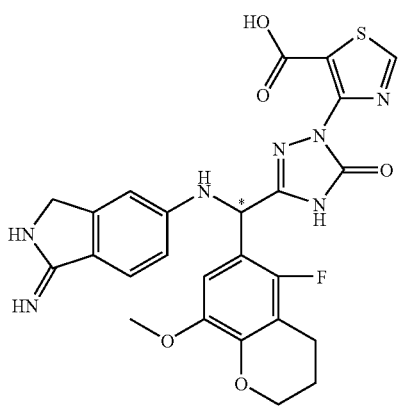

A SUMICHIRAL OA-2500 column was used for separation (optical resolution) of 4-{3-[(5-fluoro-8-methoxychroman-6-yl)-(1-imino-2,3-dihydro-1H-isoindol-5-ylamino)methyl]-5-oxo-4,5-dihydro-[1,2,4]triazol-1-yl}thiazole-5-carboxylic acid (10 mg) under the following conditions, and the first eluting enantiomer (1.35 mg) of the title compound was obtained.

$^1$H-NMR (CD$_3$OD) δ 1.99(m, 2H) 2.76(t, J=6.2 Hz, 2H) 3.73(s, 3H) 4.19(t, J=44.4 Hz, 2H) 4.64-4.91(m, 2H) 5.87(s, 1H) 6.88-6.92(m, 2H) 6.97(d, J=7.2 Hz, 1H) 7.70(d, J=8.4 Hz, 1H) 8.87(s, 1H)

HPLC retention time: 23 min. (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 30 mL/min)

Example 2

(R)- and (S)-2-(3-Aminopyridin-2-yl)-5-[(1-imino-2,3-dihydro-1H-isoindol-5-ylamino)-(8-methoxy-4H-benzo[1,3]-dioxin-6-yl)methyl]-2,4-dihydro-[1,2,4]triazol-3-one Acetate (2a) (2-Cyano-5-{[cyano-(8-methoxy-4H-benzo[1,3]-dioxin-6-yl)methyl]amino}benzyl)carbamic acid t-butyl ester

[Chemical Formula 67]

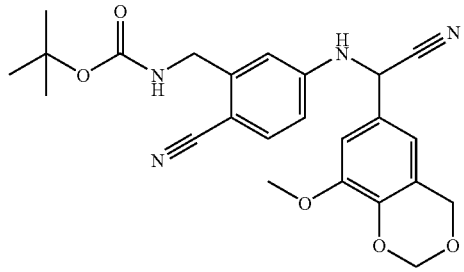

To a mixture of Yb (OTf)$_3$ (0.124 g) and THF (5 mL) there were added (5-amino-2-cyanobenzyl)carbamic acid t-butyl ester (Example (1g))(0.494 g), 8-methoxy-4H-benzo[1,3]dioxine-6-carboaldehyde (0.388 g), MS3A (0.5 g) and trimethylsilyl cyanide (0.533 mL) in that order under a nitrogen atmosphere, and the mixture was stirred at room temperature for 15 hours. Ethyl acetate (100 mL) and water (50 mL) were added to the mixture and filtration was performed with Celite. After sufficiently shaking the filtrate, the organic layer was separated off and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (0.822 g) as a colorless solid.

$^1$H-NMR (CDCl$_3$) δ 1.45(s, 9H) 3.93(s, 3H) 4.33(d, J=6.4 Hz, 2H) 4.51(d, J=7.5 Hz, 1H) 4.91(s, 2H) 5.18(br.s, 1H) 5.34(s, 2H) 5.38(d, J=7.5 Hz, 1H) 6.66(dd, J=8.4, 2.4 Hz, 1H) 6.83(s, 1H) 6.85(s, 1H) 6.91(d, J=2.4 Hz, 1H) 7.54(d, J=8.4 Hz, 1H)

(2b) (2-Cyano-5-{[(8-methoxy-4H-benzo[1,3]-dioxin-6-yl)thiocarbamoylmethyl]amino}benzyl)carbamic acid t-butyl ester

[Chemical Formula 68]

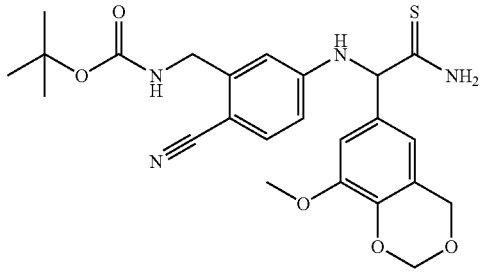

To a mixture of (2-cyano-5-{[cyano-(8-methoxy-4H-benzo[1,3]-dioxin-6-yl)methyl]amino}benzyl)carbamic acid t-butyl ester (0.822 g) and methanol (10 mL) there was added 20% aqueous ammonium sulfide (3.1 mL), and the mixture was stirred at room temperature for 15 hours. Ethyl acetate (200 mL) and water (50 mL) were added to the mixture, and after sufficiently shaking the mixture, the organic layer was separated off and washed with water (50 mL) and saturated aqueous sodium chloride (50 mL) in that order and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (0.680 g) as a colorless solid.

$^1$H-NMR (CDCl$_3$) δ 1.46(s, 9H) 3.89(s, 3H) 4.37(d, J=6.6 Hz, 2H) 4.90(s, 2H) 5.03(s, 1H) 5.31(s, 2H) 5.46(s, 10H) 6.53(d, J=8.3 Hz, 1H) 6.70(s, 1H) 6.75(s, 1H) 6.83(s, 1H) 7.44(d, J=8.3 Hz, 1H) 7.58(br.s, 1H) 7.71(br.s, 1H)

(2c) {2-[3-(t-Butoxycarbonylaminomethyl)-4-cyanophenylimino]-2-(8-methoxy-4H-benzo[1,3]-dioxin-6-yl)-1-methylsulfanylethylidene}carbamic acid methyl ester

[Chemical Formula 69]

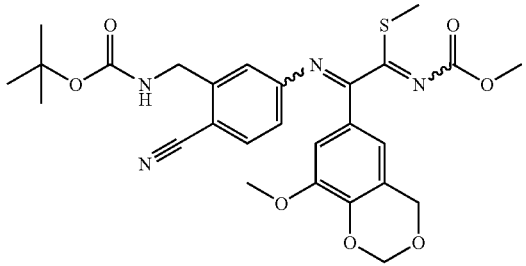

To a mixture of (2-cyano-5-{[(8-methoxy-4H-benzo[1,3]-dioxin-6-yl)thio carbamoylmethyl]amino}benzyl)carbamic acid t-butyl ester (680 mg) and acetonitrile (30 mL) there was added trimethyloxonium tetrafluoroborate (0.217 g) under a nitrogen atmosphere, and the mixture was stirred at room temperature for 1 hour. Ethyl acetate (560 mL) and saturated aqueous sodium hydrogen carbonate (200 mL) were added to the mixture, and after sufficiently shaking the mixture, the organic layer was separated off and the organic layer was dried over anhydrous magnesium sulfate. The mixture was filtered to obtain a filtrate, and the solvent in the filtrate was distilled off under reduced pressure.

Ethyl acetate (10 mL) and manganese dioxide (1.83 g) were added to the residue in that order, and the mixture was stirred at room temperature for 6 hours. The mixture was filtered through Celite and the Celite was washed with ethyl acetate (100 mL). The organic layers were combined and the solvent in the combined organic layer was distilled off under reduced pressure. Toluene (20 mL), 2,4,6-collidine (0.407 mL) and methyl chloroformate (0.195 mL) were added to the residue in that order, and the mixture was stirred at 80° C. for 8 hours under a nitrogen atmosphere. The mixture was cooled to room temperature, and then ethyl acetate (200 mL) and 1N hydrochloric acid (100 mL) were added. The mixture was sufficiently shaken, and then the organic layer was separated off, washed with saturated aqueous sodium hydrogen carbonate (100 mL) and saturated aqueous sodium chloride (100 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (0.507 g) as an off-white solid.

$^1$H-NMR (CDCl$_3$) Main isomer δ 1.45(s, 9H) 2.33(s, 3H) 3.66(s, 3H) 3.85(s, 3H) 4.51(d, J=6.5 Hz, 2H) 4.91(s, 2H) 5.10(br.s, 1H) 5.36(s, 2H) 6.99(s, 1H) 7.04(d, J=8.1 Hz, 1H) 7.20(s, 1H) 7.42(s, 1H) 7.58(d, J=8.1 Hz, 1H)

(2d) [2-Cyano-5-({(8-methoxy-4H-benzo[1,3]-dioxin-6-yl)-[1-(3-nitropyridin-2-yl)-5-oxo-4,5-dihydro-1H-[1,2,4]triazol-3-yl]methyl}amino)benzyl]carbamic acid t-butyl ester

[Chemical Formula 70]

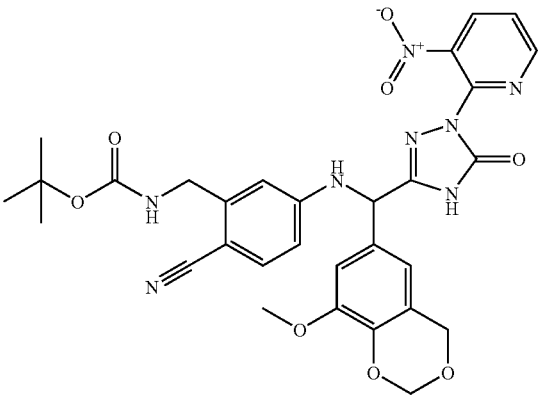

To a mixture of {2-[3-(t-butoxycarbonylaminomethyl)-4-cyanophenylimino]-2-(8-methoxy-4H-benzo[1,3]-dioxin-6-yl)-1-methylsulfanylethylidene}carbamic acid methyl ester (101 mg) and THF (2.0 mL) there were added (3-nitropyridin-2-yl)hydrazine [CAS No. 15367-16-5] (29.6 mg) and triethylamine (27.9 μL), and the mixture was stirred at 65° C. for 15 hours under a nitrogen atmosphere. The solvent in the mixture was distilled off, DMF (2.0 mL) was added to the residue, and the mixture was stirred at 85° C. for 16 hours under a nitrogen atmosphere. The solvent in the mixture was distilled off.

Methanol (5 mL) and acetic acid (52.1 μL) were added to the residue. Sodium cyanotrihydroborate (114 mg) was then added and the mixture was stirred overnight at room temperature. Water (25 mL) and ethyl acetate (50 mL) were added to the mixture, and after sufficiently shaking the mixture, the organic layer was separated off. The organic layer was washed twice with water (25 mL) and once with saturated aqueous sodium chloride (25 mL) in that order, and dried over anhydrous magnesium sulfate. The mixture was filtered to obtain a filtrate, and the solvent in the filtrate was distilled off under reduced pressure. The residue was purified by NAM silica gel column chromatography (ethyl acetate-methanol mixture) to obtain the target compound (67 mg) as an off-white solid.

$^1$H-NMR (CD$_3$OD) δ 1.45(s, 9H) 3.85(s, 3H) 4.28(br.d, J=5.7 Hz, 2H) 4.87(s, 2H) 5.23(s, 2H) 5.59(s, 1H) 6.68(dd, J=8.4, 2.3 Hz, 1H) 6.77(d, J=1.9 Hz, 1H) 6.80(d, J=2.3 Hz, 1H) 6.99(d, J=31.9 Hz, 1H) 7.08(t, J=5.7 Hz, 1H) 7.41(d, J=8.4 Hz, 1H) 7.64(dd, J=8.0, 4.8 Hz, 1H) 8.48(dd, J=8.0, 1.3 Hz, 1H) 8.76(dd, J=4.8, 1.3 Hz, 1H)

(2e) [5-({[1-(3-Aminopyridin-2-yl)-5-oxo-4,5-dihydro-1H-[1,2,4]triazol-3-yl]-(8-methoxy-4H'-benzo[1,3]-dioxin-6-yl)methyl}amino)benzyl] carbamic acid t-butyl ester

[Chemical Formula 71]

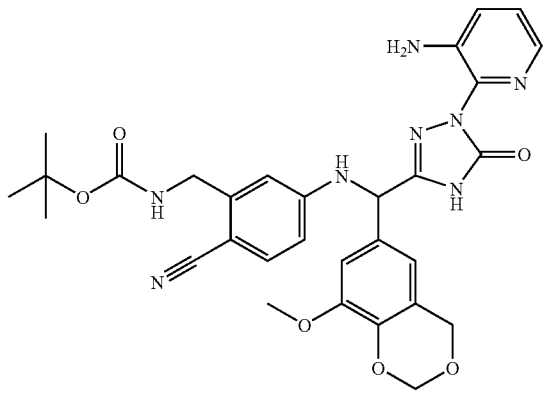

Saturated aqueous ammonium chloride (0.50 mL) and iron powder (59.8 mg) were added to [2-cyano-5-({(8-methoxy-4H-benzo[1,3]-dioxin-6-yl)-[1-(3-nitropyridin-2-yl)-5-oxo-4,5-dihydro-1H-[1,2,4]triazol-3-yl]methyl}amino)benzyl]carbamic acid t-butyl ester (67 mg) and an ethanol:water (4:1) mixed solvent (5 mL), and the mixture was heated and stirred for 4 hours at 65° C. under a nitrogen atmosphere. The mixture was filtered through Celite and the Celite was washed with ethyl acetate (50 mL). The filtrates were combined and washed three times with water (25 mL) and then with saturated aqueous sodium chloride (25 mL) in that order, and dried over anhydrous magnesium sulfate. The mixture was filtered to obtain a filtrate and the solvent in the filtrate was distilled off under reduced pressure to obtain the target compound (52 mg) as a colorless solid.

$^1$H-NMR (CD$_3$OD) δ 1.45(s, 9H) 3.83(s, 3H) 4.29(s, 2H) 4.85(s, 2H) 5.23(s, 2H) 5.57(s, 1H) 6.67(d, J=8.2 Hz, 1H) 6.78(s, 2H) 7.01(s, 1H) 7.13(br.s, 1H) 7.23(dd, J=8.0, 4.4 Hz, 1H) 7.32(d, J=8.0 Hz, 1H) 7.41(d, J=8.2 Hz, 1H) 7.81(d, J=4.4 Hz, 1H)

(2f) 2-(3-Aminopyridin-2-yl)-5-[(1-imino-2,3-dihydro-1H-isoindol-5-ylamino)-(8-methoxy-4H-benzo[1,3]-dioxin-6-yl)methyl]-2,4-dihydro-[1,2,4]triazol-3-one Acetate

[Chemical Formula 72]

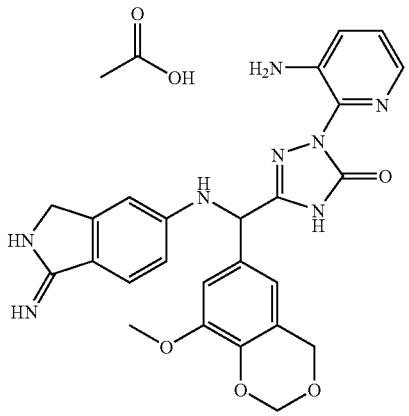

To a mixture of [5-({[1-(3-aminopyridin-2-yl)-5-oxo-4,5-dihydro-1H-[1,2,4]triazol-3-yl]-(8-methoxy-4H-benzo[1,3]-dioxin-6-yl)methyl}amino)benzyl]carbamic acid t-butyl ester (52 mg) and dichloromethane (3.0 mL) there was added TFA (1.0 mL), and the mixture was stirred at room temperature for 3 hours. Toluene (10 mL) was added to the mixture, and the solvent in the mixture was distilled off. The residue was purified by reverse-phase high performance liquid chromatography (acetonitrile/water mixed solvent, 0.1% acetic acid) to obtain the target compound (11.5 mg).

$^1$H-NMR (CD$_3$OD) δ 1.95(s, 3H) 3.85(s, 3H) 4.63(s, 2H) 4.88(s, 2H) 5.21(s, 2H) 5.65(s, 1H) 6.82(s, 1H) 6.91(s, 1H) 6.96(d, J=8.7 Hz, 1H) 7.05(s, 1H) 7.23(dd, J=8.2, 4.6 Hz, 1H) 7.34(dd, J=8.2, 1.8 Hz, 1H) 7.78(d, J=8.7 Hz, 1H) 7.82(dd, J=4.6, 1.8 Hz, 1H)

(2 g)(R)- and (S)-2-(3-Aminopyridin-2-yl)-5-[(1-imino-2,3-dihydro-1H-isoindol-5-ylamino)-(8-methoxy-4H-benzo[1,3]-dioxin-6-yl)methyl]-2,4-dihydro-[1,2,4]triazol-3-one acetate

[Chemical Formula 73]

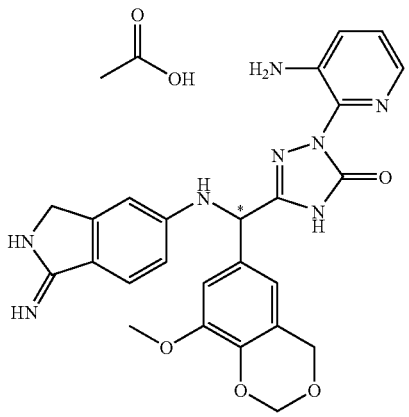

A SUMICHIRAL OA-2500 column was used for separation (optical resolution) of 2-(3-aminopyridin-2-yl)-5-[(1-imino-2,3-dihydro-1H-isoindol-5-ylamino)-(8-methoxy-4H-benzo[1,3]-dioxin-6-yl)methyl]-2,4-dihydro-[1,2,4]

triazol-3-one acetic acid salt (8 mg) under the following conditions, and the first eluting enantiomer (3.0 mg) of the title compound was obtained.

$^1$H-NMR (CD$_3$OD) δ 1.89 (S, 3H) 3.81(s, 3H) 4.59(s, 2H) 4.80-4.91(m, 2H) 5.22(s, 2H) 5.53(s, 1H) 6.82(s, 1H) 6.86(s, 1H) 6.93(dd, J=2.0, 8.8 Hz, 1H) 7.05(d, J=2.0 Hz, 1H) 7.18 (dd, J=4.4, 8.0 Hz, 1H) 7.32(dd, J=1.4, 8.0 Hz, 1H) 7.73(d, J=8.8 Hz, 1H) 7.83(d, J=1.4, 4.4 Hz, 1H)

HPLC retention time: 8 min. (Column name: SUM-ICHIRAL OA-2500, 30 mmφ×25 cm, Manufacturer: Sumika Chemical Analysis Service, Ltd., Mobile phase: 0.5 mM ammonium acetate-methanol solution, Elution rate: 20 mL/min)

Example 3

5-{[3-(2-Dimethylaminoethoxy)-5-ethyl-2-fluorophenyl]-(1-imino-2,3-dihydro-1H-isoindol-5-ylamino)methyl}-2-pyrimidin-2-yl-2,4-dihydro-1,2,4-triazol-3-one bistrifluoroacetate (3a)(5-Amino-2-bromobenzyl)carbamic acid t-butyl ester

[Chemical Formula 74]

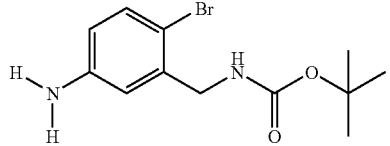

To (2-bromo-5-nitrobenzyl)carbamic acid t-butyl ester (Example (1e))(9.05 g) and an ethanol:water (25:4) mixed solvent (580 mL) there were added ammonium chloride 1.7 g and iron powder (18.3 g), and the mixture was heated to reflux for 1 hour under a nitrogen atmosphere. The mixture was filtered through Celite, and the Celite and filtered substance were washed with ethanol (100 mL), after which the washed solution was combined with the previous filtrate. The solvent in the filtrate was distilled off under reduced pressure to obtain a residue. The residue was dissolved in ethyl acetate (1 L) and water (500 mL), and the organic layer was washed with saturated aqueous sodium hydrogen carbonate (500 mL) and saturated aqueous sodium chloride (500 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (8.07 g) as an off-white solid.

$^1$H-NMR (CDCl$_3$) 1.44(s, 9H) 3.67(br.s, 2H) 4.27(d, J=5.9 Hz, 2H) 4.99(br.s, 1H) 6.46(dd, J=8.3, 3.1 Hz, 1H) 6.70(d, J=3.1 Hz, 1H) 7.25(d, J=8.3 Hz, 1H)

(3b) [2-Bromo-5-({[3-(t-butyldimethylsilanyloxy)-5-ethyl-2-fluorophenyl]cyano methyl}amino) benzyl}carbamic acid t-butyl ester

[Chemical Formula 75]

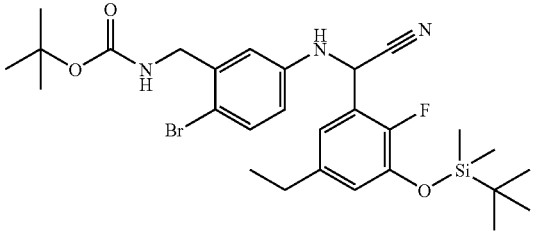

To a mixture of Yb(OTf)$_3$ (0.399 g) and dichloromethane (20 mL) there were added (5-amino-2-bromobenzyl)carbamic acid t-butyl ester (1.95 g), 3-(t-butyldimethylsilanyloxy)-5-ethyl-2-fluorobenzaldehyde (1.83 g), MS3A (2.6 g) and trimethylsilyl cyanide (1.29 mL) in that order under a nitrogen atmosphere, and the mixture was stirred at room temperature for 16 hours. The solvent was distilled off under reduced pressure, ethyl acetate (200 mL) and water (100 mL) were added to the residue, and after sufficiently shaking the mixture, the organic layer was separated off, washed with saturated aqueous sodium chloride (100 mL) and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (3.09 g) as a colorless solid.

$^1$H-NMR (CDCl$_3$) δ 0.20(s, 6H) 1.00 (s, 9H) 1.23(t, J=7.4 Hz, 3H) 1.45(s, 9H) 2.61(q, J=7.4 Hz, 2H) 4.05(d, J=8.1 Hz, 1H) 4.32(d, J=6.2 Hz, 2H) 5.01(t, J=6.2 Hz: 1H) 5.50(d, J=8.1 Hz, 1H) 6.58(dd, J=8.1, 3.1 Hz, 1H) 6.80(d, J=3.1 Hz, 1H) 6.81(dd, J=7.8, 2.3 Hz, 1H) 6.98(dd, J=5.7, 3.1 Hz, 1H) 7.40(d, J=8.1 Hz, 1H)

(3c) [2-Bromo-5-({[3-(t-butyldimethylsilanyloxy)-5-ethyl-2-fluorophenyl]thiocarbamoylmethyl}amino) benzyl]carbamic acid t-butyl ester

[Chemical Formula 76]

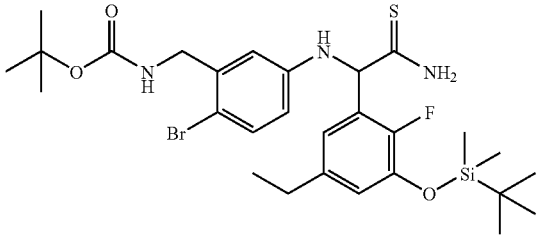

To a mixture of [2-bromo-5-({[3-(t-butyldimethylsilanyloxy)-5-ethyl-2-fluorophenyl]cyano methyl}amino) benzyl}carbamic acid t-butyl ester (3.09 g) and methanol (100 mL) there was added a 20% aqueous solution of ammonium sulfide (8.9 mL), and the mixture was stirred at room temperature for 16 hours. Ethyl acetate (200 mL) and water (400 mL) were added to the mixture, and after sufficiently shaking the mixture, the organic layer was separated off. The organic layer was washed twice with water (200 mL) and once with saturated aqueous sodium chloride (200 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (2.01 g) as an off-white solid.

$^1$H-NMR (CDCl$_3$) δ 0.19(s, 6H) 1.00(s, 9H) 1.17(t, J=7.5 Hz, 3H) 1.45(s, 9H) 2.53(q, J=7.5 Hz, 2H) 4.27(d, J=5.6 Hz, 2H) 4.81(br.s, 1H) 4.98(t, J=5.6 Hz, 1H) 5.35(s, 1H) 6.38(dd, J=8.5, 3.1 Hz, 1H) 6.69(d, J=3.1 Hz, 1H) 6.71(dd, J=7.6, 2.5 Hz, 1H) 6.98(dd, J=5.7, 2.5 Hz, 1H) 7.40(d, J=8.5 Hz, 1H) 7.53(br.s, 1H) 8.06(br.s, 1H)

(3d) {2-[4-Bromo-3-(t-butoxycarbonylaminomethyl) phenylimino)-2-[3-(t-butyldimethylsilanyloxy)-5-ethyl-2-fluorophenyl]-1-methylsulfanylethylidene}carbamic acid methyl ester

[Chemical Formula 77]

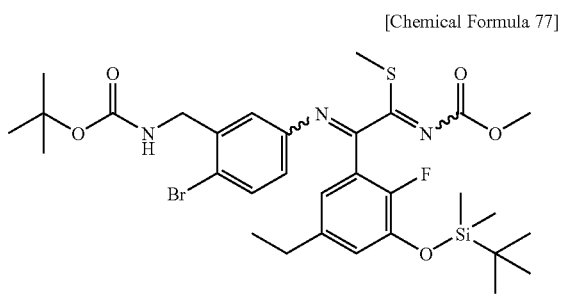

To a mixture of [2-bromo-5-({[3-(t-butyldimethylsilanyloxy)-5-ethyl-2-fluorophenyl]thiocarbamoylmethyl}amino)benzyl]carbamic acid t-butyl ester (2.46 g) and dichloromethane (200 mL) there was added trimethyloxonium tetrafluoroborate (0.667 g) under a nitrogen atmosphere, and the mixture was stirred at room temperature for 15 hours. Ethyl acetate (300 mL) and saturated aqueous sodium hydrogen carbonate (150 mL) were added, and after sufficiently shaking the mixture, the organic layer was separated off. The organic layer was washed with saturated aqueous sodium chloride (150 mL) and dried over anhydrous magnesium sulfate. The mixture was filtered to obtain a filtrate, and the solvent in the filtrate was distilled off under reduced pressure. Toluene (150 mL), 2,4,6-collidine (1.46 mL) and methyl chloroformate (0.711 mL) were added to the residue in that order, and the mixture was stirred at 85° C. for 20 hours under a nitrogen atmosphere. The mixture was cooled to room temperature, and then ethyl acetate (300 mL) and 5% sulfuric acid (200 mL) were added. The mixture was sufficiently shaken, and then the organic layer was separated off, washed with saturated aqueous sodium hydrogen carbonate (200 mL), water (200 mL) and saturated aqueous sodium chloride (200 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (0.686 g) as an off-white oil.

$^1$H-NMR (CDCl$_3$) Two main isomers δ 0.20(s, 6H) 1.01(s, 9H) 1.12(t, J=7.4 Hz, 3H) 1.46(s, 9H) 2.45(s, 3H) 2.50(q, J=7.4 Hz, 2H) 3.58(s, 3H) 4.25(d, J=6.3 Hz, 2H) 4.76(t, J=6.3 Hz, 1H) 6.41(dd, J=8.0, 2.2 Hz, 1H) 6.55(dd, J=5.6, 2.2 Hz, 1H) 6.72(dd, J=7.7, 2.2 Hz, 1H) 6.81(d, J=2.2 Hz, 1H) 7.28(d, J=8.0 Hz, 1H) δ 0.20(s, 6H) 1.01(s, 9H) 1.23(t, J=7.4 Hz, 3H) 1.45(s, 9H) 2.33(s, 3H) 2.59(q, J=7.4 Hz, 2H) 3.56(s, 3H) 4.38(d, J=6.3 Hz, 2H) 4.99(t, J=6.3 Hz, 1H) 6.86(dd, J=8.0, 2.2 Hz, 1H) 6.89(dd, J=7.7, 2.2 Hz, 1H) 7.09(d, J=2.2 Hz, 1H) 7.23(dd, J=5.6, 2.2 Hz, 1H) 7.46(d, J=8.0 Hz, 1H)

(3e) {2-[4-Bromo-3-(t-butoxycarbonylaminomethyl) phenylimino)-2-(5-ethyl-2-fluoro-3-hydroxyphenyl)-1-methylsulfanylethylidene}carbamic Acid Methyl Ester

[Chemical Formula 78]

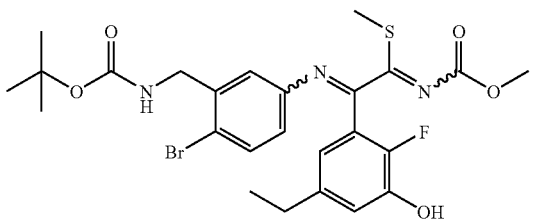

To a mixture of {2-[4-bromo-3-(t-butoxycarbonylaminomethyl)phenylimino)-2-[3-(t-butyldimethylsilanyloxy)-5-ethyl-2-fluorophenyl]-1-methylsulfanylethylidene}carbamic acid methyl ester (686 mg) and THF (25 mL) there was added a 1M THF solution (1.18 mL) of tetrabutylammonium fluoride at 0° C., under a nitrogen atmosphere. The mixture was stirred at 0° C. for 2 hours, and then ethyl acetate (200 mL) and water (100 mL) were added. The mixture was sufficiently shaken, and then the organic layer was separated off, washed twice with water (100 mL) and then with saturated aqueous sodium chloride (100 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (542 mg) as a colorless solid.

$^1$H-NMR (CDCl$_3$) Two main isomers δ 1.11(t, J=7.5 Hz, 3H) 1.47(s, 9H) 2.44(s, 3H) 2.48(q, J=7.5 Hz, 2H) 3.58(s, 3H) 4.25(d, J=6.2 Hz, 2H) 4.93(t, J=6.2 Hz, 1H) 6.02(br.s, 1H) 6.37(dd, J=8.1, 2.4 Hz, 1H) 6.55(d, J=5.6 Hz, 1H) 6.72(d, J=7.6 Hz, 1H) 6.83(d, J=2.4 Hz, 1H) 7.27(d, J=8.1 Hz, 1H) δ 1.23(t, J=7.5 Hz, 3H) 1.44(s, 9H) 2.33(s, 3H) 2.61(q, J=7.5 Hz, 2H) 3.56(s, 3H) 4.37(d, J=6.2 Hz, 2H) 4.99(t, J=6.2 Hz, 1H) 5.28(s, 1H) 6.86(dd, J=8.1, 2.4 Hz, 11H) 7.00(dd, J=7.6, 2.1 Hz, 1H) 7.09(d, J=2.4 Hz, 1H) 7.17(dd, J=5.6, 2.1 Hz, 1H) 7.46(d, J=8.1 Hz, 1H)

(3f) {2-[4-Bromo-3-(t-butoxycarbonylaminomethyl) phenylimino]-2-[3-(2-dimethylaminoethoxy)-5-ethyl-2-fluorophenyl]-1-methylsulfanylethylidene}carbamic Acid Methyl Ester

[Chemical Formula 79]

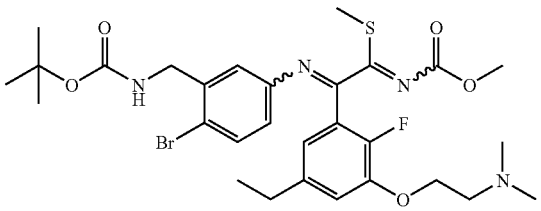

To a mixture of {2-[4-bromo-3-(t-butoxycarbonylaminomethyl)phenylimino)-2-(5-ethyl-2-fluoro-3-hydroxyphenyl)-1-methylsulfanylethylidene}carbamic acid methyl ester (542 mg) and DMF (21.6 mL) there were added potassium carbonate (257 mg) and 2-dimethylaminoethyl chloride hydrochloride (268 mg) at 0° C. in that order, under a nitrogen atmosphere. The mixture was stirred for 4 hours at 0° C., and then potassium carbonate (257 mg) and 2-dimethylaminoethyl chloride hydrochloride (268 mg) were again added in that order, stirring was continued for 4 hours at 0° C., and potassium carbonate (257 mg) and 2-dimethylaminoethyl chloride hydrochloride (268 mg) were added. The mixture was stirred overnight at room temperature, and then ethyl acetate (200 mL) and water (100 mL) were added. The mixture was sufficiently shaken, and then the organic layer was separated off, washed twice with water (100 mL) and once with saturated aqueous sodium chloride (100 mL) in that order, and dried over anhydrous magnesium sulfate. The mixture was filtered to obtain a filtrate, and the solvent in the filtrate was distilled off under reduced pressure. The residue was purified by NAM silica gel column chromatography (methanol-ethyl acetate system) to obtain the target compound (242 mg) as a colorless solid.

(3g) [2-Bromo-5-({[3-(2-dimethylaminoethoxy)-5-ethyl-2-fluorophenyl]-(5-oxo-1-pyrimidin-2-yl-4,5-dihydro-1H-[1,2,4]triazol-3-yl)methyl}amino)benzyl]carbamic Acid t-Butyl Ester Trifluoroacetate

[Chemical Formula 80]

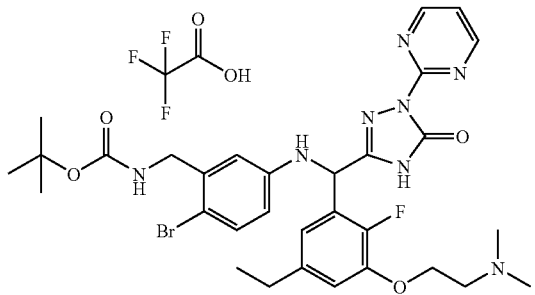

To a mixture of {2-[4-bromo-3-(t-butoxycarbonylaminomethyl)phenylimino]-2-[3-(2-dimethylaminoethoxy)-5-ethyl-2-fluorophenyl]-1-methylsulfanylethylidene}carbamic acid methyl ester (81 mg) and DMF (5.0 mL) there were added (pyrimidin-2-yl)hydrazine [CAS No. 4930-98-7] (16.2 mg) and triethylamine (20.7 µL), and the mixture was stirred at 90° C. for 16 hours under a nitrogen atmosphere. The solvent in the mixture was distilled off. Methanol (5 mL) and acetic acid (28.5 µL) were added to the residue. Sodium cyanotrihydroborate (77.9 mg) was then added to the mixture and the mixture was stirred at room temperature for 18 hours. The mixture was filtered to obtain a filtrate, and the solvent in the filtrate was distilled off under reduced pressure. The residue was purified by reverse-phase high performance liquid chromatography (acetonitrile/water mixed solvent, 0.1% trifluoroacetic acid) to obtain the target compound (11.5 mg).

$^1$H-NMR (CD$_3$OD) δ 1.18(t, J=7.4 Hz, 3H) 1.44(s, 9H) 2.60(q, J=7.4 Hz, 2H) 3.00(s, 6H) 3.61(t, J=4.7 Hz, 2H) 4.18(s, 2H) 4.41(t, J=4.7 Hz, 2H) 5.86(s, 1H) 6.53(dd, J=8.4, 2.4 Hz, 1H) 6.79(d, J=2.4 Hz, 1H) 6.97(dd, J=7.4, 2.0 Hz, 1H) 7.04(dd, J=5.6, 2.0 Hz, 1H) 7.25(d, J=8.4 Hz, 1H) 7.36(t, J=4.7 Hz, 1H) 8.76(d, J=4.7 Hz, 2H)

(3h) 5-{[3-(2-Dimethylaminoethoxy)-5-ethyl-2-fluorophenyl]-(1-imino-2,3-dihydro-1H-isoindol-5-ylamino)methyl}-2-pyrimidin-2-yl-2,4-dihydro-[1,2,4]triazol-3-one Bistrifluoroacetate

[Chemical Formula 81]

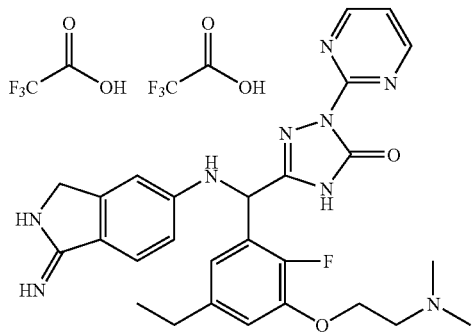

To a mixture of [2-bromo-5-({[3-(2-dimethylaminoethoxy)-5-ethyl-2-fluorophenyl]-(5-oxo-1-pyrimidin-2-yl-4,5-dihydro-1H-[1,2,4]triazol-3-yl)methyl}amino)benzyl]carbamic acid t-butyl ester trifluoroacetic acid salt (45.4 mg) and DMF (0.75 mL) there were added tris(dibenzylideneacetone)dipalladium(0)(6.1 mg), 1,1'-bis(diphenylphosphino)ferrocene (8.8 mg) and zinc cyanide (4.7 mg) under a nitrogen atmosphere, and the mixture was heated for 24 hours at 120° C. After cooling, the mixture was purified by reverse-phase high performance liquid chromatography (acetonitrile/water mixed solvent, 0.1% trifluoroacetic acid) to obtain the target compound (13.5 mg).

$^1$H-NMR (CD$_3$OD) δ 1.22(t, J=7.8 Hz, 3H) 2.64(q, J=7.8 Hz, 2H) 3.02(s, 6H) 3.64(t, J=5.5 Hz, 2H) 4.44(t, J=5.5 Hz, 2H) 4.62(d, J=18.9 Hz, 1H) 4.68(d, J=18.9 Hz, 1H) 6.04(s, 1H) 6.94(d, J=2.2 Hz, 1H) 6.97(dd, J=8.6, 2.2 Hz, 1H) 7.05(d, J=6.8 Hz, 1H) 7.07(d, J=10.4 Hz, 1H) 7.38(t, J=5.0 Hz, 1H) 7.81(d, J=8.6 Hz, 1H) 8.78(d, J=5.0 Hz, 2H)

Example 4

5-{[5-Ethyl-2-fluoro-3-(2-hydroxyethoxy)phenyl]-(1-imino-2,3-dihydro-1H-isoindol-5-ylamino)methyl}-2-pyrimidin-2-yl-2,4-dihydro-[1,2,4]triazol-3-one (4a) [2-Cyano-(5-{[cyano-(5-ethyl-2-fluoro-3-triisopropylsilanyloxy)phenyl]methyl}amino)benzyl]carbamic Acid t-Butyl Ester

[Chemical Formula 82]

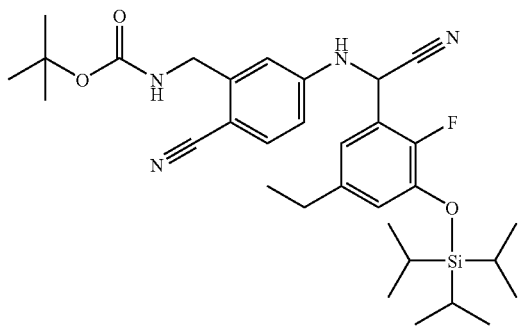

To a mixture of Yb(OTf)$_3$ (0.186 g) and dichloromethane (10 mL) there were added (5-amino-2-cyanobenzyl)carbamic acid t-butyl ester (Example (1g))(0.742 g), 3-triisopropylsilanyloxy-5-ethyl-2-fluorobenzaldehyde (0.974 g), MS3A (1 g) and trimethylsilyl cyanide (595 mg) in that order under a nitrogen atmosphere, and the mixture was stirred at room temperature for 72 hours. Ethyl acetate (100 mL) and water (100 mL) were added to the mixture and filtration was performed with Celite. The Celite and filtered substance were washed with ethyl acetate (100 mL), and the washed solution was combined with the filtrate. After sufficiently shaking the mixture, the organic layer was separated off and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (1.02 g) as a colorless solid.

$^1$H-NMR (CDCl$_3$) δ 1.10(m, 18H) 1.26(t, J=7.2 Hz, 3H) 1.28(m, 3H) 1.46(s, 9H) 2.62(q, J=7.2 Hz, 2H) 4.43(d, J=6.4 Hz, 2H) 4.51(d, J=8.0 Hz, 1H) 5.13(t, J=6.4 Hz, 1H) 5.59(d, J=8.0 Hz, 1H) 6.88(dd, J=8.5, 2.5 Hz, 1H) 6.83(br.s, 1H) 6.87(dd, J=7.8, 2.1 Hz, 1H) 6.97(dd, J=5.8, 2.1 Hz, 1H) 7.54(d, J=8.5 Hz, 1H)

(4b) [2-Cyano-(5-{[(5-ethyl-2-fluoro-3-triisopropyl-silanyloxy)phenyl]thiocarbamoylmethyl}amino) benzyl]carbamic Acid t-Butyl Ester

[Chemical Formula 83]

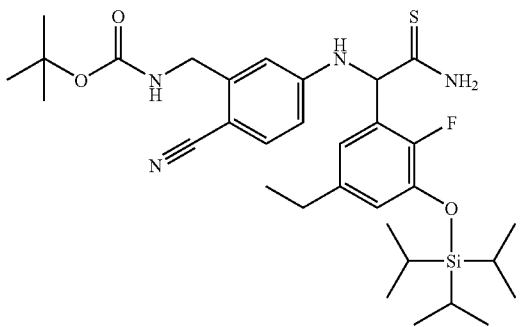

To a mixture of [2-cyano-(5-{[cyano-(5-ethyl-2-fluoro-3-triisopropylsilanyloxy)phenyl]methyl}amino)benzyl]carbamic acid t-butyl ester (1.02 g) and methanol (20 mL) there was added a 20% aqueous solution of ammonium sulfide (3.0 mL), and the mixture was stirred at room temperature for 15 hours. Ethyl acetate (200 mL) and water (100 mL) were added to the mixture, and after sufficiently shaking the mixture, the organic layer was separated off. The organic layer was washed with water (100 mL) and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (0.70 g) as a colorless solid.

$^1$H-NMR (CDCl$_3$) δ 1.10(m, 18H) 1.26(t, J=7.2 Hz, 3H) 1.28(m, 3H) 1.46(s, 9H) 2.61(q, J=7.2 Hz, 2H) 4.37(d, J=6.2 Hz, 2H) 4.51(br.s, 1H) 5.13(t, J=6.2 Hz, 1H) 5.42(s, 1H) 6.38(dd, J=8.4, 2.3 Hz, 1H) 6.73-6.76(m, 3H) 7.37(d, J=8.4 Hz, 1H) 7.44(br.s, 1H) 7.50(br.s, 1H)

(4c) {2-[3-(t-Butoxycarbonylaminomethyl)-4-cyanophenylimino]-2-(5-ethyl-2-fluoro-3-triisopropyl-silanyloxyphenyl)-1-methylsulfanylethylidene}carbamic Acid Methyl Ester

[Chemical Formula 84]

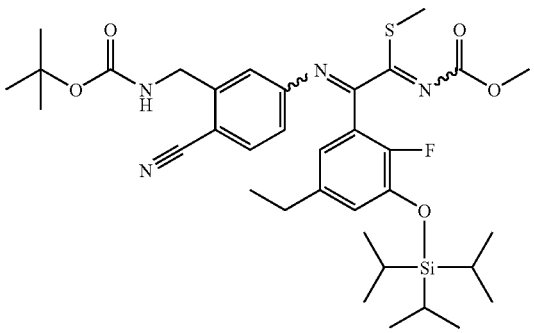

To a mixture of [2-cyano-(5-{[(5-ethyl-2-fluoro-3-triisopropylsilanyloxy)phenyl]thiocarbamoylmethyl}amino)benzyl]carbamic acid t-butyl ester (700 mg) and acetonitrile (10 mL) there was added trimethyloxonium tetrafluoroborate (0.177 g) under a nitrogen atmosphere, and the mixture was stirred at room temperature for 3 hours. Ethyl acetate (100 mL) and a 5% aqueous solution of sodium hydrogen carbonate (50 mL) were added to the mixture, and after sufficiently shaking the mixture, the organic layer was separated off. The organic layer was then washed with saturated aqueous sodium chloride (50 mL) and dried over anhydrous magnesium sulfate. The mixture was filtered to obtain a filtrate, and the solvent in the filtrate was distilled off under reduced pressure to obtain a crude product of 2-[3-(t-butoxycarbonylaminomethyl)-4-cyanophenylamino]-2-(5-ethyl-2-fluoro-3-triisopropylsilanyloxyphenyl)thioacetimidic acid methyl ester (765 mg).

$^1$H-NMR (CDCl$_3$) δ 1.10(m, 18H) 1.26(t, J=7.2 Hz, 3H) 1.28(m, 3H) 1.46(s, 9H) 2.28(s, 3H) 2.51(q, J=7.2 Hz, 2H) 4.36(d, J=6.0 Hz, 2H) 5.07(br.s, 1H) 5.35(br.s, 1H) 6.40(d, J=7.8 Hz, 1H) 6.64-6.75(m, 3H) 7.35(d, J=8.4 Hz, 1H)

Ethyl acetate (10 mL) and manganese dioxide (1.06 g) were added to this compound in that order, and the mixture was stirred at room temperature for 9 hours. The mixture was filtered through Celite, the Celite was washed with ethyl acetate (100 mL), and the washed solution was combined with the filtrate. The solvent in the mixture was distilled off under reduced pressure to obtain a crude product of 2-[3-(t-butoxycarbonylaminomethyl)-4-cyanophenylimino]-2-(5-ethyl-2-fluoro-3-triisopropylsilanyloxyphenyl)thioacetimidic acid methyl ester (662 mg).

$^1$H-NMR (CDCl$_3$) δ 1.00(m, 18H) 1.11(t, J=7.2 Hz, 3H) 1.11(m, 3H) 1.45(s, 9H) 2.43(s, 3H) 2.49(q, J=7.2 Hz, 2H) 4.36(d, J=6.3 Hz, 2H) 4.91(br.s, 1H) 6.41(dd, J=4.7, 1.6 Hz, 1H) 6.63(d, J=8.3, 1.6 Hz, 1H) 6.74(dd, J=8.3, 1.6 Hz, 1H) 6.91(d, J=1.6 Hz, 1H) 7.39(d, J=8.3 Hz, 11H)

Toluene (15 mL), 2,4,6-collidine (0.420 mL) and methyl chloroformate (0.164 mL) were added to this compound in that order, and the mixture was stirred at 85° C. for 3 hours under a nitrogen atmosphere. The mixture was cooled to room temperature, and then ethyl acetate (200 mL) and 2% sulfuric acid (200 mL) were added to the mixture. The mixture was sufficiently shaken, and then the organic layer was separated off, washed with water (200 mL) and saturated aqueous sodium chloride (200 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (0.554 g) as an off-white solid.

$^1$H-NMR (CDCl$_3$) Two main isomers δ 0.99(m, 18H) 1.11 (t, J=7.5 Hz, 3H) 1.12(m, 3H) 1.45(s, 9H) 2.46(s, 3H) 2.50(q, J=7.5 Hz, 2H) 3.61(s, 3H) 4.38(d, J=6.0 Hz, 2H) 4.90(br.s, 1H) 6.55(d, J=5.0 Hz, 1H) 6.61(d, J=8.3 Hz, 1H) 6.75(d, J=7.8 Hz, 1H) 6.90(s, 1H) 7.40(d, J=8.3 Hz, 1H) δ 1.11(m, 18H) 1.25(m, 3H) 1.26(t, J=7.5 Hz, 3H) 1.44(s, 9H) 2.32(s, 3H) 2.59(q, J=7.5 Hz, 2H) 3.58(s, 3H) 4.50(d, J=6.2 Hz, 2H) 5.09(br.s, 1H) 6.94(d, J=7.8 Hz, 1H) 7.00(d, J=8.3 Hz, 1H) 7.16(s, 1H) 7.20(d, J=5.0 Hz, 1H) 7.57(d, J=8.3 Hz, 1H)

(4d) {2-[3-(t-Butoxycarbonylaminomethyl)-4-cyanophenylimino]-2-(5-ethyl-2-fluoro-3-hydroxyphenyl)-1-methylsulfanylethylidene}carbamic Acid Methyl Ester

[Chemical Formula 85]

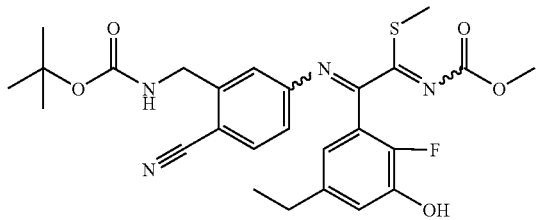

To a mixture of {2-[3-(t-butoxycarbonylaminomethyl)-4-cyanophenylimino]-2-(5-ethyl-2-fluoro-3-triisopropylsilanyloxyphenyl)-1-methylsulfanylethylidene}carbamic acid methyl ester (523 mg) and THF (10 mL) there was added a 1M THF solution of tetrabutylammonium fluoride (1.56 mL) under a nitrogen atmosphere. The mixture was stirred for 90 minutes, and then ethyl acetate (300 mL) and water (100 mL) were added. The mixture was sufficiently shaken, and then the organic layer was separated off, washed twice with water (100 mL) and once with saturated aqueous sodium chloride (100 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (346 mg) as a colorless solid.

$^1$H-NMR (CDCl$_3$) Two main isomers δ 1.11(t, J=7.2 Hz, 3H) 1.47(s, 9H) 2.47(s, 3H) 2.48(q, J=7.2 Hz, 2H) 3.60(s, 3H) 4.40(d, J=6.4 Hz, 2H) 5.09(br.s, 1H) 6.43(d, J=5.0 Hz, 1H) 6.55(d, J=8.0 Hz, 1H) 6.80(d, J=7.4 Hz, 1H) 6.95(s, 1H) 7.40(d, J=8.0 Hz, 1H) δ 1.27(t, J=7.2 Hz, 3H) 1.47(s, 9H) 2.34(s, 3H) 2.63(q, J=7.2 Hz, 2H) 3.58(s, 3H) 4.51(d, J=6.4 Hz, 2H) 5.09(br.s, 1H) 7.01(d, J=8.0 Hz, 1H) 7.03(d, J=7.4 Hz, 1H) 7.16(s, 1H) 7.19(d, J=5.0 Hz, 1l) 7.59(d, J=8.0 Hz, 1H)

(4e) {2-[3-(t-Butoxycarbonylaminomethyl)-4-cyanophenylimino]-2-[5-ethyl-2-fluoro-3-(2-triisopropylsilanyloxyethoxy)phenyl]-1-methylsulfanylethylidene}carbamic Acid Methyl Ester

[Chemical Formula 86]

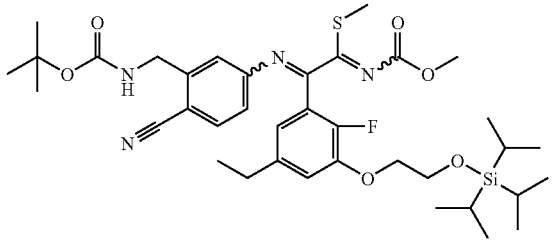

To a mixture of {2-[3-(t-butoxycarbonylaminomethyl)-4-cyanophenylimino]-2-(5-ethyl-2-fluoro-3-hydroxyphenyl)-1-methylsulfanylethylidene}carbamic acid methyl ester (346 mg) and DMF (6 mL) there were added cesium carbonate (235 mg) and (2-iodoethoxy)triisopropylsilane [CAS No. 93550-77-7] (323 mg) in that order, under a nitrogen atmosphere The mixture was stirred for 40 hours at room temperature, and then ethyl acetate (200 mL) and water (50 mL) were added. The mixture was sufficiently shaken, and then the organic layer was separated oft washed twice with water (50 mL) and once with saturated aqueous sodium chloride (50 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (406 mg) as an off-white oil.

$^1$H-NMR (CDCl$_3$) Two main isomers δ 1.10-1.26(m, 24H) 1.45(s, 9H) 2.45(s, 3H) 2.50(q, J=7.0 Hz, 2H) 3.60(s, 3H) 3.99-4.18(m, 4H) 4.39(d, J=6.2 Hz, 2H) 4.93(br.s, 1H) 6.45(br.s, 1H) 6.60(d, J=8.1 Hz, 1H) 6.83(d, J=7.5 Hz, 1H) 6.88(s, 1H) 7.40(d, J=8.1 Hz, 1H) δ 1.10-1.26(m, 24H) 1.45 (s, 9H) 2.32(s, 3H) 2.63(q, J=7.0 Hz, 2H) 3.60(s, 3H) 3.99-4.18(m, 4H) 4.51(d, J=6.2 Hz, 2H) 5.08(br.s, 1H) 6.97(d, J=8.1 Hz, 1H) 6.98(s, 1H) 7.02(d, J=7.5 Hz, 1H) 7.13(br.s, 1H) 7.57(d, J=8.1 Hz, 1H)

(4f) [2-Cyano-5-({[5-ethyl-2-fluoro-3-(2-triisopropylsilanyloxyethoxy)phenyl]-(5-oxo-1-pyrimidin-2-yl-4,5-dihydro-1H-[1,2,4]triazol-3-yl)methyl}amino)benzyl]carbamic Acid t-Butyl Ester

[Chemical Formula 87]

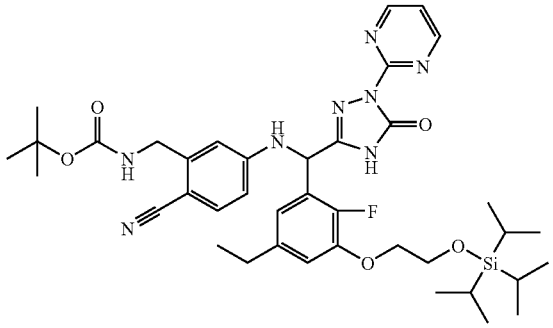

To a mixture of {2-[3-(t-butoxycarbonylaminomethyl)-4-cyanophenylimino]-2-[5-ethyl-2-fluoro-3-(2-triisopropylsilanyloxyethoxy)phenyl]-1- methylsulfanylethylidene}carbamic acid methyl ester (68 mg) and DMF (2.0 mL) there were added (pyrimidin-2-yl)hydrazine (10.8 mg) and triethylamine (14.3 μL), and the mixture was stirred at 85° C. for 10 hours under a nitrogen atmosphere. The solvent in the mixture was distilled off.

Methanol (4 mL) and acetic acid (21.4 μL) were added to the residue, Sodium cyanotrihydroborate (58.6 mg) was then added and the mixture was stirred at room temperature for 13 hours. Ethyl acetate (40 mL) and water (20 mL) were added to the mixture. The mixture was sufficiently shaken, and then the organic layer was separated oft, washed with water (20 mL) and saturated aqueous sodium chloride (20 mL) in that order, and dried over anhydrous magnesium sulfate. The mixture was filtered to obtain a filtrate, and the solvent in the filtrate was distilled off under reduced pressure. The residue was purified by silica gel column chromatography (methanol-ethyl acetate system) to obtain the target compound (56 mg) as an off-white oil.

$^1$H-NMR (CD$_3$OD) δ 1.05(d, J=6.9 Hz, 18H) 1.12(sept, J=6.9 Hz, 3H) 1.16(t, J=7.2 Hz, 3H) 1.42(s, 9H) 2.56(t, J=7.2 Hz, 2H) 4.05(t, J=4.8 Hz, 2H) 4.14(t, J=4.8 Hz, 2H) 4.28(d, J=6.2 Hz, 2H) 5.94(s, 1H) 6.66(dd, J=8.2, 2.1 Hz, 1H) 6.80(d, J=2.1 Hz, 1H) 6.87(dd, J=5.1, 2.1 Hz, 1H) 6.95(dd, J=7.4, 2.1. Hz, 1H) 7.14(t, J=6.2 Hz, 1H) 7.35(t, J=4.4 Hz, 1H) 7.40(d, J=8.2 Hz, 1H) 8.75(d, J=4.4 Hz, 2H)

(4g) [2-Cyano-5-({[5-ethyl-2-fluoro-3-(2-hydroxyethoxy)phenyl]-(5-oxo-1-pyrimidin-2-yl-4,5-dihydro-1H-[1,2,4]triazol-3-yl)methyl}amino)benzyl]carbamic Acid t-Butyl Ester

[Chemical Formula 88]

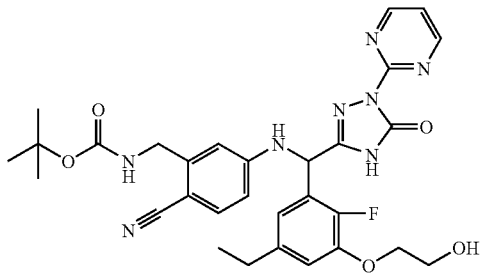

To a mixture of [2-cyano-5-({[5-ethyl-2-fluoro-3-(2-triisopropylsilanyloxyethoxy)phenyl]-(5-oxo-1-pyrimidin-2-yl-4,5-dihydro-1H-[1,2,4]triazol-3-yl)methyl}amino)benzyl]carbamic acid t-butyl ester (56 mg) and THF (4 mL) there was added a 1M THF solution of tetrabutylammonium fluoride (0.147 mL). The mixture was stirred for 4 hours, and then ethyl acetate (50 mL) and water (50 mL) were added. The mixture was sufficiently shaken, and then the organic layer was separated off, washed twice with water (50 mL) and once with saturated aqueous sodium chloride (50 mL) in that order, and dried over anhydrous magnesium sulfate. The mixture was filtered to obtain a filtrate and the solvent in the filtrate was distilled off under reduced pressure to obtain the target compound (56 mg) as a colorless oil.

$^1$H-NMR (CD$_3$OD) δ 1.05(t, J=7.2 Hz, 3H) 1.40(s, 9H) 2.38(t, J=7.2 Hz, 2H) 3.95(m, 2H) 4.04(m, 2H) 4.28(s, 2H) 5.94(s, 1H) 6.54-6.63(m, 2H) 6.76-6.82(m, 2H) 7.13(t, J=4.8 Hz, 1H) 7.31(d, J=8.2 Hz, 1H) 8.72(d, J=4.8 Hz, 2H)

(4h) 5-{[5-Ethyl-2-fluoro-3-(2-hydroxyethoxy)phenyl]-(1-imino-2,3-dihydro-1H-isoindol-5-ylamino)methyl}-2-pyrimidin-2-yl-2,4-dihydro-[1,2,4]triazol-3-one

[Chemical Formula 89]

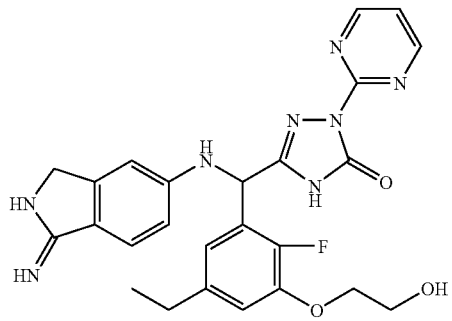

To a mixture of [2-cyano-5-({[5-ethyl-2-fluoro-3-(2-hydroxyethoxy)phenyl]-(5-oxo-1-pyrimidin-2-yl-4,5-dihydro-1H-[1,2,4]triazol-3-yl)methyl}amino)benzyl]carbamic acid t-butyl ester (34.2 mg) and dichloromethane (1.5 mL) there was added a 4N hydrogen chloride-ethyl acetate solution, and the mixture was stirred at room temperature for 4 hours. Toluene (10 mL) was added to the mixture, and the solvent in the mixture was distilled off. The residue was purified by reverse-phase high performance liquid chromatography (acetonitrile/water mixed solvent, 0.1% acetic acid) to obtain the target compound (12.0 mg).

$^1$H-NMR (CD$_3$OD) δ 1.18(t, J=7.3 Hz, 3H) 2.57(q, J=7.3 Hz, 2H) 3.89(m, 2H) 4.12(m, 4H) 5.97(s, 1H) 6.82(dd, J=8.6, 2.1 Hz, 1H) 6.94(d, J=6.6 Hz, 1H) 6.95(br.s, 1H) 6.97(dd, J=7.3, 2.1 Hz, 1H) 7.34(t, J=4.9 Hz, 1H) 7.49(d, J=8.6 Hz, 1H) 8.76(d, J=4.9 Hz, 2H)

Example 5

(R)- and (S)-5-[(1-Imino-2,3-dihydro-1H-isoindol-5-ylamino)-(S-methoxy-4H-benzo[1,3]-dioxin-6-yl)methyl]-2-pyrimidin-2-yl-2,4-dihydro-[1,2,4]-triazol-3-one acetate (5a) (2-Cyano-5-{[(8-methoxy-4H-benzo[1,3]-dioxin-6-yl)-(5-oxo-1-pyrimidin-2-yl-4,5-dihydro-1H-[1,2,4]triazol-3-yl)methyl]amino}benzyl)carbamic Acid t-Butyl Ester

[Chemical Formula 90]

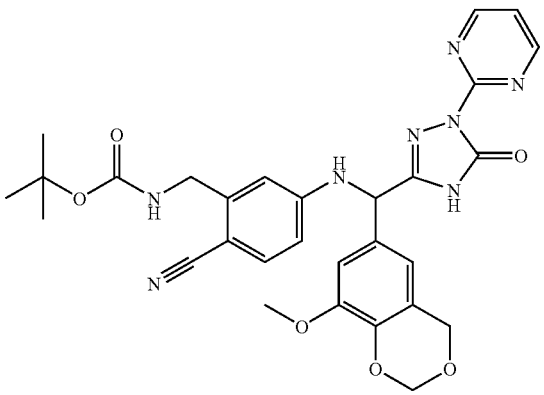

To a mixture of {2-[3-(t-butoxycarbonylaminomethyl)-4-cyanophenylimino]-2-(8-methoxy-4H-benzo[1,3]-dioxin-6-yl)-1-methylsulfanylethylidene}carbamic acid methyl ester (Example (2c))(101 mg) and THF (2.0 mL) there were added (pyrimidin-2-yl)hydrazine (21.2 mg) and triethylamine (27.9 μL), and the mixture was stirred at 65° C. for 15 hours under a nitrogen atmosphere. The solvent in the mixture was distilled off.

DMF (2.0 mL) was added to the residue, and the mixture was stirred at 85° C. for 16 hours under a nitrogen atmosphere. The solvent in the mixture was distilled off, and methanol (5 mL) and acetic acid (52.1 μL) were added to the residue. Sodium cyanotrihydroborate (114 mg) was then added to the mixture and the mixture was stirred overnight at room temperature. Water (25 mL) and ethyl acetate (50 mL) were added to the mixture, and after sufficiently shaking the mixture, the organic layer was separated off. The organic layer was washed twice with water (25 mL) and once with saturated aqueous sodium chloride (25 mL) in that order, and dried over anhydrous magnesium sulfate. The mixture was filtered to obtain a filtrate, and the solvent in the filtrate was distilled off under reduced pressure. The residue was purified by NAM silica gel column chromatography (methanol-ethyl acetate mixture) to obtain the target compound (83 mg) as an off-white solid.

$^1$H-NMR (CDCl$_3$) δ 1.34(s, 9H) 3.76(s, 3H) 4.29(d, J=6.2 Hz, 2H) 4.67(d, J=15.7 Hz, 1H) 4.73(d, J=15.7 Hz, 1H) 5.23(s, 2H) 5.74(d, J=7.9 Hz, 1H) 6.20(br.s, 1H) 6.64(dd, J=8.5, 2.1 Hz, 1H) 6.73(br.s, 1H) 6.86(br.s, 1H) 6.95(br.s, 1H) 7.20(t, J=4.6 Hz, 11H) 7.38(d, J=8.5 Hz, 1H) 8.75(d, J=4.7 Hz, 2H)

(5b)

5-[(1-Imino-2,3-dihydro-1H-isoindol-5-ylamino)-(8-methoxy-4H-benzo[1,3]-dioxin-6-yl)methyl]-2-pyrimidin-2-yl-2,4-dihydro-[1,2,4]triazol-3-one

[Chemical Formula 91]

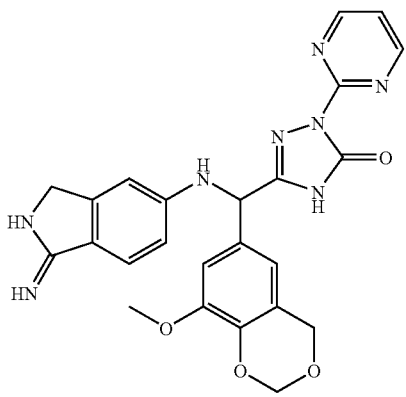

To a mixture of (2-cyano-5-{[(8-methoxy-4H-benzo[1,3]-dioxin-6-yl)-(5-oxo-1-pyrimidin-2-yl-4,5-dihydro-1H-[1,2,4]triazol-3-yl)methyl]amino}benzyl)carbamic acid t-butyl ester (83 mg) and dichloromethane (3.0 mL) there was added TFA (0.3 mL), and the mixture was stirred at room temperature for 2 hours. Toluene (10 mL) was added to the mixture, and the solvent in the mixture was distilled off. The residue was purified by reverse-phase high performance liquid chromatography (acetonitrile/water mixed solvent, 0.1% acetic acid) to obtain the target compound (33.8 mg).

$^1$H-NMR (CD$_3$OD) δ 3.77(s, 3H) 4.28(s, 2H) 4.78(d, J=15.5 Hz, 1H) 4.85(d, J=15.5 Hz, 1H) 5.22(s, 2H) 5.63(s, 1H) 6.79(d, J=1.8 Hz, 1H) 6.84(dd, J=8.7, 1.8 Hz, 1H) 6.97(d, J=1.8 Hz, 1H) 7.01(d, J=1.8 Hz, 1H) 7.35(t, J=4.7 Hz, 1H) 7.50(d, J=8.7 Hz, 1H) 8.78(d, J=4.7 Hz, 2H)

(5c)(R)- and (S)-5-[(1-Imino-2,3-dihydro-11H-isoindol-5-ylamino)-(8-methoxy-4H-benzo[1,3]-dioxin-6-yl)methyl]-2-pyrimidin-2-yl-2,4-dihydro-[1,2,4]triazol-3-one acetate

[Chemical Formula 92]

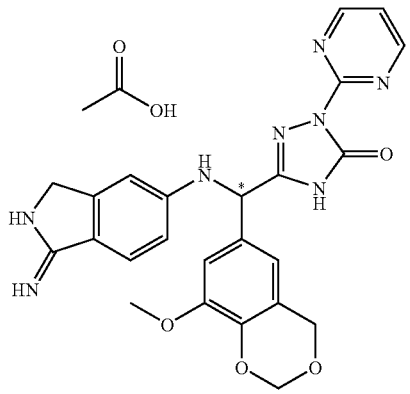

A SUMICHIRAL OA-2500 column was used for separation (optical resolution) of 5-[(1-imino-2,3-dihydro-1H-isoindol-5-ylamino)-(8-methoxy-4H-benzo[1,3]-dioxin-6-yl)methyl]-2-pyrimidin-2-yl-2,4-dihydro-[1,2,4]triazol-3-one (15 mg) under the following conditions, and the first eluting enantiomer (5.6 mg) of the title compound was obtained.

$^1$H-NMR (CD$_3$OD) δ 1.92(s, 3H) 3.81(s, 3H) 4.61(s, 2H) 4.84-4.90(m, 2H) 5.22(s, 2H) 5.59(s, 1H) 6.82(s, 1H) 6.89(s, 1H) 6.96(d, J=8.8 Hz, 1H) 7.06(s, 1H) 7.31(t, J=4.8 Hz, 1H) 7.75(d, J=8.8 Hz, 1H) 8.77(d, J=4.8 Hz, 2H)

HPLC retention time: 15 min. (Column name: SUMICHIRAL OA-2500, 30 mmφ×25 cm, Manufacturer: Sumika Chemical Analysis Service, Ltd., Mobile phase: 50 mM ammonium acetate-methanol solution, Elution rate: 40 mL/min)

Example 6

4-(3-{[2-Fluoro-3-(2-hydroxyethoxy)-5-methoxyphenyl]-(1-imino-2,3-dihydro-1H-isoindol-5-ylamino)methyl}-5-oxo-4,5-dihydro-[1,2,4]triazol-1-yl)thiazole-5-carboxylic Acid (6a) [2-Cyano-(5-{[cyano-(2-fluoro-5-methoxy-3-triisopropylsilanyloxy)phenyl]methyl}amino)benzyl]carbamic Acid t-Butyl Ester

[Chemical Formula 93]

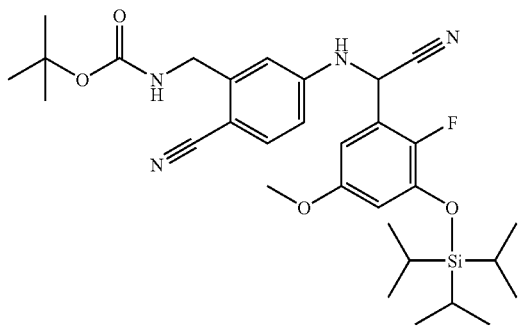

To a mixture of Yb(OTf)$_3$ (0.117 g) and THF (10 mL) there were added (5-amino-2-cyanobenzyl)carbamic acid t-butyl ester (Example (1g))(0.465 g), 2-fluoro-5-methoxy-3-triisopropylsilanyloxybenzaldehyde (0.697 g), MS3A (1 g) and trimethylsilyl cyanide (501 mg) in that order under a nitrogen atmosphere, and the mixture was stirred at room temperature for 14 hours. Ethyl acetate (300 mL) and water (200 mL) were added to the mixture and filtration was performed with Celite. After sufficiently shaking the filtrate, the organic layer was separated off and washed with saturated aqueous sodium chloride (200 mL), and then dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (0.98 g) as a colorless solid.

$^1$H-NMR (CDCl$_3$) δ 1.10(m, 18H) 1.26(m, 3H) 1.45(s, 9H) 3.80(s, 3H) 4.43(d, J=6.2 Hz, 2H) 4.54(d, J=7.9 Hz, 1H) 5.14(br.s, 1H) 5.59(d, J=7.9 Hz, 1H) 6.59(dd, J=8.2, 2.4 Hz, 1H) 6.66(br.s, 1H) 6.68(d, J=2.4 Hz, 1H) 6.84(s, 1H) 7.53(d, J=8.2 Hz, 1H)

(6b) [2-Cyano-(5-{[(2-fluoro-5-methoxy-3-triisopropylsilanyloxy)phenyl]thiocarbamoylmethyl}amino)benzyl]carbamic Acid t-Butyl Ester

[Chemical Formula 94]

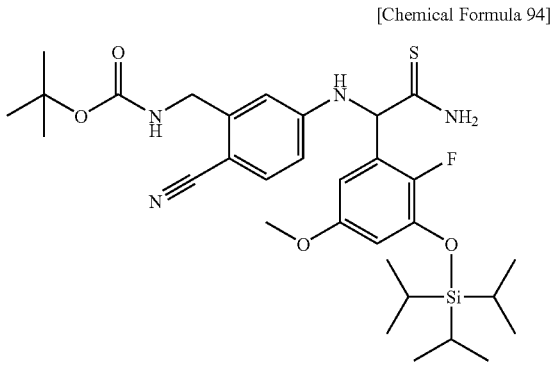

To a mixture of [2-cyano-(5-{[cyano-(2-fluoro-5-methoxy-3-triisopropylsilanyloxy)phenyl]methyl}amino)benzyl]carbamic acid t-butyl ester (980 mg), methanol (10 mL) and THF (5 mL) there was added a 20% aqueous solution of ammonium sulfide (2.86 mL), and the mixture was stirred overnight at room temperature. Ethyl acetate (300 mL) and water (200 mL) were added to the mixture, and after sufficiently shaking the mixture, the organic layer was separated off. The organic layer was washed with water (200 mL) and saturated aqueous sodium chloride (200 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (452 mg) as a colorless solid.

$^1$H-NMR (CDCl$_3$) δ 1.11(m, 18H) 1.28(m, 3H) 1.46(s, 9H) 3.68(s, 3H) 4.38(d, J=6.1 Hz, 2H) 5.08(br.s, 1H) 5.43(d, J=4.9 Hz, 1H) 5.97(br.s, 1H) 6.38(dd, J=8.1, 2.0 Hz, 1H) 6.44-6.48 (m, 3H) 6.73(s, 1H) 7.37(d, J=8.1 Hz, 1H) 7.45(s, 1H)

(6c) {2-[3-(t-Butoxycarbonylaminomethyl)-4-cyanophenylimino]-2-(2-fluoro-5-methoxy-3-triisopropylsilanyloxyphenyl)-1-methylsulfanylethylidene}carbamic Acid Methyl Ester

[Chemical Formula 95]

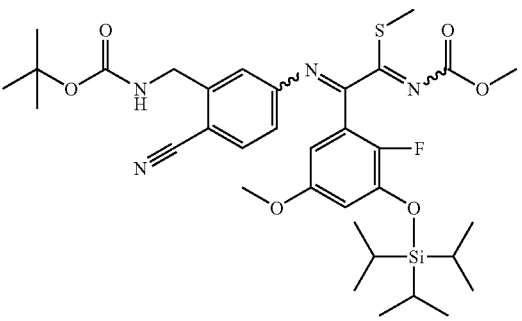

To a mixture of [2-cyano-(5-{[(2-fluoro-5-methoxy-3-triisopropylsilanyloxy)phenyl]thiocarbamoylmethyl}amino)benzyl]carbamic acid t-butyl ester (0.867 g) and acetonitrile (50 mL) there was added trimethyloxonium tetrafluoroborate (0.219 g) under a nitrogen atmosphere, and the mixture was stirred at room temperature for 1 hour. Ethyl acetate (500 mL) and saturated aqueous sodium hydrogen carbonate (200 mL) were added to the mixture, and after sufficiently shaking the mixture, the organic layer was separated off and the organic layer was dried over anhydrous magnesium sulfate. The mixture was filtered to obtain a filtrate, and the solvent in the filtrate was distilled off under reduced pressure.

Ethyl acetate (15 mL) and manganese dioxide (1.84 g) were added to the residue in that order, and the mixture was stirred at room temperature for 6 hours. The mixture was filtered through Celite, the Celite was washed with ethyl acetate (100 mL), and the washed solution was combined with the previous filtrate. The solvent in the filtrate was distilled off under reduced pressure.

Toluene (30 mL), 2,4,6-collidine (0.410 mL) and methyl chloroformate (0.196 mL) were added to the residue in that order, and the mixture was stirred at 80° C. for 8 hours under a nitrogen atmosphere. After cooling to room temperature, 2,4,6-collidine (0.205 mL) and methyl chloroformate (0.098 mL) were further added in that order and the mixture was stirred at 80° C. for 4 hours. The mixture was cooled to room temperature, and then ethyl acetate (200 mL) and 1N hydrochloric acid (100 mL) were added to the mixture. The mixture was sufficiently shaken, and then the organic layer was separated oft washed with saturated aqueous sodium hydrogen carbonate (100 mL) and saturated aqueous sodium chloride (100 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (0.542 g) as an off-white solid.

$^1$H-NMR (CDCl$_3$) Two main isomers δ 0.97-1.12(m, 21H) 1.45(s, 9H) 2.46(s, 3H) 3.61(s, 3H) 3.69(s, 3H) 4.38(d, J=6.0 Hz, 2H) 4.94(br.s, 1H) 6.25(br.s, 1H) 6.48(dd, J=7.5, 2.4 Hz, 1H) 6.61(d, J=8.1 Hz, 1H) 6.93(s, 1H) 7.41(d, J=8.1 Hz, 1H) δ 1.08-1.31(m, 2H) 1.45(s, 9H) 2.33(s, 3H) 3.58(s, 3H) 3.79 (s, 3H) 4.50(d, J=6.0 Hz, 2H) 5.10(br.s, 1H) 6.59-6.70(m, 2H) 6.99(d, J=8.1 Hz, 1H) 7.14(s, 1H) 7.57(d, J=8.1 Hz, 1H)

(6d) {2-[3-(t-Butoxycarbonylaminomethyl)-4-cyanophenylimino]-2-[2-fluoro-5-methoxy-3-(2-triisopropylsilanyloxyethoxy)phenyl]-1-methylsulfanylethylidene}carbamic Acid Methyl Ester

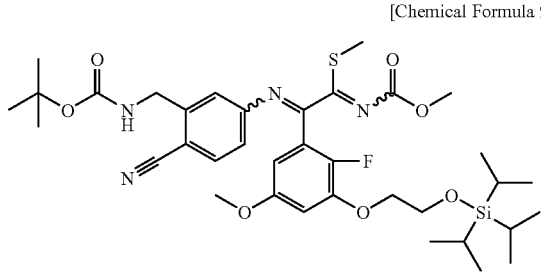

[Chemical Formula 96]

To a mixture of {2-[3-(t-butoxycarbonylaminomethyl)-4-cyanophenylimino]-2-(2-fluoro-5-methoxy-3-triisopropylsilanyloxyphenyl)-1-methylsulfanylethylidene}carbamic acid methyl ester (542 mg) and THF (10 mL) there was added a 1M THF solution of tetrabutylammonium fluoride (0.95 mL) at 0° C. under a nitrogen atmosphere. The mixture was stirred at 0° C. for 2 hours, and then ethyl acetate (200 mL) and water (50 mL) were added. The mixture was sufficiently shaken, and then the organic layer was separated off, washed twice with water (50 mL) and once with saturated aqueous sodium chloride (50 mL) in that order, and dried over anhydrous magnesium sulfate. The mixture was filtered to obtain a filtrate, and the solvent in the filtrate was distilled off under reduced pressure.

The residue was dissolved in DMF (10 mL), and then cesium carbonate (386 mg) and (2-iodoethoxy)triisopropylsilane (389 mg) were added in that order. The mixture was stirred overnight at room temperature, and then ethyl acetate (100 mL) and water (50 mL) were added. The mixture was sufficiently shaken, and then the organic layer was separated off, washed twice with water (50 mL) and then with saturated aqueous sodium chloride (50 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (278 mg) as an off-white solid.

$^1$H-NMR (CDCl$_3$) Two main isomers δ 1.03-1.30(m, 21H) 1.45(s, 9H) 2.45(s, 3H) 3.63(s, 3H) 3.68(s, 3H) 4.01-4.05(m, 4H) 4.41(d, J=5.9 Hz, 2H) 4.95(br.s, 1H) 6.14(br.s, 1H) 6.56 (dd, J=7.3, 2.4 Hz, 1H) 6.63(d, J=8.3 Hz, 1H) 6.93(s, 1H) 7.43(d, J=8.3 Hz, 1H) δ 1.03-1.30(m, 21H) 1.45(s, 9H) 2.33 (s, 3H) 3.63(s, 3H) 3.81(s, 3H) 4.01-4.05(m, 4H) 4.50(d, J=5.9 Hz, 2H) 5.09(br.s, 1H) 6.75-6.94(m, 2H) 6.97(d, J=8.3 Hz, 1H) 7.12(s, 1H) 7.58(d, J=8.3 Hz, 1H)

(6e) 4-(3-{[3-(t-Butoxycarbonylaminomethyl)-4-cyanophenylamino]-[2-fluoro-5-methoxy-3-(2-triisopropylsilanyloxyethoxy)phenyl]methyl}-5-oxo-4,5-dihydro-[1,2,4]triazol-1-yl)thiazole-5-carboxylic acid methyl ester

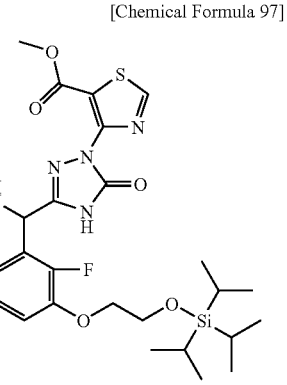

[Chemical Formula 97]

To a mixture of {2-[3-(t-butoxycarbonylaminomethyl)-4-cyanophenylimino]-2-[2-fluoro-5-methoxy-3-(2-triisopropylsilanyloxyethoxy)phenyl]-1-methylsulfanylethylidene}carbamic acid methyl ester (56 mg) and THF (2.0 mL) there were added 4-hydrazinothiazole-5-carboxylic acid methyl ester (13.9 mg) and triethylamine (11.7 μL), and the mixture was stirred at 65° C. for 14 hours under a nitrogen atmosphere. The solvent in the mixture was distilled off, DMF (2.0 mL) was added to the residue, and the mixture was stirred at 85° C. for 18 hours under a nitrogen atmosphere. The solvent in the mixture was distilled off.

Methanol (3.0 mL), THF (1.0 mL) and acetic acid (22.0 μL) were added to the residue. Sodium cyanotrihydroborate (48.1 mg) was then added to the mixture and the mixture was stirred at room temperature for 20 hours. Water (20 mL) and ethyl acetate (50 mL) were added to the mixture, and after sufficiently shaking the mixture, the organic layer was separated off. The organic layer was washed with water (20 mL) and saturated aqueous sodium chloride (20 mL) in that order, and dried over anhydrous magnesium sulfate. The mixture was filtered to obtain a filtrate, and the solvent in the filtrate was distilled off under reduced pressure. The residue was purified by NAM silica gel column chromatography (ethyl acetate-heptane mixture) to obtain the target compound (36.4 mg) as a colorless solid.

$^1$H-NMR (CD$_3$OD) δ 1.07(m, 18H) 1.15(m, 3H) 1.44(s, 9H) 3.75(s, 3H) 3.83(s, 3H) 4.06(t, J=4.8 Hz, 2H) 4.14(t, J=4.8 Hz, 2H) 4.31(d, J=6.1 Hz, 2H) 5.95(s, 1H) 6.58(dd, J=5.3, 2.2 Hz, 1H) 6.65-6.72(m, 2H) 6.79(d, J=1.9 Hz, 1H) 7.44(d, J=8.3 Hz, 1H) 9.15(s, 1H)

(6f) 4-(3-{[3-(t-Butoxycarbonylaminoomethyl)-4-cyanophenylamino]-[2-fluoro-5-methoxy-3-(2-hydroxyethoxy)phenyl]methyl}-5-oxo-4,5-dihydro-[1,2,4]triazol-1-yl)thiazole-5-carboxylic Acid Methyl Ester

[Chemical Formula 98]

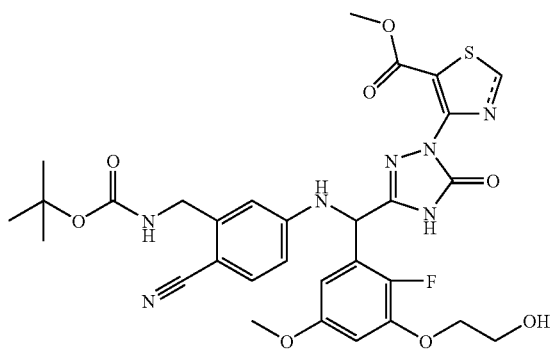

To a mixture of 4-(3-{[3-(t-butoxycarbonylaminomethyl)-4-cyanophenylamino]-[2-fluoro-5-methoxy-3-(2-triisopropylsilanyloxyethoxy)phenyl]methyl}-5-oxo-4,5-dihydro-[1,2,4]triazol-1-yl)thiazole-5-carboxylic acid methyl ester (36.4 mg) and THF (2 mL) there was added a 1M THF solution of tetrabutylammonium fluoride (0.100 mL). The mixture was stirred for 3 hours, and then ethyl acetate (30 mL) and water (15 mL) were added. The mixture was sufficiently shaken, and then the organic layer was separated off, washed with water (15 mL) and saturated aqueous sodium chloride (15 mL) in that order, and dried over anhydrous magnesium sulfate. The mixture was filtered to obtain a filtrate and the solvent in the filtrate was distilled off under reduced pressure to obtain the target compound (31 mg) as a colorless oil.

$^1$H-NMR (CD$_3$OD) δ 1.44(s, 9H) 3.74(s, 3H) 3.83(s, 3H) 3.87(t, J=4.8 Hz, 2H) 4.10(t J=4.8 Hz, 2H) 4.31(d, J=6.1 Hz, 2H) 5.95(s, 1H) 6.60(dd, J=5.2, 2.3 Hz, 1H) 6.65-6.69(m, 2H) 6.79(d, J=1.9 Hz, 1H) 7.43(d, J=8.3 Hz, 1H) 9.15(s, 11H)

(6g) 4-(3-{[2-Fluoro-3-(2-hydroxyethoxy)-5-methoxyphenyl]-(1-imino-2,3-dihydro-1H-isoindol-5-ylamino)methyl}-5-oxo-4,5-dihydro-[1,2,4]triazol-1-yl)thiazole-5-carboxylic Acid

[Chemical Formula 99]

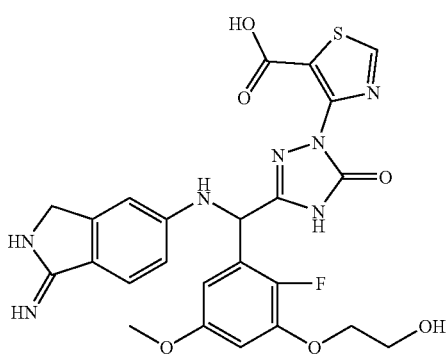

To a mixture of 4-(3-{[3-(t-butoxycarbonylaminomethyl)-4-cyanophenylamino]-[2-fluoro-5-methoxy-3-(2-hydroxyethoxy)phenyl]methyl}-5-oxo-4,5-dihydro-[1,2,4]triazol-1-yl)thiazole-5-carboxylic acid methyl ester (31 mg) and methanol (2.0 mL) there was added a 5N sodium hydroxide aqueous solution (28 μL), and the mixture was stirred overnight at room temperature. After neutralizing the mixture with acetic acid, the solvent in the mixture was distilled off under reduced pressure. Dichloromethane (2.0 mL) was added to the residue, and then a 4N hydrogen chloride-ethyl acetate solution (500 μL) was added to the mixture prior to stirring at room temperature for 15 minutes. Toluene (10 mL) was added to the mixture, and the solvent in the mixture was distilled off. The residue was purified by reverse-phase high performance liquid chromatography (acetonitrile/water mixed solvent, 0.1% acetic acid) to obtain the target compound (10 mg).

$^1$H-NMR (CD$_3$OD) δ 3.73(s, 3H) 3.88(t, J=5.1 Hz, 2H) 4.11(d, J=5.1 Hz, 2H) 4.55(d, J=18.6 Hz, 1H) 4.70(d, J=18.6 Hz, 1H) 5.94(s, 1H) 6.75-6.78(m, 2H) 6.88-6.95(m, 2H) 7.73 (d, J=8.7 Hz, 1H) 8.87(s, 1H)

Example 7

(R)- and (S)-3-{3-[(1-Imino-2,3-dihydro-1H-isoindol-5-ylamino)-(8-methoxy-4H-benzo[1,3]-dioxin-6-yl)methyl]-5-oxo-4,5-dihydro-[1,2,4]triazol-1-yl}thiophene-2-carboxylic Acid (7a) 3-(3-{[3-(t-Butoxycarbonylaminomethyl)-4-cyanophenylamino]-(8-methoxy-4H-benzo[1,3]-dioxin-6-yl)methyl}-5-oxo-4,5-dihydro-[1,2,4]triazol-1-yl)thiophene-2-carboxylic Acid Methyl Ester

[Chemical Formula 100]

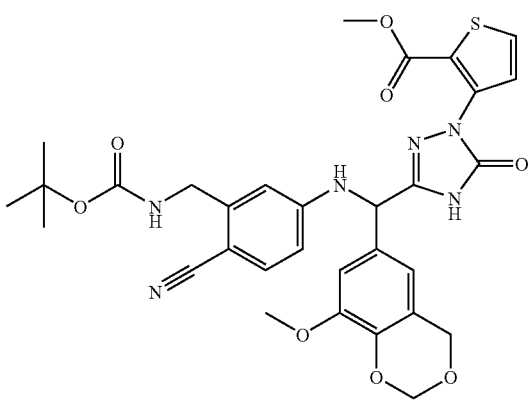

To a mixture of {2-[3-(t-butoxycarbonylaminomethyl)-4-cyanophenylimino]-2-(8-methoxy-4H-benzo[1,3]-dioxin-6-yl)-1-methylsulfanylethylidene}carbamic acid methyl ester (Example (2c))(101 mg) and THF (2.0 mL) there were added 3-hydrazinothiophene-2-carboxylic acid methyl ester (33.1 mg) and triethylamine (27.9 μL), and the mixture was stirred at 65° C. for 15 hours under a nitrogen atmosphere. The solvent in the mixture was distilled off. DMF (2.0 mL) was added to the residue, and the mixture was stirred at 85° C. for 16 hours under a nitrogen atmosphere. The solvent in the mixture was distilled off, and methanol (5 mL) and acetic acid (52.1 μL) were added to the residue. Sodium cyanotrihydroborate (114 mg) was then added to the mixture and the mixture was stirred overnight at room temperature. Water (25 mL) and ethyl acetate (50 mL) were added to the mixture, and after sufficiently shaking the mixture, the organic layer was separated off. The organic layer was washed twice with water (25 mL) and once with saturated aqueous sodium chloride (25 mL) in that order, and dried over anhydrous magnesium sulfate. The mixture was filtered to obtain a filtrate, and the solvent in the filtrate was distilled off under reduced pressure. The residue was purified by NAM silica gel column chromatography (methanol-ethyl acetate mixture) to obtain the target compound (103 mg) as a colorless solid.

¹H-NMR(CD)₃OD) δ 1.45(s, 9H) 3.77(s, 3H) 3.85(s, 3H) 4.31(d, J=5.7 Hz, 2H) 4.87(s, 2H) 5.25(s, 2H) 5.55(s, TH) 6.69(dd, J=8.4, 1.8 Hz, 1H) 6.79(d, J=1.8 Hz, 2H) 7.00(d, J=1.8 Hz, 1H) 7.23(d, J=5.4 Hz, 1H) 7.42(d, J=8.4 Hz, 1H) 7.77(d, J=5.4 Hz, 1H)

(7b) 3-{3-[(1-Imino-2,3-dihydro-1H-isoindol-5-ylamino)-(8-methoxy-4H-benzo[1,3]-dioxin-6-yl)methyl]-5-oxo-4,5-dihydro-[1,2,4]triazol-1-yl}thiophene-2-carboxylic Acid

[Chemical Formula 101]

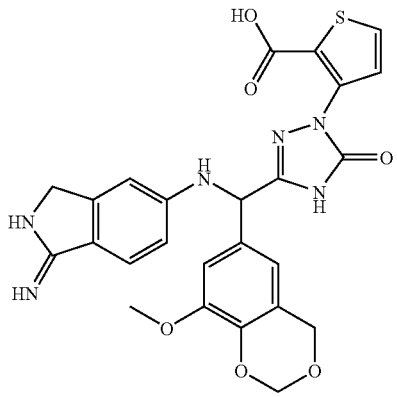

To a mixture of 3-(3-{[3-(t-butoxycarbonylaminomethyl)-4-cyanophenylamino]-(8-methoxy-4H-benzo[1,3]-dioxin-6-yl)methyl}-5-oxo-4,5-dihydro-[1,2,4]triazol-1-yl)thiophene-2-carboxylic acid methyl ester (103 mg), methanol (2.0 mL) and THF (1 mL) there was added a 5N sodium hydroxide aqueous solution (159 μL), and the mixture was stirred overnight at room temperature. After neutralizing the mixture with acetic acid, the solvent in the mixture was distilled off under reduced pressure.

Dichloromethane (4.0 mL) and TFA (1.0 mL) were added to the residue, which was then stirred at room temperature for 2 hours. Toluene (10 mL) was added to the mixture, and the solvent in the mixture was distilled off. The residue was purified by reverse-phase high performance liquid chromatography (acetonitrile/water mixed solvent, 0.1% acetic acid) to obtain the target compound (11.5 mg).

¹H-NMR (CD₃OD) δ 3.85(s, 3H) 4.55(d, J=19.1 Hz, 1H) 4.68(d, J=19.1 Hz, 1H) 4.88(s, 2H) 5.22(s, 2H) 5.55(s, 1H) 6.81(s, 1H) 6.92(s, 1H) 6.94(dd, J=8.6, 2.2 Hz, 1H) 7.05(d, J=2.2 Hz, 1H) 7.10(d, J=6.2 Hz, 1H) 7.46(d, J=6.2 Hz, 1H) 7.73(d, J=8.6 Hz, 1H)

(7c)(R)- and (S)-3-{3-[(1-Imino-2,3-dihydro-1H-isoindol-5-ylamino)-(8-methoxy-4H-benzo[1,3]-dioxin-6-yl)methyl]-5-oxo-4,5-dihydro-[1,2,4]triazol-1-yl}thiophene-2-carboxylic Acid

[Chemical Formula 102]

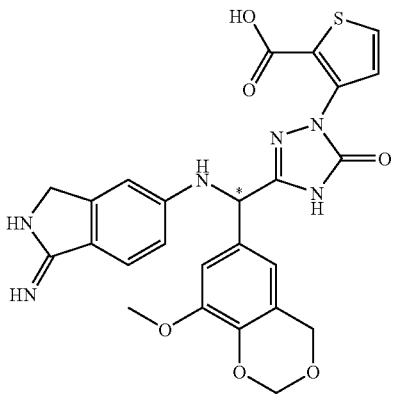

A SUMICHIRAL OA-2500 column was used for separation (optical resolution) of 3-{3-[(1-imino-2,3-dihydro-1H-isoindol-5-ylamino)-(8-methoxy-4H-benzo[1,3]-dioxin-6-yl)methyl]-5-oxo-4,5-dihydro-[1,2,4]triazol-1-yl}thiophene-2-carboxylic acid (9 mg) under the following conditions, and the first eluting enantiomer (3.1 mg) of the title compound was obtained.

¹H-NMR (CD₃OD) δ 3.84(s, 3H) 4.51-4.66(m, 4H) 4.88(s, 2H) 5.24(s, 2H) 5.54(s, 1H) 6.82(s, 1H) 6.91-6.94(m, 2H) 7.05(s, 1H) 7.08(d, J=5.0 Hz, 1H) 7.43(d, J=5.0 Hz, 1H) 7.73(d, J=8.4 Hz, 1H)

HPLC retention time: 15 min. (Column name: SUMICHIRAL OA-2500, 30 mmφ×25 cm, Manufacturer: Sumika Chemical Analysis Service, Ltd., Mobile phase: 50 mM ammonium acetate-methanol solution, Elution rate: mL/min)

Example 8

2-(2-Aminophenyl)-5-{[3-(2-dimethylaminoethoxy)-5-ethyl-2-fluorophenyl]-(1-imino-2,3-dihydro-1H-isoindol-5-ylamino)methyl}-2,4-dihydro-[1,2,4]triazol-3-one bistrifluoroacetate (8a) [2-Bromo-5-({[3-(2-dimethylaminoethoxy)-5-ethyl-2-fluorophenyl]-[1-(2-nitrophenyl)-5-oxo-4,5-dihydro-1H-[1,2,4]triazol-3-yl]methyl}amino)benzyl]carbamic Acid t-Butyl Ester Trifluoroacetate

[Chemical Formula 103]

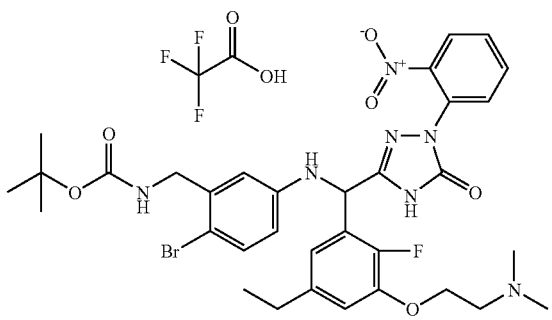

To a mixture of {2-[4-bromo-3-(t-butoxycarbonylaminomethyl)phenylimino]-2-[3-(2-dimethylaminoethoxy)-5-ethyl-2-fluorophenyl]-1-methylsulfanylethylidene}carbamic acid methyl ester (Example (3f))(161 mg) and DMF (10 mL) there was added 2-nitrophenylhydrazine (63.3 mg), and after stirring under a nitrogen atmosphere at room temperature for 72 hours, stirring was continued at 90° C. for 20 hours. The solvent in the mixture was distilled off.

Methanol (15 mL) and acetic acid (42.4 μL) were added to the residue. Sodium cyanotrihydroborate (124 mg) was then added to the mixture and the mixture was stirred at room temperature for 20 hours. The mixture was filtered to obtain a filtrate, and the solvent in the filtrate was distilled off under reduced pressure. The residue was purified by reverse-phase high performance liquid chromatography (acetonitrile/water mixed solvent, 0.1% trifluoroacetic acid) to obtain the target compound (76 mg).

$^1$H-NMR (CD$_3$OD) δ 1.23(t, J=7.5 Hz, 3H) 1.45(s, 9H) 2.64(q, J=7.5 Hz, 2H) 3.03(s, 6H) 3.64(t, J=5.6 Hz, 2H) 4.18(br.s, 2H) 4.45(t, J=5.6 Hz, 2H) 5.84(s, 1H) 6.54(dd, J=8.5, 2.3 Hz, 1H) 6.77(d, J=2.3 Hz, 1H) 7.01-7.05(m, 2H) 7.26(d, J=8.5 Hz, 1H) 7.57(td, J=8.1, 1.1 Hz, 1H) 7.69(dd, J=8.1, 1.1 Hz, 1H) 7.76(td, J=8.1, 1.1 Hz, 1H) 7.97(dd, J=8.1, 1.1 Hz, 1H)

(8b) [5-({[1-(2-Aminophenyl)-5-oxo-4,5-dihydro-1H-[1,2,4]triazol-3-yl]-[3-(2-dimethylaminoethoxy)-5-ethyl-2-fluorophenyl]methyl}amino)-2-bromobenzyl]carbamic Acid t-butyl Ester Trifluoroacetate

[Chemical Formula 104]

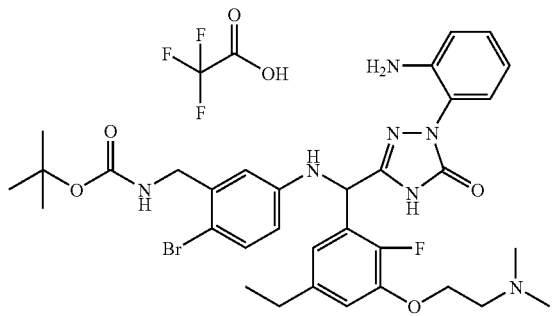

Iron powder (70 mg) was added to [2-bromo-5-({[3-(2-dimethylaminoethoxy)-5-ethyl-2-fluorophenyl]-[1-(2-nitrophenyl)-5-oxo-4,5-dihydro-1H-[1,2,4]triazol-3-yl]methyl}amino)benzyl] carbamic acid t-butyl ester trifluoroacetic acid salt (76 mg) and a methanol:acetic acid:water (1:1:1) mixed solvent (6 mL) under a nitrogen atmosphere, and the mixture was heated for 18 hours at 60° C. The mixture was filtered to obtain a filtrate, and the solvent in the filtrate was distilled off under reduced pressure. The residue was purified by reverse-phase high performance liquid chromatography (acetonitrile/water mixed solvent, 0.1% trifluoroacetic acid) to obtain the target compound (44 mg) as a colorless oil.

$^1$H-NMR (CD$_3$OD) δ 1.22(t, J=7.6 Hz, 3H) 1.45(s, 9H) 2.64(q, J=7.6 Hz, 2H) 3.00(s, 6H) 3.62(m, 2H) 4.18(br.s, 2H) 4.42(t, J=5.6 Hz, 2H) 5.88(s, 1H) 6.55(dd, J=8.4, 2.4 Hz, 1H) 6.72(dd, J=8.4, 2.9 Hz, 1H) 6.79(d, J=2.4 Hz, 1H) 7.01-7.12 (m, 5H) 7.26(d, J=8.4 Hz, 1H)

(8c) 2-(2-Aminophenyl)-5-{[3-(2-dimethyl amino ethoxy)-5-ethyl-2-fluorophenyl]-(1-imino-2,3-dihydro-1H-isoindol-5-ylamino)methyl}-2,4-dihydro-[1,2,4]triazol-3-one Bistrifluoroacetate

[Chemical Formula 105]

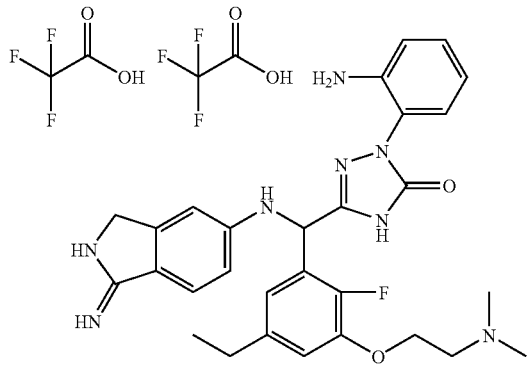

To a mixture of [5-({[1-(2-aminophenyl)-5-oxo-4,5-dihydro-1H-[1,2,4]triazol-3-yl]-[3-(2-dimethylaminoethoxy)-5-ethyl-2-fluorophenyl]methyl}amino)-2-bromobenzyl]carbamic acid t-butyl ester trifluoroacetic acid salt (44 mg) in DMF (0.5 mL) there were added tris(dibenzylideneacetone)dipalladium(0)(5.8 mg), 1,1'-bis(diphenylphosphino)ferrocene (8.4 mg) and zinc cyanide (4.4 mg) under a nitrogen atmosphere, and the mixture was heated for 20 hours at 120° C. After cooling the mixture, the mixture was purified by reverse-phase high performance liquid chromatography (acetonitrile/water mixed solvent, 0.1% trifluoroacetic acid) to obtain the target compound (12.6 mg).

$^1$H-NMR (CD$_3$OD) δ 1.21(t, J=7.9 Hz, 3H) 2.64(q, J=7.9 Hz, 2H) 3.01(s, 6H) 3.63(t, J=5.5 Hz, 2H) 4.44(t, J=5.5 Hz, 2H) 4.62(d, J=18.9 Hz, 1H) 4.68(d, J=18.9 Hz, 1H) 6.05(s, 1H) 6.82(td, J=7.3, 1.6 Hz, 1H) 6.92-6.98(m, 3H) 7.03(dd, J=6.4, 1.6 Hz, 1H) 7.08(dd, J=7.3, 1.6 Hz, 1H) 7.17(td, J=7.3, 1.6 Hz, 1H) 7.22(dd, J=7.3, 1.6 Hz, 11) 7.81(d, J=8.3 Hz, 1H)

Example 9

5-{3-[(2-Fluoro-4,5-dimethoxyphenyl)-(1-imino-2,3-dihydro-1H-isoindol-5-ylamino)methyl]-5-oxo-4,5-dihydro-[1,2,4]triazol-1-yl}-3H-imidazole-4-carboxylic Acid (9a) (2-Cyano-5-{[cyano-(2-fluoro-4,5-dimethoxyphenyl)methyl]amino}benzyl) carbamic Acid t-Butyl Ester

[Chemical Formula 106]

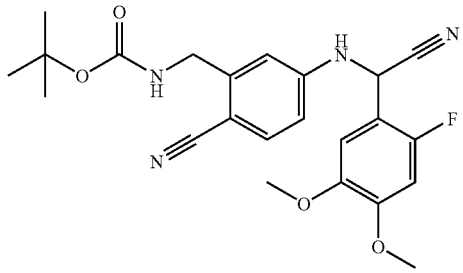

To a mixture of Yb(OTf)$_3$(0.124 g) and THF (5 mL) there were added (5-amino-2-cyanobenzyl)carbamic acid t-butyl ester (Example (1g))(0.494 g), 2-fluoro-4,5-dimethoxybenzaldehyde (0.368 g), MS3A (1 g) and trimethylsilyl cyanide (533 mg) in that order under a nitrogen atmosphere, and the mixture was stirred at room temperature for 14 hours. Ethyl acetate (100 mL) and water (50 mL) were added to the mixture and filtration was performed with Celite. After sufficiently shaking the mixture, the organic layer was separated off and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (0.749 g) as a colorless solid.

$^1$H-NMR (CDCl$_3$) δ 1.45(s, 9H) 3.81(s, 3H) 3.83(s, 3H) 4.43(d, J=5.7 Hz, 2H) 4.52(d, J=7.4 Hz, 1H) 5.16(br.s, 1H) 5.58(d, J=7.4 Hz, 1H) 6.69(dd, J=8.6, 2.7 Hz, 1H) 6.73(d, J=11.2 Hz, 1H) 6.84(s, 1H) 7.02(d, J=6.8 Hz, 1H) 7.55(d, J=8.6 Hz, 1H)

(9b) [2-Cyano-(5-{[(2-fluoro-4,5-dimethoxyphenyl)thiocarbamoyl]methyl}amino)benzyl]carbamic acid t-butyl ester

[Chemical Formula 107]

To a mixture of (2-cyano-5-{[cyano-(2-fluoro-4,5-dimethoxyphenyl)methyl]amino}benzyl)carbamic acid t-butyl ester (749 mg) and methanol (10 mL) there was added a 20% aqueous solution of ammonium sulfide (2.9 mL), and the mixture was stirred at room temperature for 15 hours. Ethyl acetate (200 mL) and water (50 mL) were added to the mixture, and after sufficiently shaking the mixture, the organic layer was separated off. The organic layer was washed with water (50 mL) and saturated aqueous sodium chloride (50 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (699 mg) as a colorless solid.

$^1$H-NMR (CDCl$_3$) δ 1.45(s, 9H) 3.80(s, 3H) 3.87(s, 3H) 4.37(d, J=5.9 Hz, 2H) 5.07(br.s, 1H) 5.41(d, J=6.5 Hz, 1H) 5.92(br.s, 1H) 6.45(d, J=8.5 Hz, 1H) 6.69(d, J=11.6 Hz, 1H) 6.71(s, 1H) 6.82(d, J=7.2 Hz, 1H) 7.40(d, J=8.5 Hz, 1H) 7.46(s, 2H)

(9c) {2-[3-(t-Butoxycarbonylaminomethyl)-4-cyanophenylimino]-2-(2-fluoro-4,5-dimethoxyphenyl)-1-methylsulfanylethylidene}carbamic Acid Methyl Ester

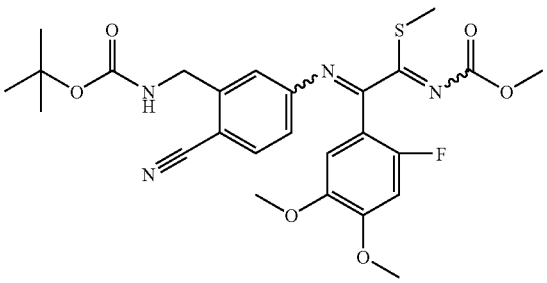

[Chemical Formula 108]

To a mixture of [2-cyano-(5-{[(2-fluoro-4,5-dimethoxyphenyl)thiocarbamoyl]methyl}amino)benzyl]carbamic acid t-butyl ester (0.357 g) and acetonitrile (10 mL) there was added trimethyloxonium tetrafluoroborate (0.116 g) under a nitrogen atmosphere, and the mixture was stirred at room temperature for 20 minutes. Ethyl acetate (100 mL) and saturated aqueous sodium hydrogen carbonate (50 mL) were added to the mixture, the mixture was sufficiently shaken, and then the organic layer was separated off, washed with saturated aqueous sodium chloride (50 mL) and dried over anhydrous magnesium sulfate. The mixture was filtered to obtain a filtrate, and the solvent in the filtrate was distilled off under reduced pressure. Ethyl acetate (5 mL) and manganese dioxide (0.65 g) were added to the residue in that order, and the mixture was stirred at room temperature for 5 hours. The mixture was filtered through Celite, the Celite was washed with ethyl acetate (50 mL), and the washed solution was combined with the filtrate. The solvent in the filtrate was distilled off under reduced pressure. Toluene (8 mL), 2,4,6-collidine (0.218 mL) and methyl chloroformate (0.104 mL) were added to the residue in that order, and the mixture was stirred at 80° C. for 8 hours under a nitrogen atmosphere. The mixture was cooled to room temperature, and then ethyl acetate (100 mL) and 1N hydrochloric acid (50 mL) were added. The mixture was sufficiently shaken, and then the organic layer was separated off, washed with saturated aqueous sodium hydrogen carbonate (50 mL) and saturated aqueous sodium chloride (50 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (0.274 g) as an off-white solid.

$^1$H-NMR (CDCl$_3$) Main isomer 1.45(s, 9H) 2.33(s, 3H) 3.64(s, 3H) 3.82(s, 3H) 3.83(s, 3H) 4.51(d, J=6.5 Hz, 2H) 5.11(br.s, 1H) 6.62(d, J=11.9 Hz, 1H) 6.97(d, J=8.2 Hz, 1H) 7.13(s, 1H) 7.42(d, J=7.0 Hz, 1H) 7.58(d, J=8.2 Hz, 1H)

(9d) 3-Allyl-5-(3-{[3-(t-butoxycarbonylaminomethyl)-4-cyanophenylamino]-(2-fluoro-4,5-dimethoxyphenyl)methyl}-5-oxo-4,5-dihydro-[1,2,4]triazol-1-yl)-3H-imidazole-4-carboxylic Acid Ethyl Ester

[Chemical Formula 109]

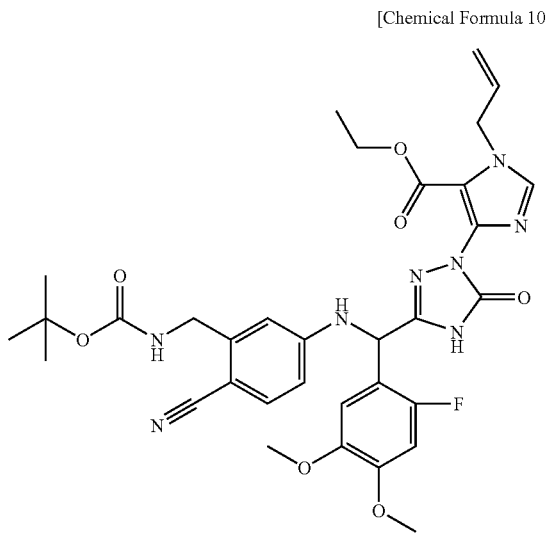

To a mixture of {2-[3-(t-butoxycarbonylaminomethyl)-4-cyanophenylimino]-2-(2-fluoro-4,5-dimethoxyphenyl)-1-methylsulfanylethylidene}carbamic acid methyl ester (67 mg) in DMF (3 mL) there were added triethylamine (0.036 mL) and 3-allyl-5-hydrazino-3H-imidazole-4-carboxylic acid ethyl ester (33 mg) under a nitrogen atmosphere, and the mixture was stirred at 85° C. for 24 hours. The solvent in the mixture was distilled off.

Methanol (6.15 mL) and acetic acid (42.4 μL) were added to the residue. Sodium cyanotrihydroborate (61.8 mg) was then added to the mixture and the mixture was stirred at room temperature for 20 hours. The mixture was purified by reverse-phase high performance liquid chromatography (acetonitrile/water mixed solvent, 0.1% acetic acid) to obtain the target compound (17 mg).

$^1$H-NMR (CD$_3$OD) δ 1.10(t, J=7.0 Hz, 3H) 1.45(s, 9H) 3.77(s, 3H) 3.83(s, 3H) 4.15(q, J=7.0 Hz, 2H) 4.30(m, 2H) 5.00(d, J=6.0 Hz, 2H) 5.14(dd, J=17.3, 1.5 Hz, 1H) 5.23(dd, J=10.9, 1.5 Hz, 1H) 5.87(s, 1H) 6.01-6.10(m, 1H) 6.68(dd, J=8.2, 2.2 Hz, 1H) 6.80(d, J=2.2 Hz, 1H) 6.85(d, J=12.2 Hz, 1H) 7.05(d, J=7.0 Hz, 1H) 7.43(d, J=8.2 Hz, 1H) 7.92(s, 1H)

(9e) 3-Allyl-5-(3-{[3-(t-butoxycarbonylaminomethyl)-4-cyanophenylamino]-(2-fluoro-4,5-dimethoxyphenyl)methyl}-5-oxo-4,5-dihydro-[1,2,4]triazol-1-yl)-3H-imidazole-4-carboxylic Acid

[Chemical Formula 110]

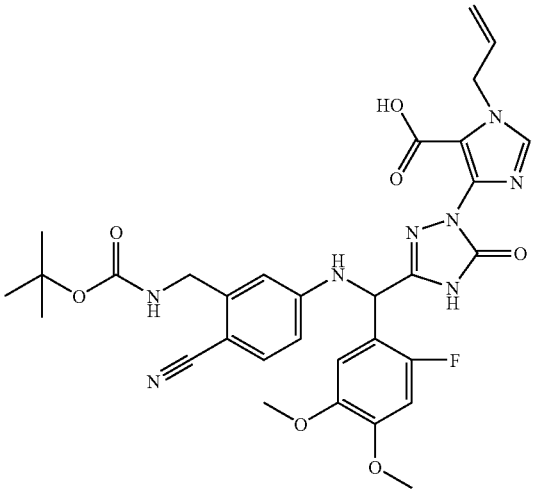

To a mixture of 3-allyl-5-(3-{[3-(t-butoxycarbonylaminomethyl)-4-cyanophenylamino]-(2-fluoro-4,5-dimethoxyphenyl)methyl}-5-oxo-4,5-dihydro-[1,2,4]triazol-1-yl)-3H-imidazole-4-carboxylic acid ethyl ester (17 mg) and methanol (1 mL) there was added a 5N sodium hydroxide aqueous solution (0.10 mL), and the mixture was stirred overnight at room temperature. The mixture was purified by reverse-phase high performance liquid chromatography (acetonitrile/water mixed solvent, 0.1% acetic acid) to obtain the target compound (2.5 mg).

$^1$H-NMR (CD$_3$OD) δ 1.45(s, 9H) 3.77(s, 3H) 3.83(s, 3H) 4.28(d, J=16.2 Hz, 1H) 4.35(d, J=16.2 Hz, 1H) 5.04(d, J=6.1 Hz, 2H) 5.16(dd, J=17.5, 1.5 Hz, 1H) 5.22(dd, J=10.7, 1.5 Hz, 1H) 5.85(s, 1H) 6.02-60.11(m, 1H) 6.66(dd, J=8.2, 2.2 Hz, 1H) 6.77(d, J=2.2 Hz, 1H) 6.83(d, J=11.6 Hz, 1H) 7.01(d, J=7.2 Hz, 1H) 7.41(d, J=8.2 Hz, 1H) 7.81(s, 1H)

(9f) 5-{3-[(2-Fluoro-4,5-dimethoxyphenyl)-(1-imino-2,3-dihydro-1H-isoindol-5-ylamino)methyl]-5-oxo-4,5-dihydro-[1,2,4]triazol-1-yl}-3H-imidazole-4-carboxylic Acid

[Chemical Formula 111]

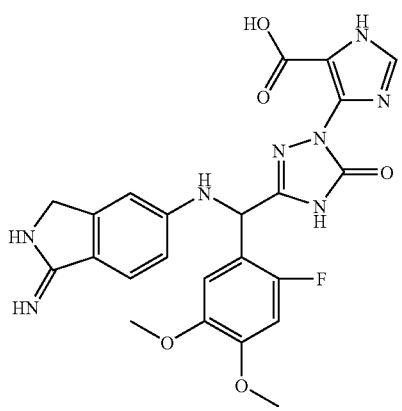

To a mixture of 3-allyl-5-(3-{[3-(t-butoxycarbonylaminomethyl)-4-cyanophenylamino]-(2-fluoro-4,5-dimethoxyphenyl)methyl}-5-oxo-4,5-dihydro-[1,2,4]triazol-1-yl)-

3H-imidazole-4-carboxylic acid (2.5 mg) in dichloromethane (2 mL) there were added tetrakis(triphenylphosphine)palladium(0)(0.5 mg) and 1,3-dimethylbarbituric acid (1.5 mg) under a nitrogen atmosphere, and the mixture was stirred overnight at room temperature. Trifluoroacetic acid (0.4 mL) was added, the mixture was stirred at room temperature for 30 minutes, and then toluene (10 mL) was added to the mixture and the solvent in the mixture was distilled off. The residue was purified by reverse-phase high performance liquid chromatography (acetonitrile/water mixed solvent, 0.1% acetic acid) to obtain the target compound (0.25 mg).

¹H-NMR (CD₃OD) δ 3.84(s, 3H) 3.85(s, 3H) 4.14(d, J=14.3 Hz, 1H) 4.27(d, J=14.3 Hz, 1H) 5.72(s, 1H) 6.89(d, J=2.0 Hz, 1H) 6.90(d, J=11.5 Hz, 1H) 6.93(dd, J=8.5, 2.0 Hz, 1H) 7.06 (d, J=6.5 Hz, 1H) 7.48(d, J=8.5 Hz, 1H) 7.62(s, 1H)

Example 10

(R)- and (S)-2-(2-Aminophenyl)-5-[(2-fluoro-4,5-dimethoxyphenyl)-(1-imino-2,3-dihydro-1H-isoindol-5-ylamino)methyl]-2,4-dihydro-[1,2,4]-triazol-3-one Acetate (10a) (2-Bromo-5-{[cyano-(2-fluoro-4,5-dimethoxyphenyl)methyl]amino}benzyl) carbamic Acid t-Butyl Ester

[Chemical Formula 112]

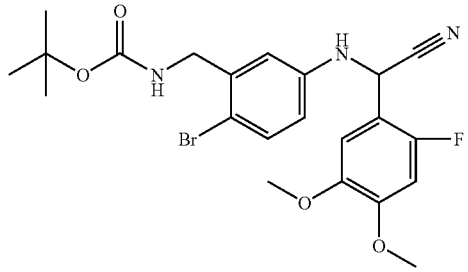

To a mixture of Yb(OTf)₃(0.399 g) and dichloromethane (25 mL) there were added (5-amino-2-bromobenzyl)carbamic acid t-butyl ester (Example (3a))(1.95 g), 2-fluoro-4,5-dimethoxybenzaldehyde (1.19 g), MS3A (2.58 g) and trimethylsilyl cyanide (1.29 mL) in that order under a nitrogen atmosphere, and the mixture was stirred at room temperature for 16 hours. The solvent in the mixture was distilled off under reduced pressure, ethyl acetate (200 mL) and water (100 mL) were added to the residue, and after sufficiently shaking the mixture, the organic layer was separated off, washed with saturated aqueous sodium chloride (100 mL) and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (2.98 g) as a colorless solid.

¹H-NMR (CDCl₃) δ 1.45(s, 9H) 3.89(s, 3H) 3.91(s, 3H) 4.33(d, J=6.1 Hz, 2H) 5.11(br.s, 1H) 5.49(s, 1H) 6.58(dd, J=8.7, 2.7 Hz, 1H) 6.70(d, J=11.4 Hz, 1H) 6.81(s, 1H) 7.01(d, J=6.9 Hz, 1H) 7.40(d, J=8.7 Hz, 1H)

(10b) (2-Bromo-5-{[(2-fluoro-4,5-dimethoxyphenyl)thiocarbamoylmethyl]amino}benzyl)carbamic Acid t-Butyl Ester

[Chemical Formula 113]

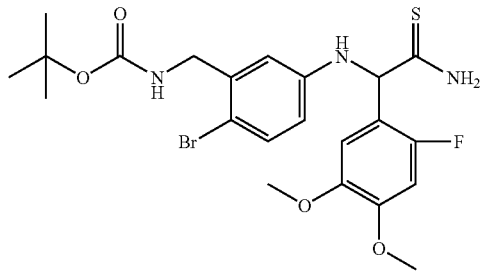

To a mixture of (2-bromo-5-{[cyano-(2-fluoro-4,5-dimethoxyphenyl)methyl]amino}benzyl) carbamic acid t-butyl ester (2.96 g) and methanol (50 mL) there was added a 20% aqueous solution of ammonium sulfide (10.3 mL), and the mixture was stirred at room temperature for 16 hours. Ethyl acetate (200 mL) and water (400 mL) were added to the mixture, and after sufficiently shaking the mixture, the organic layer was separated off. The organic layer was washed twice with water (200 mL) and once with saturated aqueous sodium chloride (200 mL) in that order, and dried over anhydrous magnesium sulfate. The mixture was filtered to obtain a filtrate and the solvent in the filtrate was distilled off under reduced pressure to obtain the target compound (3.01 g) as an off-white solid.

¹H-NMR (CDCl₃) δ 1.45(s, 9H) 3.82(s, 3H) 3.86(s, 3H) 4.27(d, J=5.9 Hz, 2H) 4.98(br.s, 1H) 5.32(s, 1H) 5.92(br.s, 1H) 6.39(dd, J=8.3, 2.6 Hz, 1H) 6.67(d, J=11.3 Hz, 1H) 6.70(d, J=2.6 Hz, 1H) 6.83(d, J=6.9 Hz, 1H) 7.30(d, J=8.3 Hz, 1H) 7.50(s, 1H) 7.93(s, 1H)

(10c) {2-[4-Bromo-3-(t-butoxycarbonylaminomethyl)phenyl]amino}-2-(2-fluoro-4,5-dimethoxyphenyl)thioacetimidic Acid Methyl Ester

[Chemical Formula 114]

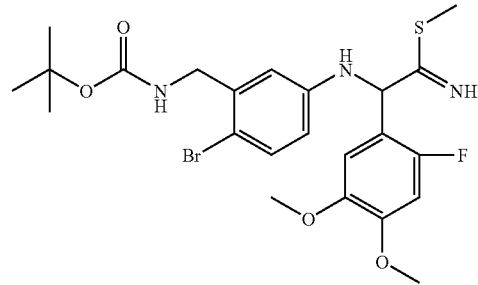

To a mixture of (2-bromo-5-{[(2-fluoro-4,5-dimethoxyphenyl)thiocarbamoylmethyl]amino}benzyl)carbamic acid t-butyl ester (3.02 g) and dichloromethane (200 mL) there was added trimethyloxonium tetrafluoroborate (0.971 g) under a nitrogen atmosphere, and the mixture was stirred at room temperature for 15 hours. Ethyl acetate (300 mL) and saturated aqueous sodium hydrogen carbonate (150 mL) were added to the mixture, the mixture was sufficiently shaken, and then the organic layer was separated off, washed with saturated aqueous sodium chloride (150 mL) and dried over anhydrous magnesium sulfate. The mixture was filtered to obtain a filtrate and the solvent in the filtrate was distilled off under reduced pressure to obtain the target compound (3.03 g) as an off-white solid.

¹H-NMR (CDCl₃) δ 1.45(s, 9H) 2.30(s, 3H) 3.80(s, 3H) 3.86(s, 3H) 4.28(d, J=5.9 Hz, 2H) 4.98(br.s, 1H) 5.30(br.s, 1H) 5.92(br.s, 1H) 6.39(d, J=8.0 Hz, 1H) 6.61-6.80(m, 3H) 7.30(br.s, 1H)

(10d) {2-[4-Bromo-3-(t-butoxycarbonylaminomethyl)phenylimino]-2-(2-fluoro-4,5-dimethoxyphenyl)-1-methylsulfanylethylidene}carbamic Acid Methyl Ester

[Chemical Formula 115]

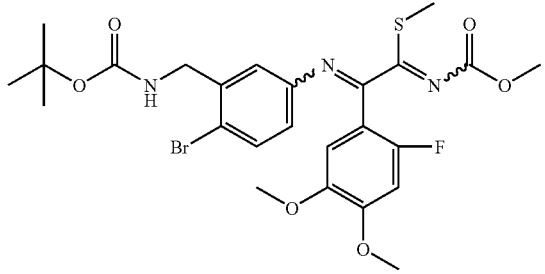

To a mixture of {2-[4-bromo-3-(t-butoxycarbonylaminomethyl)phenyl]amino}-2-(2-fluoro-4,5-dimethoxyphenyl)-thioacetimidic acid methyl ester (3.03 g) and toluene (150 mL) there were added 2,4,6-collidine (2.22 mL) and methyl chloroformate (1.06 mL) in that order, and the mixture was stirred under a nitrogen atmosphere at 85° C. for 20 hours. The mixture was cooled to room temperature, and then ethyl acetate (300 mL) and a 5% aqueous solution of sulfuric acid (200 mL) were added. The mixture was sufficiently shaken, and then the organic layer was separated off, washed with saturated aqueous sodium hydrogen carbonate (200 mL), water (200 mL) and saturated aqueous sodium chloride (200 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (0.590 g).

¹H-NMR (CDCl₃) Main isomer δ 1.45(s, 9H) 2.46(s, 3H) 3.58(s, 3H) 3.84(s, 3H) 3.95(s, 3H) 4.29(d, J=6.4 Hz, 2H) 4.85(br.s, 1H) 6.60(d, J=11.2 Hz, 1H) 6.81(d, J=8.0 Hz, 1H) 7.06(s, 1H) 7.42(d, J=7.0 Hz, 1H) 7.46(d, J=8.0 Hz, 1H)

(10e) [2-Bromo-5-({(2-fluoro-4,5-dimethoxyphenyl)-[1-(2-nitrophenyl)-5-oxo-4,5-dihydro-1H-[1,2,4]triazol-3-yl]methyl}amino)benzyl]carbamic Acid t-Butyl Ester

[Chemical Formula 116]

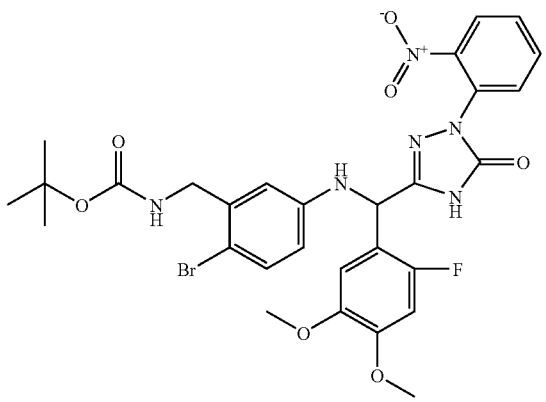

To a mixture of {2-[4-bromo-3-(t-butoxycarbonylaminomethyl)phenylimino]-2-(2-fluoro-4,5-dimethoxyphenyl)-1-methylsulfanylethylidene}carbamic acid methyl ester (492 mg) in DMF (25 mL) there was added 2-nitrophenylhydrazine (185 mg), and the mixture was stirred under a nitrogen atmosphere, at room temperature for 72 hours, and then at 90° C. for 20 hours. The solvent in the mixture was distilled off.

Methanol (20 mL) and acetic acid (94.4 μL) were added to the residue. Sodium cyanotrihydroborate (413 mg) was then added to the mixture and the mixture was stirred at room temperature for 20 hours. The mixture was filtered to obtain a filtrate, and the solvent in the filtrate was distilled off under reduced pressure. Ethyl acetate (100 mL) and water (50 mL) were added to the residue, and after sufficiently shaking the mixture, the organic layer was separated off and washed twice with water (50 mL) and once with saturated aqueous sodium chloride (50 mL) in that order and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (232 mg).

¹H-NMR (CD₃OD) δ 1.44(s, 9H) 3.81(s, 3H) 3.82(s, 3H) 4.20(m, 2H) 5.79(s, 1H) 6.56(dd, J=8.7, 2.3 Hz, 1H) 6.76(d, J=2.3 Hz, 1H) 6.82(d, J=11.7 Hz, 1H) 7.03(d, J=6.6 Hz, 1H) 7.26(d, J=8.7 Hz, 1H) 7.55(td, J=7.6, 1.4 Hz, 1H) 7.69(dd, J=7.6, 1.4 Hz, 1H) 7.74(td, J=7.6, 1.4 Hz, 1H) 7.98(dd, J=7.6, 1.4 Hz, 1H)

(10f) [5-({[1-(2-Aminophenyl)-5-oxo-4,5-dihydro-1H-[1,2,4]triazol-3-yl]-(2-fluoro-4,5-dimethoxyphenyl)methyl}amino)-2-bromobenzyl]carbamic Acid t-Butyl Ester

[Chemical Formula 117]

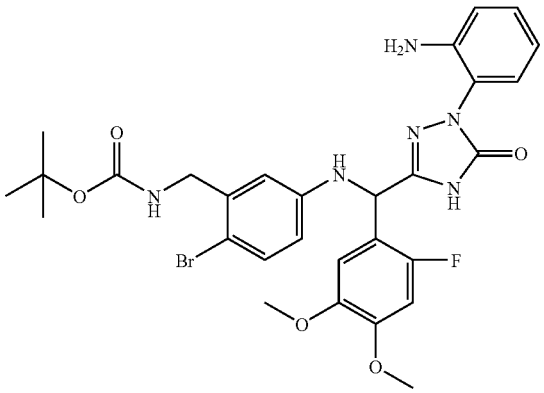

Iron powder (231 mg) was added to [2-bromo-5-({(2-fluoro-4,5-dimethoxyphenyl)-[1-(2-nitrophenyl)-5-oxo-4,5-dihydro-1H-[1,2,4]triazol-3-yl]methyl}amino)benzyl]carbamic acid t-butyl ester (232 mg) and a methanol:acetic acid: water (1:1:1) mixed solvent (24 mL), and the mixture was heated for 18 hours at 60° C. under a nitrogen atmosphere. The solvent in the mixture was distilled off under reduced pressure, and ethyl acetate (100 mL) and water (25 mL) were added to the residue. Sodium hydrogen carbonate was gradually added to the mixture to adjust the pH to 8. After sufficiently shaking the mixture, the organic layer was separated off and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (147 mg) as an off-white solid.

¹H-NMR (CDCl₃) δ 1.42(s, 9H) 3.64(s, 3H) 3.79(s, 3H) 4.24(d, J=6.9 Hz, 2H) 4.96(d, J=5.8 Hz, 1H) 5.06(t, J=6.9 Hz, 1H) 5.68(d, J=5.8 Hz, 1H) 6.49(dd, J=8.4, 2.2 Hz, 1H) 6.68(d, J=11.3 Hz, 1H) 6.72(br.s, 1H) 6.81(d, J=7.6 Hz, 1H) 6.83(t, J=7.6 Hz, 1H) 6.93(d, J=6.5 Hz, 1H) 7.15(t, J=7.6 Hz, 1H) 7.23(d, J=8.4 Hz, 1H) 7.30(d, J=7.6 Hz, 1H) 9.99(br.s, 1H) 11.84(br.s, 2H)

(10 g) 2-(2-Aminophenyl)-5-[(2-fluoro-4,5-dimethoxyphenyl)-(1-imino-2,3-dihydro-1H-isoindol-5-ylamino)methyl]-2,4-dihydro-[1,2,4]triazol-3-one trifluoroacetate

[Chemical Formula 118]

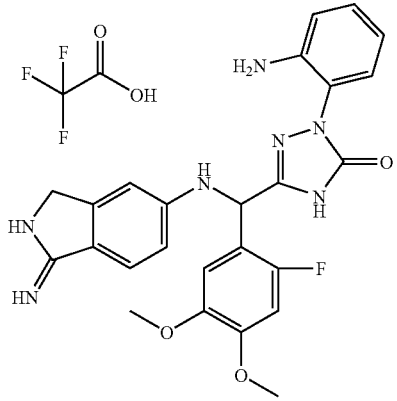

To a mixture of [5-({[1-(2-aminophenyl)-5-oxo-4,5-dihydro-1H-[1,2,4]triazol-3-yl]-(2-fluoro-4,5-dimethoxyphenyl)methyl}amino)-2-bromobenzyl] carbamic acid t-butyl ester (147 mg) and DMF (1 mL) there were added tris(dibenzylideneacetone)dipalladium(0)(20.9 mg), 1,1'-bis(diphenylphosphino)ferrocene (30.3 mg) and zinc cyanide (16.1 mg) under a nitrogen atmosphere, and the mixture was heated for 20 hours at 120° C. After cooling the mixture, the mixture was purified by reverse-phase high performance liquid chromatography (acetonitrile/water mixed solvent, 0.1% trifluoroacetic acid) to obtain the target compound (19.1 mg).

¹H-NMR (CD₃OD) δ 3.78(s, 3H) 3.84(s, 3H) 4.63(d, J=21.0 Hz, 1H) 4.68(d, J=21.0 Hz, 1H) 6.00(s, 1H) 6.88(d, J=11.1 Hz, 1H) 6.91(dd, J=8.4, 1.8 Hz, 1H) 6.93(d, J=1.8 Hz, 1H) 6.96(td, J=7.4 Hz, 1.8 Hz, 1H) 7.01(dd, J=7.4, 1.8 Hz, 1H) 7.05(d, J=6.6 Hz, 1H) 7.21(td, J=7.4 Hz, 1.8 Hz, 1H) 7.32(dd, J=7.4, 1.8 Hz, 1H) 7.80(d, J=8.4 Hz, 1H)

(10h)(R)- and (S)-2-(2-Aminophenyl)-5-[(2-fluoro-4,5-dimethoxyphenyl)-(1-imino-2,3-dihydro-1H-isoindol-5-ylamino)methyl]-2,4-dihydro-[1,2,4]triazol-3-one acetate

[Chemical Formula 119]

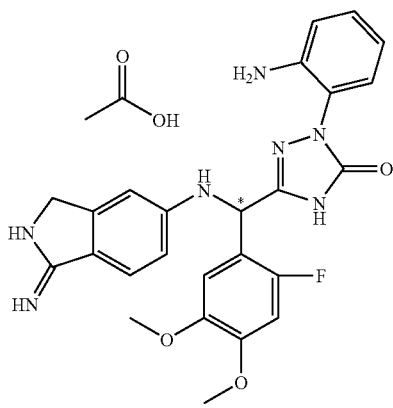

A SUMICHIRAL OA-2500 column was used for separation (optical resolution) of 2-(2-aminophenyl)-5-[(2-fluoro-4,5-dimethoxyphenyl)-(1-imino-2,3-dihydro-1 H-isoindol-5-ylamino)methyl]-2,4-dihydro-[1,2,4]triazol-3-one trifluoroacetic acid salt (60 mg) under the following conditions, and the first eluting enantiomer (13.0 mg) of the title compound was obtained.

¹H-NMR (CD₃OD) δ1.95(s, 3H) 3.72(s, 3H) 3.81(s, 3H) 4.59(s, 2H) 5.93(s, 1H) 6.73(td, J=8.0, 1.7 Hz, 1H) 6.83(d, J=12.2 Hz, 1H) 6.87(dd, J=8.0, 1.7 Hz, 1H) 6.89(d, J=2.1 Hz, 1H) 6.94(dd, J=8.7, 2.1 Hz, 1H) 7.08(d, J=6.6 Hz, 1H) 7.11(td, J=8.0 Hz, 1.7 Hz, 1H) 7.23(dd, J=8.0, 1.7 Hz, 1H) 7.75(d, J=8.7 Hz, 1H)

HPLC retention time: 23 min. (Column name: SUMICHIRAL OA-2500, 20 mmφ×25 cm, Manufacturer: Sumika Chemical Analysis Service, Ltd., Mobile phase: 0.05 M ammonium acetate-methanol solution, Elution rate: 5 mL/min)

Example 11

4-(3-{[2-Fluoro-3-(2-hydroxyethoxy)-5-methoxyphenyl]-(1-imino-2,3-dihydro-1H-isoindol-5-ylamino)methyl}-5-oxo-4,5-dihydro-[1,2,4]triazol-1-yl)oxazole-5-carboxylic acid (11a) 4-Bromo-2-triisopropylsilanyloxazole-5-carboaldehyde

[Chemical Formula 120]

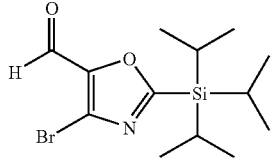

To a mixture of N,N,N'-trimethylethylenediamine (2.86 g) and THF (80 mL) there were added dropwise a 2.6 M hexane solution of n-butyllithium (8.46 mL), and 2-triisopropylsilanyloxazole-5-carboaldehyde [CAS No. 869542-45-0] (5.08 g), in that order at −20° C. under a nitrogen atmosphere. After stirring the mixture at −20° C. for 3 hours, the 2.6 M hexane solution of n-butyllithium (8.46 mL) was again added dropwise, stirring was continued at −20° C. for 3 hours, and then the mixture was cooled to −75° C. and 1,2-dibromotetrafluoroethane (7.12 mL) was added. The mixture was returned to room temperature, and then ethyl acetate (300 mL) and an aqueous ammonium chloride solution (300 mL) were added. After sufficiently shaking the mixture, the organic layer was separated off and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (1.94 g) as a brown liquid.

¹H-NMR (CDCl₃) 1.14(d, J=7.5 Hz, 18H) 1.44(sept, J=7.5 Hz, 3H) 9.84(s, 1H)

(11b) 4-Bromooxazole-5-carboxylic Acid Methyl Ester

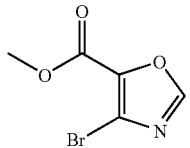

[Chemical Formula 121]

To a mixture of 4-bromo-2-triisopropylsilanyloxazole-5-carboaldehyde (1.94 g) and methanol (40 mL) there were added sodium cyanide (1.43 g) and manganese dioxide (10.2 g) in that order, and the mixture was stirred overnight at room temperature. The mixture was filtered through Celite, the Celite was washed with ethyl acetate (200 mL), and the washed solution was combined with the filtrate. After sufficiently shaking the mixture, the organic layer was separated off and washed with a 1N aqueous sodium hydroxide solution (200 mL), and then dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (0.435 g) as a colorless solid.

$^1$H-NMR (CDCl$_3$) 3.94(s, 3H) 7.93(s, 1H)

(11c) 4-(N,N'-di-t-Butoxycarbonyl)hydrazinooxazole-5-carboxylic Acid Methyl Ester

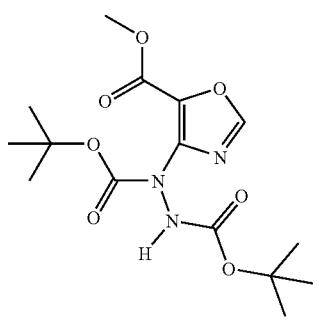

[Chemical Formula 122]

To a mixture of 4-bromooxazole-5-carboxylic acid methyl ester (435 mg) and toluene (5 mL) there were added tris(dibenzylideneacetone)dipalladium(0)(77.3 mg), 1,1'-bis(diphenylphosphino)ferrocene (140 mg), cesium carbonate (687 mg) and di-t-butyl-1,2-hydrazinodicarboxylic acid (490 mg) under a nitrogen atmosphere, and the mixture was heated for 14 hours at 95° C. After cooling the mixture, ethyl acetate (300 mL) and water (100 mL) were added, and after sufficient shaking, the organic layer was separated off and washed with saturated aqueous sodium chloride (100 mL) and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (370 mg) as an off-white solid.

$^1$H-NMR (CDCl$_3$) 1.49(s, 9H) 1.51(s, 9H) 3.94(s, 3H) 7.86(s, 1H)

(11d) 4-Hydrazinooxazole-5-carboxylic Acid Methyl Ester

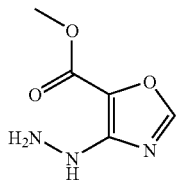

[Chemical Formula 123]

To a mixture of 4-(N,N'-di-t-butoxycarbonyl)hydrazinooxazole-5-carboxylic acid methyl ester (297 mg) and dichloromethane (10 mL) there was added dropwise a 1 M dichloromethane solution of tin tetrachloride (4.16 mL) under a nitrogen atmosphere, and the mixture was stirred overnight at room temperature. After adding ethyl acetate (80 mL) and a small amount of saturated aqueous ammonia to the mixture, a 5N aqueous sodium hydroxide solution was further added to alkaline. After sufficiently shaking the mixture, the organic layer was separated off and the aqueous layer was extracted with ethyl acetate (40 mL). The extract was combined with the previous organic layer and dried over anhydrous magnesium sulfate. The mixture was filtered to obtain a filtrate, and the solvent in the filtrate was distilled off under reduced pressure. The residue was purified by silica gel column chromatography (methanol-ethyl acetate mixture) to obtain the target compound (52 mg) as a colorless solid.

$^1$H-NMR (CDCl$_3$) 3.91(s, 3H) 4.00(br.s, 2H) 4.04(br.s, 1H) 7.71(s, 1H)

(11e) 4-(3-{[3-(t-Butoxycarbonylaminomethyl)-4-cyanophenylamino]-[2-fluoro-5-methoxy-3-(2-triisopropylsilanyloxyethoxy)phenyl]methyl}-5-oxo-4,5-dihydro-[1,2,4]triazol-1-yl)oxazole-5-carboxylic acid methyl ester

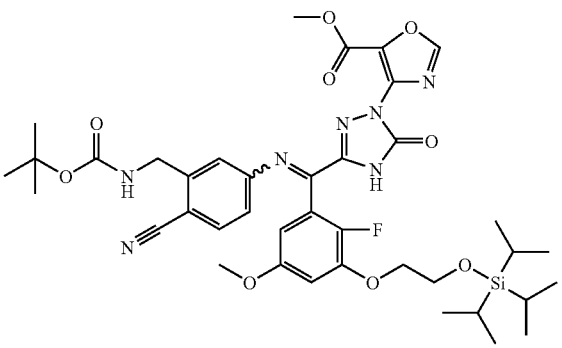

[Chemical Formula 124]

To a mixture of {2-[3-(t-butoxycarbonylaminomethyl)-4-cyanophenylimino]-2-[2-fluoro-5-methoxy-3-(2-triisopropylsilanyloxyethoxy)phenyl]-1-methylsulfanylethylidene}carbamic acid methyl ester (Example (6d))(56 mg) and THF (2.0 mL) there were added 4-hydrazinooxazole-5-carboxylic acid methyl ester (12.6 mg) and triethylamine (11.7 µL), and the mixture was stirred at 65° C. for 14 hours under a nitrogen atmosphere. The solvent in the mixture was distilled off, DMF (2.0 mL) was added to the residue, and the mixture was stirred at 85° C. for 18 hours under a nitrogen atmosphere. The solvent in the mixture was distilled off.

Methanol (3.0 mL), THF (1.0 mL) and acetic acid (22.0 μL) were added to the residue. Sodium cyanotrihydroborate (48.1 mg) was then added to the mixture and the mixture was stirred at room temperature for 20 hours. Water (20 mL) and ethyl acetate (50 mL) were added to the mixture, and after sufficiently shaking the mixture, the organic layer was separated off. The organic layer was washed with water (20 mL) and saturated aqueous sodium chloride (20 mL) in that order, and dried over anhydrous magnesium sulfate. The mixture was filtered to obtain a filtrate, and the solvent in the filtrate was distilled off under reduced pressure. The residue was purified by NAM silica gel column chromatography (ethyl acetate-heptane mixture) to obtain the target compound (41.1 mg) as a colorless solid.

$^1$H-NMR (CD$_3$OD) δ 1.07(m, 1H) 1.25(m, 3H) 1.44(s, 9H) 3.74(s, 3H) 3.85(s, 3H) 4.07(q, J=4.7 Hz, 2H) 4.14(t, J=4.7 Hz, 2H) 4.31(br.s, 2H) 5.94(s, 1H) 6.57(dd, J=5.0, 2.3 Hz, 1H) 6.66-6.69(m, 2H) 6.79(d, J=2.0 Hz, 1H) 7.11(br.t, J=5.7 Hz, 1H) 7.44(d, J=8.6 Hz, 1H) 8.43(s, 1H)

(11f) 4-(3-{[3-(t-Butoxycarbonylaminomethyl)-4-cyanophenylamino]-[2-fluoro-3-(2-hydroxyethoxy)-5-methoxyphenyl]methyl}-5-oxo-4,5-dihydro-[1,2,4]triazol-1-yl)oxazole-5-carboxylic Acid Methyl Ester

[Chemical Formula 125]

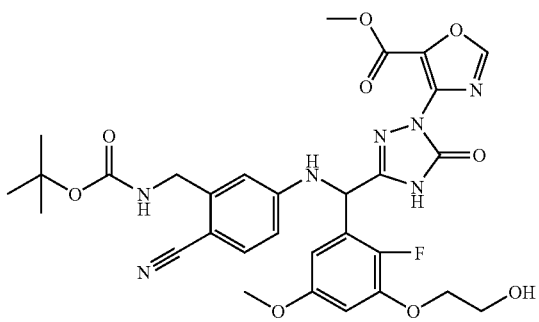

To a mixture of 4-(3-{[3-(t-butoxycarbonylaminomethyl)-4-cyanophenylamino]-[2-fluoro-5-methoxy-3-(2-triisopropylsilanyloxyethoxy)phenyl]methyl}-5-oxo-4,5-dihydro-[1,2,4]triazol-1-yl)oxazole-5-carboxylic acid methyl ester (41.1 mg) and THF (2 mL) there was added a 1M THF solution of tetrabutylammonium fluoride (0.100 mL). The mixture was stirred for 3 hours, and then ethyl acetate (30 mL) and water (15 mL) were added. The mixture was sufficiently shaken, and then the organic layer was separated off, washed with water (15 mL) and saturated aqueous sodium chloride (15 mL) in that order, and dried over anhydrous magnesium sulfate. The mixture was filtered to obtain a filtrate and the solvent in the filtrate was distilled off under reduced pressure to obtain the target compound (39.1 mg) as a colorless oil.

$^1$H-NMR (CD$_3$OD) δ 1.44(s, 9H) 3.73(s, 3H) 3.84(s, 3H) 3.87(t, J=5.0 Hz, 2H) 4.10(t, J=5.0 Hz, 2H) 4.31(br.s, 2H) 5.93(s, 1H) 6.58(dd, J=5.0, 2.3 Hz, 1H) 6.64-6.68(m, 2H) 6.79(d, J=2.0 Hz, 1H) 7.43(d, J=8.5 Hz, 1H) 8.41(s, 1H)

(11g) 4-(3-{[2-Fluoro-3-(2-hydroxyethoxy)-5-methoxyphenyl]-(1-imino-2,3-dihydro-1H-isoindol-5-ylamino)methyl}-5-oxo-4,5-dihydro-[1,2,4]triazol-1-yl)oxazole-5-carboxylic acid

[Chemical Formula 126]

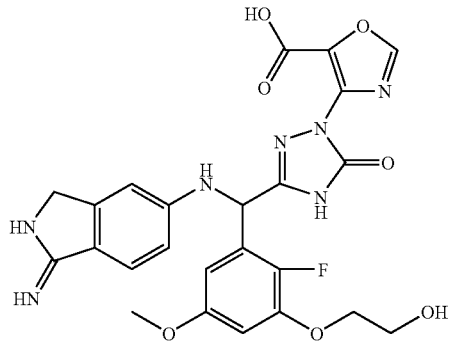

To a mixture of 4-(3-{[3-(t-butoxycarbonylaminomethyl)-4-cyanophenylamino]-[2-fluoro-3-(2-hydroxyethoxy)-5-methoxyphenyl]methyl}-5-oxo-4,5-dihydro-[1,2,4]triazol-1-yl)oxazole-5-carboxylic acid methyl ester (39 mg) and methanol (2.0 mL) there was added a 5 M sodium hydroxide aqueous solution (28 μL), and the mixture was stirred overnight at room temperature. After neutralizing the mixture with acetic acid, the solvent in the mixture was distilled off under reduced pressure. Dichloromethane (2.0 mL) was added to the residue, and then a 4M hydrogen chloride-ethyl acetate solution (500 μL) was added to the solution prior to stirring at room temperature for 15 minutes. Toluene (10 mL) was added to the mixture, and the solvent in the mixture was distilled off. The residue was purified by reverse-phase high performance liquid chromatography (acetonitrile/water mixed solvent, 0.1% acetic acid) to obtain the target compound (8.5 mg).

$^1$H-NMR (CD$_3$OD) δ 3.73(s, 3H) 3.88(t, J=4.8 Hz, 2H) 4.11(d, J=4.8 Hz, 2H) 4.58(d, J=17.2 Hz, 1H) 4.67(d, J=17.2 Hz, 1H) 5.94(s, 1H) 6.64(dd, J=5.7, 2.5 Hz, 1H) 6.66(dd, J=7.8, 2.5 Hz, 1H) 6.86-6.95(m, 2H) 7.75(d, J=8.6 Hz, 1H) 8.38(s, 1H)

Example 12

5-[(2-Fluoro-4,5-dimethoxyphenyl-(1-imino-2,3-dihydro-1H-isoindol-5-yl amino)methyl]-2-(1-oxy-pyridin-2-yl)-2,4-dihydro-[1,2,4]triazol-3-one (12a) [2-Cyano-5-({(2-fluoro-4,5-dimethoxyphenyl)-[5-oxo-1-(1-oxypyridin-2-yl)-4,5-dihydro-1H-[1,2,4]triazol-3-yl]methyl}amino)benzyl]carbamic Acid t-Butyl Ester

[Chemical Formula 127]

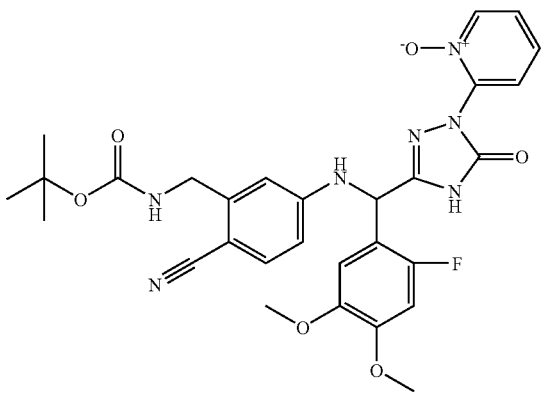

The target compound (6.9 mg) was obtained by the same procedure under the same reaction conditions as Example (9d), except that (1-oxypyridin-2-yl)hydrazine (25.8 mg) was used instead of the 3-allyl-5-hydrazino-3H-imidazole-4-carboxylic acid ethyl ester in Example (9d).

¹H-NMR (CD₃OD) δ 1.42(s, 9H) 3.77(s, 3H) 3.83(s, 3H) 4.27(d, J=16.4 Hz, 1H) 4.36(d, J=16.4 Hz, 1H) 5.86(s, 1H) 6.69(dd, J=8.5, 2.1 Hz, 1H) 6.80(d, J=2.1 Hz, 1H) 6.85(d, J=11.4 Hz, 1H) 7.05(d, J=6.6 Hz, 1H) 7.41(d, J=8.5 Hz, 1H) 7.59-7.64(m, 2H) 7.74-7.78(m, 1H) 8.45-8.49(m, 1H)

(12b) 5-[(2-Fluoro-4,5-dimethoxyphenyl)-(1-imino-2,3-dihydro-1H-isoindol-5-yl amino)methyl]-2-(1-oxypyridin-2-yl)-2,4-dihydro-[1,2,4]triazol-3-one

[Chemical Formula 128]

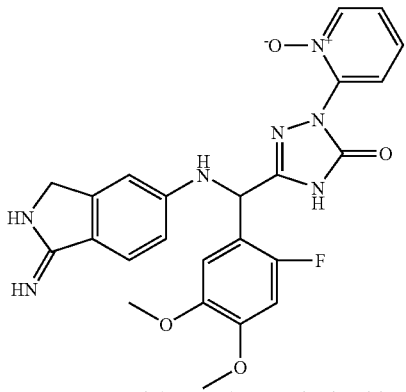

The target compound (4.0 mg) was obtained by the same procedure under the same reaction conditions as Example (2f), except that [2-cyano-5-({(2-fluoro-4,5-dimethoxyphenyl)-[5-oxo-1-(1-oxypyridin-2-yl)-4,5-dihydro-1H-[1,2,4]triazol-3-yl]methyl}amino)benzyl]carbamic acid t-butyl ester (6.9 mg) was used instead of the [5-({[1-(3-aminopyridin-2-yl)-5-oxo-4,5-dihydro-1H-[1,2,4]triazol-3-yl]-(8-methoxy-4H-benzo[1,3]-dioxin-6-yl)methyl}amino)benzyl]carbamic acid t-butyl ester in Example (2f).

¹H-NMR (CD₃OD) δ 3.83(s, 3H) 3.85(s, 3H) 4.20(d, J=14.6 Hz, 1H) 4.25(d, J=14.6 Hz, 1H) 5.90(s, 1H) 6.90(d, J=12.0 Hz, 1H) 6.91(dd, J=8.8, 2.0 Hz, 1H) 6.93(d, J=2.0 Hz, 1H) 7.07(d, J=6.3 Hz, 1H) 7.55(d, J=8.8 Hz, 1H) 7.59-7.64 (m, 2H) 7.88(dd, J=7.6, 2.8 Hz, 11H) 8.49(dd, J=6.7, 1.4 Hz, 1H)

Example 13

2-{3-[(2-Fluoro-4,5-dimethoxyphenyl)-(1-imino-2,3-dihydro-1H-isoindol-5-ylamino)methyl]-5-oxo-4,5-dihydro-[1,2,4]triazol-1-yl}benzoic Acid Trifluoroacetate (13a) 2-(3-((4-Bromo-3-(t-butoxycarbonylaminomethyl)phenylamino)-(2-fluoro-4,5-dimethoxyphenyl)methyl)-5-oxo-4,5-dihydro-[1,2,4]triazol-1-yl)benzoic Acid

[Chemical Formula 129]

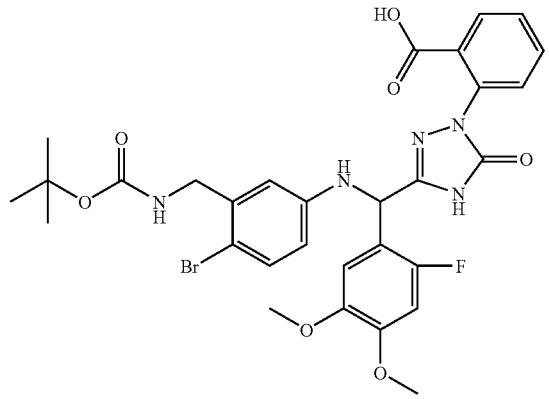

The target compound (142 mg) was obtained by the same procedure under the same reaction conditions as Example (10e), except that 2-hydrazinobenzoic acid hydrochloride (105 mg) was used instead of the 2-nitrophenylhydrazine in Example (10e).

¹H-NMR (CD₃OD) δ 1.44(s, 9H) 3.79(s, 3H) 3.83(s, 3H) 4.16(d, J=14.7 Hz, 1H) 4.23(d, J=14.7 Hz, 1H) 5.76(s, 1H) 6.56(dd, J=8.7, 3.1 Hz, 1H) 6.75(d, J=3.1 Hz, 1H) 6.82(d, J=11.8 Hz, 1H) 7.07(d, J=6.9 Hz, 1H) 7.26(d, J=8.7 Hz, 1H) 7.49(td, J=7.5, 1.6 Hz, 1H) 7.50(dd, J=7.5, 1.6 Hz, 1H) 7.62 (td, J=7.5, 1.6 Hz, 1H) 7.93(dd, J=7.5, 1.6 Hz, 1H)

(13b) 2-{3-[(2-Fluoro-4,5-dimethoxyphenyl)-(1-imino-2,3-dihydro-1H-isoindol-5-ylamino)methyl]-5-oxo-4,5-dihydro-[1,2,4]triazol-1-yl}benzoic Acid Trifluoroacetate

[Chemical Formula 130]

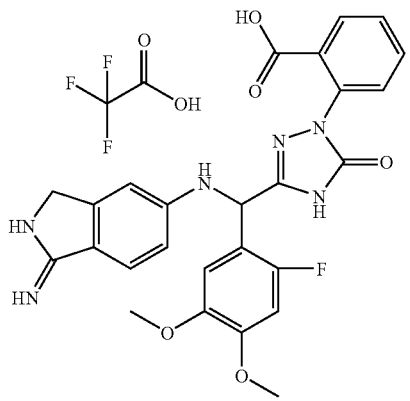

The target compound (11 mg) was obtained by the same procedure under the same reaction conditions as Example (10 g), except that 2-(3-{[4-bromo-3-(t-butoxycarbonylaminomethyl)phenylamino]-(2-fluoro-4,5-dimethoxyphenyl)methyl}-5-oxo-4,5-dihydro-[1,2,4]triazol-1-yl)benzoic acid (57 mg) was used instead of the [5-({[1-(2-aminophenyl)-5-oxo-4,5-dihydro-1H-[1,2,4]triazol-3-yl]-(2-fluoro-4,5-dimethoxyphenyl)methyl}amino)-2-bromobenzyl]carbamic acid t-butyl ester in Example (10g).

¹H-NMR (CD₃OD) δ 3.81(s, 3H) 3.83(s, 3H) 4.65(d, J=21.1 Hz, 1H) 4.72(d, J=21.1 Hz, 1H) 5.95(s, 1H) 6.88(d, J=11.6 Hz, 1H) 6.94(s, 1H) 6.96(dd, J=8.7, 2.4 Hz, 1H) 7.07(d, J=6.5 Hz, 11) 7.50(m, 2H) 7.65(td, J=8.7, 2.4 Hz, 1H) 7.80(d, J=8.7 Hz, 1H) 7.98(dd, J=8.7, 2.4 Hz, 1H)

Example 14

5-[(2-Fluoro-3,5-dimethoxyphenyl)-(1-imino-2,3-dihydro-1H-isoindol-5-yl amino)methyl]-2-(2-nitrophenyl)-2,4-dihydro-[1,2,4]triazol-3-one Trifluoro Acetate (14a)(2-Bromo-5-nitrobenzyl)carbamic acid 2-trimethylsilanylethyl ester

[Chemical Formula 131]

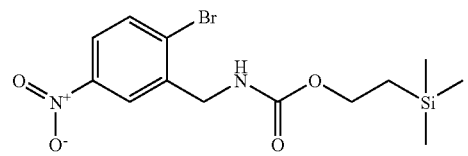

To a mixture of 2-bromo-5-nitrobenzylamine (Example (1d))(2.77 g) and dichloromethane (80 mL) there were added triethylamine (1.72 mL) and 2-trimethylsilanylethyl 4-nitrophenyl carbonate [CAS No. 80149-80-0] (3.5 g), and the mixture was stirred at room temperature for 64 hours. Ethyl acetate (300 mL) and water (300 mL) were added to the mixture, and after sufficiently shaking, the organic layer was separated off and washed with a 1N aqueous sodium hydroxide solution (300 mL) and saturated aqueous sodium chloride (300 mL) in that order, and dried over anhydrous magnesium sulfate. The mixture was filtered to obtain a filtrate, and the solvent in the filtrate was distilled off under reduced pressure. The residue was purified by silica gel column chromatography (ethyl acetate-heptane mixture) to obtain the target compound (1.69 g) as a colorless solid.

$^1$H-NMR (CDCl$_3$) δ 0.06(s, 9H) 1.01(m, 2H) 4.20(m, 2H) 4.49(d, J=6.4 Hz, 2H) 5.26(br.s, 1H) 7.73(d, J=8.4 Hz, 1H) 8.00(dd, J=8.4, 2.0 Hz, 1H) 8.25(d, J=2.0 Hz, 1H)

(14b)(2-Cyano-5-nitrobenzyl)carbamic acid 2-trimethylsilanylethyl Ester

[Chemical Formula 132]

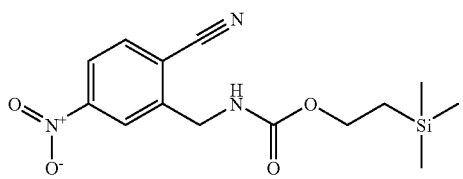

The target compound (0.92 g) was obtained as an off-white solid by the same procedure under the same reaction conditions as Example (1f), except that (2-bromo-5-nitrobenzyl)carbamic acid 2-trimethylsilanylethyl ester (1.69 g) was used instead of the (2-bromo-5-nitrobenzyl)carbamic acid t-butyl ester in Example (1f).

$^1$H-NMR (CDCl$_3$) δ 0.06(s, 91H) 1.01(m, 2H) 4.20(m, 2H) 4.64(d, J=6.4 Hz, 2H) 5.38(br.s, 1H) 7.87(d, J=8.0 Hz, 1H) 8.25(dd, J=8.0, 2.0 Hz, 1H) 8.39(d, J=2.0 Hz, 1H)

(14c)(5-Amino-2-cyanobenzyl)carbamic Acid 2-trimethylsilanylethyl Ester

[Chemical Formula 133]

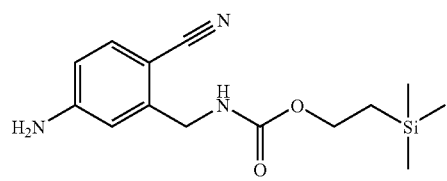

The target compound (738 mg) was obtained by the same procedure under the same reaction conditions as Example (1g), except that (2-cyano-5-nitrobenzyl)carbamic acid 2-trimethylsilanylethyl ester (917 mg) was used instead of the (2-cyano-5-nitrobenzyl)carbamic acid t-butyl ester in Example (1g).

$^1$H-NMR (CDCl$_3$) δ 0.06(s, 9H) 0.99(m, 2H) 4.18(m, 2H) 4.43(d, J=6.4 Hz, 2H) 5.21(br.s, 1H) 6.53(dd, J=8.4, 2.5 Hz, 1H) 6.73(br.s, 1H) 7.40(d, J=8.4 Hz, 1H)

(14d) (2-Cyano-5-{[cyano-(2-fluoro-3,5-dimethoxyphenyl)methyl]amino}benzyl) carbamic acid 2-trimethylsilanylethyl Ester

[Chemical Formula 134]

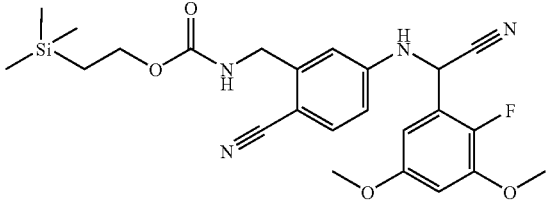

The target compound (438 mg) was obtained by the same procedure under the same reaction conditions as Example (1 h), except that (5-amino-2-cyanobenzyl)carbamic acid 2-trimethylsilanylethyl ester (369 mg) was used instead of the (5-amino-2-cyanobenzyl)carbamic acid t-butyl ester and 2-fluoro-3,5-dimethoxybenzaldehyde (234 mg) was used instead of the 5-fluoro-8-methoxychroman-6-carboaldehyde in Example (1 h).

$^1$H-NMR (CDCl$_3$) δ 0.04(s, 9H) 0.99(m, 2H) 3.83(s, 3H) 3.89(s, 3H) 4.17(m, 2H) 4.47(d, J=6.5 Hz, 2H) 4.61(d, J=7.6 Hz, 1H) 5.25(br.t, J=6.5 Hz, 1H) 5.62(d, J=7.6 Hz, 1H) 6.61-6.63(m, 2H) 6.69(dd, J=8.4, 2.4 Hz, 1H) 6.85(br.s, 1H) 7.54(d, J=8.4 Hz, 1H)

(14e) (2-Cyano-5-{[(2-fluoro-3,5-dimethoxyphenyl)thiocarbamoylmethyl]amino}benzyl)carbamic acid 2-trimethylsilanylethyl Ester

[Chemical Formula 135]

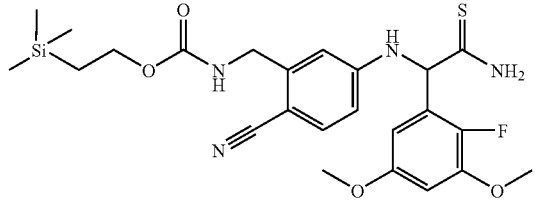

The target compound (153 mg) was obtained by the same procedure under the same reaction conditions as Example (1i), except that (2-cyano-5-{[cyano-(2-fluoro-3,5-dimethoxyphenyl)methyl]amino}benzyl) carbamic acid 2-trimethylsilanylethyl ester (438 mg) was used instead of the (2-cyano-5-{[cyano-(5-fluoro-8-methoxychroman-6-yl)methyl]amino}benzyl)carbamic acid t-butyl ester in Example (1i).

$^1$H-NMR (CDCl$_3$) δ 0.05(s, 911) 1.00(m, 2H) 3.72(s, 3H) 3.89(s, 3H) 4.18(m, 2H) 4.41(d, J=6.4 Hz, 2H) 5.17(br.t, J=6.4 Hz, 1H) 5.46(s, 1H) 6.39-6.43(m, 2H) 6.49(dd, J=7.9, 2.6 Hz, 1H) 6.72(br.s, 1H) 7.38(d, J=7.9 Hz, 1H) 7.45(br.s, 2H)

(14f) (2-{4-Cyano-3-[(2-trimethylsilanylethoxycarbonylamino)methyl]phenylimino}-2-(2-fluoro-3,5-dimethoxyphenyl)-1-methylsulfanylethylidene)carbamic Acid Methyl Ester

[Chemical Formula 136]

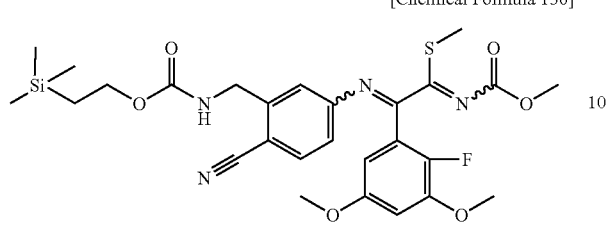

The target compound (78 mg) was obtained by the same procedure under the same reaction conditions as Example (1j), except that (2-cyano-5-{[(2-fluoro-3,5-dimethoxyphenyl)thiocarbamoylmethyl]amino}benzyl)carbamic acid 2-trimethylsilanylethyl ester (153 mg) was used instead of the (2-cyano-5-{[(5-fluoro-8-methoxychroman-6-yl)thiocarbamoylmethyl]amino}benzyl)carbamic acid t-butyl ester in Example (1j).

$^1$H-NMR (CDCl$_3$) Two main isomers δ 0.03 or 0.05(s, 9H) 0.95-1.02(m, 211) 2.46(s, 311) 3.63(s, 3H) 3.69(s, 311) 3.83 or 3.89(s, 3H) 4.16-4.19(m, 2H) 4.43(d, J=6.0 Hz, 2H) 5.10 (br.t, J=6.0 Hz, 1H) 6.14(br.s, 1H) 6.30(dd, J=7.2, 2.6 Hz, 1H) 6.66(d, J=7.5 Hz, 1H) 6.89-6.94(m, 1H) 7.45(d, J=7.5 Hz, 1H) δ 0.03 or 0.05(s, 9H) 0.95-1.02(m, 2H) 2.33(s, 3H) 3.63 (s, 3H) 3.79(s, 3H) 3.83 or 3.89(s, 3H) 4.16-4.19(m, 2H) 4.55(d, J=6.0 Hz, 211) 5.24(br.t, J=6.0 Hz, 1H) 6.69-6.73(m, 1H) 6.91-6.95(m, 1H) 6.97(d, J=7.5 Hz, 11H) 7.14(s, 1H) 7.59(d, J=7.5 Hz, 1H)

(14 g) [2-Cyano-5-({(2-fluoro-3,5-dimethoxyphenyl)-[1-(2-nitrophenyl)-5-oxo-4,5-dihydro-1H-[1,2,4]triazol-3-yl]methyl}amino)benzyl]carbamic Acid 2-trimethylsilanylethyl Ester

[Chemical Formula 137]

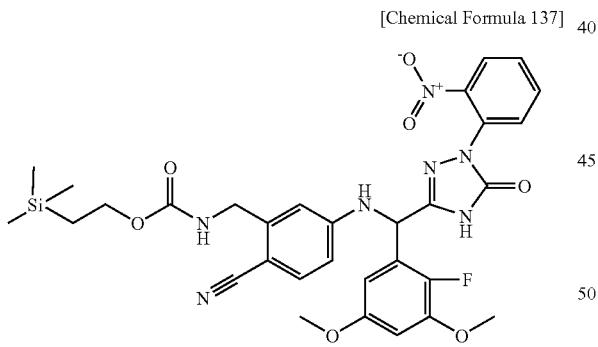

The target compound (30 mg) was obtained by the same procedure under the same reaction conditions as Example (8a), except that (2-{4-cyano-3-[(2-trimethylsilanylethoxycarbonylamino)methyl]phenylimino}-2-(2-fluoro-3,5-dimethoxyphenyl)-1-methylsulfanylethylidene)carbamic acid methyl ester (20 mg) was used instead of the {2-[4-bromo-3-(t-butoxycarbonylaminomethyl)phenylimino]-2-[3-(2-dimethylaminoethoxy)-5-ethyl-2-fluorophenyl]-1-methylsulfanylethylidene}carbamic acid methyl ester in Example (8a).

$^1$H-NMR (CD$_3$OD) δ 0.04(s, 9H) 0.94-0.99(m, 2H) 3.75(s, 3H) 3.83(s, 3H) 4.06-4.12(m, 2H) 4.33(s, 2H) 5.91(s, 1H) 6.51(dd, J=5.3, 2.8 Hz, 1H) 6.61(dd, J=7.2, 2.8 Hz, 1H) 6.67(dd, J=8.5, 2.1 Hz, 1H) 6.75(d, J=2.11 Hz, 1H) 7.40(d, J=8.5 Hz, 1H) 7.53-7.77(m, 3H) 7.95(d, J=7.7 Hz, 1H)

(14h) 5-[(2-Fluoro-3,5-dimethoxyphenyl)-(1-imino-2,3-dihydro-1H-isoindol-5-yl amino)methyl]-2-(2-nitrophenyl)-2,4-dihydro-[1,2,4]triazol-3-one trifluoroacetate

[Chemical Formula 138]

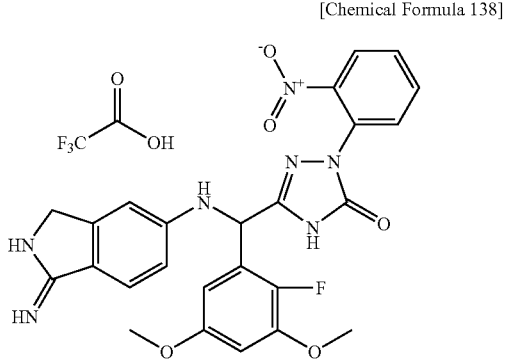

To a mixture of [2-cyano-5-({(2-fluoro-3,5-dimethoxyphenyl)-[1-(2-nitrophenyl)-5-oxo-4,5-dihydro-1H-[1,2,4]triazol-3-yl]methyl}amino)benzyl]carbamic acid 2-trimethylsilanylethyl ester (30.2 mg) and acetonitrile (2 mL) there was added a 1M THF solution of tetrabutylammonium fluoride (0.10 mL) under a nitrogen atmosphere, and the mixture was heated for 4 hours at 50° C. The mixture was cooled to room temperature, and the solvent in the mixture was distilled off. The residue was purified by reverse-phase high performance liquid chromatography (acetonitrile/water mixed solvent, 0.1% trifluoroacetic acid) to obtain the target compound (1.3 mg).

$^1$H-NMR (CD$_3$OD) δ 3.79(s, 3H) 3.88(s, 3H) 4.68(s, 2H) 6.00(s, 1H) 6.58(br.s, 1H) 6.70(br.s, 1H) 6.92(s, 1H) 6.99(d, J=8.6 Hz, 1H) 7.60(t, J=7.7 Hz, 1H) 7.70(d, J=7.7 Hz, 1H) 7.75-7.82(m, 2H) 8.01(d, J=7.7 Hz, 1H)

Example 15

3-{3-[(2-Fluoro-4,5-dimethoxyphenyl-(1-imino-2,3-dihydro-1H-isoindol-5-ylamino)methyl]-5-oxo-4,5-dihydro-[1,2,4]triazol-1-yl}-1H-pyrazole-4-carboxylic Acid

(15a) 3-(3-{[3-(t-Butoxycarbonylaminomethyl)-4-cyanophenylamino]-(2-fluoro-4,5-dimethoxyphenyl)methyl}-5-oxo-4,5-dihydro-[1,2,4]triazol-1-yl)-1H-pyrazole-4-carboxylic Acid Ethyl Ester

[Chemical Formula 139]

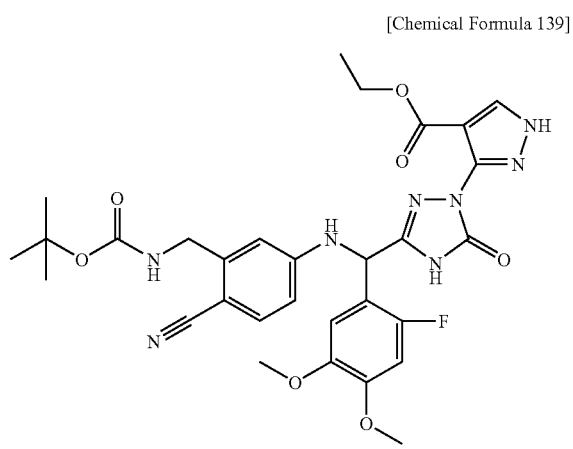

The target compound (20 mg) was obtained by the same procedure under the same reaction conditions as Example (9d), except that 3-hydrazino-1H-pyrazole-4-carboxylic acid ethyl ester bishydrochloride (33 mg) was used instead of the 3-allyl-5-hydrazino-3H-imidazole-4-carboxylic acid ethyl ester in Example (9d).

¹H-NMR (CD₃OD) δ 1.20(t, J=7.4 Hz, 3H) 1.45(s, 9H) 3.79(s, 3H) 3.84(s, 3H) 4.16(m, 2H) 4.26(d, J=15.4 Hz, 1H) 4.35(d, J=15.4 Hz, 1H) 5.87(s, 1H) 6.68(dd, J=8.3, 2.2 Hz, 1H) 6.79(d, J=2.2 Hz, 1H) 6.85(d, J=11.5 Hz, 1H) 7.04(d, J=7.3 Hz, 1H) 7.42(d, J=8.3 Hz, 1H) 8.24(s, 1H)

(15b)

3-{3-[(2-Fluoro-4,5-dimethoxyphenyl)-(1-imino-2,3-dihydro-1H-isoindol-5-ylamino)methyl]-5-oxo-4,5-dihydro-[1,2,4]triazol-1-yl}-1H-pyrazole-4-carboxylic Acid

[Chemical Formula 140]

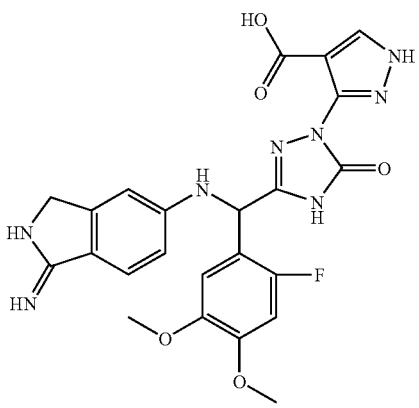

To a mixture of 3-(3-{[3-(t-butoxycarbonylaminomethyl)-4-cyanophenylamino]-(2-fluoro-4,5-dimethoxyphenyl)methyl}-5-oxo-4,5-dihydro-[1,2,4]triazol-1-yl)-1H-pyrazole-4-carboxylic acid ethyl ester (20 mg) and acetonitrile there were added triethylamine (0.035 mL) and di-t-butyl dicarbonate, and the mixture was stirred overnight at room temperature.

The solvent in the mixture was distilled off.

Methanol (1 mL) and a 5N sodium hydroxide aqueous solution (0.031 mL) were added to the residue, and the mixture was stirred overnight at room temperature. The solvent in the mixture was distilled off, and then dichloromethane (2 mL) and trifluoroacetic acid (0.4 mL) were added to the residue and the mixture was stirred at room temperature for 3 hours. Toluene (10 mL) was added, the solvent in the mixture was distilled off, and the residue was purified by reverse-phase high performance liquid chromatography (acetonitrile/water mixed solvent, 0.1% acetic acid) to obtain the target compound (0.5 mg).

¹H-NMR (CD₃OD) δ 3.79(s, 3H) 3.83(s, 3H) 4.61(d, J=19.2 Hz, 1H) 4.73(d, J=19.2 Hz, 1H) 5.91(s, 1H) 6.85(d, J=11.5 Hz, 1H) 6.91(d, J=2.0 Hz, 1H) 6.93(dd, J=8.4, 2.0 Hz, 1H) 7.07(d, J=6.9 Hz, 1H) 7.76(d, J=8.4 Hz, 1H) 8.04(s, 1H)

Example 16

(R)- and (S)-2-(3-Aminopyridin-2-yl)-5-{[5-ethyl-2-fluoro-3-(2-hydroxyethoxy)phenyl]-(1-imino-2,3-dihydro-1H-isoindol-5-ylamino)methyl}-2,4-dihydro-[1,2,4]triazol-3-one Acetate (16a) [2-Cyano-5-({[5-ethyl-2-fluoro-3-(2-triisopropylsilanyloxyethoxy)phenyl]-[1-(3-nitropyridin-2-yl)-5-oxo-4,5-dihydro-1H-[1,2,4]triazol-3-yl]methyl}amino)benzyl]carbamic Acid t-Butyl Ester

[Chemical Formula 141]

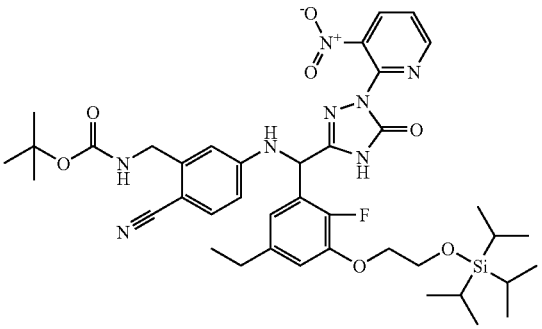

The target compound (38 mg) was obtained by the same procedure under the same reaction conditions as Example (4f), except that (3-nitropyridin-2-yl)hydrazine [CAS No. 15367-16-5] (15.1 mg) was used instead of the (pyrimidin-2-yl)hydrazine in Example (4f).

¹H-NMR (CD₃OD) δ 1.06(m, 18H) 1.10(m, 3H) 1.19(t, J=7.6 Hz, 3H) 1.46(s, 9H) 2.60(q, J=7.6 Hz, 2H) 4.06(t, J=4.8 Hz, 2H) 4.16(t, J=4.8 Hz, 2H) 4.30(m, 2H) 5.95(s, 1H) 6.68 (dd, J=8.4, 2.2 Hz, 1H) 6.80(d, J=2.2 Hz, 1H) 6.87(dd, J=5.9, 2.5 Hz, 1H) 6.97(dd, J=7.7, 2.5 Hz, 1H) 7.09(br.s, 1H) 7.41(d, J=8.4 Hz, 1H) 7.64(dd, J=7.9, 4.4 Hz, 1H) 8.47(dd, J=7.9, 1.5 Hz, 1H) 8.75(dd, J=4.4, 1.5 Hz, 1H)

(16b) [2-Cyano-5-({[5-ethyl-2-fluoro-3-(2-hydroxyethoxy)phenyl]-[1-(3-nitropyridin-2-yl)-5-oxo-4,5-dihydro-1H-[1,2,4]triazol-3-yl]methyl}amino)benzyl]carbamic Acid t-Butyl Ester

[Chemical Formula 142]

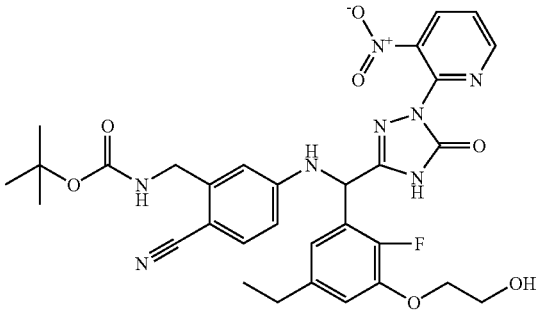

The target compound (38 mg) was obtained by the same procedure under the same reaction conditions as Example (4g), except that [2-cyano-5-({[5-ethyl-2-fluoro-3-(2-triisopropylsilanyloxyethoxy)phenyl]-[1-(3-nitropyridin-2-yl)-5-oxo-4,5-dihydro-1H-[1,2,4]triazol-3-yl]methyl}amino)benzyl]carbamic acid t-butyl ester (38 mg) was used instead of the [2-cyano-5-({[5-ethyl-2-fluoro-3-(2-triisopropylsilanyloxyethoxy)phenyl]-(5-oxo-1-pyrimidin-2-yl-4,5-dihydro-1H-[1,2,4]triazol-3-yl)methyl}amino)benzyl]carbamic acid t-butyl ester in Example (4 g).

$^1$H-NMR (CDCl$_3$) δ 1.26(t, J=7.6 Hz, 3H) 1.46(s, 9H) 2.49(q, J=7.6 Hz, 2H) 3.95(m, 2H) 4.10(m, 2H) 4.34(d, J=6.0 Hz, 2H) 5.23(br.s, 1H) 5.75(br.s, 1H) 5.82(br.s, 1H) 6.56(br.s, 1H) 6.71(d, J=7.5 Hz, 1H) 6.76(s, 1H) 6.81(d, J=4.7 Hz, 1H) 7.35(d, J=8.6 Hz, 1H) 7.47(dd, J=8.0, 4.2 Hz, 1H) 8.33(dd, J=8.0, 1.5 Hz, 1H) 8.74(dd, J=4.2, 1.5 Hz, 1H)

(16c) [5-({[1-(3-Aminopyridin-2-yl)-5-oxo-4,5-dihydro-1H-[1,2,4]triazol-3-yl]-[5-ethyl-2-fluoro-3-(2-hydroxyethoxy)phenyl]methyl}amino)-2-cyanobenzyl]Carbamic Acid t-Butyl Ester

[Chemical Formula 143]

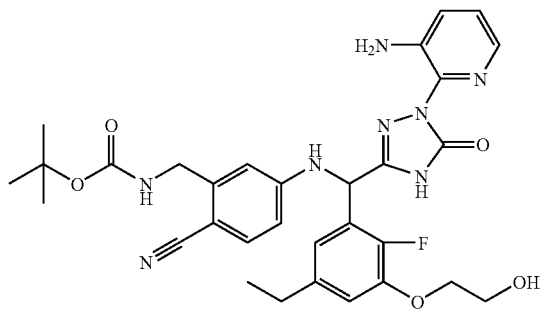

The target compound (40 mg) was obtained by the same procedure under the same reaction conditions as Example (2e), except that [2-cyano-5-({[5-ethyl-2-fluoro-3-(2-hydroxyethoxy)phenyl]-[1-(3-nitropyridin-2-yl)-5-oxo-4,5-dihydro-1H-[1,2,4]triazol-3-yl]methyl}amino)benzyl]carbamic acid t-butyl ester (38 mg) was used instead of the [2-cyano-5-({(8-methoxy-4H-benzo[1,3]-dioxin-6-yl)-[1-(3-nitropyridin-2-yl)-5-oxo-4,5-dihydro-1H-[1,2,4]triazol-3-yl]methyl}amino)benzyl]carbamic acid t-butyl ester in Example (2e).

$^1$H-NMR (CD$_3$OD) δ 1.26(t, J=7.6 Hz, 3H) 1.46(s, 911) 2.49(q, J=7.6 Hz, 2H) 3.79(m, 2H) 4.02(m, 2H) 4.21(s, 2H) 5.86(s, 1H) 6.59(d, J=8.4 Hz, 1H) 6.69(s, 1H) 6.79-6.87(m, 2H) 7.11(dd, J=7.6, 3.1 Hz, 1H) 7.21(d, J=7.5 Hz, 1H) 7.32(d, J=8.4 Hz, 1H) 7.70(d, J=4.4 Hz, 1H)

(16d) 2-(3-Aminopyridin-2-yl)-5-{[5-ethyl-2-fluoro-3-(2-hydroxyethoxy)phenyl]-(1-imino-2,3-dihydro-1H-isoindol-5-ylamino)methyl}-2,4-dihydro-[1,2,4]triazol-3-one Acetate

[Chemical Formula 144]

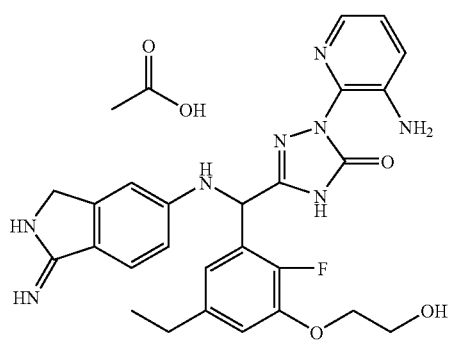

The target compound (11 mg) was obtained by the same procedure under the same reaction conditions as Example (4h), except that [5-({[1-(3-aminopyridin-2-yl)-5-oxo-4,5-dihydro-1H-[1,2,4]triazol-3-yl]-[5-ethyl-2-fluoro-3-(2-hydroxyethoxy)phenyl]methyl}amino)-2-cyanobenzyl]carbamic acid t-butyl ester (40 mg) was used instead of the [2-cyano-5-({[5-ethyl-2-fluoro-3-(2-hydroxyethoxy)phenyl]-(5-oxo-1-pyrimidin-2-yl-4,5-dihydro-1H-[1,2,4]triazol-3-yl)methyl}amino)benzyl]carbamic acid t-butyl ester in Example (4h).

$^1$H-NMR (CD$_3$OD) δ 1.19(t, J=7.6 Hz, 3H) 1.95(s, 3H) 2.60(q, J=7.6 Hz, 2H) 3.89(t, J=4.8 Hz, 2H) 4.12(t, J=4.8 Hz, 2H) 4.64(s, 2H) 6.02(s, 1H) 6.92-6.99(m, 4H) 7.22(dd, J=7.8, 5.0 Hz, 1H) 7.33(d, J=7.8 Hz, 1H) 7.78(d, J=8.5 Hz, 1H) 7.81(d, J=5.0 Hz, 1H)

(16e)(R)- and (S)-2-(3-Aminopyridin-2-yl)-5-{[5-ethyl-2-fluoro-3-(2-hydroxyethoxy)phenyl]-(1-imino-2,3-dihydro-1H-isoindol-5-ylamino)methyl}-2,4-dihydro-[1,2,4]triazol-3-one Acetate

[Chemical Formula 145]

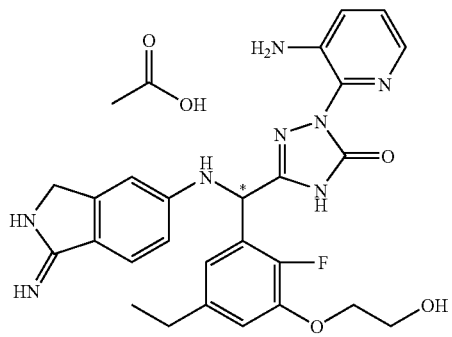

A SUMICHIRAL OA-2500 column was used for separation (optical resolution) of 2-(3-aminopyridin-2-yl)-5-{[5-ethyl-2-fluoro-3-(2-hydroxyethoxy)phenyl]-(1-imino-2,3-dihydro-11H-isoindol-5-ylamino)methyl}-2,4-dihydro-[1,2,4]triazol-3-one acetic acid salt (8.5 mg) under the following conditions, and the first eluting enantiomer (3.03 mg) of the title compound was obtained.

$^1$H-NMR (CD$_3$OD) δ 1.18(t, J=7.6 Hz, 3H) 1.91(s, 3H) 2.58(q, J=7.6 Hz, 2H) 3.88(t, J=4.6 Hz, 2H) 4.12(t, J=4.6 Hz, 2H) 4.62(s, 2H) 5.99(s, 1H) 6.91-6.96(m, 4H) 7.20(dd, J=4.4, 8.0 Hz, 1H) 7.32(dd, J=1.6, 8.0 Hz, 1H) 7.77(d, J=8.4 Hz, 1H) 7.81(dd, J=1.6, 4.4 Hz, 1H)

HPLC retention time: 7 min. (Column name: SUMICHIRAL OA-2500, 30 mmφ×25 cm, Manufacturer: Sumika Chemical Analysis Service, Ltd., Mobile phase: 50 mM ammonium acetate-methanol solution, Elution rate: 25 mL/min)

Example 17

(R)- and (S)-3-(3-{[5-Ethyl-2-fluoro-3-(2-hydroxyethoxy)phenyl]-(1-imino-2,3-dihydro-1H-isoindol-5-ylamino)methyl}-5-oxo-4,5-dihydro-[1,2,4]triazol-1-yl)thiophene-2-carboxylic Acid

(17a) 3-(3-{[3-(t-Butoxycarbonylaminomethyl)-4-cyanophenylamino]-[5-ethyl-2-fluoro-3-(2-triisopropylsilanyloxyethoxy)phenyl]methyl}-5-oxo-4,5-dihydro-[1,2,4]triazol-1-yl)thiophene-2-carboxylic acid methyl Ester

[Chemical Formula 146]

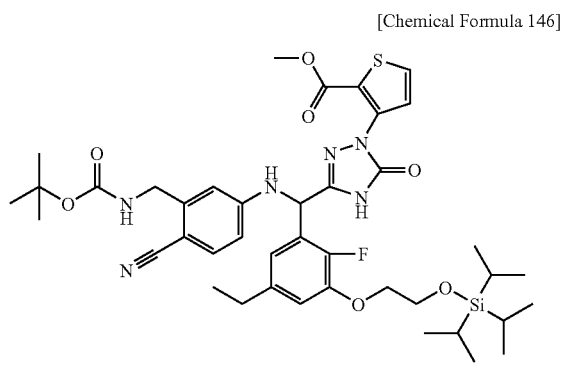

The target compound (45 mg) was obtained by the same procedure under the same reaction conditions as Example (4f), except that 3-hydrazinothiophene-2-carboxylic acid methyl ester [CAS No. 75681-13-9] (16.8 mg) was used instead of the (pyrimidin-2-yl)hydrazine in Example (4f).

$^1$H-NMR (CD$_3$OD) δ 1.06(m, 18H) 1.10(m, 3H) 119(t, J=7.5 Hz, 3H) 1.46(s, 9H) 2.60(q, J=7.5 Hz, 2H) 3.76(s, 3H) 4.06(t, J=4.7 Hz, 2H) 4.16(t, J=4.7 Hz, 2H) 4.31(m, 2H) 5.90(s, 1H) 6.68(dd, J=8.7, 2.3 Hz, 1H) 6.78(d, J=2.3 Hz, 1H) 6.89(dd, J=5.9, 2.5 Hz, 1H) 6.98(dd, J=7.9, 2.5 Hz, 1H) 7.07(br.s, 1H) 7.20(d, J=5.2 Hz, 1H) 7.42(d, J=8.7 Hz, 1H) 7.75(d, J=5.2 Hz, 1H)

(17b) 3-(3-{[3-(t-Butoxycarbonylaminomethyl)-4-cyanophenylamino]-[5-ethyl-2-fluoro-3-(2-hydroxyethoxy)phenyl]methyl}-5-oxo-4,5-dihydro-[1,2,4]triazol-1-yl)thiophene-2-carboxylic Acid Methyl Ester

[Chemical Formula 147]

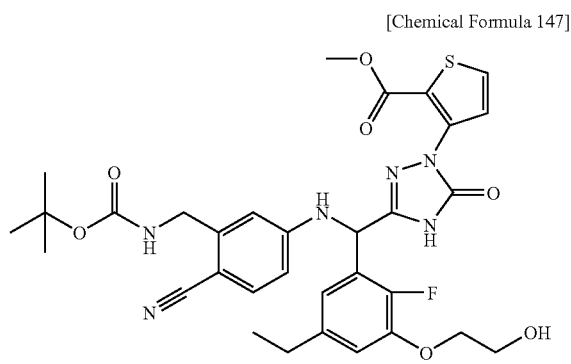

The target compound (31 mg) was obtained by the same procedure under the same reaction conditions as Example (4g), except that 3-(3-{[3-(t-butoxycarbonylaminomethyl)-4-cyanophenylamino]-[5-ethyl-2-fluoro-3-(2-triisopropylsilanyloxyethoxy)phenyl]methyl}-5-oxo-4,5-dihydro-[1,2,4]triazol-1-yl)thiophene-2-carboxylic acid methyl ester (45 mg) was used instead of the [2-cyano-5-({[5-ethyl-2-fluoro-3-(2-triisopropylsilanyloxyethoxy)phenyl]-(5-oxo-1-pyrimidin-2-yl-4,5-dihydro-1H-[1,2,4]triazol-3-yl)methyl}amino)benzyl]carbamic acid t-butyl ester in Example (4g).

$^1$H-NMR (CD$_3$OD) δ 1.20(t, J=7.6 Hz, 3H) 1.34(s, 9H) 2.51(q, J=7.6 Hz, 2H) 3.67(s, 3H) 3.78(t, J=5.0 Hz, 2H) 4.16(t, J=5.0 Hz, 2H) 4.24(m, 2H) 5.81(s, 1H) 6.59(dd, J=8.7, 2.2 Hz, 1H) 6.69(d, J=2.2 Hz, 1H) 6.81(dd, J=5.5, 2.5 Hz, 1H) 6.88(dd, J=8.0, 2.5 Hz, 1H) 7.10(d, J=5.1 Hz, 1H) 7.33(d, J=8.7 Hz, 1H) 7.65(d, J=5.1 Hz, 1H)

(17c) 3-(3-{[5-Ethyl-2-fluoro-3-(2-hydroxyethoxy)phenyl]-(1-imino-2,3-dihydro-1H-isoindol-5-ylamino)methyl}-5-oxo-4,5-dihydro-[1,2,4]-triazol-1-yl)thiophene-2-carboxylic Acid

[Chemical Formula 148]

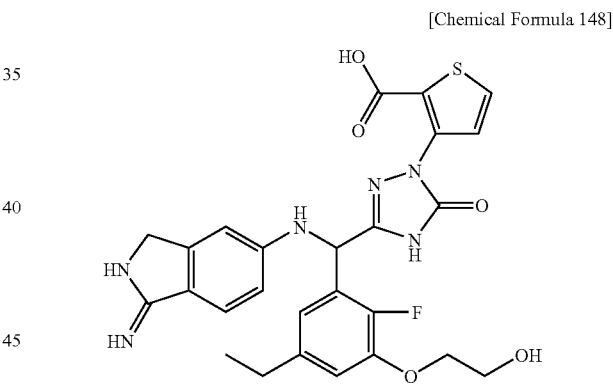

A mixture of 3-(3-{[3-(t-butoxycarbonylaminomethyl)-4-cyanophenylamino]-[5-ethyl-2-fluoro-3-(2-hydroxyethoxy)phenyl]methyl}-5-oxo-4,5-dihydro-[1,2,4]triazol-1-yl)thiophene-2-carboxylic acid methyl ester (31 mg), a methanol:THF (2:1) mixed solvent (1.5 mL) and a 5N sodium hydroxide aqueous solution (0.1 mL) was heated for 14 hours at 65° C. under a nitrogen atmosphere. Acetic acid was added to the mixture, which was then purified by reverse-phase high performance liquid chromatography (acetonitrile/water mixed solvent, 0.1% acetic acid) to obtain the target compound (9.0 mg).

$^1$H-NMR (CD$_3$OD) δ 1.19(t, J=7.6 Hz, 3H) 2.60(q, J=7.6 Hz, 2H) 3.88(t, J=4.8 Hz, 2H) 4.13(d, J=4.8 Hz, 2H) 4.59(d, J=18.0 Hz, 1H) 4.72(d, J=18.0 Hz, 1H) 5.96(s, 1H) 6.90-6.99 (m, 4H) 7.10(d, J=5.4 Hz, 1H) 7.46(d, J=5.4 Hz, 1H) 7.75(d, J=8.8 Hz, 1H)

(17d)(R)- and (S)-3-(3-{[5-Ethyl-2-fluoro-3-(2-hydroxyethoxy)phenyl]-(1-imino-2,3-dihydro-1H-isoindol-5-ylamino)methyl}-5-oxo-4,5-dihydro-[1,2,4]triazol-1-yl)thiophene-2-carboxylic Acid

[Chemical Formula 149]

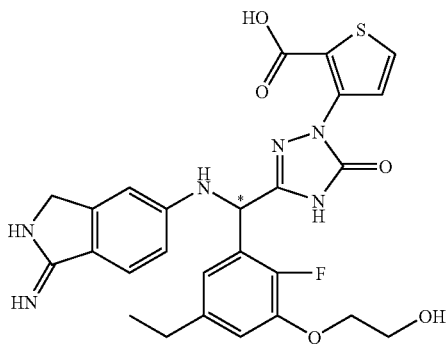

A SUMICHIRAL OA-2500 column was used for separation (optical resolution) of 3-(3-{[5-ethyl-2-fluoro-3-(2-hydroxyethoxy)phenyl]-(1-imino-2,3-dihydro-1H-isoindol-5-ylamino)methyl}-5-oxo-4,5-dihydro-[1,2,4]triazol-1-yl)thiophene-2-carboxylic acid (7.5 mg) under the following conditions, and the first eluting enantiomer (1.17 mg) of the title compound was obtained.

$^1$H-NMR (CD$_3$OD) δ 1.16(t, J=7.6 Hz, 3H) 2.57(q, J=7.6 Hz, 2H) 3.89(t, J=4.8 Hz, 2H) 4.12(t, J=4.8 Hz, 2H) 4.54-4.64(m, 2H) 5.91(s, 1H) 6.88-6.91(m, 2H) 6.95-7.00(m, 2H) 7.07(d, J=5.0 Hz, 1H) 7.42(d, J=5.0 Hz, 1H) 7.68(d, J=8.4 Hz, 1H)

HPLC retention time: 15 min. (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 30 mL/min)

Pharmacological Test Example 1

Inhibiting Activity Against Clotting Factor VIIa
(1) Method

A dimethyl sulfoxide (DMSO) solution was prepared with an invention compound concentration of 10 mmol/L (10 mmol/L compound solution).

One packet of tris-hydroxymethylaminomethane-preset (hereinafter referred to as "Tris preset")(Product of Sigma Corp., Catalog No. T8293), 8.8 g of sodium chloride (NaCl) and 1 g of bovine serum albumin (hereinafter abbreviated as "BSA") were dissolved in 1 L of water to prepare a Tris-BSA buffer (100 mmol/L Tris, 0.15 mol/L NaCl, 0.1% BSA, pH 7.4).

The Tris-BSA buffering solution (180 μL) was added to the aforementioned 10 mmol/L compound solution (20 μL). The mixture was provided for a 10-fold dilution series using the aforementioned Tris-BSA buffering solution to prepare solutions with compound concentrations of 1.0 mmol/L, 100, 10, 1, 0.1, 0.01 and 0.001 μmol/L (1.0 mmol-0.001 μmol/L compound solutions).

As a control, a solution was prepared by 10-fold dilution of DMSO with the Tris-BSA buffer (hereinafter referred to as "control 10% solution").

After dissolving one pack of Tris-Preset, NaCl (8.8 g) and BSA (1 g) in water (approximately 900 mL), a 1 mol/L calcium chloride (CaCl$_2$) aqueous solution (15 mL) and a 1 mg/mL Cephalin aqueous solution (30 mL) were added, and water was added to a total volume of 1 L. To this solution there was added a human tissue factor (hereinafter, "TF") sample (product of Calbiochem, Catalog No. 612151)(450 μg) to a TF sample concentration of 10 nmol/L, and then a human clotting factor VIIa (hereinafter, "Factor VIIa") purified sample (product of Enzyme Research Laboratories, Catalog No. HFVIIa)(250 μg) was added to a Factor VIIa purified sample concentration of 5 nmol/L, to prepare an enzyme solution (100 mmol/L Tris-HCl, 0.15 mol/L NaCl, 15 mmol/L CaCl$_2$, 30 μg/mL Cephalin, 1 mg/mL BSA, 10 nmol/L TF, 5 nmol/L Factor VIIa).

To 110 μL of this enzyme solution there was added 15 μL of each of the 1.0-mmol-0.001 μmol/L compound solutions, and then 25 μL of a 1.0 mmol/L synthetic chromogenic substrate solution (Spectrozyme FVIIa, product of American Diagnostica, Catalog No. 217L) was added and the mixture was allowed to stand at room temperature for 40 minutes. The amount of 4-nitroanilide released into the solution was quantified by spectrophotometry (405 nm).

A control 10% solution was used in place of the compound solution for measurement in the same manner as a control.

The enzyme reaction inhibition was determined based on this measurement in the presence of the compounds of the invention from 100 μmol/L to 0.1 nmol/L. The IC50 value of each compound as an index of inhibiting activity against clotting factor VIIa was calculated based on nonlinear regression analysis of the enzyme reaction inhibition at each compound concentration.

(2) Results

Table 1 shows the IC50 values (IC50 FVIIa (μM)) for inhibiting activity of each compound against clotting factor VIIa.

TABLE 1

|  | IC50 of FVIIa (μM) |
| --- | --- |
| Example 1 | 0.038 |
| Example 2 | 0.013 |
| Example 3 | 0.025 |
| Example 4 | 0.014 |
| Example 5 | 0.020 |
| Example 6 | 0.123 |
| Example 7 | 0.003 |
| Example 8 | 0.015 |
| Example 9 | 0.042 |
| Example 10 | 0.012 |
| Example 11 | 0.242 |
| Example 12 | 0.163 |
| Example 13 | 0.004 |
| Example 14 | 0.013 |
| Example 15 | 0.207 |
| Example 16 | 0.003 |
| Example 17 | 0.002 |

INDUSTRIAL APPLICABILITY

Since the compounds of the invention have excellent inhibitory action against blood clotting, and are safer with suitable physicochemical stability, they are useful as medicaments, and especially as therapeutic or prophylactic medicaments for diseases associated with thrombus formation.

What is claimed is:

1. A compound of formula (1), or a salt thereof:

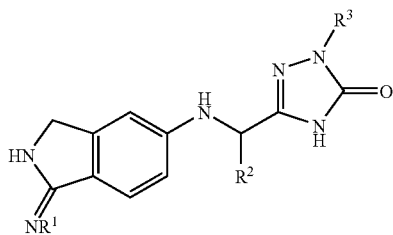

wherein
$R^1$ is hydrogen;
$R^2$ is
a C6-10 aryl optionally substituted by 1-5 substituents selected from Group A1 below or
a 9- to 12-membered benzene-fused cyclic group optionally substituted by 1-5 substituents selected from Group A1 below; and
$R^3$ is
a C6-10 aryl optionally substituted by 1-5 substituents selected from Group A1 below or
a 5- to 10-membered heteroaryl group optionally substituted by 1-5 substituents selected from Group A1 below,
wherein Group A1 is selected from the group consisting of
hydroxyl,
halogen,
cyano,
nitro,
oxo,
C1-6 alkyl optionally substituted by 1-3 substituents selected from Group B1 below,
C3-8 cycloalkyl optionally substituted by 1-5 substituents selected from Group B1 below,
C2-6 alkenyl,
C2-6 alkynyl,
C1-6 alkoxy optionally substituted by 1-3 substituents selected from Group B1 below,
C3-8 cycloalkyloxy optionally substituted by 1-5 substituents selected from Group B1 below,
C2-6 alkenyloxy,
C2-6 alkynyloxy,
C1-6 alkylthio,
C1-6 alkylsulfinyl,
C1-6 alkylsulfonyl,
C1-6 alkylsulfonyloxy,
C6-10 aryl optionally substituted by 1-5 substituents selected from Group B1 below,
C6-10 aryloxy optionally substituted by 1-5 substituents selected from Group B1 below,
5- to 10-membered heteroaryl group optionally substituted by 1-5 substituents selected from Group B1 below,
5- to 10-membered heteroaryloxy optionally substituted by 1-5 substituents selected from Group B1 below,
a 5- or 6-membered non-aromatic heterocyclic group optionally substituted by 1-5 substituents selected from Group B1 below,
5- or 6-membered non-aromatic heterocyclooxy optionally substituted by 1-5 substituents selected from Group B1 below,
—$NR^{1'}$—$R^{2'}$, and
—CO—$R^{3'}$;
where $R^{1'}$ and $R^{2'}$ each independently is
hydrogen,
C1-6 alkyl optionally substituted by 1-3 substituents selected from Group B1 below,
C2-6 alkenyl,
C2-7 alkylcarbonyl optionally substituted by 1-3 substituents selected from Group B1 below,
C2-7 alkoxycarbonyl optionally substituted by 1-3 substituents selected from Group B1 below,
C1-6 alkylsulfonyl optionally substituted by 1-3 substituents selected from Group B1 below,
carbamoyl,
aminosulfonyl,
C6-10 aryl optionally substituted by 1-5 substituents selected from Group B1 below, or
5- to 10-membered heteroaryl group optionally substituted by 1-5 substituents selected from Group B1 below, and
$R^{3'}$ is
hydroxyl,
C1-6 alkyl optionally substituted by 1-3 substituents selected from Group B1 below,
C1-6 alkoxy optionally substituted by 1-3 substituents selected from Group B1 below,
amino,
mono(C1-6 alkyl)amino optionally substituted by 1-3 substituents selected from Group B1 below, or
di(C1-6 alkyl)amino optionally substituted by 1-3 substituents selected from Group B1 below,
wherein Group B1 is selected from the group consisting of
hydroxyl,
halogen,
cyano,
oxo,
C1-6 alkoxy optionally substituted by halogen,
C3-8 cycloalkyl,
amino,
mono(C1-6 alkyl)amino,
di(C1-6 alkyl)amino,
carbamoyl,
mono(C1-6 alkyl)aminocarbonyl,
di(C1-6 alkyl)aminocarbonyl,
C6-10 aryl optionally substituted by 1-5 substituents selected from Group C1 below, and
5- 10-membered heteroaryl group optionally substituted by 1-5 substituents selected from Group C1 below,
wherein Group C1 is selected from the group consisting of halogen, C1-6 alkyl, and C1-6 alkoxy.

2. The compound or salt thereof of claim 1, which is the compound of formula (1-1), or a salt thereof:

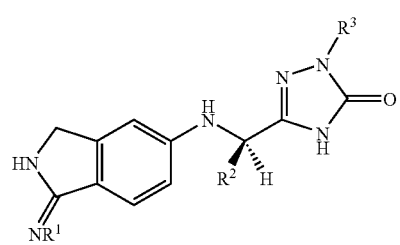

wherein $R^1$, $R^2$ and $R^3$ have the same definitions as $R^1$, $R^2$ and $R^3$ in claim 1.

3. The compound or salt thereof of claim 1, which is the compound of formula (1-2), or a salt thereof:

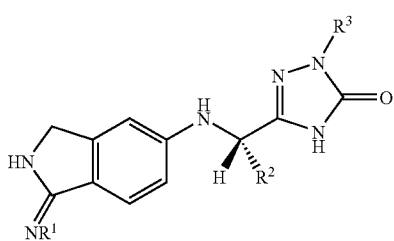

(1-2)

wherein $R^1$, $R^2$ and $R^3$ have the same definitions as $R^1$, $R^2$ and $R^3$ in claim 1.

4. The compound or a salt thereof according to claim 1, wherein $R^2$ is
phenyl optionally substituted by 1-4 substituents selected from Group D1 below or
a 9- to 12-membered benzene-fused cyclic group optionally substituted by 1-4 substituents selected from Group D1 below,
wherein Group D1 is selected from the group consisting of
hydroxyl,
halogen,
C1-6 alkyl optionally substituted by 1-3 substituents selected from Group D2 below,
C2-6 alkenyl,
C2-6 alkynyl,
C1-6 alkoxy optionally substituted by 1-3 substituents selected from Group D2 below,
C2-6 alkenyloxy,
C1-6 alkylsulfonyloxy, 5- or 6-membered non-aromatic heterocyclooxy optionally substituted by 1-3 substituents selected from Group D2 below, and
C2-7 alkylcarbonyl,
wherein Group D2 is selected from the group consisting of
hydroxyl,
halogen,
cyano,
oxo,
C1-6 alkoxy optionally substituted by halogen,
mono(C1-6 alkyl) amino,
di(C1-6 alkyl) amino,
mono(C1-6 alkyl) aminocarbonyl, and
di(C1-6 alkyl) aminocarbonyl.

5. The compound or a salt thereof according to claim 1, wherein $R^2$ is
phenyl optionally substituted by 1-4 substituents selected from Group D1 below,
wherein Group D1 is selected from the group consisting of
hydroxyl,
halogen,
C1-6 alkyl optionally substituted by 1-3 substituents selected from Group D2 below,
C2-6 alkenyl,
C2-6 alkynyl,
C1-6 alkoxy optionally substituted by 1-3 substituents selected from Group D2 below,
C2-6 alkenyloxy,
C1-6 alkylsulfonyloxy,
5- or 6-membered non-aromatic heterocyclooxy optionally substituted by 1-3 substituents selected from Group D2 below, and
C2-7 alkylcarbonyl,
wherein Group D2 is selected from the group consisting of
hydroxyl,
halogen,
cyano,
oxo,
C1-6 alkoxy optionally substituted by halogen,
mono(C1-6 alkyl) amino,
mono(C1-6 alkyl) aminocarbonyl, and
di(C1-6 alkyl) aminocarbonyl.

6. The compound or a salt thereof according to claim 1, wherein $R^2$ is
phenyl optionally substituted by 2-3 substituents selected from Group D3 below,
wherein Group D3 is selected from the group consisting of
fluorine,
chlorine,
methyl optionally substituted by 1 substituent selected from Group D4 below,
ethyl optionally substituted by 1 substituent selected from Group D4 below,
vinyl,
ethynyl,
methoxy optionally substituted by 1 or 2 substituents selected from Group D4 below,
ethoxy optionally substituted by 1 or 2 substituents selected from Group D4 below,
1-propyloxy optionally substituted by 1 or 2 substituents selected from Group D4 below,
2-propyloxy optionally substituted by 1 or 2 substituents selected from Group D4 below,
allyloxy,
tetrahydrofuryloxy,
tetrahydropyranyloxy, and
acetyl,
wherein Group D4 is selected from the group consisting of
hydroxyl,
fluorine,
cyano,
methoxy,
methylamino,
dimethylamino,
methylaminocarbonyl, and
dimethylaminocarbonyl.

7. The compound or a salt thereof according to claim 1, wherein $R^2$ is a group of the following formula:

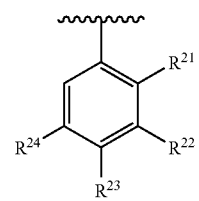

wherein $R^{21}$ is
hydrogen,
benzyloxy,
fluorine or
chlorine;
$R^{22}$ is
hydrogen,
hydroxyl,
methyl optionally substituted by 1 substituent selected from Group D5 below, ethyl optionally substituted by 1 substituent selected from Group D5 below,
methoxy optionally substituted by 1 substituent selected from Group D5 below,
ethoxy optionally substituted by 1 or 2 substituents selected from Group D5 below,
1-propyloxy optionally substituted by 1 substituent selected from Group D5 below,
2-propyloxy optionally substituted by 1 substituent selected from Group D5 below,
allyloxy,
tetrahydrofuryloxy,
tetrahydropyranyloxy, or
acetyl;
$R^{23}$ is
hydrogen,
fluorine,
hydroxyl,
methoxy optionally substituted by 1 substituent selected from Group D6 below,
ethoxy optionally substituted by 1 substituent selected from Group D6 below, or
2-propyloxy optionally substituted by 1 substituent selected from Group D6 below, and
$R^{24}$ is
hydrogen,
fluorine,
hydroxyl,
methyl optionally substituted by 1 substituent selected from Group D7 below,
ethyl,
vinyl,
ethynyl,
methoxy optionally substituted by 1 substituent selected from Group D7 below,
ethoxy optionally substituted by 1 substituent selected from Group D7 below,
2-propyloxy, or
allyloxy,
wherein Group D5 is selected from the group consisting of
hydroxyl,
fluorine,
cyano,
methoxy,
dimethylamino,
dimethylaminocarbonyl,
2-fluoroethoxy and
2-hydroxyethoxy,
wherein Group D6 consists of
fluorine,
cyano,
methoxy,
dimethylamino,
methylaminocarbonyl, and
dimethylaminocarbonyl,
wherein Group D7 is selected from the group consisting of hydroxyl, fluorine, cyano, and ethoxy having one methoxy.

8. The compound or a salt thereof according to claim 7, wherein $R^{21}$ is hydrogen or fluorine.

9. The compound or a salt thereof according to claim 7, wherein $R^{22}$ is hydrogen, hydroxyl, cyanomethyl, methoxymethyl, methoxy, dimethylaminocarbonylmethoxy, ethoxy, 2-fluoroethoxy, 2-hydroxyethoxy, 2-methoxyethoxy, 2-(dimethylamino)ethoxy, tetrahydrofuryloxy, tetrahydropyranyloxy, fluoromethoxy, 3-hydroxypropyloxy, 2-fluoroethoxymethyl or 2-hydroxyethoxymethyl.

10. The compound or a salt thereof according to claim 7, wherein $R^{23}$ is hydrogen, fluorine, methoxy, cyanomethoxy, ethoxy, 2-propyloxy or 2-methoxyethoxy.

11. The compound or a salt thereof according to claim 7, wherein $R^{24}$ is hydrogen, hydroxyl, methyl, ethyl, vinyl, ethynyl, methoxy, ethoxy, or 2-fluoroethoxy.

12. The compound or a salt thereof according to claim 1, wherein $R^2$ is a 9- to 12-membered benzene-fused cyclic group optionally substituted by 1-4 substituents selected from Group D1 below,
wherein Group D1 is selected from group consisting of
hydroxyl,
halogen,
C1-6 alkyl optionally substituted by 1-3 substituents selected from Group D2 below,
C2-6 alkenyl,
C2-6 alkynyl,
C1-6 alkoxy optionally substituted by 1-3 substituents selected from Group D2 below,
C2-6 alkenyloxy,
C1-6 alkylsulfonyloxy,
5- or 6-membered non-aromatic heterocyclooxy optionally substituted by 1-3 substituents selected from Group D2 below, and
C2-7 alkylcarbonyl,
wherein Group D2 is selected from the group consisting of
hydroxyl,
halogen,
cyano,
oxo,
C1-6 alkoxy optionally substituted by halogen,
mono(C1-6 alkyl) amino,
di(C1-6 alkyl) amino,
mono(C1-6 alkyl) aminocarbonyl, and
di(C1-6 alkyl) aminocarbonyl.

13. The compound or a salt thereof according to claim 1, wherein $R^2$ is a group of the following formula:

wherein $R^{27}$ is hydrogen or halogen;
$R^{28}$ is
hydrogen,
hydroxyl,
halogen,
C1-6 alkyl optionally substituted by 1-3 substituents selected from Group D8 below,
C2-6 alkenyl,
C2-6 alkynyl,
C1-6 alkoxy optionally substituted by 1-3 substituents selected from Group D8 below, or
C2-7 alkylcarbonyl;
$R^{29}$ is
hydrogen,
cyano, C1-6 alkyl optionally substituted by 1-3 substituents selected from Group D8 below,
C1-6 alkoxy optionally substituted by 1-3 substituents selected from Group D8 below, or
carbamoyl;
X is
carbon optionally substituted by 1-2 substituents selected from Group D8 below,
nitrogen optionally substituted by 1substituents selected from Group D8 below, or oxygen;
m is an integer from 0 to 3 and n is an integer from 0 to 2, with the proviso that the sum of m and n is 1-4; and
Rings A and B optionally contain one double bond in the ring and are optionally substituted by an oxo group on the ring,
wherein Group D8 is selected from the group consisting of
hydrogen,
hydroxyl,
halogen,
C1-6 alkoxy,
mono(C1-6 alkyl)amino,
di(C1-6 alkyl)amino,
mono(C1-6 alkyl) aminocarbonyl,
di(C1-6 alkyl)aminocarbonyl, and
C1-6 alkyl optionally substituted by halogen.

14. The compound or a salt thereof according to claim 13, wherein $R^2$ is a group of the following formula:

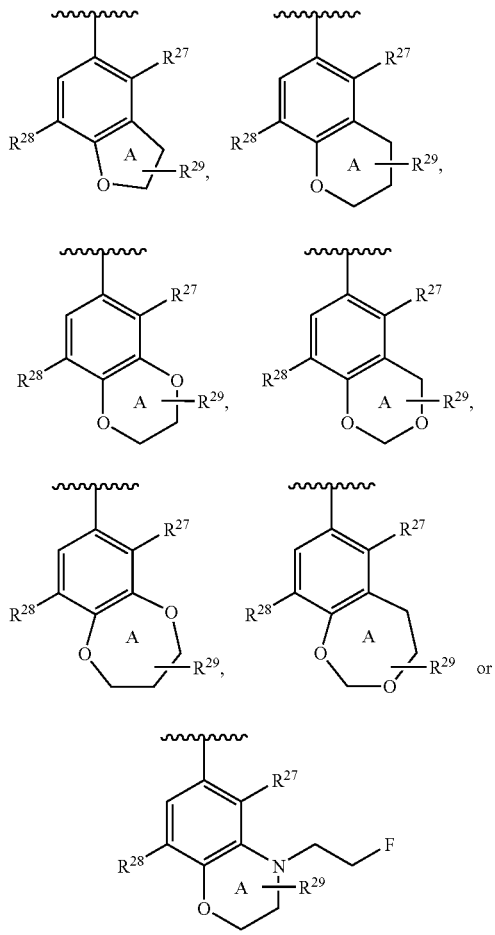

wherein $R^{27}$ is hydrogen or halogen;
$R^{28}$ is
hydrogen,
hydroxyl,
C1-6 alkyl optionally substituted by 1-3 substituents selected from Group D8 below,
C2-6 alkenyl,
C2-6 alkynyl,
C1-6 alkoxy optionally substituted by 1-3 substituents selected from Group D8 below, or
C2-7 alkylcarbonyl;
$R^{29}$ is
hydrogen,
cyano,
C1-6 alkyl optionally substituted by 1-3 substituents selected from Group D8 below,
C1-6 alkoxy optionally substituted by 1-3 substituents selected from Group D8 below, or
aminocarbonyl;
and Ring A is optionally substituted by an oxo group on the ring,
wherein Group D8 is selected from the group consisting of
hydrogen,
hydroxyl,
halogen,
C1-6 alkoxy,
mono(C1-6 alkyl)amino,
di(C1-6 alkyl)amino,
mono(C1-6 alkyl)aminocarbonyl,
di(C1-6 alkyl)aminocarbonyl, and
C1-6 alkyl optionally substituted by halogen.

15. The compound or a salt thereof according to claim 14, wherein $R^{28}$ is methyl, ethyl, methoxy, ethoxy, vinyl or ethynyl.

16. The compound or a salt thereof according to claim 14, wherein $R^{29}$ is hydrogen.

17. The compound or a salt thereof according to claim 1, wherein $R^3$ is
phenyl optionally substituted by substituted by 1-3 substituents selected from Group E1 below,
pyridyl optionally substituted by substituted by 1-3 substituents selected from Group E1 below,
N-oxypyridyl optionally substituted by substituted by 1-3 substituents selected from Group E1 below,
pyrimidinyl optionally substituted by 1-3 substituents selected from Group E1 below,
pyrazolyl optionally substituted by 1 or 2 substituents selected from Group E1 below,
imidazolyl optionally substituted by 1 or 2 substituents selected from Group E1 below,
thiazolyl optionally substituted by 1 or 2 substituents selected from Group E1 below,
thienyl optionally substituted by 1-3 substituents selected from Group E1below, or
oxazolyl optionally substituted by 1-3 substituents selected from Group E1below,
wherein Group E1 is selected from the group consisting of
hydroxyl,
halogen,
cyano,
C1-6 alkyl,
C1-6 alkoxy,
—NH-$R^{21r}$, and
—CO-$R^{31r}$;
where $R^{21r}$ is
hydrogen,
C1-6 alkyl,
C2-6 alkenyl,
C2-7 alkylcarbonyl optionally substituted by 1-3 substituents selected from Group E2 below, C2-7 alkoxycarbonyl optionally substituted by 1-3 substituents selected from Group E2 below,
C1-6 alkylsulfonyl,
Carbamoyl, or
aminosulfonyl, and
$R^{31t}$ is
hydroxyl,
C1-6 alkyl,
C1-6 alkoxy,
amino,
mono(C1-6 alkyl)amino, or
di(C1-6 alkyl)amino,
wherein Group E2 is selected from the group consisting of hydroxyl, C1-6 alkoxy, and C3-8 cycloalkyl.

18. The compound or a salt thereof according to claim 1, wherein $R^3$ is
phenyl optionally substituted by 1 or 2 substituents selected from Group E3 below,
pyridyl optionally substituted by 1 or 2 substituents selected from Group E3 below,
N-oxypyridyl optionally substituted by 1 or 2 substituents selected from Group E3 below,
pyrimidinyl optionally substituted by 1 or 2 substituents selected from Group E3 below,
pyrazolyl optionally substituted by 1 or 2 substituents selected from Group E3 below,
imidazolyl optionally having substituted by 1 or 2 substituents selected from Group E3 below,
thiazolyl optionally substituted by 1 or 2 substituents selected from Group E3 below,
thienyl optionally substituted by 1 or 2 substituents selected from Group E3 below, or
oxazolyl optionally substituted by 1 or 2 substituents selected from Group E3 below,
wherein Group E3 is selected from the group consisting of halogen,
C1-6 alkyl,
C1-6 alkoxy,
—NH—$R^{22t}$,
nitro, and
—CO—$R^{32t}$;
wherein $R^{22t}$ is hydrogen or C2-7 alkoxycarbonyl, and $R^{32t}$ is hydroxyl, C1-6 alkoxy or amino.

19. The compound or a salt thereof according to claim 1, wherein $R^3$ is
phenyl optionally substituted by one group selected from Group E4 below,
pyridyl optionally substituted by one group selected from Group E5 below,
N-oxypyridyl,
pyrazinyl,
pyridazinyl,
pyrimidinyl,
pyrazolyl optionally substituted by one group selected from Group E4 below,
imidazolyl optionally substituted by one group selected from Group E4 below,
thiazolyl optionally substituted by one group selected from Group E4 below,
thienyl optionally substituted by one group selected from Group E4 below, or
oxazolyl optionally having substituted by one group selected from Group E4
wherein Group E4 is selected from the group consisting of methoxy,
—NH—$R^{22t}$,
nitro,
carboxyl,
carbamoyl,
methoxycarbonyl, and
methoxycarbonylamino,
where $R^{22t}$ is hydrogen or C2-7 alkoxycarbonyl,
wherein Group E5 is selected from the group consisting of fluorine, methyl, methoxy, and amino.

20. A pharmaceutical composition comprising a compound or a salt thereof according to claim 1 an a pharmaceutically acceptable excipient.

21. An agent for the inhibition of clotting factor VIIa which comprises a compound or a salt thereof according to claim 1.

22. The compound of claim 1, selected from the group consisting of:

2-(3-aminopyridin-2-yl)-5-[(1-imino-2,3-dihydro-1H-isoindol-5-ylamino)-(8-methoxy-4H-benzo[1,3]dioxin-6-yl)methyl]-2,4-dihydro-1,2,4-triazol-3-one

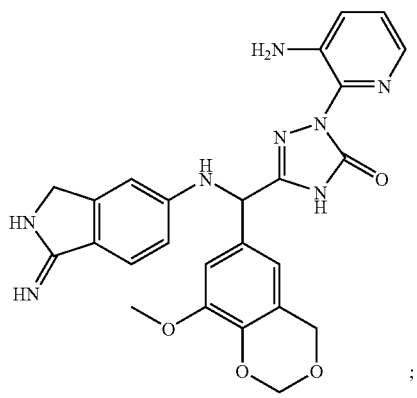

;

5-[(1-imino-2,3-dihydro-1H-isoindol-5-ylamino)-(8-methoxy-4H-benzo[1,3]dioxin-6-yl)methyl]-2-pyrimidin-2-yl-2,4-dihydro-1,2,4-triazol-3-one

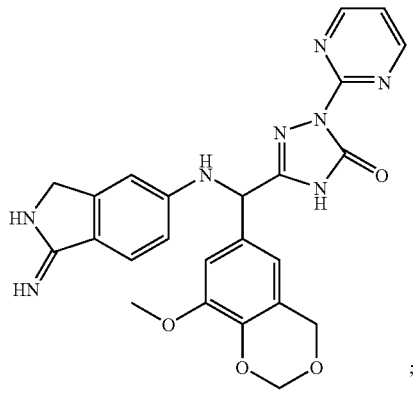

;

2-(3-aminopyridin-2-yl)-5-{[5-ethyl-2-fluoro-3(2-hydroxyethoxy)phenyl]-(1-imino-2,3-dihydro-1H-isoindol-5-ylamino)methyl}-2,4-dihydro-1,2,4-triazol-3-one

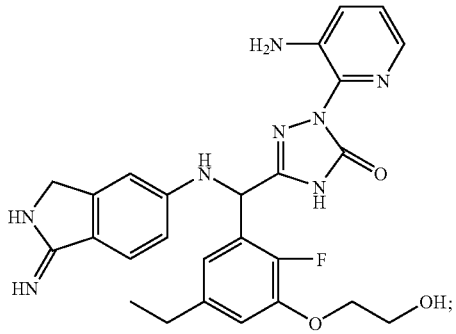

and pharmaceutically acceptable salts thereof.

23. The compound of claim 22, wherein said compound is 2-(3-aminopyridin-2-yl)-5-[(1-imino-2,3-dihydro-1H-isoindol-5-ylamino)-(8-methoxy-4H-benzo[1,3]dioxin-6-yl)methyl]-2,4-dihydro-1,2,4-triazol-3-one

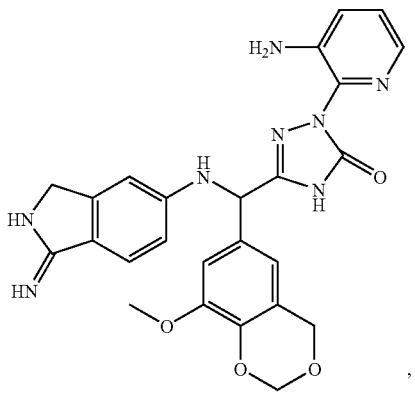

or a pharmaceutically acceptable salt thereof.

24. The compound of claim 22, wherein said compound is 5-[(1-imino-2,3-dihydro-1H-isoindol-5-ylamino)-(8-methoxy-4H-benzo[1,3]dioxin-6-yl)methyl]-2-pyrimidin-2-yl-2,4-dihydro-1,2,4-triazol-3-one

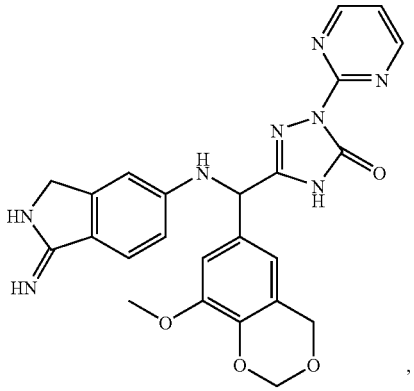

or a pharmaceutically acceptable salt thereof.

25. The compound of claim 22, wherein said compound is 2-(3-aminopyridin-2-yl)-5-{[5-ethyl-2-fluoro-3(2-hydroxyethoxy)phenyl]-(1-imino-2,3-dihydro-1H-isoindol-5-ylamino)methyl}-2,4-dihydro-1,2,4-triazol-3-one

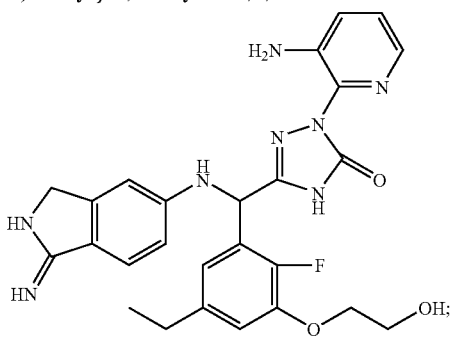

or a pharmaceutically acceptable salt thereof.

* * * * *